(12) United States Patent
Block et al.

(10) Patent No.: US 12,122,836 B2
(45) Date of Patent: Oct. 22, 2024

(54) FUSION PROTEINS OF HUMAN PROTEIN FRAGMENTS TO CREATE ORDERLY MULTIMERIZED IMMUNOGLOBULIN Fc COMPOSITIONS WITH ENHANCED COMPLEMENT BINDING

(71) Applicant: Gliknik Inc., Baltimore, MD (US)

(72) Inventors: David S. Block, Baltimore, MD (US); Henrik Olsen, Baltimore, MD (US)

(73) Assignee: Gliknik Inc., Baltimore, MD (US)

( * ) Notice: Subject to any disclaimer, the term of this patent is extended or adjusted under 35 U.S.C. 154(b) by 497 days.

(21) Appl. No.: 15/878,509

(22) Filed: Jan. 24, 2018

(65) Prior Publication Data

US 2018/0244772 A1     Aug. 30, 2018

Related U.S. Application Data

(63) Continuation of application No. PCT/US2016/043746, filed on Jul. 22, 2016.

(60) Provisional application No. 62/196,478, filed on Jul. 24, 2015.

(51) Int. Cl.
| | |
|---|---|
| C07K 16/28 | (2006.01) |
| C07K 16/00 | (2006.01) |
| A61K 38/17 | (2006.01) |
| A61K 39/00 | (2006.01) |
| A61P 37/06 | (2006.01) |
| A61P 37/08 | (2006.01) |

(52) U.S. Cl.
CPC ............ *C07K 16/283* (2013.01); *C07K 16/00* (2013.01); *C07K 16/2803* (2013.01); *A61K 38/1774* (2013.01); *A61K 2039/505* (2013.01); *A61P 37/06* (2018.01); *A61P 37/08* (2018.01); *C07K 2317/35* (2013.01); *C07K 2317/52* (2013.01); *C07K 2317/524* (2013.01); *C07K 2317/526* (2013.01); *C07K 2317/53* (2013.01); *C07K 2317/734* (2013.01); *C07K 2317/92* (2013.01); *C07K 2317/94* (2013.01); *C07K 2319/00* (2013.01); *C07K 2319/30* (2013.01); *C07K 2319/73* (2013.01)

(58) Field of Classification Search
None
See application file for complete search history.

(56) References Cited

U.S. PATENT DOCUMENTS

| | | | |
|---|---|---|---|
| 5,648,260 A * | 7/1997 | Winter .................. | C07K 16/00 435/69.6 |
| 5,681,566 A | 10/1997 | Stevenson | |
| 5,877,396 A | 3/1999 | Ravetch et al. | |
| 6,004,781 A | 12/1999 | Seed | |
| 6,194,551 B1 * | 2/2001 | Idusogie ............ | C07K 16/2896 530/389.1 |
| 6,660,266 B1 | 12/2003 | Mosser et al. | |
| 6,737,056 B1 | 5/2004 | Presta | |
| 7,148,321 B2 | 12/2006 | Gillies et al. | |
| 7,511,121 B2 | 3/2009 | Arnason et al. | |
| 7,524,487 B2 | 4/2009 | Mosser et al. | |
| 7,666,622 B2 | 2/2010 | Sharma et al. | |
| 8,147,835 B2 | 4/2012 | Ledbetter et al. | |
| 8,258,263 B2 | 9/2012 | Morrison et al. | |
| 8,680,237 B2 | 3/2014 | Strome et al. | |
| 8,815,237 B2 | 8/2014 | Wittrup et al. | |
| 9,512,208 B2 | 12/2016 | Strome et al. | |
| 9,512,210 B2 | 12/2016 | Strome et al. | |
| 9,683,044 B2 | 6/2017 | Block et al. | |
| 9,926,362 B2 | 3/2018 | Strome et al. | |
| 10,208,105 B2 | 2/2019 | Strome et al. | |
| 10,851,154 B2 | 12/2020 | Strome et al. | |
| 10,941,191 B2 | 3/2021 | Strome et al. | |
| 11,034,775 B2 | 6/2021 | Olsen et al. | |
| 11,117,940 B2 | 9/2021 | Block et al. | |
| 11,331,372 B2 | 5/2022 | Block et al. | |
| 2002/0115157 A1 | 8/2002 | Davis et al. | |
| 2002/0142374 A1 | 10/2002 | Gallo et al. | |
| 2002/0147326 A1 | 10/2002 | Chaikin et al. | |
| 2003/0044423 A1 | 3/2003 | Gillies et al. | |
| 2003/0118592 A1 | 6/2003 | Ledbetter et al. | |
| 2003/0216546 A1 | 11/2003 | Tykocinski et al. | |
| 2003/0235578 A1 | 12/2003 | Stinson et al. | |
| 2004/0062763 A1 | 4/2004 | Mosser et al. | |
| 2004/0110226 A1 | 6/2004 | Lazar et al. | |
| 2004/0147731 A1 | 7/2004 | Parkos | |
| 2004/0151725 A1 | 8/2004 | Gray et al. | |

(Continued)

FOREIGN PATENT DOCUMENTS

| | | |
|---|---|---|
| AU | 2015200330 B2 | 10/2016 |
| CN | 101835802 A | 9/2010 |

(Continued)

OTHER PUBLICATIONS

Schneider et al (MI, 51:66-72, 2012).*
Borrok et al (ACS CB, 7:1596-1602, 2012).*
Beurskens et al (Blood, 122(21):375, 2013).*
Skolnick et al. (Trends in Biotechnology, 18: 34-39, 2000).*
By Jones (Pharmacogenomics Journal, 1:126-134, 2001).*
Tosatto et al (Current Pharmaceutical Design, 12:2067-2086, 2006).*
Czajkowsky et al (SR, 5:9526, 1-11, 2015).*
Diebolder et al (Science, 343:1260-1263, 2014).*
Passeri et al (Int. J. Mol. Sci. 2022, 23, 13954).*
Cummings et al (Journal of Alzheimer's Disease 67 (2019) 779-794).*
Rodriguez de Cordoba et al (Immunobiology, 217(11):1034-1046, 2012).*

(Continued)

*Primary Examiner* — Brad Duffy
(74) *Attorney, Agent, or Firm* — COOLEY LLP

(57) ABSTRACT

The current invention involves a series of fully recombinant multimerized forms of immunoglobulin Fc which thereby present polyvalent immunoglobulin Fc to immune cell receptors. The fusion proteins exist as both homodimeric and highly ordered multimeric fractions, termed stradomers. The invention involves stradomers that increase multimerization and bind preferentially to complement and that are useful in the treatment and prevention of disease.

10 Claims, 86 Drawing Sheets
Specification includes a Sequence Listing.

(56) References Cited

U.S. PATENT DOCUMENTS

| | | |
|---|---|---|
| 2004/0265321 A1 | 12/2004 | Johnson et al. |
| 2005/0033029 A1 | 2/2005 | Lu |
| 2005/0249723 A1 | 11/2005 | Lazar |
| 2006/0074225 A1 | 4/2006 | Chamberlain et al. |
| 2006/0263856 A1 | 11/2006 | Gillies et al. |
| 2006/0275254 A1 | 12/2006 | Kim et al. |
| 2007/0128111 A1 | 6/2007 | Reilly et al. |
| 2007/0269369 A1 | 11/2007 | Gegg et al. |
| 2008/0242845 A1* | 10/2008 | Lazar .............. C07K 16/2893 530/387.3 |
| 2008/0260738 A1 | 10/2008 | Moore et al. |
| 2008/0267980 A1 | 10/2008 | Tomlinson et al. |
| 2009/0104210 A1 | 4/2009 | Tota et al. |
| 2009/0117133 A1 | 5/2009 | Arnason et al. |
| 2009/0136485 A1 | 5/2009 | Chu et al. |
| 2009/0175867 A1 | 7/2009 | Thompson et al. |
| 2009/0217401 A1 | 8/2009 | Korman et al. |
| 2009/0252729 A1 | 10/2009 | Farrington et al. |
| 2009/0258031 A1 | 10/2009 | Karrer et al. |
| 2009/0304696 A1 | 12/2009 | Lawson et al. |
| 2009/0304715 A1 | 12/2009 | Masuho et al. |
| 2010/0048877 A1 | 2/2010 | Ruker et al. |
| 2010/0093979 A1 | 4/2010 | Lazar |
| 2010/0143353 A1 | 6/2010 | Mosser et al. |
| 2010/0158909 A1 | 6/2010 | Mcdonagh et al. |
| 2010/0227805 A1 | 9/2010 | Karin et al. |
| 2010/0239633 A1 | 9/2010 | Strome et al. |
| 2011/0243966 A1 | 10/2011 | Farrington et al. |
| 2011/0305697 A1 | 12/2011 | Walczak |
| 2012/0100099 A1 | 4/2012 | Wang et al. |
| 2012/0100140 A1 | 4/2012 | Reyes et al. |
| 2012/0149876 A1 | 6/2012 | Von Kreudenstein et al. |
| 2012/0283417 A1 | 11/2012 | Mosser et al. |
| 2012/0309941 A1 | 12/2012 | Strome et al. |
| 2013/0156765 A1 | 6/2013 | Block et al. |
| 2013/0266579 A1* | 10/2013 | Wei .............. A61P 25/00 424/158.1 |
| 2014/0072582 A1 | 3/2014 | Block et al. |
| 2014/0105913 A1 | 4/2014 | Strome et al. |
| 2014/0120581 A1* | 5/2014 | Niwa .............. C07K 16/2887 435/69.6 |
| 2014/0335075 A1 | 11/2014 | Strome et al. |
| 2014/0370012 A1 | 12/2014 | Block et al. |
| 2015/0056185 A1 | 2/2015 | Strome et al. |
| 2015/0071948 A1* | 3/2015 | Lazar .............. A61K 47/68 424/178.1 |
| 2015/0166636 A1 | 6/2015 | Igawa et al. |
| 2015/0218236 A1 | 8/2015 | Pleass |
| 2015/0353636 A1 | 12/2015 | Parren et al. |
| 2016/0229913 A1 | 8/2016 | Bosques et al. |
| 2016/0280768 A1 | 9/2016 | Strome et al. |
| 2016/0355570 A1 | 12/2016 | Strome et al. |
| 2017/0008951 A1 | 1/2017 | Block et al. |
| 2017/0029505 A1 | 2/2017 | Griffin et al. |
| 2017/0081406 A1 | 3/2017 | Fallah-arani et al. |
| 2017/0088603 A1 | 3/2017 | Fallah-arani et al. |
| 2018/0002388 A1 | 1/2018 | Block et al. |
| 2018/0094061 A1 | 4/2018 | Block et al. |
| 2018/0186862 A1 | 7/2018 | Strome et al. |
| 2019/0194357 A1 | 6/2019 | Olsen et al. |
| 2019/0218275 A1 | 7/2019 | Strome et al. |
| 2019/0389941 A1 | 12/2019 | Block et al. |
| 2021/0277091 A1 | 9/2021 | Strome et al. |
| 2022/0056087 A1 | 2/2022 | Block et al. |
| 2022/0241372 A1 | 8/2022 | Block et al. |

FOREIGN PATENT DOCUMENTS

| | | |
|---|---|---|
| CN | 103260640 A | 8/2013 |
| EP | 0553667 A1 | 8/1993 |
| EP | 0439540 B1 | 6/1995 |
| EP | 2006305 A9 | 7/2009 |
| JP | 2013-543483 A | 12/2013 |
| KR | 20130043171 A | 4/2013 |
| RU | 2549676 C2 | 4/2015 |
| WO | WO 1990/004413 A1 | 5/1990 |
| WO | WO 1994/003191 A1 | 2/1994 |
| WO | WO 1994/015640 A1 | 7/1994 |
| WO | WO 2000/009560 A2 | 2/2000 |
| WO | WO 2002/056910 A1 | 7/2002 |
| WO | WO 2002/072605 A2 | 9/2002 |
| WO | WO 2002/072608 A2 | 9/2002 |
| WO | WO 2003/010202 A1 | 2/2003 |
| WO | WO 2003/051933 A1 | 6/2003 |
| WO | WO 2003/074679 A2 | 9/2003 |
| WO | WO 2003/105898 A1 | 12/2003 |
| WO | WO 2004/062619 A2 | 7/2004 |
| WO | WO 2005/000895 A2 | 1/2005 |
| WO | WO 2005/007809 A2 | 1/2005 |
| WO | WO 2005/077981 A2 | 8/2005 |
| WO | WO 2005/089503 A2 | 9/2005 |
| WO | WO 2006/008739 A2 | 1/2006 |
| WO | WO 2006/061650 A2 | 6/2006 |
| WO | WO 2006/071206 A2 | 7/2006 |
| WO | WO 2006/074199 A1 | 7/2006 |
| WO | WO 2007/021129 A1 | 2/2007 |
| WO | WO 2007/100083 A1 | 9/2007 |
| WO | WO 2008/114011 A2 | 9/2008 |
| WO | WO 2008/138131 A1 | 11/2008 |
| WO | WO 2008/151088 A2 | 12/2008 |
| WO | WO 2008/157378 A2 | 12/2008 |
| WO | WO 2009/079242 A2 | 6/2009 |
| WO | WO 2010/065578 A2 | 6/2010 |
| WO | WO 2011/060242 A2 | 5/2011 |
| WO | WO 2011/073692 A1 | 6/2011 |
| WO | WO 2011/091078 A2 | 7/2011 |
| WO | WO 2012/001647 A2 | 1/2012 |
| WO | WO 2012/016073 A2 | 2/2012 |
| WO | WO 2013/112986 A1 | 8/2013 |
| WO | WO 2014/006217 A1 | 1/2014 |
| WO | WO 2014/031646 A2 | 2/2014 |
| WO | WO 2015/132364 A1 | 9/2015 |
| WO | WO 2015/158867 A1 | 10/2015 |
| WO | WO 2016/009232 A1 | 1/2016 |
| WO | WO 2016/073917 A1 | 5/2016 |
| WO | WO 2016/139365 A1 | 9/2016 |
| WO | WO 2017/005767 A1 | 1/2017 |
| WO | WO 2017/013203 A1 | 1/2017 |
| WO | WO 2017/019565 A1 | 2/2017 |
| WO | WO 2017/036905 A1 | 3/2017 |
| WO | WO-2017176651 A1 | 10/2017 |
| WO | WO 2017/214321 A1 | 12/2017 |
| WO | WO 2018/018047 A2 | 1/2018 |
| WO | WO-2018107082 A1 | 6/2018 |

OTHER PUBLICATIONS

"Synthetic peptides with high biochemical activity," downloaded on Sep. 7, 2012 from http://www.genosphere-biotech.com/Long-Active-Peptides.html, 1 page.

Abaza, et al., "Effect of amino acid substitutions outside an antigenic site on protein binding to monoclonal antibodies of predetermined specificity obtained by peptide immunization: demonstration with region 94-100 (antigenic site 3) of myoglobin." Journal of Protein Chemistry (1992); 11 (5): 433-444.

Alegre and Fallarino, "Mechanisms of CTLA-4-Ig in tolerane induction." Curr. Pharmaceutical Design (2006); 12 (2): 149-160.

Anderson, C. A. et al., "Cutting Edge: Biasing immune responses by directing antigen to macrophage Fcγ receptors." J. Immunology (2002); 168: 3697-3701.

Andreson, et al., "Product Equivalence Study Comparing the Tolerability, Pharmacokinetics, and Pharmacodynamics of Various Human Immunoglobulin-G Formulations." The Journal of Clinical Pharmacology (2000); 40 (7): 722-730.

Arase, et al., "Association with FcRγ Is Essential for Activation Signal through NKR-P1 (CD161) in Natural Killer (NK) Cells and NK1.1+ T Cells." Journal of Experimental Medicine (1997); 186 (12): 1957-1963.

Arduin, et al., "Highly reduced binding to high and low affinity mouse Fc gamma receptors by L234A/L235A and N297A Fc mutations engineered into mouse lgG2a." Molecular Immunology (2015); 63 (2): 456-463.

(56) References Cited

OTHER PUBLICATIONS

Asanuma, et al., "Multimerization and collagen binding of vitronectin is modulated by its glycosylation." International Congress Series (2001); vol. 1223, pp. 97-101.
Aslan, et al., "Plasmon light scattering in biology and medicine: new sensing approaches, visions and perspectives." Current Opinion in Chemical Biology (2005); 9 (5): 538-544.
Aubin, et al., "Indirect inhibition of in vivo and in vitro T-cell responses by intravenous immunoglobulins due to impaired antigen presentation." Blood (2010); 115 (9): 1727-1734.
Augeber, et al., "Are aggregates of IgG the effective part of high-dose immunoglobulin therapy in adult idiopathic thrombocytopenia purpura (ITP)?" Blut (1985); 50: 249-252.
Bánki, et al., "Cross-Linking of CD32 Induces Maturation of Human Monocyte-Derived Dendritic Cells Via NF-κB Signaling Pathway." The Journal of Immunology (2003); 170 (8): 3963-3970.
Barrionuevo, et al., "Immune complex-FcγR interaction modulates monocyte/macrophage molecules involved in inflammation and immune response." Clin. Exp. Immunol. (2013); 133 (2): 200-207.
Bazin, et al., "Tetramolecular immune complexes are more efficient than IVIg to prevent antibody-dependent in vitro and in vivo and in in vivo phagocytosis of blood cells." British J. Haematol. (2004); 127 (1): 90-96.
Boyle, et al., "Human Antibodies Fix Complement to Inhibit Plasmodium falciparum Invasion of Erythrocytes and Are Associated with Protection against Malaria." Immunity (2015); 42 (3): 580-590.
Boyle, J.J., et al., "Solid-Phase Immunoglobulins IgG and IgM Activate Macrophages with Solid-Phase IgM Acting via a Novel Scavenger Receptor A Pathway." The American Journal of Pathology (2012); 181 (1): 347-361.
Braathen, R., et al., "The Carboxyl-terminal Domains of IgA and IgM Direct Isotype-specific Polymerization and Interaction with the Polymeric Immunoglobulin Receptor." The Journal of Biological Chemistry (2002); 277 (45): 42755-42762.
Bruhns, et al., "Specificity and affinity of human Fc receptors and their polymorphic variants for human IgG subclasses." Blood (2009); 113 (16): 3716-3725.
Burton, "Immunoglobulin G: Functional sites." Molecular Immunology (1985); 22 (3): 161-206.
Campbell, A. M., "Monoclonal Antibody Technology," In Laboratory Techniques in Biochemistry and Molecular Biology (1984); vol. 13, Elsevier Science Publishers, pp. 1-32.
Caron, et al., "Engineered Humanized Dimeric Forms of IgG are More Effective Antibodies." J. Exp. Med. (1992); 176: 1191-1195.
Chang, et al., "Intravenous immunoglobulins reverse acute vasoocclusive crises in sickle cell mice through rapid inhibition of neutrophil adhesion." Blood (2008); 111: 915-923.
Chappel, et al., "Identification of the Fcγ receptor class I binding site in human IgG through the use of recombinant IgG1/IgG2 hybrid and point-mutated antibodies." Proc. Natl. Acad. Sci. USA (1991); 88: 9036-9040.
Chougnet, et al., "Molecular analysis of decreased interleukin-12 production in person infected with human immunodeficiency virus." J. Infectious Diseases (1996); 174: 46-53.
Chu, et al., "Inhibition of B cell receptor-mediated activation of primary human B cells by coengagement of CD19 and FcγRIIb with Fc-engineered antibodies." Molecular Immunology (2008); 45 (15): 3926-3933.
Cohen, P., "Systemic Autoimmunity," In Fundamental Immunology, 4th edition, Philadelphia, Lippencot-Raven Publishers, pp. 1067-1088 (1999).
Colman, et al., "Effects of amino acid sequence changes on antibody-antigen interactions," Research in Immunology (1994); 145 (1): 33-36.
Constantine, M. M., et al., "Intravenous immunoglobulin utilization in the Canadian Atlantic provinces: a report of the Atlantic Collaborative Intravenous Immune Globulin utilization working group." Transfusion (2007); 47: 2072-2080.

Davidson, et al, "T helper cell1-type CD4+ T cells, but not B cells, mediate colitis in interleukin 10-deficient mice." J. Exp. Med. (1996); 184: 241-251.
Davis, et al., "Differential B cell expression of mouse Fc receptor homologs." International Immunology (2004); 16 (9): 1343-1353.
Davis, et al., "Intermolecular disulfide bonding in IgM: effects of replacing cysteine residues in the μ heavy chain." EMBO J. (1989); 8 (9): 2519-2526.
Debre, et al., "Infusion of Fcγ fragments for treatment of children with acute immune thrombocytopeni purpura." Lancet (1993); 342: 945-949.
Deo, Y. M. et al., "Clinical significance of IgG Fc receptors and FcγR-directed immunotherapies." Immunology Today (1997); 18 (3) : 127-135.
Dinarello, C. A., "Proinflammatory and anti-inflammatory cytokines as mediators in the pathogenesis of septic shock." Chest (1997); 112: 321S-329S.
European examination report mailed May 18, 2011 in co-pending European application No. 08769936.9, 7 pages.
European Search Report, EP appl. No. 13169230.3, 15 pages (Oct. 25, 2013).
Extended European Search Report for EP 13830394.6, dated Mar. 4, 2016, 9 pages.
Fan, et al., "Production of multivalent protein binders using a self-trimerizing collagen-like peptide scaffold." The FASEB Journal (2008); 22 (11): 3795-2804.
Flanagan, et al., "Soluble Fc Fusion Proteins for Biomedical Research." Meth. Mol. Biol. (2007); 378: 33-52.
Garratty, "Severe reactions associated with transfusion of patients with sickle cell disease." Transfusion (1997); 37 (4): 357-361.
Gavin, et al., "Cutting Edge: Identification of the Mouse IgG3 Receptor: Implications for Antibody Effector Function at the Interface Between Innate and Adaptive Immunity." J. Immunol. (1998); 160 (1): 20-23.
Gerber, et al., "Reversing Lipopolysaccharide Toxicity by Ligating the Macrophage Fcγ Receptors." J. Immunology (2001); 166: 6861-6868.
Ghielmetti, et al., "Gene expression profiling of the effects of intravenous immunoglobulin in human whole blood." Molecular Immunology (2006); 43 (7): 939-949.
Gliknik website. www.gliknik.com/research/stradomer.php, 2012.
Goldenberg, "Multiple Sclerosis Review." P&T (2012); 37(3): 175-184.
Gralnick, et al., "Role of carbohydrate in multimeric structure of factor VIII/von Willebrand factor protein." PNAS (1983); 80 (9): 2771-2774.
Greenwood et al., "Engineering multiple domains forms of the therapeutic antibody CAMPATH-1H: Effect on complement Lysis," Ther. Immunol. (1994); 1(5):247-255.
Ha, et al., "Isolation and characterization of IgG1 with asymmetrical Fc glycosylation." Glycobiology (2011); 21 (8): 1087-1096.
Harbury, et al. "A switch between two-, three-, and four-stranded coiled coils in GCN4 leucine zipper mutants." Science (1993); 262: 1401-1407.
Hart, et al., "Comparison of the suppressive effects of interleukin-10 and interleukin-4 on synovial fluid macrophages and blood monocytes from patients with inflammatory arthritis." Immunology (1995); 84: 536-542.
Hu, et al., "Targeting tumor vasculature endothelial cells and tumor cells for immunotherapy of human melanoma in a mouse xenograft model." PNAS (1999); 96 (14): 8161-8166.
Huang, et al., "In vitro study of combination of rhOPG-Fc and alendronate on inhibition osteoclast." Zhonghua Wai Ke Za Zhi (2005); 43(12):812-816. (Abstract Only, Article In Chinese).
Hughes-Jones and Gardner, "Reaction between the isolated globular sub-units of the complement component C1q and IgG-complexes." Mol Immunol. (1979); 16 (9): 697-701.
International Preliminary Report on Patentability for International Application No. PCT/US2015/059574, dated May 9, 2017, 12 pages.
International Preliminary Report on Patentability for International Application No. PCT/US2016/043746, dated Jan. 30, 2018, 9 pages.

(56) References Cited

OTHER PUBLICATIONS

International Preliminary Report on Patentability for PCT/US2013/023404, 17 pages, mailed Jul. 29, 2014.
International Preliminary Report on Patentability for PCT/US2013/055800, 23 pages, mailed Feb. 24, 2015.
International Preliminary Report on Patentability, mailed Jan. 29, 2013 in International application No. PCT/US2011/045768, 10 pages.
International Preliminary Report on Patentability, PCT appln. No. PCT/US2008/065428, 8 pages, mailed Dec. 1, 2009.
International Search Report and Written Opinion for International Application No. PCT/US2011/045768, 15 pages, mailed Mar. 8, 2012.
International Search Report and Written Opinion for International Application No. PCT/US2015/059574, mailed Feb. 3, 2016, 14 pages.
International Search Report and Written Opinion for International Application No. PCT/US2016/043746, mailed Jan. 17, 2017, 13 pages.
International Search Report for PCT/US2008/065428, 5 pages, mailed Feb. 10, 2009.
International Search Report for PCT/US2013/023404, 4 pages, mailed Apr. 15, 2013.
International Search Report for PCT/US2013/055800, 7 pages, mailed Mar. 4, 2014.
Jain, et al., "Fully recombinant IgG2a Fc multimers (stradomers) effectively treat collagen-induced arthritis and prevent idiopathic thrombocytopenia purpura in mice." Arthritis Res. Ther. (2012); 14 (4): R192, 12 pages.
Jain, et al., "Tumour antigen targeted monoclonal antibodies incorporating a novel multimerisation domain significantly enhance antibody dependent cellular cytotoxicity against colon cancer." European Journal of Cancer (2013); 49 (15): 3344-3352.
Jefferis, et al., "Interaction sites on human IgG-Fc for FcγR: current models." Immunol. Lett. (2002); 82 (1-2): 57-65.
Kacskovics, et al., "Fc receptors in livestock species." Vet. Immunol. Immunopathol. (2004); 102: 351-362.
Landschulz, et al., "The Leucine Zipper: A Hypothetical Structure Common to a New Class of DNA Binding Proteins." Science (1988); 240: 1759-1764.
Lee, J. K. "Determination of the Molecular Size Distribution of Immunoglobulin G (IgG) In Intravenous IgG-Albumin Formulations By High-Performance Liquid Chromatography." Journal of Chromatography (1988); 444: 141-152.
Lemieux and Bazin, "Autoantibody-Induced Formation of Immune Complexes in Normal Human Serum." Curr. Pharm Design (2006); 12: 173-179.
Levinson, D. R., "Intravenous Immune Globulin: medicare payment and availability." Report to DHHS, OEI-03-05-00404 (2007).
Liew, "TH1 and TH2 cells: a historical perspective." Nature Reviews, Immunology (2002);2: 55-60.
Lucas, et al., "ERK activation following macrophage FcγR ligation leads to chromatin modifications at the IL-10 locus." Journal of Immunology (2005); 175: 469-477.
Lund, et al., "Multiple Interactions of IgG with Its Core Oligosaccharide Can Modulate Recognition by Complement and Human Fcγ Receptor I and Influence the Synthesis of Its Oligosaccharide Chains." J. Immunol. (1996); 157: 4963-4969.
Meijer, et al., "Pharmacokinetics of Murine Anti-Human CD3 Antibodies in Man Are Determined by the Disappearance of Target Antigen." Journal of Pharmacology and Experimental Therapeutics (2002); 300 (1): 346-353.
Mendel and Mendel, "'Non-specific' binding. The problem, and a solution." Biochemical Journal (1985); 228 (1): 269-272.
Mihaesco and Seligmann, "Papain Digestion Fragments of Human IGM Globulins." Journal of Experimental Medicine (1968); 127 (3): 431-453.

Mimoto, et al., Engineered antibody Fc variant with selectively enhanced FcγRIIb binding over both FcγRIIa$^{R131}$ and FcγRIIa$^{H131}$. Protein Engineering, Design and Selection (2013); 26 (10): 589-598.
Monoclonal antibody 13-1 heavy chain-mouse, GenBank Accession # PC4436 (Date: Feb. 4, 1998).
Moore, et al., "Engineered Fc variant antibodies with enhanced ability to recruit complement and mediate effector functions." mABs (2010); 2: 2, 181-189.
Morris, et al., "Development and characterization of recombinant human Fc:OX40L fusion protein linked via a coiled-coil trimerization domain." Molecular Immunology (2007); 44 (12): 3112-3121.
Mosser, D. M., "The Many Faces of Macrophage Activation." J. Leukocyte Biology (2003); 73: 209-212.
Mosser, et al., "Interleukin-10: new perspectives on an old cytokine." Immunological Reviews (2008); 226 (1): 205-218.
Mössner, et al., "Increasing the efficacy of CD20 antibody therapy through the engineering of a new type II anti-CD20 antibody with enhanced direct and immune effector cell-mediated B-cell cytotoxicity." Blood (2010); 115 (22): 4393-4402.
Nagashima, et al., "Enhanced antibody-dependent cellular phagocytosis by chimeric monoclonal antibodies with tandemly repeated Fc domains." Journal of Bioscience and Bioengineering (2011); 111 (4): 391-396.
Nagashima, et al., "Fc Taryotaika ni yoru Kokassei Kotai." Proc. 126th Ann. Meet. Pharm. Soc. Japan 126:107 (abstract No. P28[S]am-551) (2006).
Nagashima, et al., "Tandemly repeated Fc domain augments binding avidities of antibodies for Fcγ receptors, resulting in enhanced antibody-dependent cellular cytotoxicity." Mol. Immunol. (2008); 45: 2752-2763.
Ngo, et al., "Computational complexity, protein structure prediction, and the levinthal paradox," in the Protein Folding Problem and Tertiary Structure Prediction, Boston: Birkhauser, pp. 433 and 492-495 (1994).
Nimmerjahn and Ravetch, "The antiinflammatory activity of IgG: the intravenous IgG paradox." Journal of Experimental Medicine (2007); 204 (1): 11-15.
Nimmerjahn and Ravetch, "Antibody-mediated modulation of immune responses." Immunological Rev. (2010); 236: 265-275.
Ong, et al., "How to accelerate the endothelialization of stents." Archives de maladies du coeur et des vaisseaux (2005); 98 (2): 123-126.
O'Shea, et al., "Evidence that the leucine zipper is a coiled coil." Science (1989); 243 (4890): 538-542.
Oyama, et al., "A Case of Autoimmune-Related Retinopathy and Optic Neuropathy Syndrome Treated by Autologous Nonmyeloablative Hematopoietic Stem Cell Transplantation." Journal of Neuro-Ophthalmology (2009); 29 (1): 43-49.
Partial European Search Report, EP appl. No. 13169230.3, 8 pages (Jul. 31, 2013).
Proceedings of the 126th Annual Meeting of the Pharmaceutical Society of Japan, No. 126 2006, p. 107 (P28[S]am-551) (and Machine translation of pertinent portions), 4 pages.
Ratcliffe et al., "Measurement of the binding activity of defined IgG aggregates to macrophage Fc receptors," Immunology Letters, 7(2):73-76 (1983).
Reeth et al., "Positive selection vectors to generate fused genes for the expression of his-tagged proteins." BioTechniques (1998); 25: 898-904.
Reff and Heard, "A review of modifications to recombinant antibodies: attempt to increase efficacy in oncology applications." Crit. Rev. Oncol./Hematol. (2001); 40: 25-35.
Reid and Porter, "Subunit composition and structure of subcomponent C1q of the first component of human complement." Biochemical Journal (1976); 155 (1): 19-23.
Rudikoff, et al. "Single amino acid substitution altering antigen-binding specificity." Proceedings of the National Academy of Sciences (1982); 79.6: 1979-1983.
Salfield, "Isotype selection in antibody engineering." Nat. Biotechnol. (2007); 25: 1369-1372.

(56) References Cited

OTHER PUBLICATIONS

Sazinsky, et al., "Aglycosylated immunoglobulin $G_1$ variants productively engage activating Fc receptors." PNAS (2008); 105 (51): 20167-20172.
Schuurman, et al., "The inter-heavy chain disulfide bonds of IgG4 are in equilibrium with intra-chain disulfide bonds." Mol. Immunol. (2001); 38: 1-8.
Shields, et al., "High Resolution Mapping of the Binding Site on Human IgG1 for FcγRI, FCγRII, FCγRIII, and FcRn and Design of IgG1 Variants with Improved Binding to the FcγR*," J. Biol. Chem. (2001); 276: 6591-6604.
Shields, et al., "Lack of Fucose on Human IgG1 N-Linked Oligosaccharide Improves Binding to Human FcγRIII and Antibody-dependent Cellular Toxicity." The Journal of Biological Chemistry (2002); 277 (30): 26733-26740.
Siragam, et al., "Can antibodies with specificity for soluble antigens mimic the therapeutic effects of intravenous IgG in the treatment of autoimmune disease?" The Journal of Clinical Investigation (2005); 115 (1): 155-160.
Siragam, et al., "Intravenous immunoglobulin ameliorates ITP via activating Fcγ receptors on dendritc cells." Nature Med. (2006); 12(6):668-692.
Smith and Morrison, "Recombinant polymeric IgG: an approach to engineering more potent antibodies." Biotechnol. (1994); 12: 683-688.
Smith, et al., "Addition of a μ-tailpiece to IgG results in polymeric antibodies with enhanced effector functions including complement-mediated cytolysis by IgG4." J. Immunol. (1995); 154: 2226-2236.
Song, et al., "Monoclonal IgG can ameliorate immune thrombocytopenia in a murine model of ITP: an alternative to IVIG." Blood (2002); 101 (9): 3708-3713.
Stegall, et al., "Terminal Complement Inhibition Decreases Antibody-Mediated Rejection in Sensitized Renal Transplant Recipients." American Journal of Transplantation (2011); 11 (11): 2405-2413.
Stevenson, G. T. et al., "Engineered antibody for treating lymphoma." Recent Res. Canc. Res. (2002); 159: 104-112.
Sundaram, et al., "Lipopolysaccharide-induced suppression of erythrocyte binding and phagocytosis via FcγRI, FcγRII, FcγRIII, and CR3 receptors in murine macrophages." J. Leukocyte Biology (1993); 54: 81-88.
Supplemental European Search Report for EP 08769936.9, mailed May 26, 2010, 9 pages.
Supplementary European Search Report, EP appl. 11813204.2, 6 pages (Jul. 3, 2015).
Supplementary European Search Report, EP appl. 13741129.4, 5 pages (Nov. 4, 2015).
Sutterwala, et al., "Reversal of Proinflammatory Responses by Ligating the macrophage Fcγ Receptor Type I." Journal of Experimental Medicine (1998); 188 (1): 217-222.
Sutterwala, et al., "Selective Suppression of Interleukin-12 Induction After Macrophage Receptor Litigation." J. Exp. Med. (1985); 185: 1977-1985.
Tai, et al., "Potent in vitro and in vivo activity of an Fc-engineered humanized anti-HM1.24 antibody against multiple myeloma with augmented effector function." Blood (2012); 119 (9): 2074-2082.
Tankersley, D. L., "Dimer Formation In immunoglobulin Preparations and Speculations On the Mechanism of Action of Intravenous Immune Globulin in Autoimmune Diseases." Immunological Reviews (1994); 39: 159-172.
Teeling, et al., "Therapeutic efficacy of intravenous immunoglobulin preparations depends on the immunoglobulin G dimers: studies in experimental immune thrombocytopenia." Blood (2001); 98 (4): 1095-1099.
Tha-In, et al., "Modulation of the cellular immune system by intravenous immunoglobulin." Trends Immunol. (2008); 29 (12): 608-615.
Thiruppathi, et al., "Recombinant IgG2a Fc (M045) multimers effectively suppress experimental autoimmune myasthenia gravis." J. Autoimmunity (2014); 52 (2): 64-73.

Tremblay, et al., "Picogram doses of lipopolysaccharide exacerbate antibody-mediated thrombocytopenia and reduce the therapeutic efficacy of intravenous immunoglobulins in mice." British Journal of Hematology (2007); 139: 297-302.
Turhan, et al., "Intravenous immune globulin prevents venular vaso-occlusion in sickle cell mice by inhibiting leukocyte adhesion and the interactions between sickle erythrocytes and adherent leukocytes." Blood (2004); 103: 2397-2400.
Vajdos, et al. "Comprehensive functional maps of the antigen-binding site of an anti-ErbB2 antibody obtained with shotgun scanning mutagenesis." Journal of Molecular Biology (2002); 320 (2): 415-428.
Van Noort and Amor, "Cell Biology of Autoimmune Diseases." International Review of Cytology (1998); 178: 127-205.
Vialtel, et al., "Nucleation-controlled Polymerization of human Monoclonal Immunoglobulin G Cryoglobulins." The Journal of Biological Chemistry (1982); 257 (7): 3811-3818.
Vidarsson, et al., "IgG subclasses and allotypes: from structure to effector functions." Frontiers in Immunology (2014); 5 (1): 1-17.
Weber, et al., "B-cell activation influences T-cell polarization and outcome of anti-CD20 B-cell depletion in central nervous system autoimmunity." Annals of Neurology (2010); 68 (3): 369-383.
Wright and Morrison, "Effect of C2-Associated Carbohydrate Structure on Ig Effector Function: Studies with Chimeric Mouse-Human IgG1 Antibodies in Glycosylation Mutants of Chinese Hamster Ovary Cells." The Journal of Immunology (1998); 160 (7): 3393-3402.
Wright, et al., "Dimeric, Trimeric and Tetrameric Complexes of Immunoglobulin G Fix Complement." Biochem. J. (1980); 187: 775-780.
Written Opinion of the International Searching Authority, PCT appln. No. PCT/US2008/065428, 7 pages, mailed Feb. 11, 2009.
Written Opinion of the International Searching Authority, PCT appl. No. PCT/US2013/023404, 16 pages, mailed Apr. 15, 2013.
Written Opinion of the International Searching Authority, PCT appl. No. PCT/US2013/0055800, 22 pages, mailed Mar. 4, 2014.
Yoo, et al. "Human IgG2 can form covalent dimers." The Journal of Immunology (2003); 170 (6): 3134-3138.
Zang, C., "Annual founders week deemed a 'huge success,'" VOICE University of Maryland, pp. 1-5, http://umvoice.com/2011/12/annual-founders-week-deemed-a-huge-success/, visited website Dec. 10, 2012.
Zhang, et al., "Alteration in the IL-2 signal peptide affects secretion of proteins in vitro and in vivo." Journal Gene Medicine (2005); 7: 354-365.
Zhang, et al., "Dynamic and transient remodeling of the macrophages IL-10 promoter during transcription." Journal of Immunology (2006); 177: 1282-1288.
U.S. Appl. No. 13/470,105 (abandoned).
U.S. Appl. No. 13/812,269 (abandoned).
U.S. Appl. No. 14/109,384 (abandoned).
U.S. Appl. No. 15/177,061 (pending).
U.S. Appl. No. 15/199,416 (pending).
U.S. Appl. No. 15/370,675 (abandoned).
U.S. Appl. No. 15/642,175 (pending).
U.S. Appl. No. 15/900,211 (pending).
U.S. Pat. No. 8,680,237 (issued Mar. 25, 2014).
U.S. Pat. No. 9,512,208 (issued Dec. 6, 2016).
U.S. Pat. No. 9,512,210 (issued Dec. 6, 2016).
U.S. Pat. No. 9,926,362 (issued Mar. 27, 2018).
Blundell, et al., "Engineering the fragment crystallizable (Fc) region of human IgG1 multimers and monomers to fine-tune interactions with sialic acid-dependent receptors." Journal of Biological Chemistry (2017); 292: 12994-13007.
Czajkowsky, D.M., et al., "Fc-fusion proteins: new developments and future perspectives. EMBO Molecular Medicine (Oct. 2012); 4(10): 1015-1028. Epub Jul. 26, 2012.
Diebolder, et al., "Complement is activated by IgG hexamers assembled at the cell surface." Science (Mar. 2014); 343(6176): 1260-1263.
Extended European Search Report for EP Application No. 16831166.0, dated Feb. 11, 2019, 8 pages.

(56) References Cited

OTHER PUBLICATIONS

Extended European Search Report for European Patent Application No. 18166541.5, dated Oct. 18, 2018, 9 pages.
Extended European Search Report for Eurpean Patent Application No. 17810971.6, dated Dec. 16, 2019, 8 pages.
Ghumra, et al., "Structural requirements for the interaction of human IgM and IgA with the human Fcα/μ receptor." Eur. J. Immunol. (2009); 39 (4): 1147-1156.
International Preliminary Report on Patentability for International Application No. PCT/US2017/036425, dated Dec. 11, 2018, 8 pages.
International Preliminary Report on Patentability for International Application No. PCT/US2017/043538, dated Jan. 22, 2019, 9 pages.
International Search Report and Written Opinion for International Application No. PCT/US2017/036425, mailed Oct. 31, 2017, 13 pages.
International Search Report and Written Opinion for International Application No. PCT/US2017/043538, mailed Jan. 5, 2018, 13 pages.
Liu and May, "Disulfide bond structures of IgG molecules." mAbs (Jan.-Feb. 2012); 4(1): 17-23. Epub Jan. 1, 2012.
Lund, et al., "Multiple binding sites on the CH2 domain of IgG for mouse Fc gamma R11." Mol Immunol. (Jan. 1992); 29(1): 53-59.
Mekhaiel, et al., "Polymeric human Fc-fusion proteins with modified effector functions." Scientific Reports (2011); 1: 124, pp. 1-11.
Mimura, et al., "Role of Oligosaccharide Residues of IgG1-Fc in FcγRIIb Binding." Journal of Biological Chemistry (Sep. 2001); 276(49): 45539-45547.
Opposition Proceedings No. 2012392760, Notice of Opposition filed by Gliknik, Inc. on Oct. 2, 2018, in Australian Patent Application No. 2012392760 in the name of Liverpool School of Tropical Medicine, 2 pages.
Opposition Proceedings No. 2012392760, Statement of Grounds and Particulars of Opposition filed by Gliknik, Inc. on Jan. 2, 2019, in Australian Patent Application No. 2012392760 in the name of Liverpool School of Tropical Medicine, 11 pages.
Opposition Proceedings No. 2012392760 (Australian Patent Application No. 2012392760 in the name of Liverpool School of Tropical Medicine) filed by Gliknik, Inc. on Jan. 2, 2019, Evidence in Answer in Opposition, Declaration of Anthony Lawrence Shaw (and exhibits ALS-18 and ALS-19 and exhibits ALS-18 and ALS-19) dated and filed Sep. 4, 2019, 14 pages.
Opposition Proceedings No. 2012392760 (Australian Patent Application No. 2012392760 in the name of Liverpool School of Tropical Medicine) filed by Gliknik, Inc. on Jan. 2, 2019, Applicant's Evidence in Answer, Declaration of Sarah Cox (and Exhibit SC1), dated Jul. 2, 2019, and filed Jul. 3, 2019, 36 pages.
Opposition Proceedings No. 2012392760 (Australian Patent Application No. 2012392760 in the name of Liverpool School of Tropical Medicine) filed by Gliknik, Inc. on Jan. 2, 2019, Applicant's Evidence in Answer, Declaration of Dr Beate Peter (and Exhibits BP1-BP9) dated Jul. 2, 2019, and filed Jul. 3, 2019, 147 pages.
Reeck, et al., "'Homology' in proteins and nucleic acids: a terminology muddle and a way out of it." Cell (Aug. 1987); 50(5): 667.
Samuelsson, A., et al., "Anti-inflammatory Activity of IVIG Mediated Through the Inhibitory Fc Receptor." Science (Jan. 2001); 291(5503): 484-486.
Saphire, et al., "Crystal structure of a neutralizing human IGG against HIV-1: a template for vaccine design." Science (Aug. 2001); 293(5532): 1155-1159.
Saphire, et al., "Crystallization and preliminary structure determination of an intact human immunoglobulin, b12: an antibody that broadly neutralizes primary isolates of HIV-1." Acta Cryst. (2001); D57: 168-171.
Sørensen, et al., "Effect of the IgM and IgA secretory tailpieces on polymerization and secretion of IgM and IgG." The Journal of Immunology (Apr. 1996); 156(8): 2858-2865.
Spirig, et al., "rIgG1 Fc Hexamer Inhibits Antibody-Mediated Autoimmune Disease via Effects on Complement and FcgRs". J Immunol. (Apr. 15, 2018); 200(8): 2542-2553. Epub Mar. 12, 2018.
Wei, Xiaoshan et al., "Proteomics studies of autoimmune diseases of the nervous system." Journal of Apoplexy and Nervous Diseases (2009); vol. 26, No. 5, pp. 630-632, and English summary / abstract, 4 pages.
White, D.M., et al., "Design and expression of polymeric immunoglobulin fusion proteins: a strategy for targeting low-affinity Fc gamma receptors." Protein Expression and Purification (Apr. 2001); 21(3): 446-455.
Woof, et al., "Human antibody-Fc receptor interactions illuminated by crystal structures." Nat Rev Immunol. (Feb. 2004); 4(2): 89-99.
Wu, et al., "Structural basis for enhanced neutralization of HIV-1 by a dimeric IgG form of the glycan-recognizing antibody 2G12." Cell Rep. (Dec. 2013); 5(5): 1443-1455.
Allen, et al., "Interchain disulfide bonding in human IgG2 antibodies probed by site-directed mutagenesis". Biochemistry (2009); 48(17):3755-3766.
Chen, et al., "Fusion protein linkers: Property, design and functionality". Advanced Drug Delivery Reviews (Oct. 15, 2013); 65(10); 1357-1369.
De Jong, et al., "A Novel Platform for the Potentiation of Therapeutic Antibodies Based on Antigen-Dependent Formation of IgG Hexamers at the Cell Surface". PLoS Biol. (Jan. 6, 2016); 14(1): e1002344. eCollection Jan. 2016.
De Taeye, et al., "The Ligands for Human IgG and Their Effector Functions ". Antibodies (2019); 8(2): 30, 18 pages.
Extended European Search Report for European Patent Application No. 17832021.4, dated Feb. 26, 2020, 11 pages.
Maeda, et al., "Engineering of Functional Chimeric Protein G-Vargula Luciferase". Analytical Biochemistry (Jul. 1, 1997); 249(2): 147-152.
Orlando, M., "Modification of proteins and low molecular weight substances with hydroxyethyl starch (HES)", Inaugural Dissertation, Giesen, 2003, 191 pages.
Subedi and Barb, "The Structural Role of Antibody N-Glycosylation in Receptor Interactions". Structure (Sep. 1, 2015); 23(9): 1573-1583. Epub Jul. 23, 2015.
Wang, et al., "Molecular Basis of Assembly and Activation of Complement Component C1 in Complex with Immunoglobulin G1 and Antigen". Mol Cell. (Jul. 7, 2016); 63(1): 135-145. Epub Jun. 16, 2016.
Bazin, et al., "Reversal of immune thrombocytopenia in mice by cross-linking human immunoglobulin G with a high-affinity monoclonal antibody". Br J Haematol. (Oct. 2006); 135(1): 97-100. Epub Aug. 22, 2006.
Bleeker, et al., "Vasoactive side effects of intravenous immunoglobulin preparations in a rat model and their treatment with recombinant platelet-activating factor acetylhydrolase". Blood (Mar. 1, 2000);95(5): 1856-1861.
Clynes, Raphael, "Immune complexes as therapy for autoimmunity". J. Clin. Invest. (2005); 115(1): 25-27.
Extended European Search Report for EP Application No. 16831166, dated Apr. 21, 2021, 6 pages.
Rudnick and Adams, "Affinity and Avidity in Antibody-Based Tumor Targeting." Cancer Biotherapy and Radiopharmaceuticals (2009); 24 (2): 155-161.
Stewart, R., et al., "The role of Fc gamma receptors in the activity of immunomodulatory antibodies for cancer." Journal for ImmunoTherapy of Cancer (2014); 2: 29, 10 pages.
Dalakas, et al., "A Controlled Trial of High-Dose Intravenous Immune Globulin Infusions as Treatment for Dermatomyositis." The New England Journal of Medicine (Dec. 30, 1993); 329(27): 1993-2000.
Gajdos, et al., "High-Dose Intravenous Gammaglobulin for Myasthenia Gravis." The Lancet (1984); 323 (8373): 406-407.
Jayne, et al., "Treatment of systemic vasculitis with pooled intravenous immunoglobulin." The Lancet (May 11, 1991); 337(8750): 1137-1139.
Jin and Balthasar, "Mechanisms of Intravenous Immunoglobulin Action in Immune Thrombocytopenia Purpura." Human Immunology (Apr. 2005); 66(4): 403-410.
Jukes, et al., "A Newly Developed Chemically Crosslinked Dextran-Poly(Ethylene Glycol) Hydrogel for Cartilage Tissue Engineering." Tissue Engineering Part A (2010); 16(2): 565-573.

(56) References Cited

OTHER PUBLICATIONS

LeHoang, et al., "Intravenous immunoglobulin (IVIg) for the treatment of birdshot retinochoroidopathy." Journal Ocular Immunology and Inflammation (Mar. 2000); 8(1): 49-57.
Nimmerjahn and Ravetch, "Fcγ receptors as regulators of immune responses." Nature Reviews Immunology (2008); 8: 34-47.
Rowley, et al., "Engineered hexavalent Fc proteins with enhanced Fc-gamma receptor avidity provide insights into immune-complex interactions." Communications Biology (2018); 1: 146, pp. 1-12.
Rütter and Luger, "High-dose intravenous immunoglobulins: An approach to treat severe immune-mediated and autoimmune diseases of the skin". J Am Acad Dermatol. (Jun. 2001); 44(6): 1010-1024.
Sultan, et al., "Anti-idiotypic suppression of autoantibodies to factor VIII (antihaemophilic factor) by high-dose intravenous gammaglobulin." The Lancet (Oct. 6, 1984); 2(8406): 765-768.
Van Der Mech, et al., "A Randomized Trial Comparing Intravenous Immune Globulin and Plasma Exchange in Guillain-Barr Syndrome." The New England Journal of Medicine (Apr. 23, 1992); 326(17): 1123-1129.
Zafranskaya, et al., "Interferon-therapy reduces CD4+ and CD8+ T-cell reactivity in multiple sclerosis." Immunology (May 2007); 121(1): 29-39. Epub Dec. 18, 2006.
Brønsted, et al., "Crosslinked dextran—a new capsule material for colon targeting of drugs." Journal of Controlled Release (Apr. 30, 1998); 53(1-3): 7-13.
Muller, S. et al., "Spliceosomal Peptide P140 for Immunotherapy of Systemic Lupus Erythematosus: Results of an Early Phase II Clinical Trial," Arthritis Rheum. Dec. 2008; 58(12): 3873-3883.

\* cited by examiner

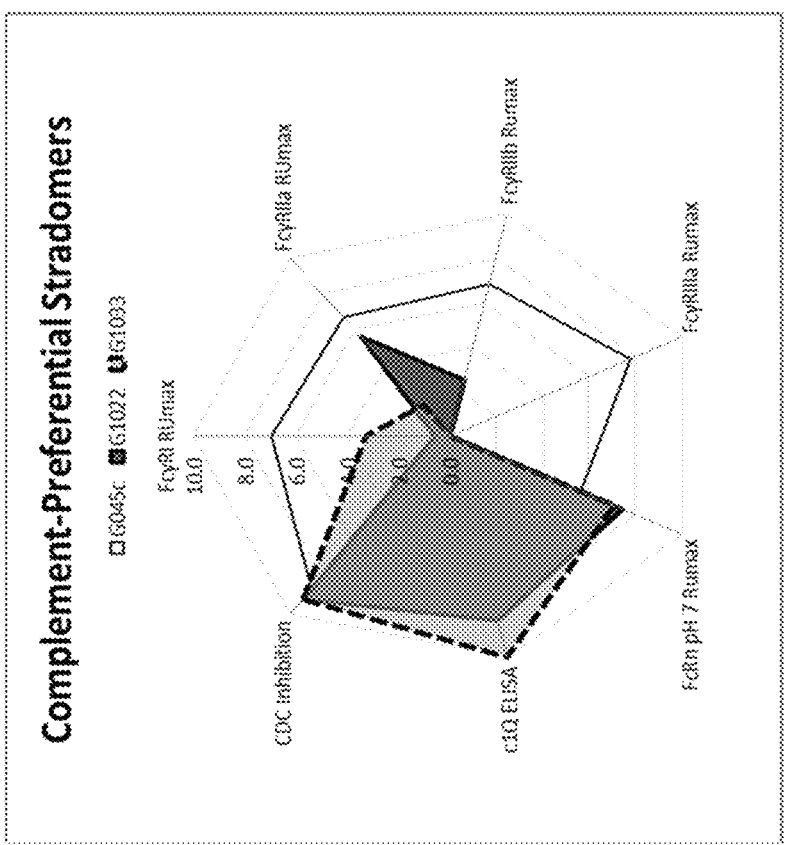

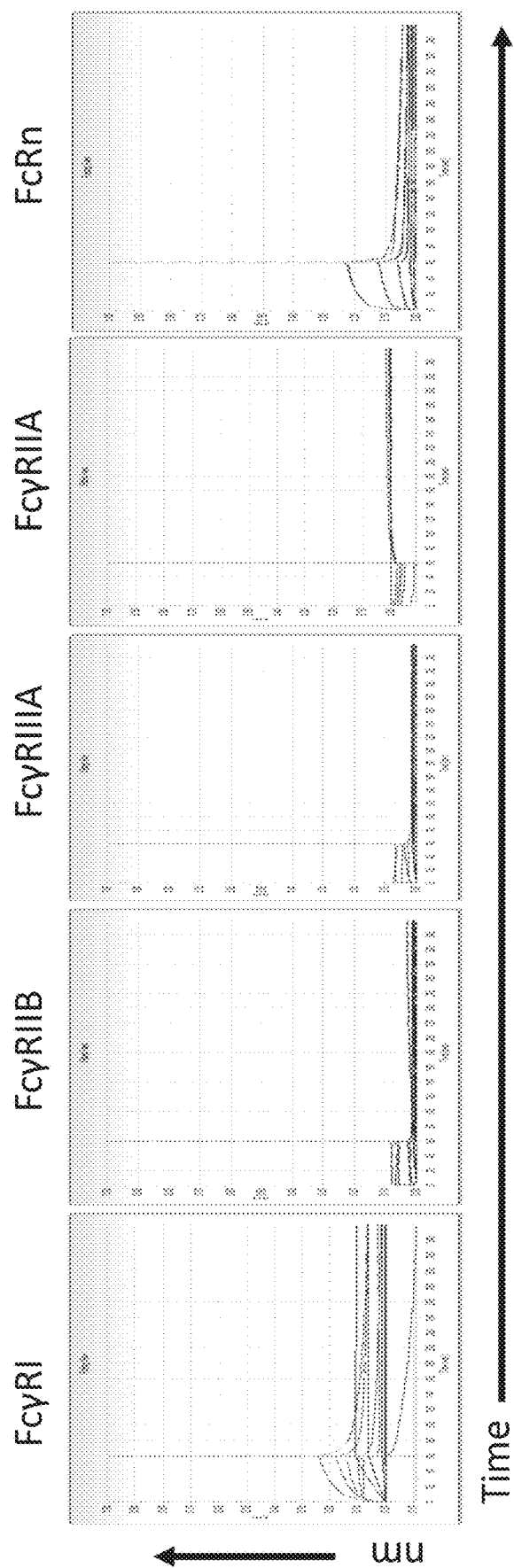

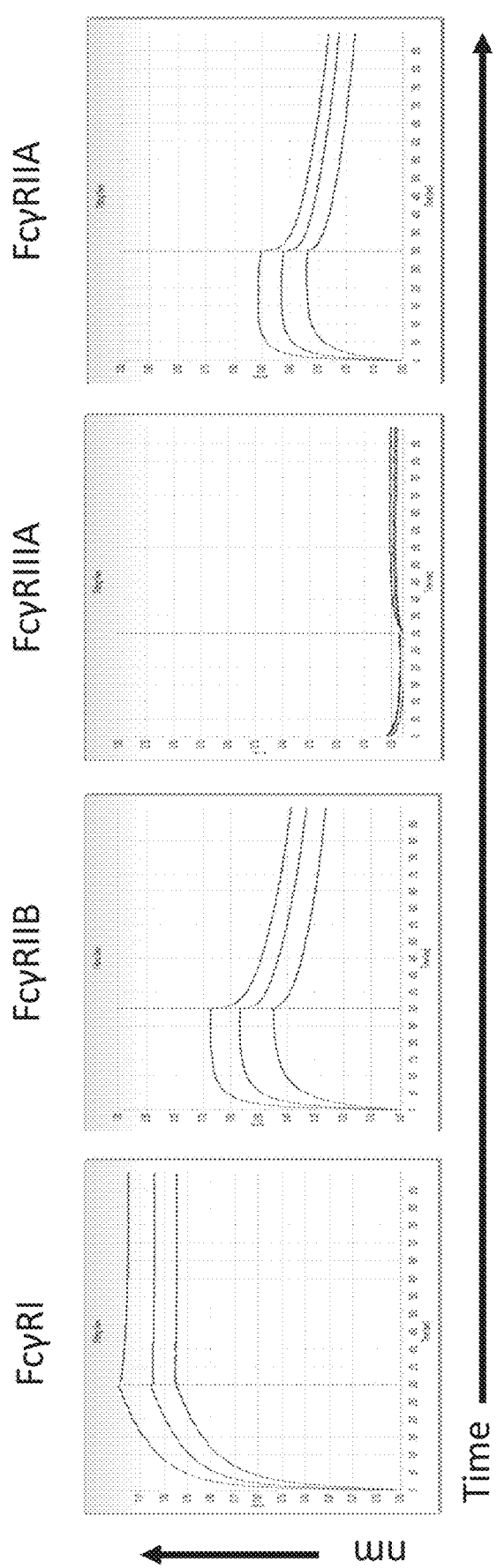

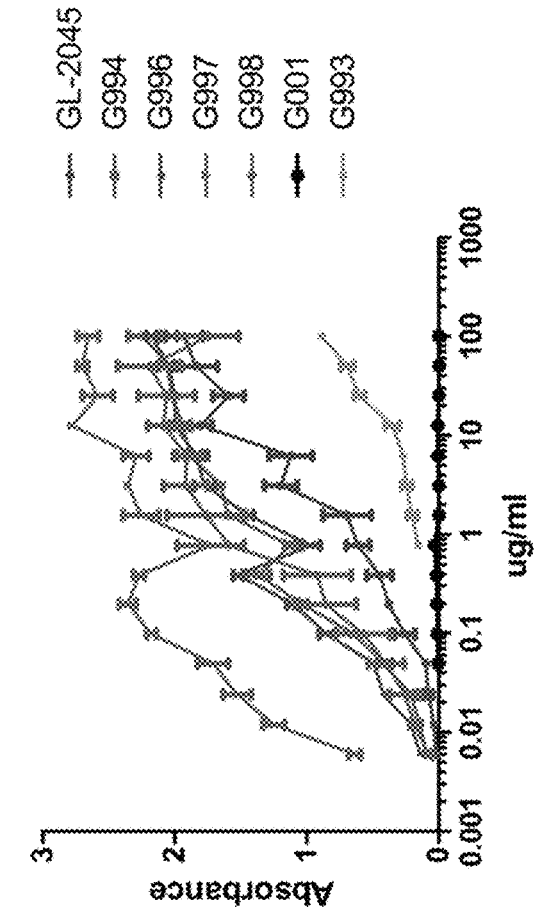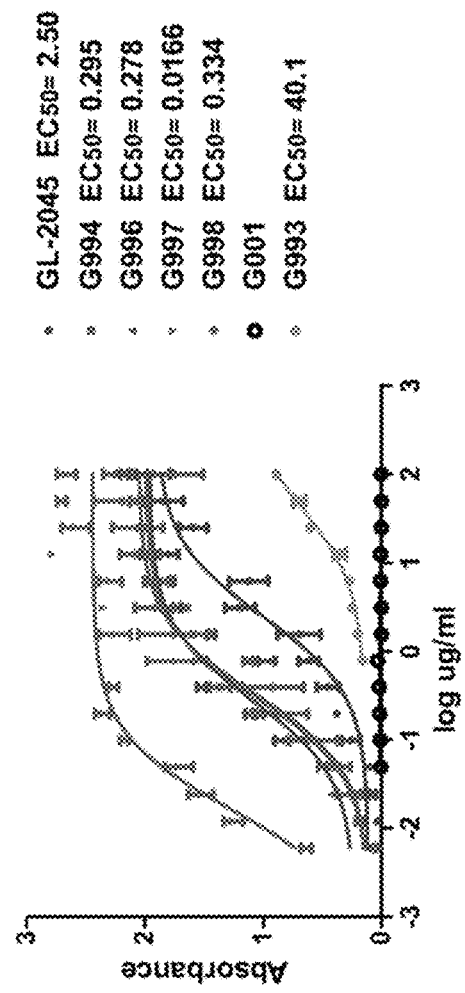
Fig. 31A
Fig. 31B

Fig. 36A (SEQ ID NO: 3)

```
216 EPKSCDKTHT CPPCPAPELL GGPSVFLFPP KPKDTLMISR TPEVTCVVVD VSHEDPEVKF
276 NWYVDGVEVH NAKTKPREEQ YNSTYRVVSV LTVLHQDWLN GKEYKCKVSN KALPAPIEKT
336 ISKAKGQPRE PQVYTLPPSR DELTKNQVSL TCLVKGFYPS DIAVEWESNG QPENNYKTTP
396 PVLDSDGSFF LYSKLTVDKS RWQQGNVFSC SVMHEALHNH YTQKSLSLSP GK
```

Fig. 36B (SEQ ID NO: 2)

```
216 EPKSCDKTHT CPPCPAPELL GGPSVFLFPP KPKDTLMISR TPEVTCVVVD VSHEDPEVKF
276 NWYVDGVEVH NAKTKPREEQ YNSTYRVVSV LTVLHQDWLN GKEYKCKVSN KALPAPIEKT
336 ISKAKGQPRE PQVYTLPPSR EEMTKNQVSL TCLVKGFYPS DIAVEWESNG QPENNYKTTP
396 PVLDSDGSFF LYSKLTVDKS RWQQGNVFSC SVMHEALHNH YTQKSLSLSP GK
```

G998 40 mg/kg

Diseased PBS control mice

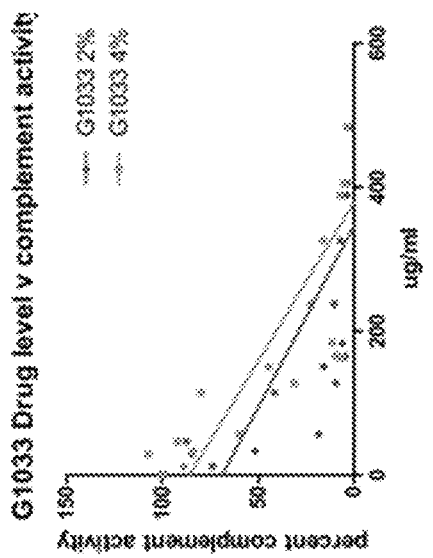
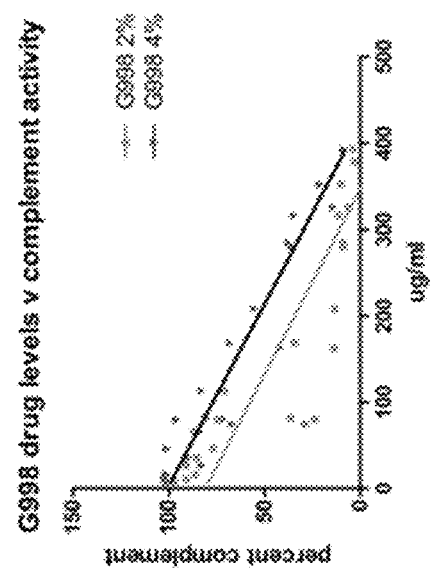
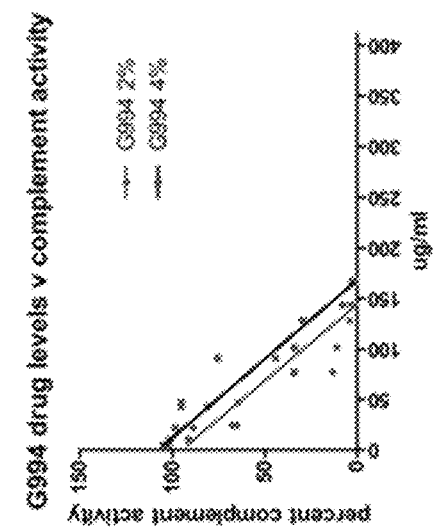
Fig. 47B

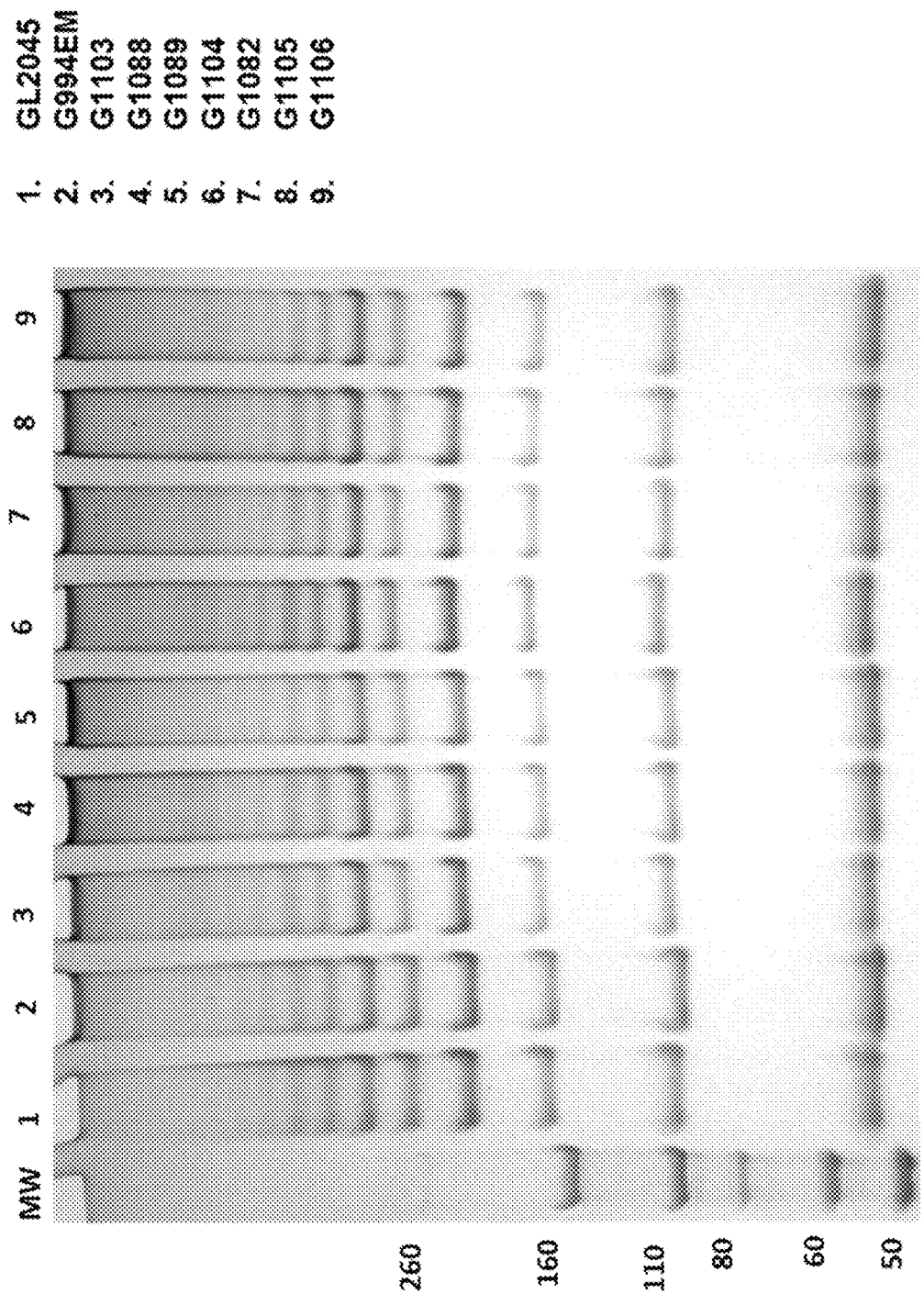

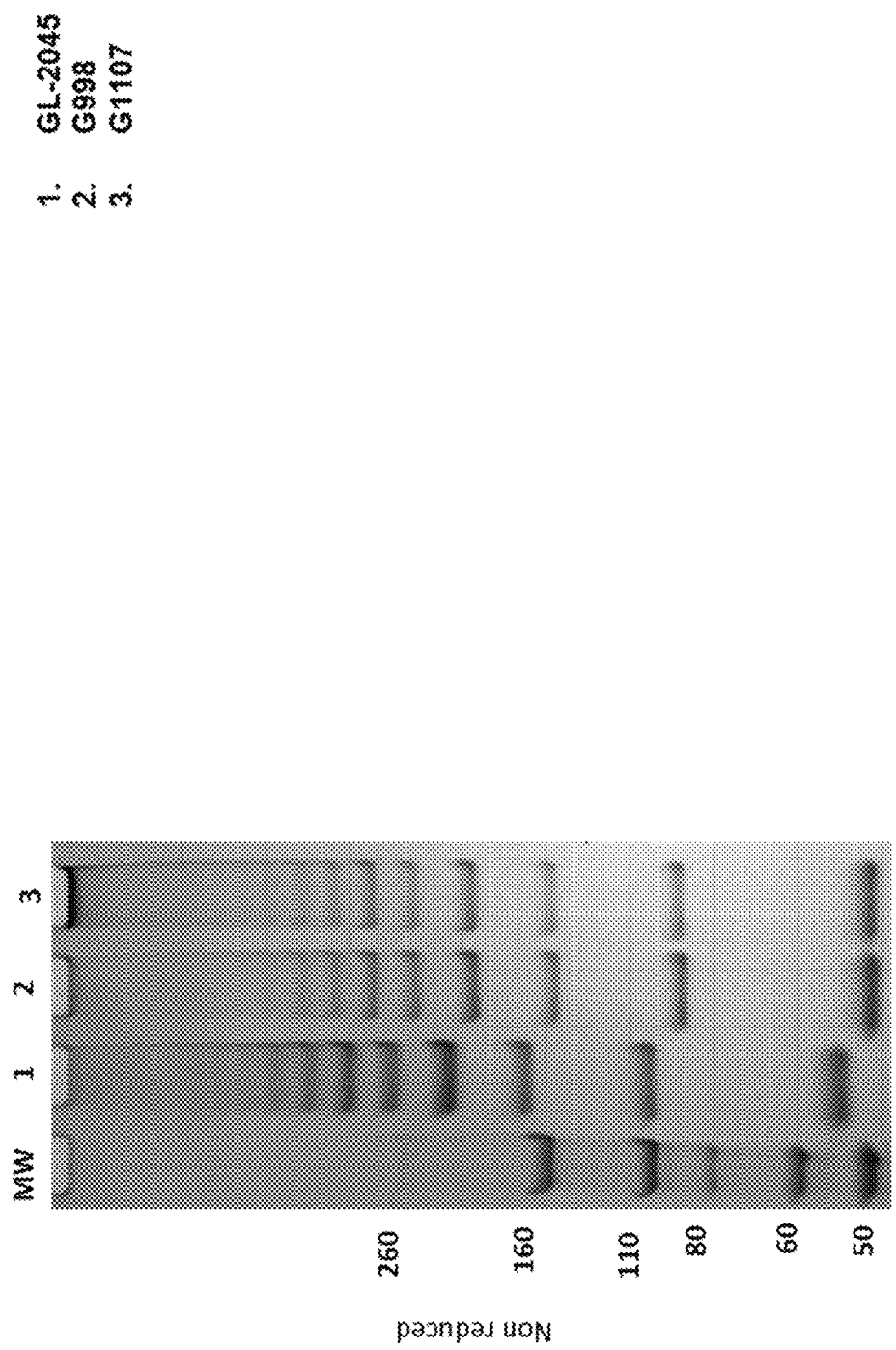

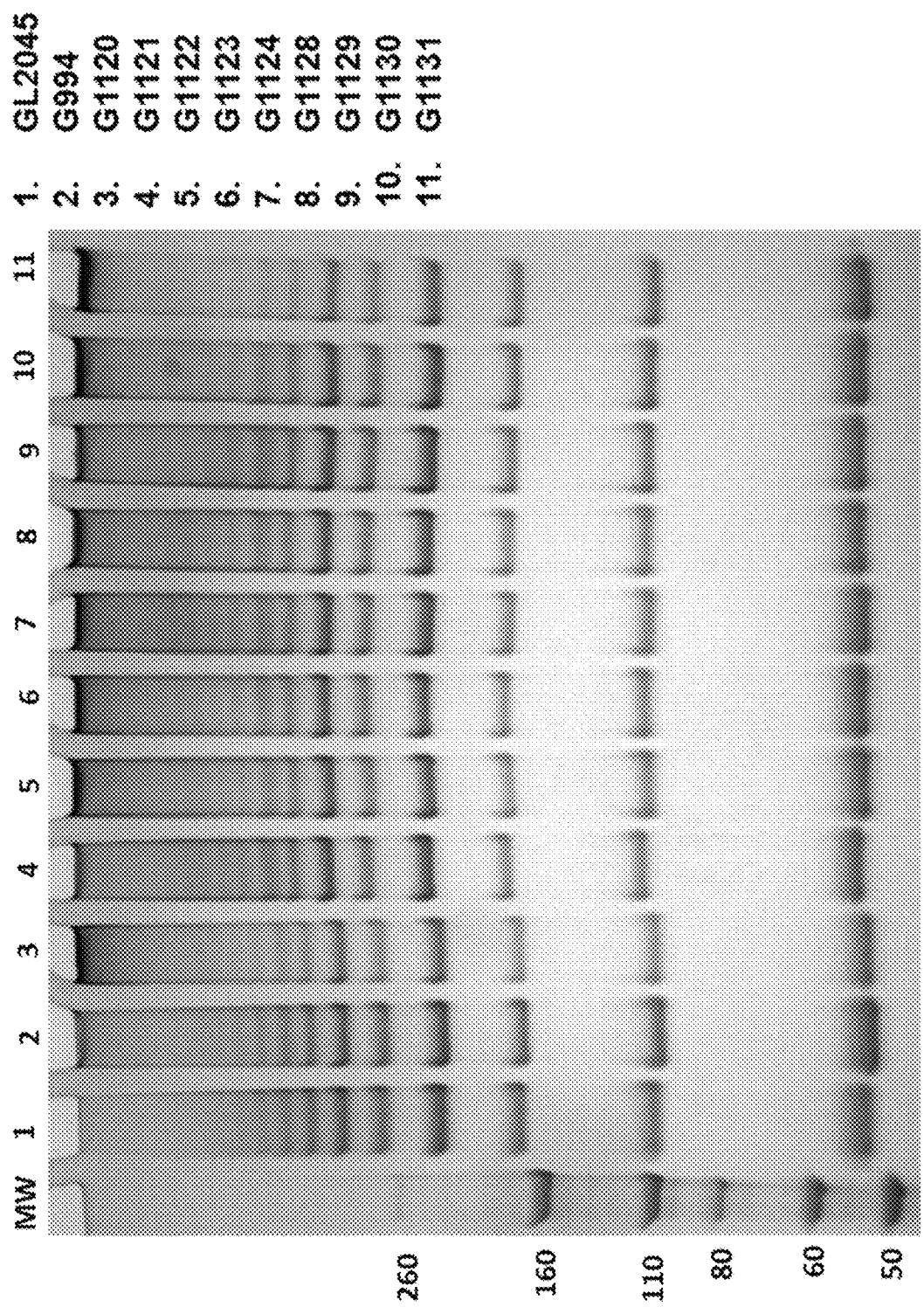

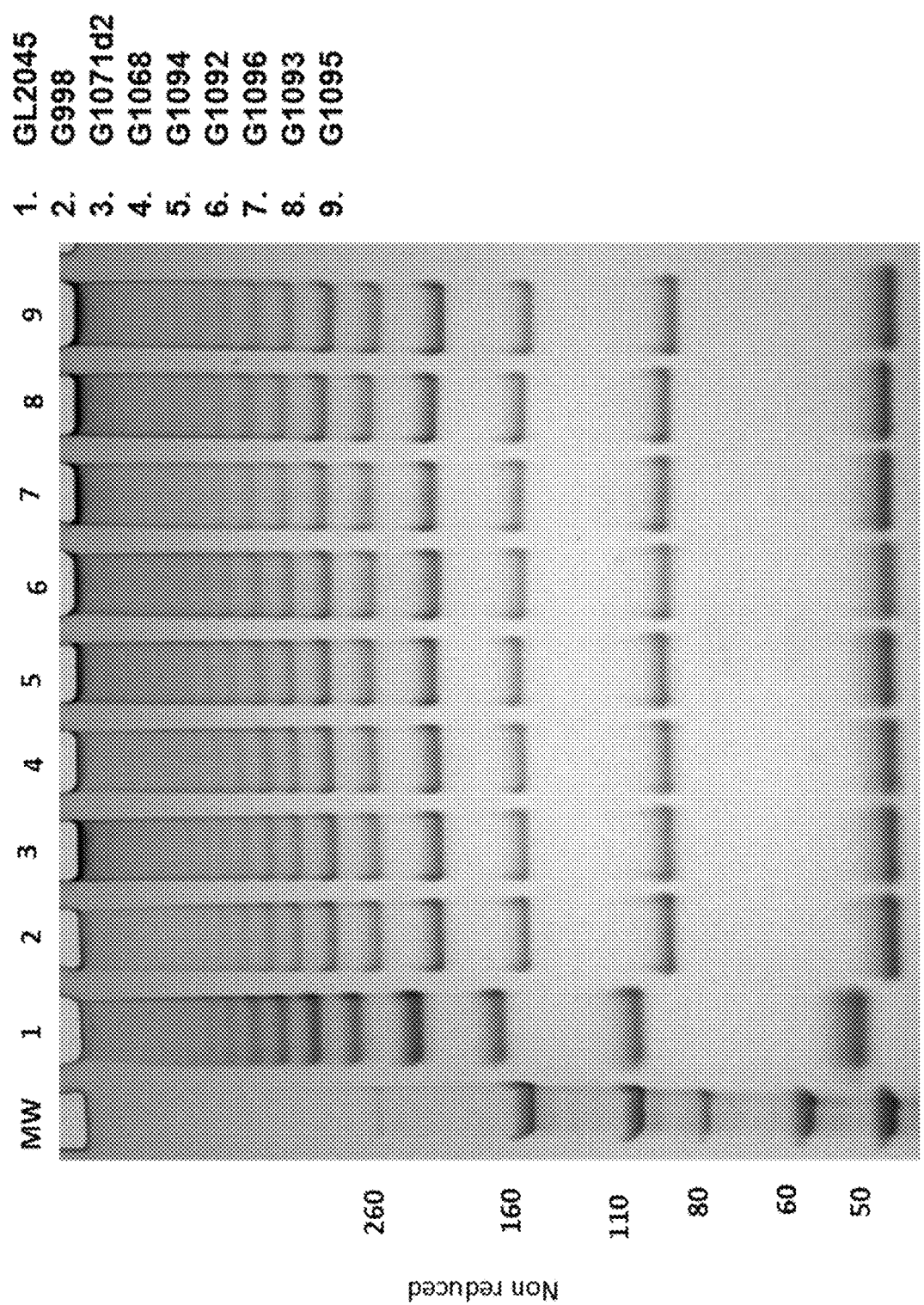

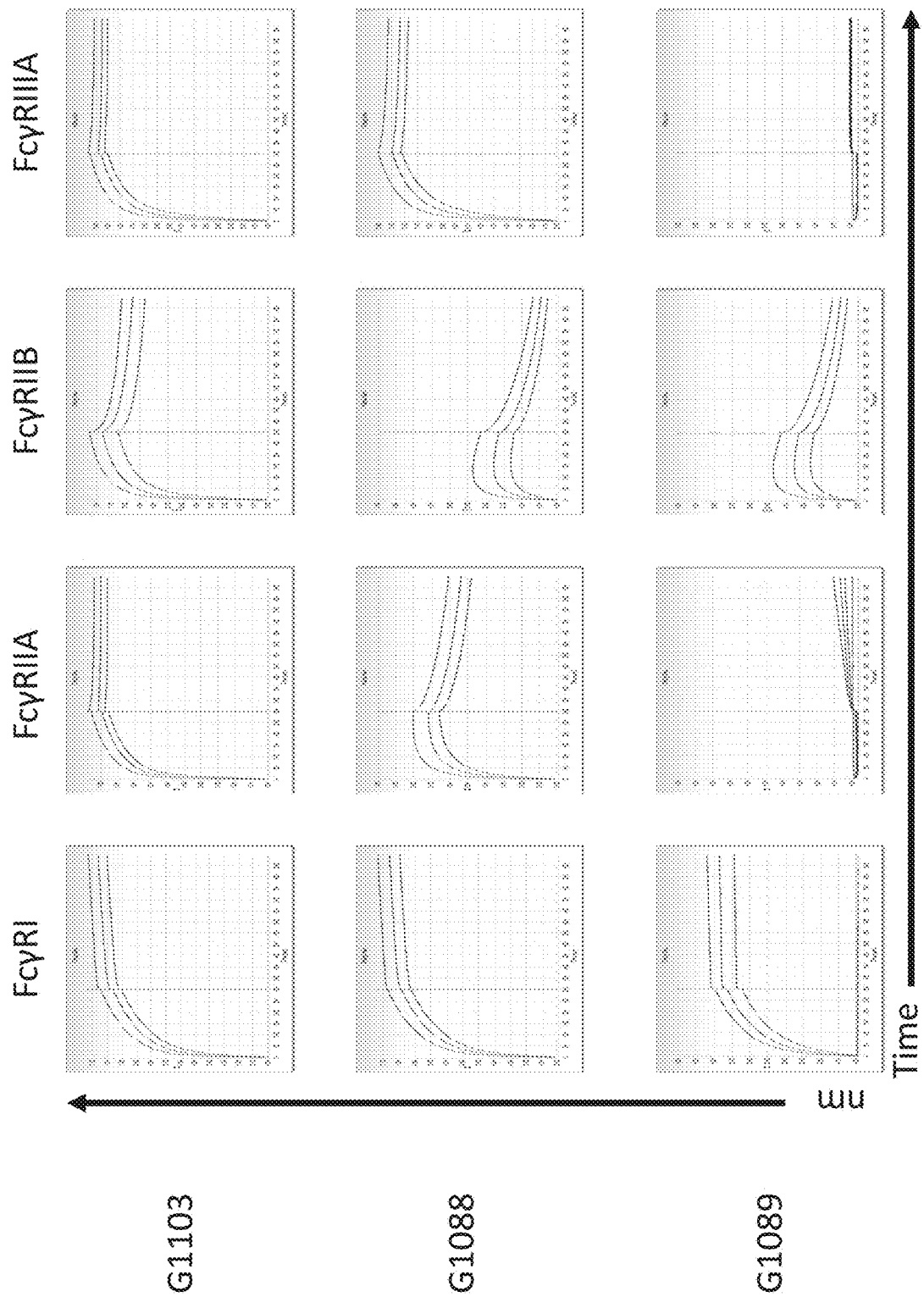

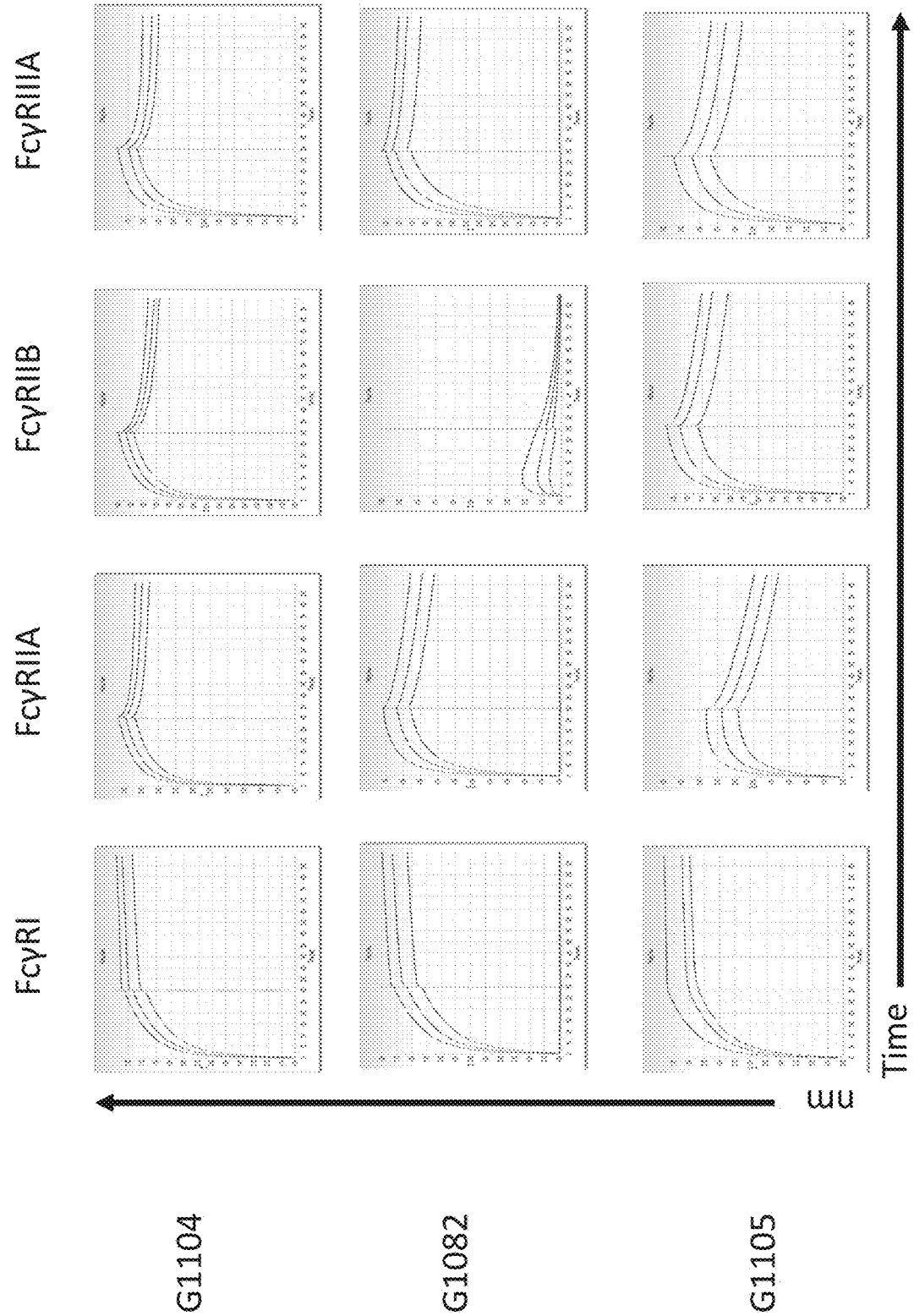

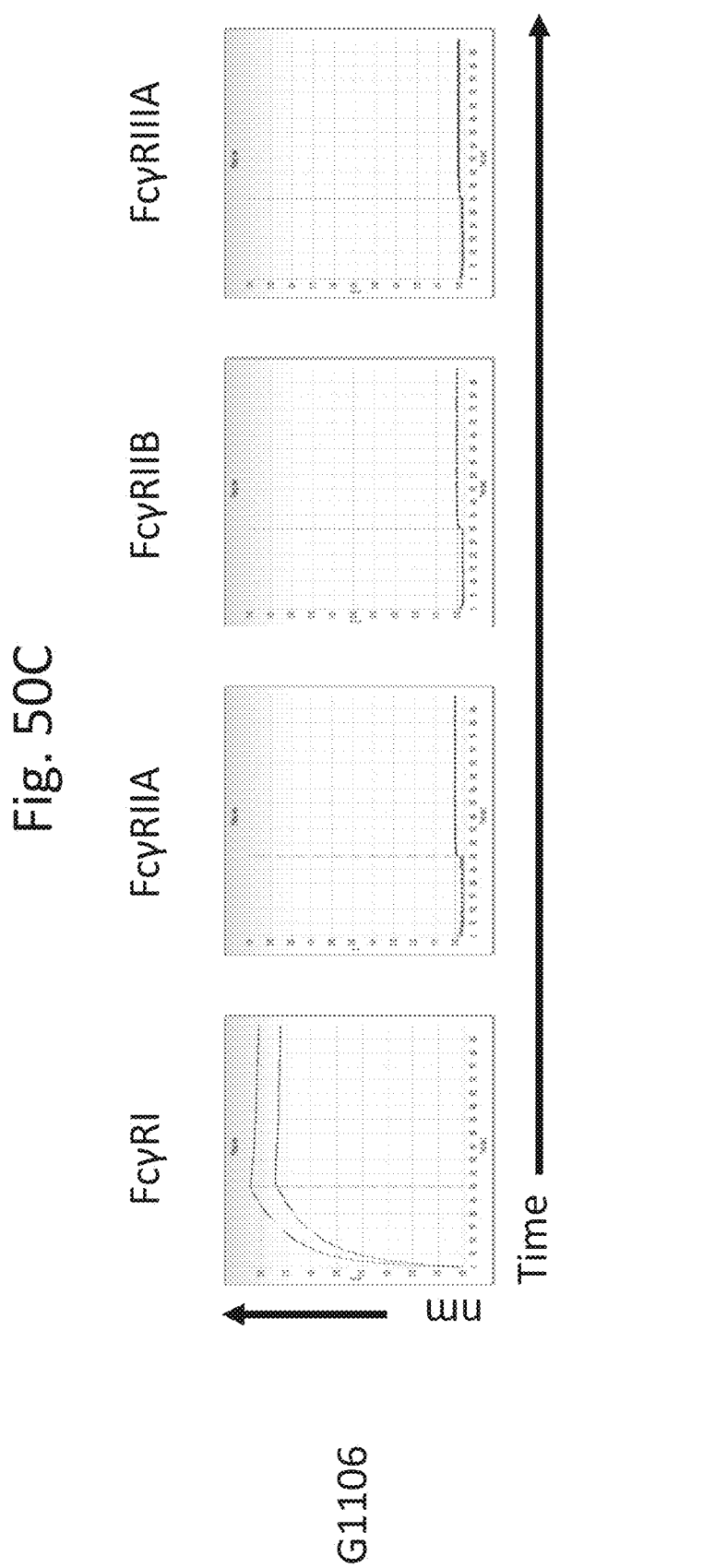

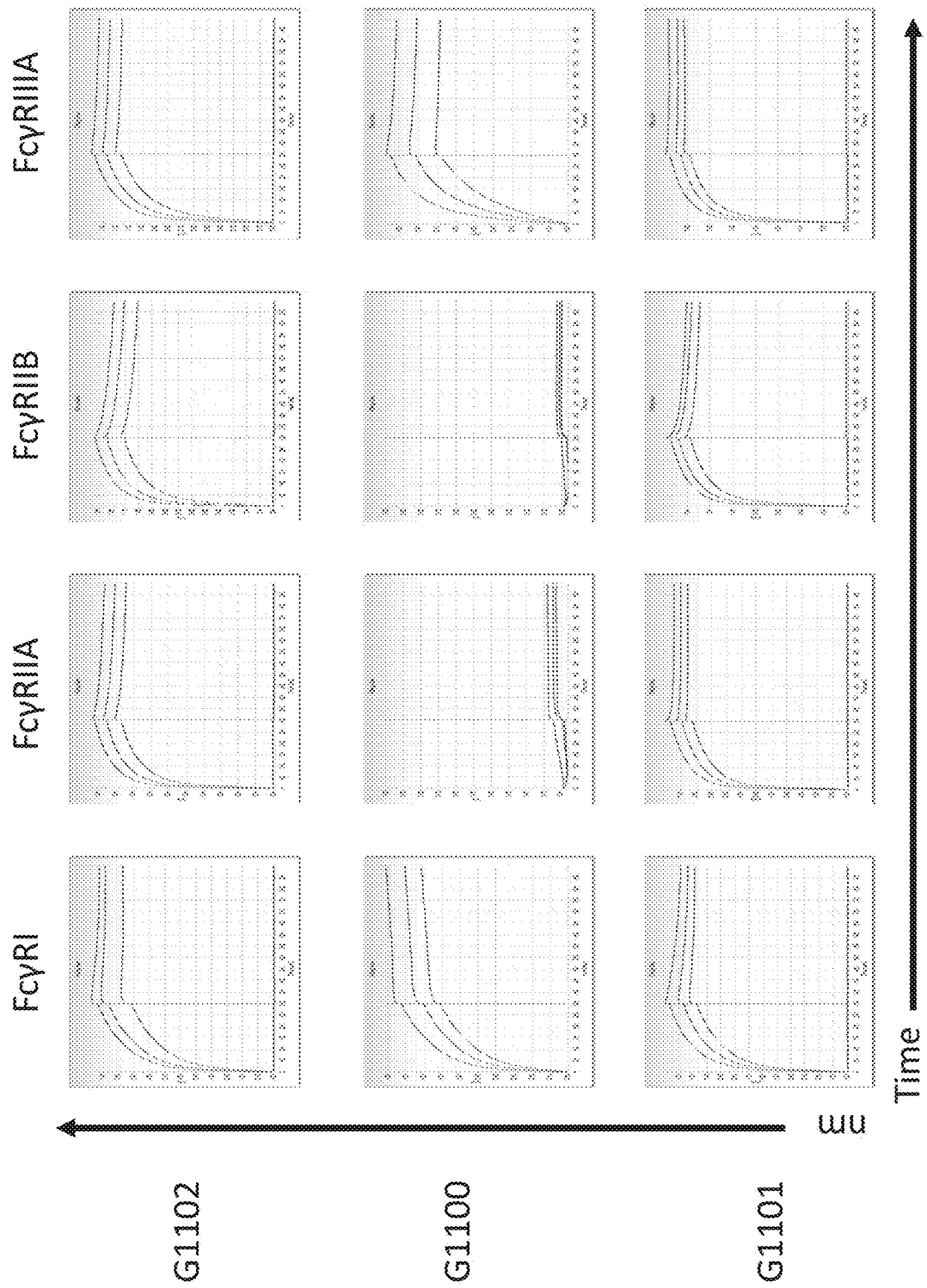

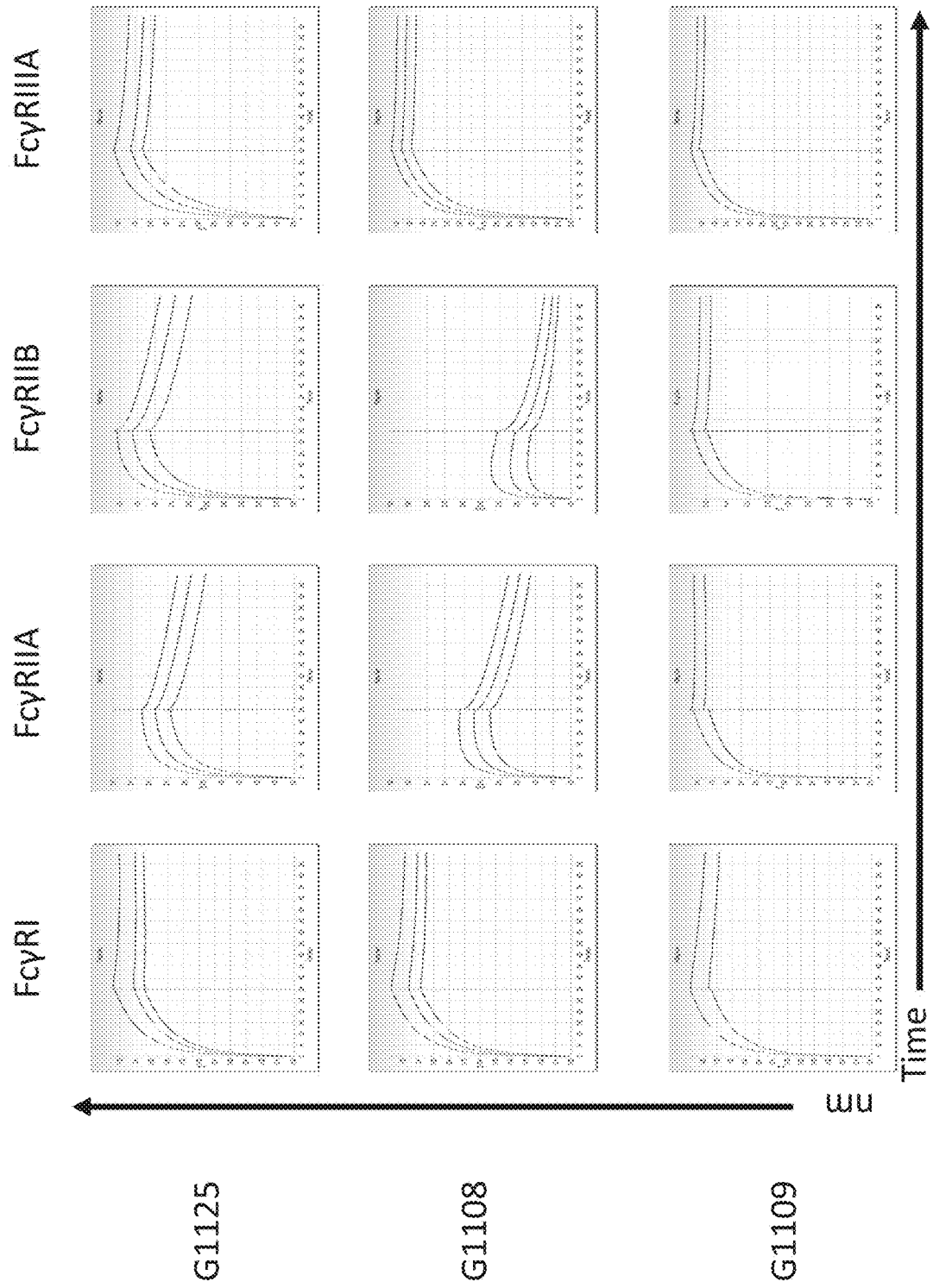

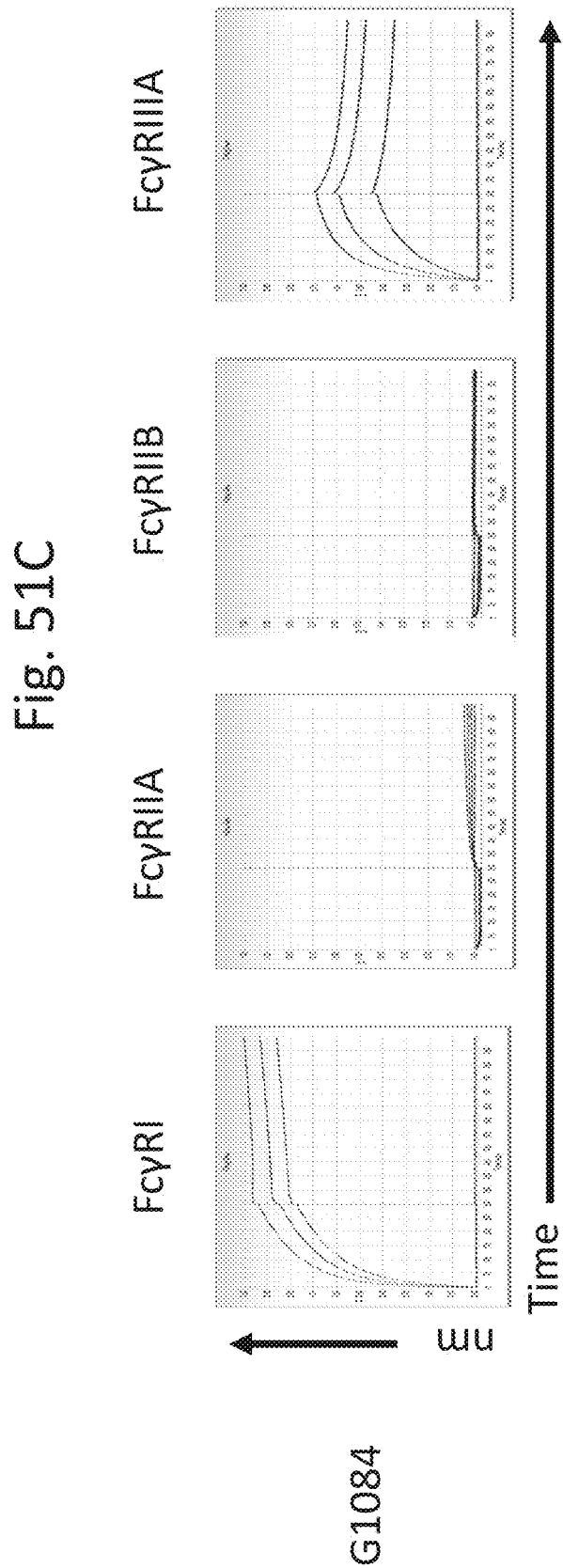

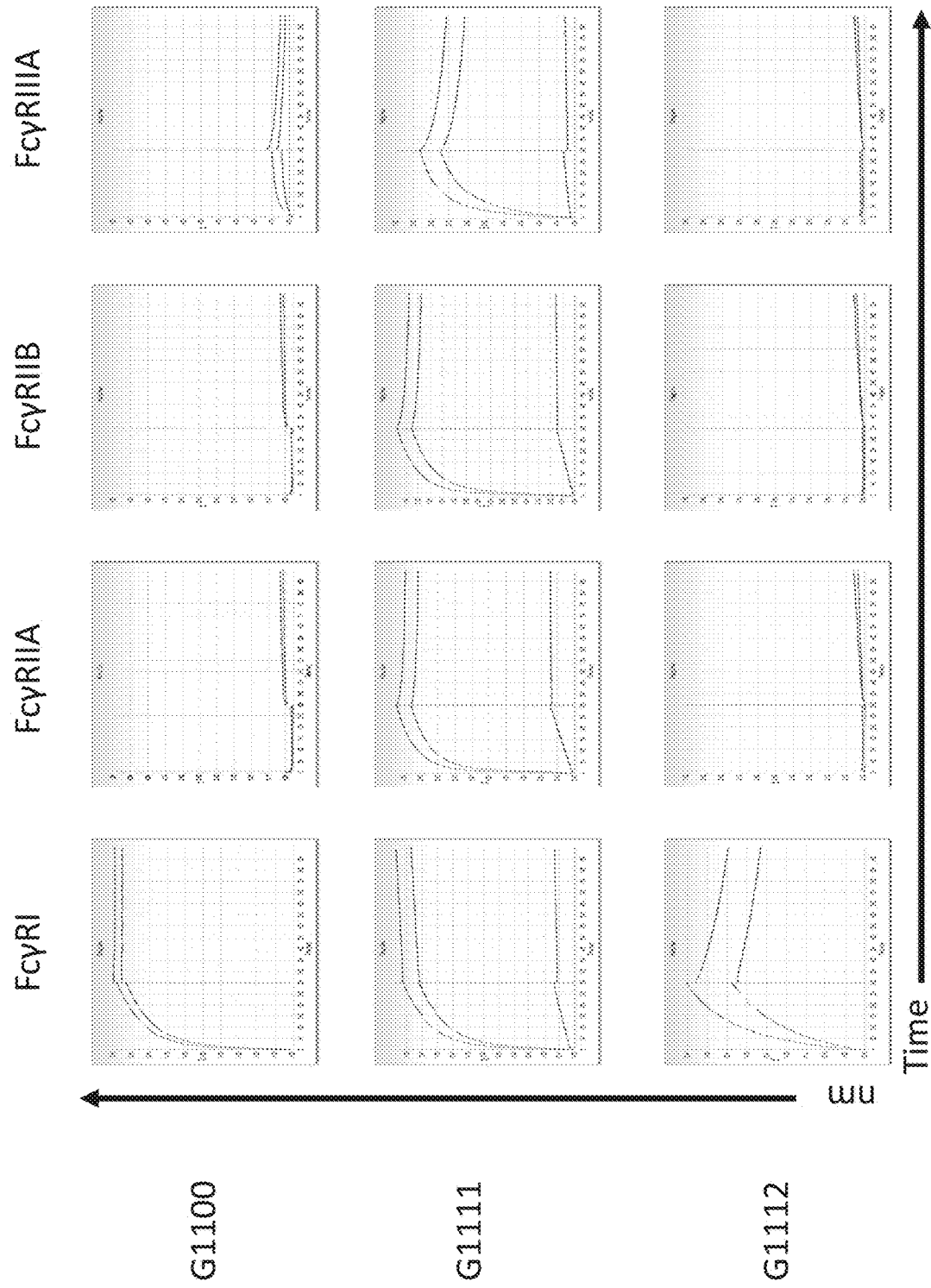

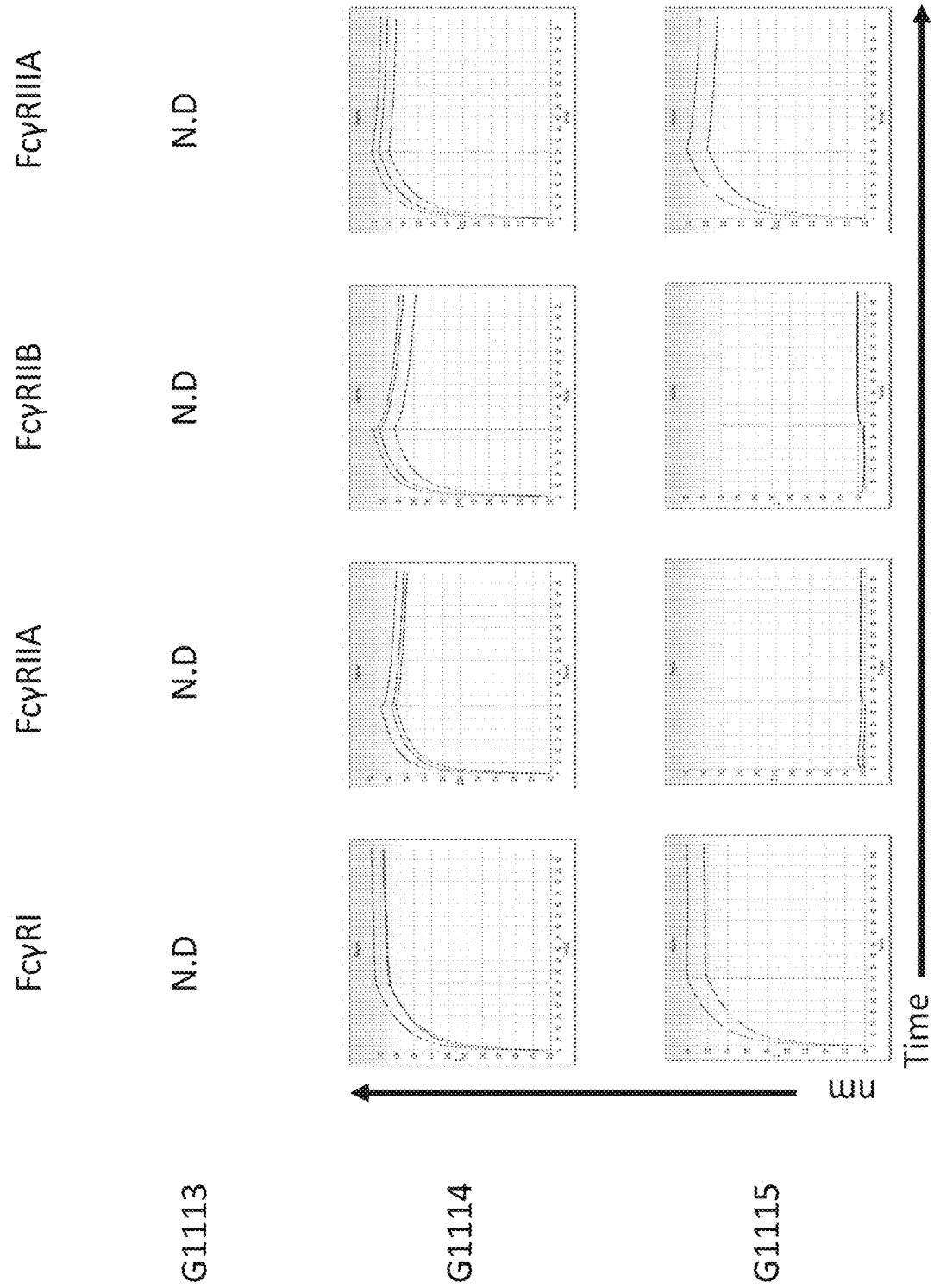

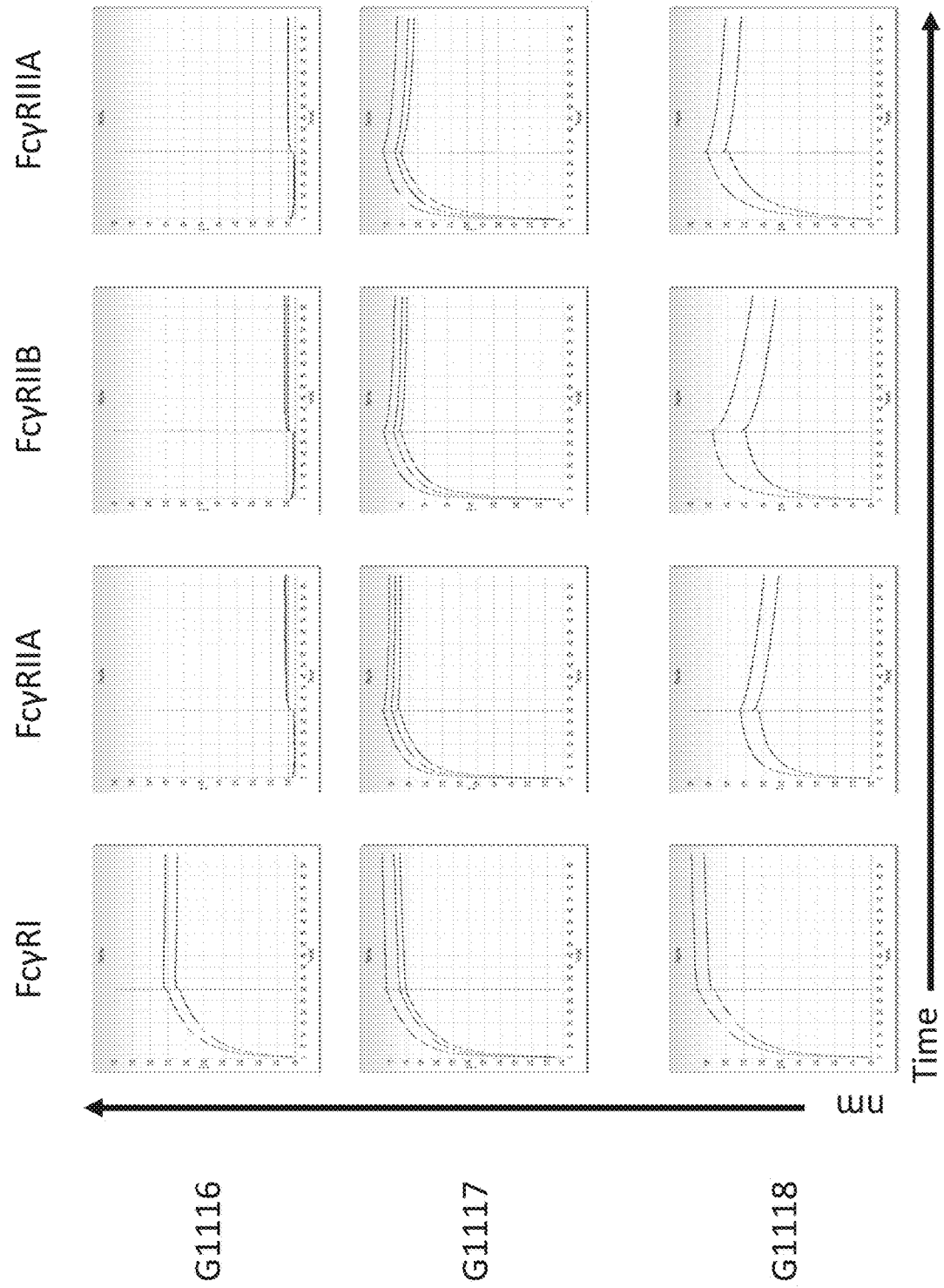

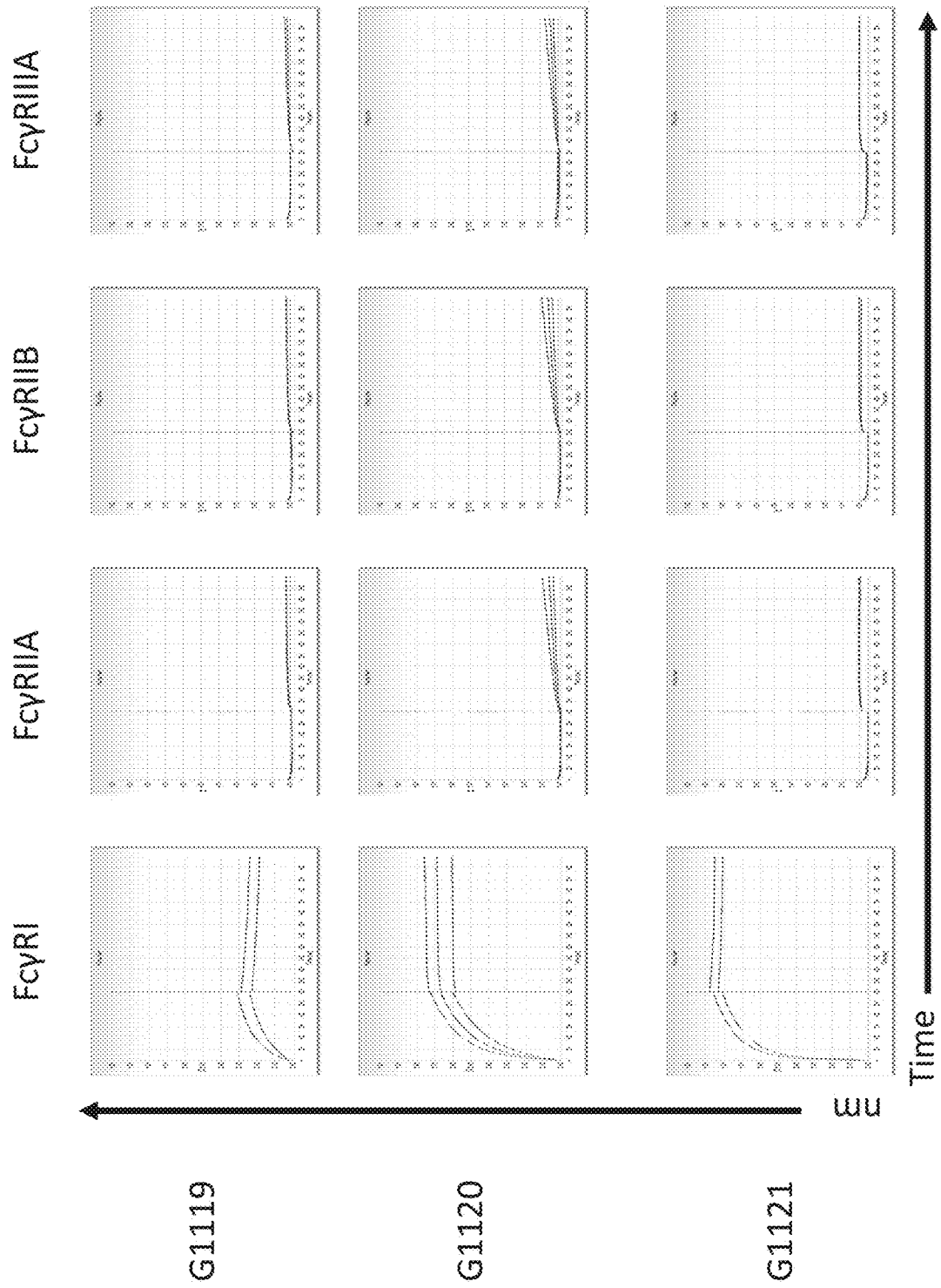

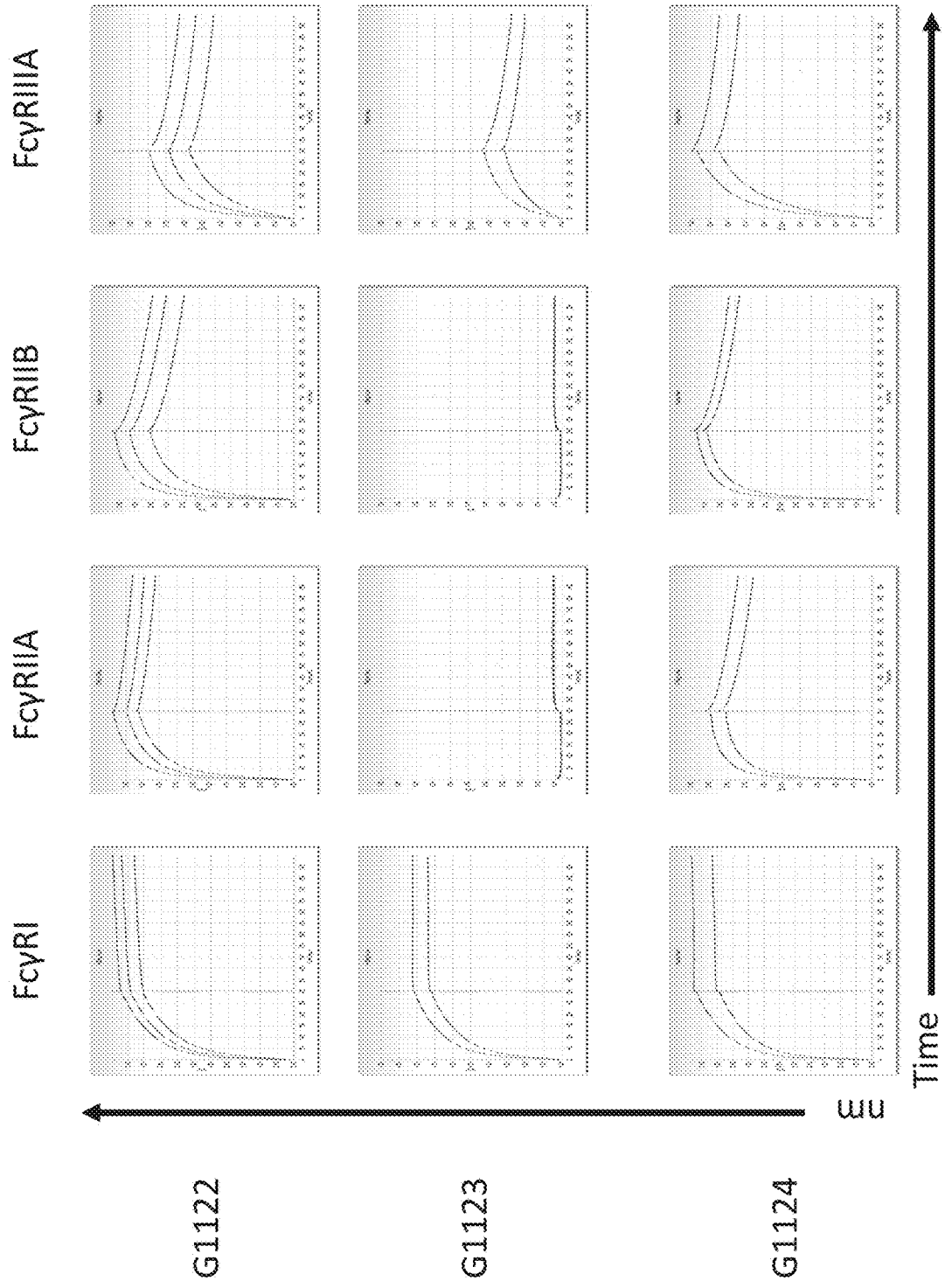

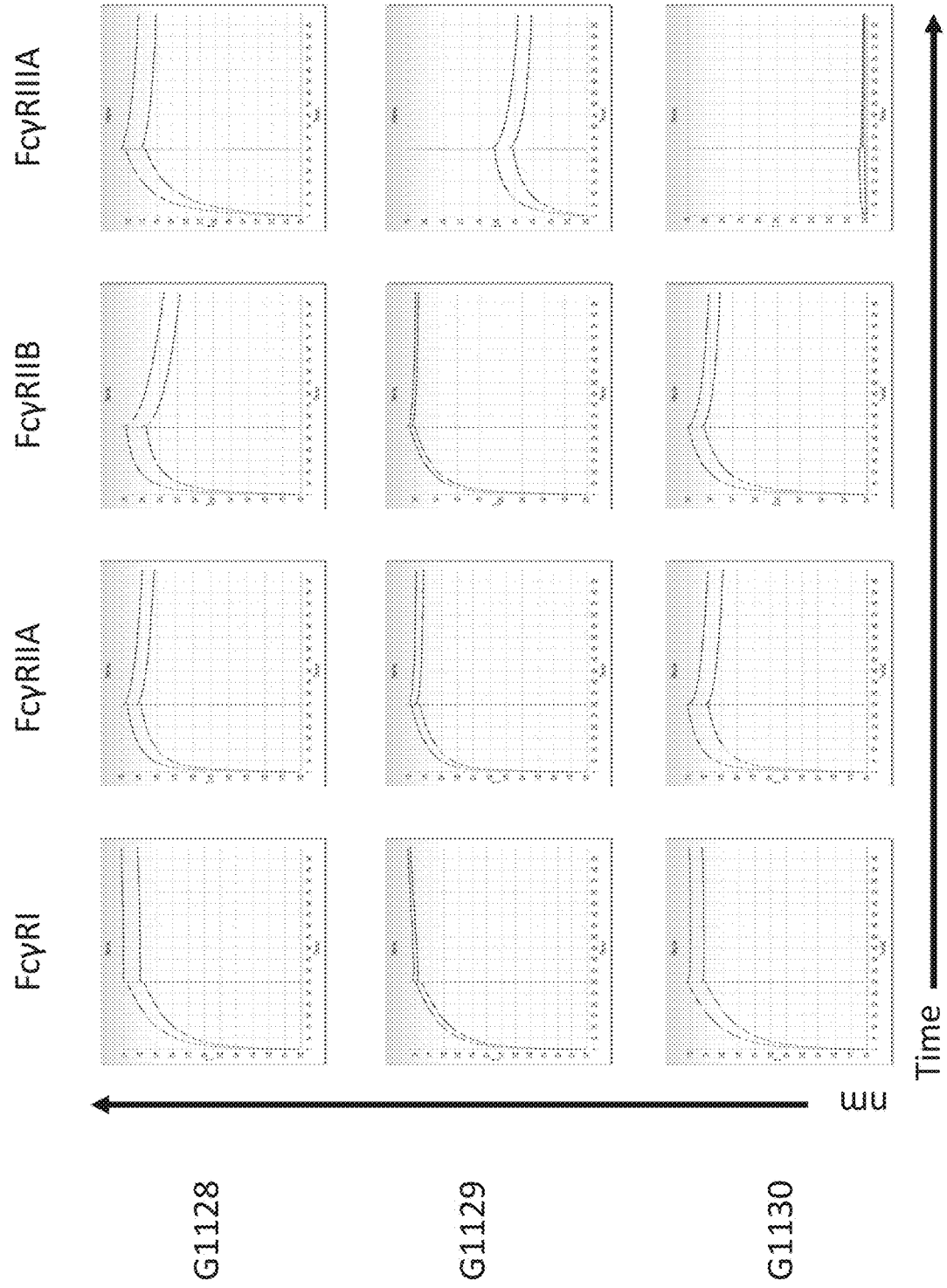

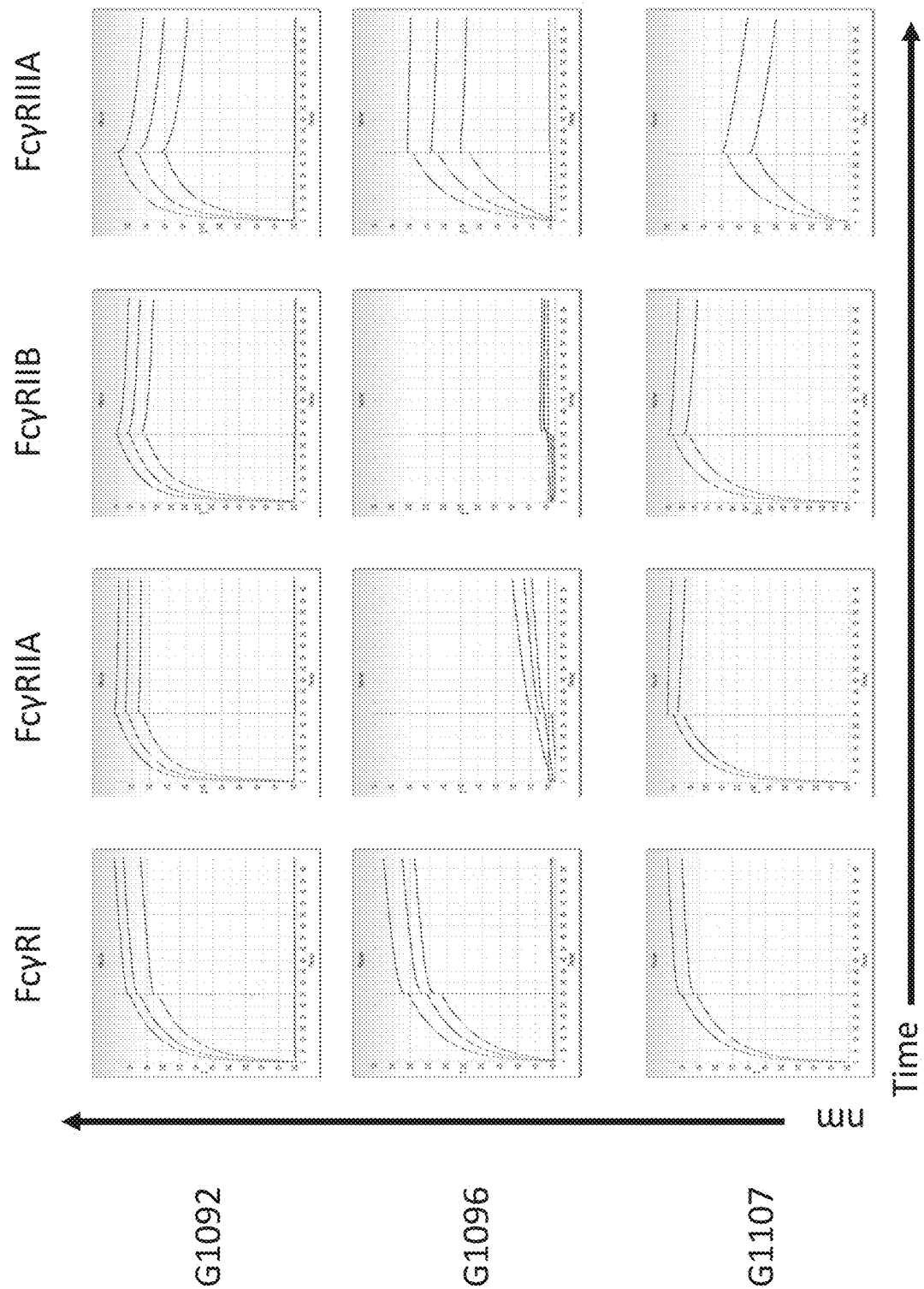

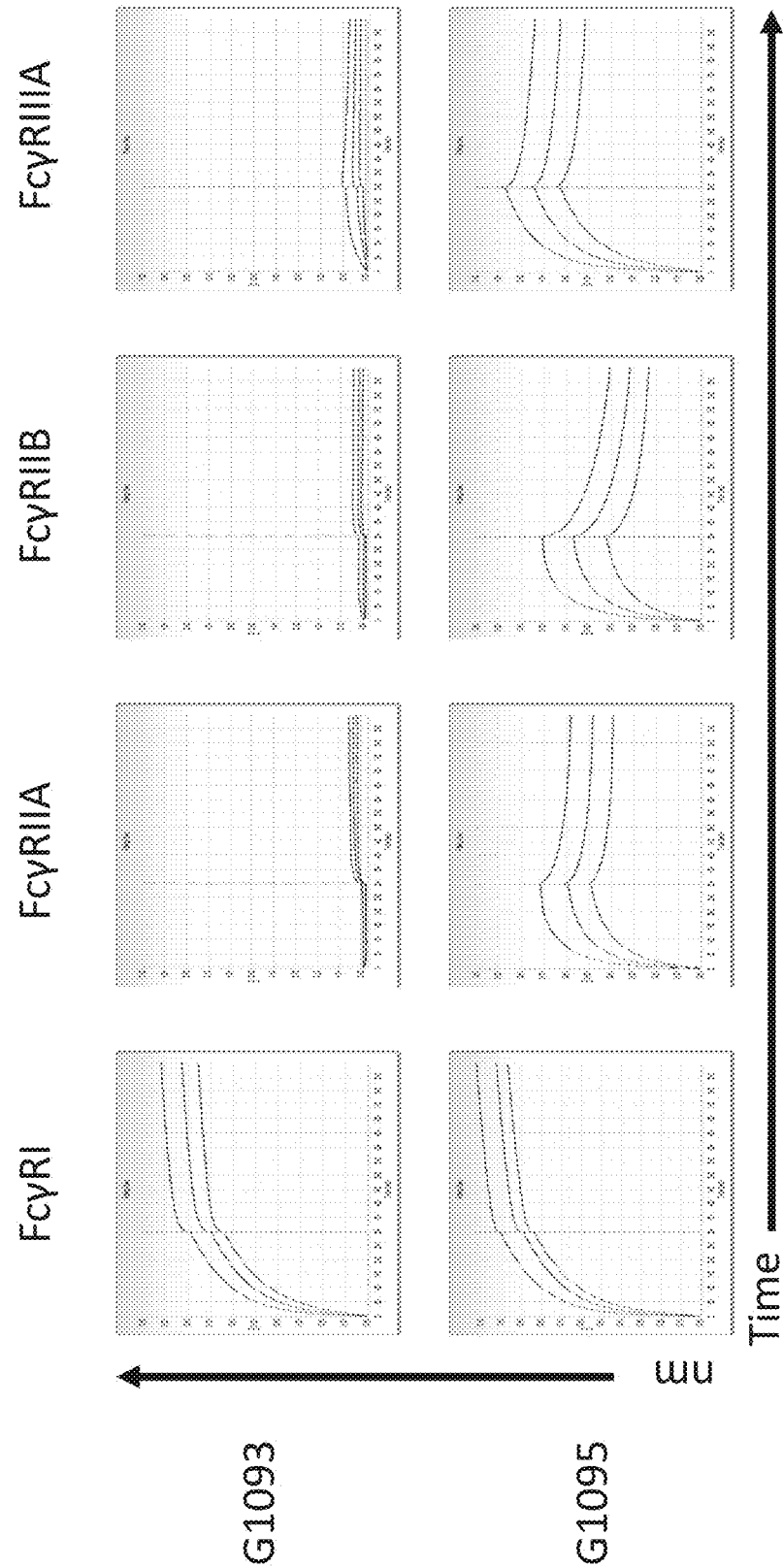

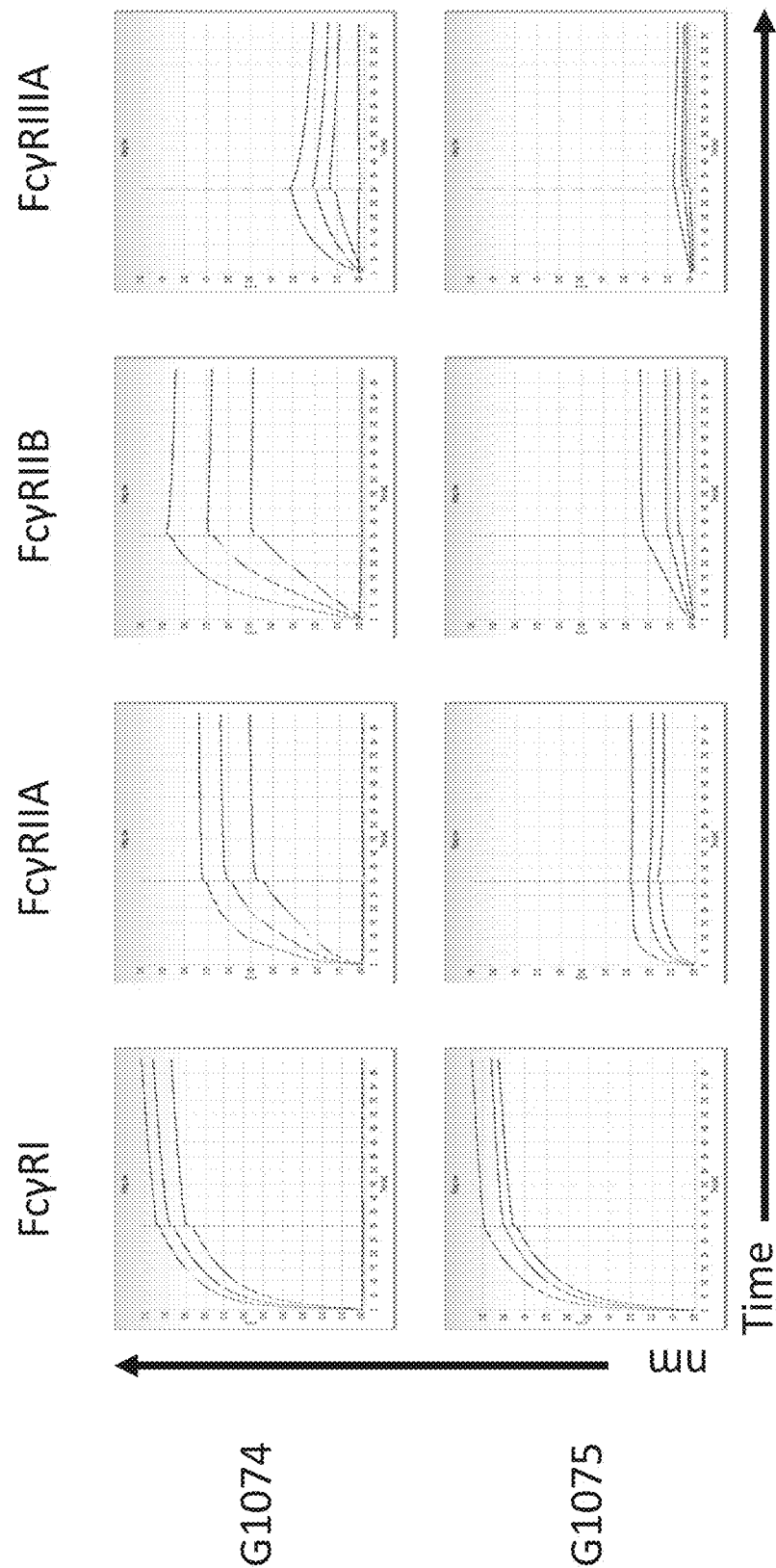

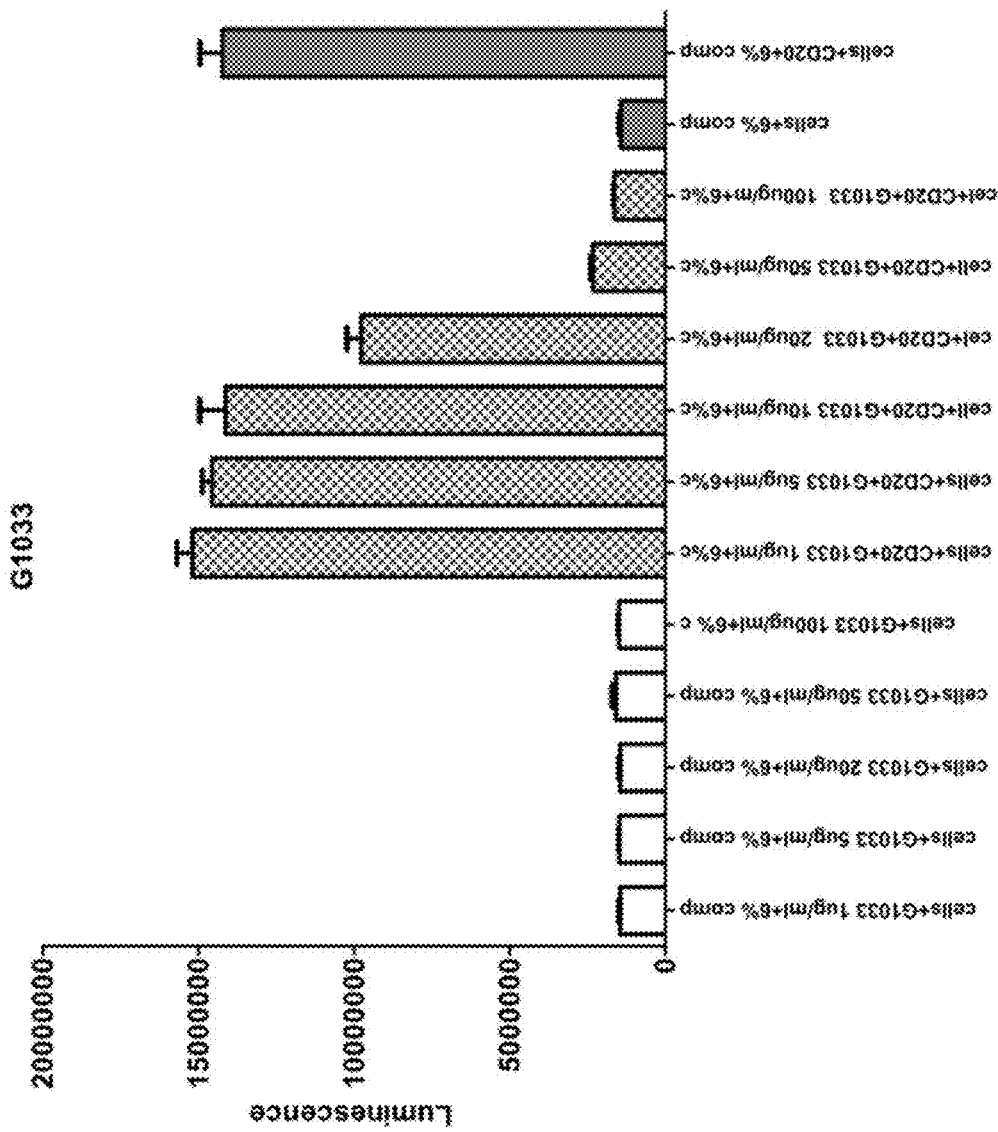

FUSION PROTEINS OF HUMAN PROTEIN FRAGMENTS TO CREATE ORDERLY MULTIMERIZED IMMUNOGLOBULIN Fc COMPOSITIONS WITH ENHANCED COMPLEMENT BINDING

CROSS-REFERENCE TO RELATED APPLICATIONS

This application is a continuation of and claims priority to International PCT Application No. PCT/US2016/043746, filed Jul. 22, 2016, which claims priority to U.S. Provisional Application No. 62/196,478, filed Jul. 24, 2015, the contents of which are incorporated herein by reference in their entireties.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: GLIK_015_01US_SeqList_ST25.txt, date recorded: Jan. 22, 2018, file size 193 kilobytes).

FIELD OF THE INVENTION

This invention relates generally to the fields of immunology, autoimmunity, inflammation, and tumor immunology. More specifically, the present invention relates to biologically active biomimetic molecules comprising immunoglobulin Fc domains that exhibit altered Fc receptor binding and retained or enhanced binding to elements of the complement system, compositions comprising such biomimetics, and methods of making and using such biomimetics. The invention further relates to treating or preventing pathological conditions such as complement-mediated diseases, autoimmune diseases, inflammatory diseases, blood disorders, and cancers.

BACKGROUND OF THE INVENTION

The complement system is a part of the immune system that is involved in target cell lysis and phagocytosis of antigens. There are three main complement pathways currently known: the classical pathway, the alternative pathway, and the lectin binding pathway. The classical complement pathway is activated once the protein C1q binds to one or more molecules of intact immunoglobulin IgM, or at least two molecules of intact immunoglobulin IgG1, IgG2, or IgG3 (Janeway's Immunobiology, $8^{th}$ Ed., Murphy ed., Garland Science, 2012, Chapter 10). Complement activation leads to complement-dependent cytotoxicity (CDC). Alterations in the Fc region of monoclonal antibodies have been shown to enhance or decrease the affinity of complement binding (Moore et al., *MAbs.* 2(2): 181-9 (2010). However, this work was done in the context of a monoclonal antibody and was therefore dependent, at least in part, on target specificity of the Fab and was without the context of binding avidity.

Excessive complement activation and/or deposition can be detrimental and is associated with many diseases including myasthenia gravis, hemolytic uremic syndrome (HUS), and paroxysmal nocturnal hemoglobinuria (PNH). The aging brain is associated with dramatically increased levels of complement component C1q (Stephan et al., *J. Neuroscience,* 14 Aug. 2013, 33(33): 13460-13474). The complement system is profoundly involved in the pathogenesis of acetylcholine receptor antibody-related Myasthenia gravis (Tüzün and Christadoss, *Autoimmun Rev.* 2013 July; 12(9): 904-11. doi: 10.1016/j.autrev.2013.03.003). A number of findings from immunological, genetic, and protein biochemical studies indicate that the complement system plays an essential role in the etiology of Age-Related Macular Degeneration (Weber et al., *Dtsch Arztebl Int.,* 2014 February; 111(8): 133-138). There is strong evidence that both the classical and the alternative pathways of complement are pathologically activated during Rheumatoid Arthritis as well as in animal models for Rheumatoid Arthritis (Okroj et al., *Ann Med.* 2007; 39(7):517-30).

The classical, alternative, and lectin pathways are activated in a sequential manner and all three pathways are involved in systemic disease. Activation of the complement system is involved in the pathogenesis of the systemic autoimmune diseases. Activation via the classical pathway has long been recognized in immune complex-mediated diseases such as cryoglobulinemic vasculitis and systemic lupus erythematosus (Chen et al., *Journal of Autoimmunity,* 2009). Complement activation through both the alternative and lectin pathways is found in patients with Henoch-Schönlein purpura nephritis and IgA Nephropathy (Hisano et al., *Am J Kidney Dis* 2005; 45:295e302). The importance of complement in membranous nephropathy, one of the most common causes of adult nephrotic syndrome, is well described. Membranous nephropathy is marked by glomerular subepithelial immune deposits. Studies in Heymann nephritis, an experimental model of membranous nephropathy, have demonstrated that these deposits locally activate complement to cause podocyte injury, culminating in cytoskeletal reorganization, loss of slit diaphragms, and proteinuria (Beck et al., The Role of Complement in Membranous Nephropathy. *Semin Nephrol* 2013 November; 33(6):531-42).

Activation of complement is an extraordinarily complex process with new components of the cascade still being discovered many decades after the process was initially thought to be understood. The first step in the classical pathway complement cascade is the binding of C1q to the antibody. (Duncan A R, Winter G., Nature. 1988 Apr. 21; 332(6166):738-40).

Binding of non-aggregated antibody to C3 or to C3b is not thought to occur through complement activation in plasma, but is thought to be maintained primarily by complexes of the activation product $C3b_2$ with IgG (Lutz H U, Jelezarova E, Mol Immunol. 2006 January; 43(1-2):2-12). However, during activation of the alternative pathway of complement by immune aggregates containing IgG antibody, the alpha'-chain of C3b may become covalently bound at one or two sites in the Fd portion of the heavy chain of IgG (i.e. that portion of the heavy chain which is included in the Fab fragment) (K J Gadd and K B Reid, Biochem J. May 1, 1981; 195(2): 471-480). Complement components C4a, C3a, C5a, and Membrane Attack Complex have historically been commonly referred to as Complement Split Products or Anaphylatoxins. However, the literature now makes clear that C4a (Xie et al., International Immunopharmacology 12 (2012) 158-168), C3a (Coulthard and Woodruff, *J Immunol* 2015; 194:3542-3548), and C5a (Nishise et al., *Therapeutic Apheresis and Dialysis* 13(6):509-514 and Gerard et al., *J. Biol Chem.* 280(48):39677-39680, 2005) are in certain circumstances anti-inflammatory and not associated with an escalation of the cascade.

A predominant therapy on the market at this time for treatment of complement-mediated diseases is the anti-C5 antibody eculizumab which binds C5 and inhibits its cleavage to C5a and C5b-9, partially inhibiting the progression of the complement cascade downstream and associated inflammatory and thrombotic responses. However, it does not have a direct impact on upstream complement components such as C1q, C1R, C1S, C1-like complex, or on C4, C4a, C4b, C2, C1, C4b2, C2b, C4b2a, C3, C3a, or C3b which are components of the lectin pathway, classical pathway, and alternative pathway upstream of complement cascade component C5 and which may be preferential targets for treating disease. In contrast, normal immunoglobulins and monoclonal antibodies do bind C1q and other targets upstream of C5. Thus, there is a need in the art for improved methods for treating complement-mediated diseases through binding of upstream complement cascade components and consequent modulation of the complement cascade. There is a further need in the art for improved methods for treating complement-mediated diseases with an immunoglobulin Fc-comprising compound that binds hexameric C1q with avidity, not just with affinity, and further which does so without significant avidity binding to low affinity Fc receptors.

Native immunoglobulin IgG1 Fc binds more than a dozen ligands naturally, one of which is complement factor C1q. Other IgG1 Fc ligands without limitation include the canonical Fc receptors, neonatal receptor FcRn, iron, Protein A, FcRL1-6, TRIM21, and DC-SIGN. Soluble homodimeric IgG1 naturally binds C1q with affinity that is too low to be functional (CA Diebolder et. al., Science March 2014; 343(6176):1260-1263) and with a high dissociation rate (Gaboriaud et. al., J. Biol. Chem. 2003 Nov. 21; 278(47): 46974-82). However, when the IgG1 is fixed to an antigen target through its Fab, a conformational change occurs (M. Oda et. al., Int. Immunol. (2003) 15 (3): 417-426) and binding affinity to C1q increases.

Moreover, as IgG1 accumulates at the site of an antigen, multiple immunoglobulin Fc are presented to C1q, resulting in more avid binding at the antigen binding site. As C1q is hexameric with six Fc binding sites (K B Reid., Behring Inst Mitt. 1989 July; (84):8-19), the binding of aggregated IgG1 is of high avidity (Diebolder, 2014). Thus, densely bound IgG1 binds C1q not only with the affinity of a homodimeric immunoglobulin but also with avidity resulting in Complement Dependent Cytotoxicity, in addition to being available to cross-link Fc receptors with resultant Antibody Dependent Cell Cytotoxicity (ADCC) and Antibody Dependent Cell Phagocytosis (ADCP). The resulting functional response of the binding of clusters of bound Fc to hexameric C1q is activation of the classical complement pathway with formation of C1qC1rC1s and cleavage of C4 to C4a and C4b. Soluble aggregates of IgG1, which occur both naturally at very low concentrations (Soltis and Hasz, J Clin Lab Immunol. 1982 October; 9(1):13-7) and in pooled human Intravenous Immunoglobulin (IVIG) (A. Herrera et. al., J. All Clin Immunol, 84(1):556-561), present unbound polyvalent IgG1 Fc to its ligands, including low affinity Fc receptors and C1q. Soluble (i.e. not cell bound) aggregates of IgG1 thereby bind hexameric C1q with avidity. The binding of soluble C1q to soluble aggregates of IgG1 (i.e. not cell bound) may inhibit the downstream activation of the complement cascade, including inhibition of CDC.

Pooled human IVIG, which is pooled from tens of thousands of blood donors, contains a very small and variable portion (0.1-5%) of IgG1 aggregates that mimic the natural effect of soluble aggregates of native IgG1. IVIG binds C1q and has been demonstrated to be clinically useful in complement-mediated diseases such as Myasthenia gravis. IVIG, however, has all the attendant risks of being a blood product, is not recombinantly produced, has poorly controlled amounts of IgG1 aggregates, and is comprised primarily of inactive fractions for treating complement-mediated diseases. What is more, IVIG treatment also often leads to an unwanted proinflammatory response by binding to low affinity Fc receptors (Andresen et. al., J Clin Pharmacol 2000; 40:722-730 and Ghielmetti et. al., Mol Immunol 43 (2006) 939-949). There is a need for novel, consistent, recombinantly-produced therapies that mimic the natural process of aggregated soluble IgG1 Fc acting as a complement sink by avidly binding C1q, while at the same time avoiding unwanted pro-inflammatory responses by preferentially binding to complement components over other natural ligands including low affinity Fc receptors.

SUMMARY OF THE INVENTION

The present invention relates to biologically active fusion protein biomimetic molecules comprising one or more human immunoglobulin Fc domains and one or more multimerization domains, wherein the Fc domain portion of the fusion protein comprises one or more point mutations. In one aspect, the biomimetic molecules preferentially bind one or more complement components relative to a normal non-aggregated human immunoglobulin Fc. In some embodiments, preferential binding to one or more complement components is achieved by the Fc domain of the biomimetic having reduced binding to canonical Fc Receptors relative to normal non-aggregated immunoglobulin Fc or alternatively normal aggregated immunoglobulin Fc. In some embodiments, the biologically active fusion protein biomimetic molecules comprise stradomer units. Compositions comprising the biologically active fusion protein biomimetics and methods for using the same are provided.

In one aspect, the present disclosure provides a stradomer unit comprising at least one IgG1 Fc domain having one or more point mutations corresponding to at least one of positions 267, 268, and/or 324 of the IgG1 Fc domain. In some embodiments, the stradomer unit further comprises at least one multimerization domain. In some embodiments, the amino acid at position 267 is mutated from serine (Ser; S) to any other amino acid. In further embodiments, the amino acid at position 267 is mutated to glutamic acid (Glu; E). In some embodiments, the amino acid at position 268 is mutated from histidine (His; H) to any other amino acid. In further embodiments, the amino acid at position 268 is mutated to phenylalanine (Phe; F). In some embodiments, the amino acid at position 324 is mutated from serine to any other amino acid. In further embodiments, the amino acid at position 324 is mutated to threonine (Thr; T). In some embodiments, the Fc domain of the stradomer unit comprises point mutations at positions 267, 268, and 324. In further embodiments, the Fc domain comprises the point mutations S267E, H268F, and S324T.

In some embodiments, the stradomer unit comprises an IgG1 Fc domain having an amino acid sequence comprising point mutations at positions 267, 268, and/or 324 and further comprising at least one point mutation at position 233 and/or 234 and/or 235 and/or 236 and/or 238 and/or 265 and/or 297 and/or 299 and/or 328. In one embodiment, the amino acid at position 297 is mutated from asparagine (Asn; N) to any other amino acid. In a further embodiment, the amino acid at position 297 is mutated to alanine (Ala; A). In one embodiment, the amino acid at position 299 is mutated from threonine (T) to any other amino acid other than serine or cysteine. In a further embodiment, the amino acid at position 299 is mutated to alanine (Ala; A). In one embodiment, the amino acid at position 238 is mutated from proline (Pro; P) to any other amino acid. In a further embodiment, the amino acid at position 238 is mutated to aspartic acid (Asp; D). In one embodiment, the amino acid at position 233 is mutated from glutamic acid (Glu; E) to any other amino acid. In a further embodiment, the amino acid at position 233 is mutated to proline (Pro; P). In another embodiment, the amino acid at position 236 is mutated from glycine (Gly; G) to any other amino acid. In a further embodiment, the amino acid at position 236 is mutated to arginine (Arg; R). In one embodiment, the amino acid at position 236 is deleted. In one embodiment, the amino acid at position 234 is mutated from leucine (Leu; L) to any other amino acid. In a further embodiment, the amino acid at position 234 is mutated to valine (Val; V) or alanine (Ala; A). In another embodiment, the amino acid at position 235 is mutated from leucine (Leu; L) to any other amino acid. In a further embodiment, the amino acid at position 235 is mutated to alanine (Ala; A). In one embodiment, the amino acid at position 265 is mutated from aspartic acid (Asp; D) to any other amino acid. In a further embodiment, the amino acid at position 265 is mutated to alanine (Ala; A). In another embodiment, the amino acid at position 265 is mutated to tryptophan (Trp; W). In one embodiment, the amino acid at position 297 is mutated from asparagine (Asn; N) to any other amino acid. In one embodiment, the amino acid at position 297 is mutated to alanine (Ala; A). In one embodiment, the amino acid at position 297 is mutated to glutamine (Gln; Q). In one embodiment, the amino acid at position 299 is mutated from threonine (Thr; T) to any other amino acid, other than serine (Ser; S) or cysteine (Cys; C). In one embodiment, the amino acid at position 299 is mutated to alanine. In one embodiment, the amino acid at position 298 is mutated to any amino acid other than proline. In one embodiment, the amino acid at position 328 is mutated from leucine (Leu; L) to any other amino acid. In a further embodiment, the amino acid at position 328 is mutated to phenylalanine (Phe; F).

In some embodiments, the Fc domain of the stradomer unit comprises point mutations at positions 267, 268, 297, and 324. In further embodiments, the Fc domain comprises the point mutations S267E, H268F, N297A, and S324T.

In some embodiments, the Fc domain of the stradomer unit comprises point mutations at positions 234, 235, 267, 268, and 324. In further embodiments, the Fc domain comprises the point mutations L234V, L235A, S267E, H268F, and S324T.

In some embodiments, the Fc domain of the stradomer unit comprises point mutations at positions 234, 235, 267, 268, 297, and 324. In further embodiments, the Fc domain comprises the point mutations L234V, L235A, S267E, H268F, N297A, and S324T.

In some embodiments, the Fc domain of the stradomer unit comprises point mutations at of positions 233, 234, 235, 267, 268, and 324, and deletion of the amino acid at position 236. In further embodiments, the Fc domain comprises the point mutations E233P, L234A, L235A, S267E, H268F, and S324T, and deletion of the amino acid at position 236.

In some embodiments, the Fc domain of the stradomer unit comprises point mutations at of positions 233, 234, 235, 267, 268, 297, and 324. In further embodiments, the Fc domain comprises the point mutations E233P, L234A, L235A, S267E, H268F, N297A, and S324T.

In some embodiments, the Fc domain of the stradomer unit comprises a point mutation at positions 265, 267, 268, and 324. In further embodiments, the Fc domain comprises the point mutations D265A, S267E, H268F, and S324T.

In some embodiments, the Fc domain of the stradomer unit comprises a point mutation at positions 238, 267, 268, and 324. In further embodiments, the Fc domain comprises the point mutations P238D, S267E, H268F, and S324T.

In some embodiments, the Fc domain of the stradomer unit comprises a point mutation at positions 238, 267, 268, 297, and 324. In further embodiments, the Fc domain comprises the point mutations P238D, S267E, H268F, N297A, and S324T.

In some embodiments, the Fc domain of the stradomer unit comprises a point mutation at positions 236, 267, 268, and 324. In further embodiments, the Fc domain comprises the point mutations G236R, S267E, H268F, and S324T.

In some embodiments, the Fc domain of the stradomer unit comprises a point mutation at positions 233, 236, 267, 268, and 324. In further embodiments, the Fc domain comprises the point mutations E233P, G236R, S267E, H268F, and S324T.

In some embodiments, the Fc domain of the stradomer unit comprises a point mutation at positions 233, 236, 267, 268, 324, and 328. In further embodiments, the Fc domain comprises the point mutations E233P, G236R, S267E, H268F, S324T, and L328F.

In some embodiments, the Fc domain of the stradomer unit comprises a point mutation at positions 238, 265, 267, 268, and 324. In further embodiments, the Fc domain comprises the point mutations P238D, D265G, S267E, H268F, and S324T. In other embodiments, the Fc domain comprises the point mutations P238D, D265W, S267E, H268F, and S324T.

In some embodiments, the Fc domain of the stradomer unit comprises a point mutation at positions 267, 268, 324, and 328. In further embodiments, the Fc domain comprises the point mutations S267E, H268F, S324T, and L328F.

In some embodiments, the Fc domain of the stradomer unit comprises a point mutation at positions 233, 234, 235, 267, 268, 297, 324, and 328, and deletion of the amino acid at position 236. In further embodiments, the Fc domain comprises the point mutations E233P, L234V, L235A, S267E, H268F, N297A, S324T, and L328F, and deletion of the amino acid at position 236.

In some embodiments, the Fc domain of the stradomer unit comprises a point mutation at positions 233, 268, and 324. In further embodiments, the Fc domain comprises the point mutations E233P, H268F, and S324T.

In some embodiments, the Fc domain of the stradomer unit comprises a point mutation at positions 233, 268, 297, and 324. In further embodiments, the Fc domain comprises the point mutations E233P, H268F, S324T and a point mutation at position 297 other than N297A or N297Q.

In some embodiments, the Fc domain of the stradomer unit comprises a point mutation at positions 233, 268, 299, and 324. In further embodiments, the Fc domain comprises the point mutations E233P, H268F, S324T and a point mutation at position 299 other than T299S and T299C. In some embodiments, the Fc domain of the stradomer unit comprises the point mutations E233P, H268F, S324T, and T299A.

In some embodiments, the Fc domain of the stradomer unit comprises point mutations at positions 233, 268, 324, and 267. In some embodiments, the Fc domain of the stradomer unit comprises the point mutations E233P, H268F, S324T, and a point mutation at position 267 other than the point mutation S267E.

In some embodiments, the Fc domain of the stradomer unit comprises point mutations at positions 233, 268, 324, 267, and 297. In further embodiments, the Fc domain of the stradomer unit comprises the point mutations E233P, H268F, S324T, a point mutation at position 267 other than the point mutation S267E, and a point mutation at position 297 other than the point mutation N297A and N297Q. In further embodiments, the Fc domain of the stradomer unit comprises mutations at positions 233, 268, 324, 267, and 297. In further embodiments, the Fc domain of the stradomer unit comprises the point mutations E233P, H268F, S324T, a point mutation at position 267 other than the point mutation S267E, a point mutation at position 297 other than the point mutation N297A and N297Q, and a point mutation at position 299 other than the point mutations T299S and T299C. In further embodiments, the mutation at position 299 is T299A.

In some embodiments, the Fc domain of the stradomer unit comprises point mutations at positions 233, 268, 324, 267, and 236. In some embodiments, the Fc domain of the stradomer unit comprises the point mutations E233P, H268F, S324T, a point mutation at position 267 other than S267E, and a point mutation at position 236 other than G236R.

In some embodiments, the Fc domain of the stradomer unit comprises point mutations at positions 233, 268, 324, 267, 236, and 297. In some embodiments, the Fc domain of the stradomer unit comprises the point mutations E233P, H268F, S324T, a point mutation at position 267 other than S267E, a point mutation at position 236 other than G236R, and a point mutation at position 297 other than N297A and N297Q.

In some embodiments, the Fc domain of the stradomer unit comprises point mutations at positions 233, 268, 324, 267, 236, and 299, wherein the point mutation at position 299 is a point mutation other than T299S and T299C. In some embodiments, the Fc domain of the stradomer unit comprises the point mutations E233P, H268F, S324T, a point mutation at position 267 other than S267E, a point mutation at position 236 other than G236R, and T299A.

In some embodiments, the Fc domain of the stradomer unit comprises point mutations at at least one of positions 267, 268, and/or 324 and further comprises a point mutation at three or more of positions 233, 235, 236, 267, 268, 297, 299, and/or 324. In some embodiments, the Fc domain of the stradomer unit comprises point mutations at at least one of positions 267, 268, and/or 324 and further comprises a point mutation at three or more of positions 233, 235 other than L235H, 236 other than 236R, 267 other than S267E, 268, 297 other than N297A, or alternatively 299, and/or 324.

In one embodiment, the stradomer comprises a multimerization domain, wherein the multimerization domain is selected from the group consisting of an IgG2 hinge, an isoleucine zipper and a GPP domain and is capable of multimerizing said stradomer units. In some embodiments, the multimerization domain creates multimers of said stradomer units. In further embodiments, the multimers of said stradomer units are high order multimers.

In some embodiments, the stradomer comprises, from amino to carboxy terminus, a leader sequence; an Fc domain comprising an IgG1 hinge, IgG1 CH2, and IgG1 CH3; and an IgG2 hinge, wherein the stradomer comprises one or more point mutations as provided herein. In a further embodiment, the leader sequence is cleaved upon expression. Therefore, in another embodiment, there is provided a stradomer comprising, from amino to carboxy terminus, an Fc domain comprising an IgG1 hinge, IgG1 CH2, and IgG1 CH3; and an IgG2 hinge, wherein the stradomer comprises one or more point mutations as provided herein. In one embodiment, the stradomer comprises an amino acid sequence selected from the group consisting of SEQ ID NOs: 10-16, 18-63, and 65-77, or a functional variant thereof.

In some embodiments, the stradomer comprises, from amino to carboxy terminus, a leader sequence; an IgG2 hinge; and an Fc domain comprising an IgG1 hinge, IgG1 CH2, and IgG1 CH3, wherein the stradomer comprises one or more point mutations provided herein. In a further embodiment, the leader sequence is cleaved upon expression. Therefore, in another embodiment, there is provided a stradomer comprising, from amino to carboxy terminus, an IgG2 hinge; and an Fc domain comprising an IgG1 hinge, IgG1 CH2, and IgG1 CH3, wherein the stradomer comprises one or more point mutations provided herein. In one embodiment, the stradomer comprises an amino acid sequence selected from SEQ ID NO: 17 and SEQ ID NO: 64, or a functional variant thereof.

In some embodiments, the stradomer comprises, from amino to carboxy terminus, a leader sequence; an IgG2 hinge; and an Fc domain comprising an IgG1 CH2 and IgG1 CH3, wherein the stradomer comprises one or more point mutations provided herein. In a further embodiment, the leader sequence is cleaved upon expression. Therefore, in another embodiment, there is provided a stradomer comprising, from amino to carboxy terminus, an IgG2 hinge; and an Fc domain comprising an IgG1 CH2 and IgG1 CH3, wherein the stradomer comprises one or more point mutations provided herein.

In one embodiment, the stradomer unit further comprises one or more amino acid linker sequence. In a further embodiment, the linker is cleavable. In a further embodiment, the linker is protease sensitive. In one embodiment, the linker is cleaved by a protease that is predominantly intracellular. In a further embodiment, the linker is cleaved by a protease that is predominantly present in the Golgi and the Endoplasmic Reticulum. In one embodiment, the linker is cleaved by furin. In another embodiment, the linker is cleaved by a protease that is predominantly an organ-specific protease such as, for example, the brain-related protease neuropsin. In another embodiment, the linker is cleaved by a protease that is predominantly a tumor-specific protease, such as, for example, metalloproteinase 9 and urokinase plasminogen activator.

In some embodiments, the stradomer unit exhibits preferential binding to complement relative to FcγRI, FcγRII including FcγRIIa and/or FcγRIIb, and/or FcγRIII. In certain embodiments, the stradomer unit exhibits reduced binding to a low affinity Fcγ Receptor. In other embodiments, the stradomer unit exhibits reduced binding to FcγRI, FcγRII including FcγRIIa and/or FcγRIIb, and/or FcγRIII relative to a stradomer of the same structure that does not comprise a point mutation at one or more of positions 267, 268 and/or 324.

In certain embodiments, the stradomer unit comprises a mutation at 297, 298, or 299 and retains binding to C1q, inhibits CDC, and retains binding to FcγRI or to a low affinity Fcγ Receptor including FcγRIIa, FcγRIIb and/or FcγRIII.

In one aspect, the present disclosure provides a cluster stradomer comprising two or more stradomer units as disclosed herein. For example, in some embodiments, the present disclosure provides a cluster stradomer comprising two or more stradomer units comprising an IgG1 Fc domain having an amino acid sequence comprising point mutations at positions 267, 268, and/or 324. In further embodiments, the two or more stradomer units further comprise at least one point mutation at position 233 and/or 234 and/or 235 and/or 236 and/or 238 and/or 265 and/or 297 and/or 299 and/or 328. In some embodiments, the two or more stradomer units comprise a deletion of the amino acid at position 236.

In some embodiments, the stradomers provided herein are used to treat or prevent diseases and disorders including but not limited to complement-mediated diseases, autoimmune diseases, inflammatory diseases, allergies, B-cell mediated diseases, antibody-mediated diseases, renal disorders, and blood disorders.

In some embodiments, the antibody-mediated disease is selected from the group consisting of Goodpasture's disease; solid organ transplantation rejection; neuromyelitis optica; neuromyotonia; limbic encephalitis; Morvan's fibrillary chorea syndrome; myasthenia gravis; Lambert Eaton myasthenic syndrome; autonomic neuropathy; Alzheimer's Disease; atherosclerosis; Parkinson's Disease; stiff person syndrome or hyperekplexia; recurrent spontaneous abortion; Hughes syndrome; systemic lupus erythematosus; autoimmune cerebellar ataxia; connective tissue diseases including scleroderma, Sjogren's syndrome; polymyositis; rheumatoid arthritis; polyarteritis nodosa; CREST syndrome; endocarditis; Hashimoto's thyroiditis; mixed connective tissue disease; channelopathies; Pediatric Autoimmune Neuropsychiatric Disorders Associated with Streptococcal infections (PANDAS); clinical conditions associated with antibodies against N-methyl-D-aspartate receptors especially NR1, contactin-associated protein 2, AMPAR, GluR1/GluR2, glutamic acid decarboxylase, GlyR alpha 1a, acetylcholine receptor, VGCC P/Q-type, VGKC, MuSK, GABA(B)R; aquaporin-4; and pemphigus. In some embodiments, the autoimmune disease is arthritis.

In some embodiments, the complement-mediated disease is selected from the group consisting of myasthenia gravis, hemolytic uremic syndrome (HUS), atypical hemolytic uremic syndrome (aHUS), paroxysmal nocturnal hemoglobinuria (PNH), neuromyelitis optica, antibody-mediated rejection of allografts, nephropathy including membranous nephropathy, and nephritis including membranoproliferative glomerulonephritis (MPGN) and lupus nephritis.

In some embodiments, the blood disorder is an anemia, such as sickle cell diseases, including Hemoglobin SS, Hemoglobin SC, Hemoglobin Sβ⁰ thalassemia, Hemoglobin Sβ⁺ thalassemia, Hemoglobin SD, and Hemoglobin SE. In some embodiments, the inflammatory disorder is Age-Related Macular Degeneration, Alzheimer's Disease, Amyotrophic Lateral Sclerosis, or Parkinson's Disease.

In some embodiments, the stradomers provided herein are administered to a subject in need thereof. In further embodiments, the stradomers provided herein are administered intravenously, subcutaneously, orally, intraperitoneally, sublingually, buccally, transdermally, by subdermal implant, or intramuscularly.

In some embodiments, the present disclosure provides stradomers useful in treating or preventing autoimmune-related vision loss or hearing loss, such as noise-induced or age-related hearing loss. In another embodiment, the provided stradomers are useful in reducing inflammation or autoimmune responses related to device implantation, such as implantation of cochlear or other hearing devices.

BRIEF DESCRIPTION OF THE FIGURES

FIG. 6A-FIG. 6B provide a radar graph of the RUmax for each Fc receptor, C1q ELISA, and CDC inhibition data for G045c and complement-preferential stradomers G1022 and G1033 (FIG. 6A) and a radar graph of the RU at 300 seconds (RU300s) for each Fc receptor for G045c and complement-preferential stradomers G1022 and G1033 (FIG. 6B).

FIG. 13 shows the binding of stradomer G989 to FcγRI, FcγRIIb, FcγRIIIa, FcγRIIa, and FcRn, as measured by biolayer interferometry.

FIG. 19 (bottom row of panels) also shows the binding of stradomer G996 to mouse FcγRIIb, FcγRIII, and FcγRIV.

FIG. 23 shows the binding of stradomer G1043 to FcγRT, FcγRIIb, FcγRIIIa, or FcγRIIa, as measured by biolayer interferometry.

FIG. 31A-FIG. 31B show the binding of negative control G001, parent stradomer GL-2045, G993, G997, G998, G996, and G994 to C1q, as measured by absorbance at increasing concentrations of stradomer in an ELISA assay (FIG. 31A) and the log-transformed data and the $EC_{50}$ values for each of the tested stradomers. EC50 values are shown in µg/mL (FIG. 31B).

FIG. 36A-FIG. 36B provide the sequences of the human IgG1 Fc domain, DEL (FIG. 36A; SEQ ID NO: 3) and EEM (FIG. 36B; SEQ ID NO: 2) polymorphs.

In FIG. 38A, (G) refers to glomeruli with thickened basement membrane; (B) refers to the basophilic tubules and interstitial infiltrates; and the arrows point to dilated tubules with proteinaceous fluid. FIG. 36B shows the non-lesioned glomeruli and tubules in the G998 treated animal.

FIG. 44A provides all data points collected in the study for each complement preferential stradomer. FIG. 44B focuses in on the lower part of the curve (lower drug concentrations).

FIG. 47A-FIG. 47B show the correlation between drug level and complement activity for each of the compounds tested in the study. FIG. 47A shows all data points collected in the experiment, and FIG. 47B shows the first part of the curve, with lower drug concentrations. For G994, the x-axis intercept value is 144 and 168 μg/ml for 2% and 4% serum. $R^2$ values for the correlation is 0.866 and 0.835. For G998 the x intercept value is 425 and 347 μg/ml with $R^2$ values of 0.925 and 0.743 for 2% and 4% serum. For G1033 the x intercept is 346 and 379 μg/ml with R2 values of 0.584 and 0.714.

FIG. 48A-FIG. 48G are gels showing that, like the parent compound GL-2045 on which the tested derivative stradomer compound was based (G994 or G998) the derivative stradomer compounds form multimers. Compounds GL-2045, G994, G1103, G1088, G1089, G1104, G1082, G1105, and G1106 are shown in FIG. 48A. Compounds GL-2045, G994, G1102, G1100, G1101, G1125, G1108, G1109, and G1084 are shown in FIG. 48B. Compounds GL-2045, G998, and G1107 are shown in FIG. 48C. Compounds GL-2045, G994, G1110, G1111, G1112, G1114, G1115, G1116, G1117, G1118, and G1119 are shown in FIG. 48D. Compounds GL-2045, G994, G1120, G1121, G1122, G1123, G1124, G1128, G1129, G1130, and G1131 are shown in FIG. 48E. Compounds GL-2045, G998, G1071d2, G1068, G1094, G1092, G1096, G1093, and G1095 are shown in FIG. 48F. Compounds GL-2045, G998, G1069, G1070, G1132, G1075, and G1075 are shown in FIG. 48G.

-FIG. 50C shows the binding of stradomer G1103, G1088, G1089, G1104, G1082, G1105, and G1106 to FcγRT, FcγRIIA, FcγRIIB, or FcγRIII, as measured by biolayer interferometry (ForteBio Octet).

FIG. 51A-FIG. 51C shows the binding of stradomer G1102, G1100, G1101, G1125, G1108, G1109, and G1084 to FcγRT, FcγRIIA, FcγRIIB, or FcγRIII, as measured by biolayer interferometry (ForteBio Octet).

FIG. 52A-FIG. 52G shows the binding of stradomer G1100, G1111, G1112, G1113, G1114, G1115, G1116, G1117, G1118, G1119, G1120, G1121, G1122, G1123, G1124, G1128, G1129, G1130, and G1131 to FcγRT, FcγRIIA, FcγRIIB, or FcγRIII, as measured by biolayer interferometry (ForteBio Octet).

FIG. 53A-FIG. 53C shows the binding of stradomer G1071d2, G1068, G1094, G1092, G1096, G1107, G1093, and G1095 to FcγRI, FcγRIIA, FcγRIIB, or FcγRIII, as measured by biolayer interferometry (ForteBio Octet).

FIG. 54A-FIG. 54B shows the binding of stradomer G1069, G1070, G1132, G1074, and G1075 to FcγRI, FcγRIIA, FcγRIIB, or FcγRIII, as measured by biolayer interferometry (ForteBio Octet).

FIG. 63 shows CDC inhibition data for G1033. CD20 denotes addition of the CD20 antibody. "6%" denotes addition of 6% serum complement. Controls includes cells plus addition of G996 only (50 and 100 μg/ml), cells plus serum ("+6%"), and cells plus serum plus antibody ("cells+CD20+6%").

DETAILED DESCRIPTION OF THE INVENTION

Figure 1:
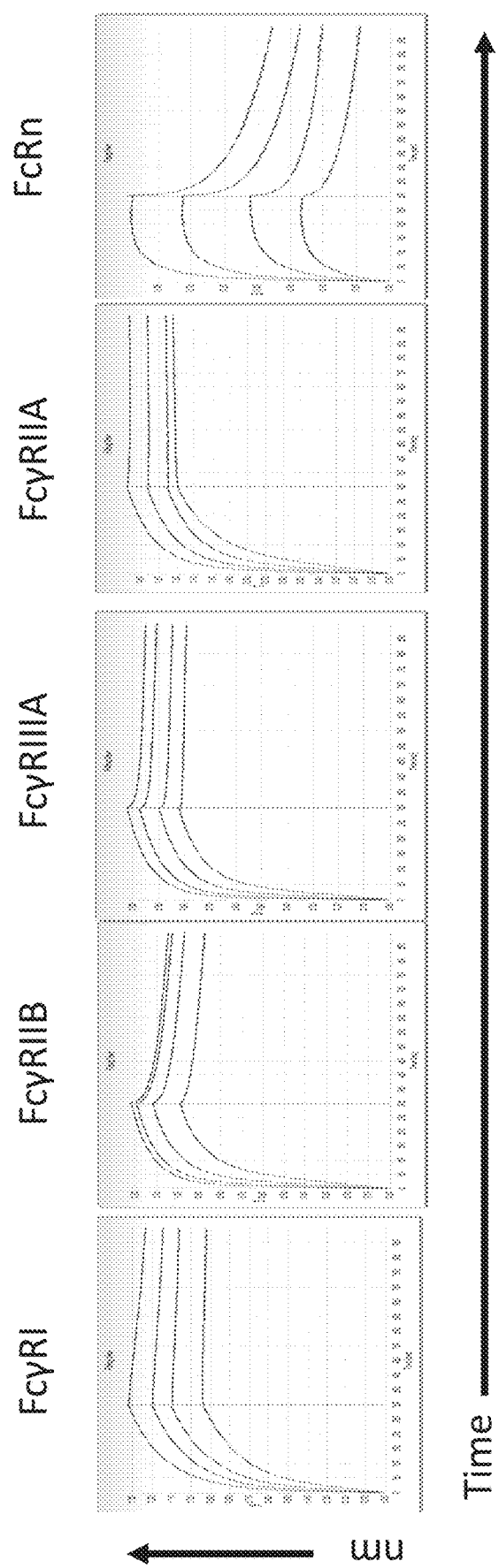
FIG. 1 shows the binding of stradomer GL-2045 to FcγRI, FcγRIIb, FcγRIIIa, FcγRIIa, or FcRn, as measured by biolayer interferometry (ForteBio Octet).

The approach to rational molecular design for immune modulating compounds described herein includes recombinant and/or biochemical creation of immunologically active biomimetic(s) which exhibit retained, preferential, or enhanced binding to complement. In one embodiment, the compositions provided herein enhance complement binding by increasing the ratio of binding to complement relative to binding to Fc receptors. In one embodiment, the compositions provided herein exhibit diminished or absent binding to one or several FcγRs. In another embodiment, the compositions provided herein exhibit diminished or absent binding to FcRn. In one embodiment, the compositions provided herein bind complement, and exhibit diminished or absent binding to certain FcγRs as well as FcRn. The compositions provided herein have utility for treating, for example, complement-mediated diseases and complement-associated diseases. The compositions provided herein also exhibit multimerization. In one embodiment, the compositions provided herein exhibit retained or enhanced multimerization relative to previously described biomimetics.

WO 2008/151088 discloses using linked immunoglobulin Fc domains to create orderly multimerized immunoglobulin Fc biomimetics of hIVIG (biologically active ordered multimers known as stradomers), which include short sequences including restriction sites and affinity tags between individual components of the stradomer, for the treatment of pathological conditions including autoimmune diseases and other inflammatory conditions. See WO 2008/151088 and U.S. Pat. No. 8,680,237, the contents of each of which are incorporated by reference in their entirety. WO 2012/016073 discloses stradomers wherein the individual components are directly linked, rather than separated by restriction sites or affinity tags. See WO 2012/016073 and US Appl. Publ. No. 2013/0156765, the contents of each of which are incorporated by reference in their entirety. WO 2012/016073 also specifically discloses a multimerizing stradomer (GL-2045) comprising an IgG1Fc domain with an IgG2 hinge multimerization domain directly linked to its C-terminus, which exhibits enhanced multimerization and complement binding relative to the N-terminal linked construct (G019, described in WO2008/151088). The stradomer units described herein comprise one or more point mutations in the Fc region of GL-2045 result in either enhanced complement binding and/or selective or increased complement binding relative to canonical Fc gamma receptor binding as compared to previously described molecules.

G045c and G019 have previously been described (See WO 2012/016073). The structure of G045c is: IgG1 Hinge—IgG1CH2 IgG1 CH3—IgG2 Hinge and G045c is provided as SEQ ID NO: 7 and 8.

The terms "G045c," "GL-2045," are used interchangeably herein. G045c has the structure: IgG1 Hinge—IgG1CH2 IgG1 CH3—IgG2 Hinge. As used herein, the term "stradomer on the G045c background" and the like refers to a stradomer having the structure of IgG1 Hinge—IgG1CH2 IgG1 CH3—IgG2 Hinge (SEQ ID NO: 7 or 8). The structure of G019 is: IgG2 Hinge—IgG1 Hinge—IgG1 CH2—IgG1 CH3. As used herein, the term "stradomer on the G019 background" and the like refers to a stradomer having the structure of IgG2 Hinge—IgG1 Hinge—IgG1 CH2—IgG1 CH3 (SEQ ID NO: 9). One of skill in the art will understand that the amino acid sequences of both GL-2045 and G019 comprise an amino terminal leader sequence (SEQ ID NO: 1) which is cleaved upon expression of the mature protein.

Mutations in the Fc regions of full antibody molecules have predictable results with respect to antibody characteristics and function. See, for example, Shields et al., *Journal of Biological Chemistry*, 276; 6591 (2001). In particular, Moore et al. have demonstrated that the triple mutation S267E, H268F, and/or S324T in the Fc region of a monoclonal antibody reliably increases the ratio of complement binding of a monoclonal antibody relative to canonical Fcγreceptor or FcRn binding (*Mabs* 2:2; 18 (2010)). However, the present inventors herein disclose compounds in which the mutations S267E, H268F, and/or S324T in the Fc region of a multimerizing stradomer, including the triple mutation S267E/H268F/S324T, actually and quite surprisingly are associated with lack of binding to C1q and thus do NOT increase the ratio of complement binding relative to canonical Fcγreceptor binding (e.g. G999, G1024, G1030, G1031, G1040, G1044, and G1048).

Figure 61:
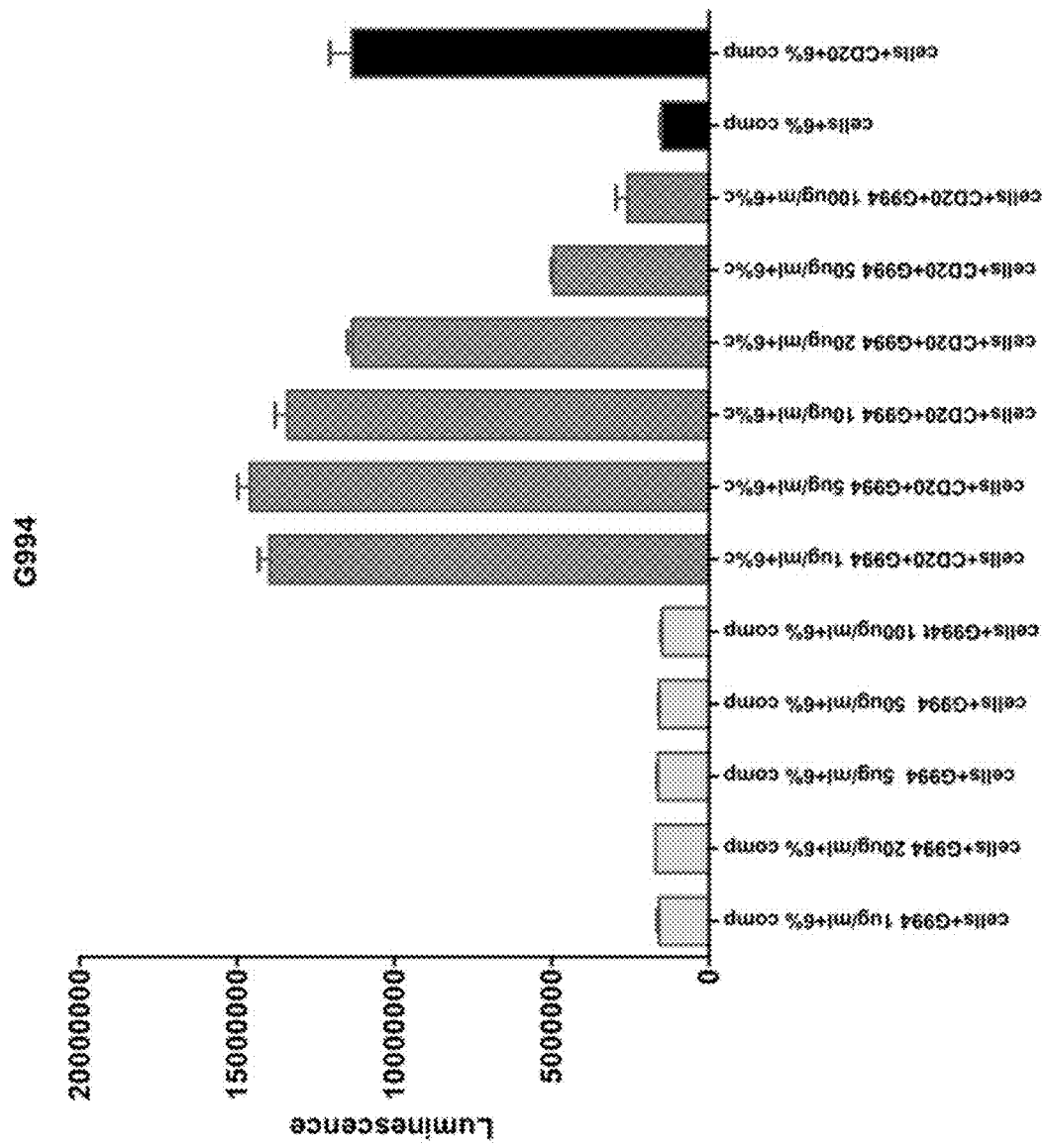
FIG. 61 shows CDC inhibition data for G994. CD20 denotes addition of the CD20 antibody. "6%" denotes addition of 6% serum complement. Controls includes cells plus addition of G996 only (50 and 100 μg/ml), cells plus serum ("+6%"), and cells plus serum plus antibody ("cells+CD20+6%").
Figure 62:
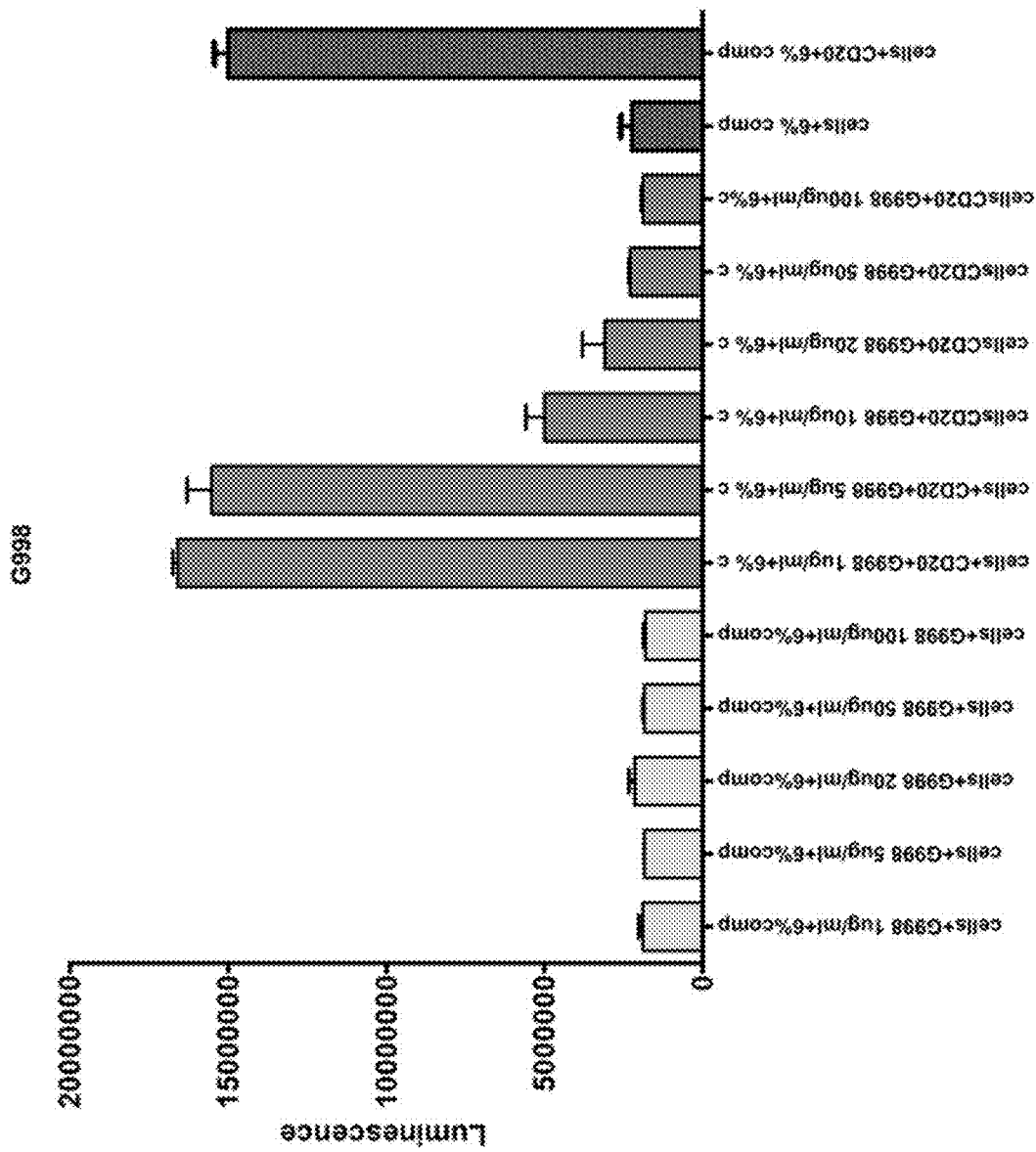
FIG. 62 shows CDC inhibition data for G998. CD20 denotes addition of the CD20 antibody. "6%" denotes addition of 6% serum complement. Controls includes cells plus addition of G996 only (50 and 100 μg/ml), cells plus serum ("+6%"), and cells plus serum plus antibody ("cells+CD20+6%").

It is well established that specific mutations to monoclonal antibodies that increase C1q binding (such as S267E, H268F, and/or S324T described by Moore et. al.) thereby increase CDC (Moore et. al. 2010). The present inventors herein describe numerous compounds which, by incorporating these same mutations in the context of a multimerizing stradomer are associated not only with no increase in CDC but also with no inherent CDC at all. Moreover, and shockingly given that these mutations are associated with increased CDC in the context of a mAb, the inventors demonstrate herein that the compounds of the present invention incorporating these same mutations actually inhibit CDC in a concentration-dependent manner (e.g. G994, G998, and many others, FIGS. 61-63).

Further, in the context of an antibody, a point mutation introduced at position 297 of the Fc domain has been reported to decrease binding to the high affinity and low affinity canonical Fcγreceptors (Robert L. Shields, et al. High Resolution Mapping of the Binding Site on Human IgG1 for FcγRI, FcγRII, FcγRIII, and FcRn and Design of IgG1 Variants with Improved Binding to the FcγR. J. Biol. Chem., February 2001; 276: 6591-6604). Similarly, in the context of a monoclonal antibody, a point mutation introduced at position 299 of the Fc domain has been shown to variably affect binding to FcγRs (e.g., reduce binding to FcγRIIIa and maintain FcγRIIa binding) and further inhibit binding to C1q (Sazinsky et al. Aglycosylated immunoglobulin $G_1$ variants productively engage activating Fc receptors. Proc Natl Acad Sci USA. 2008 Dec. 23; 105(51): 20167-20172; PCT/US2008/085757). In the context of specific multimerizing stradomers, a point mutation at position 297 or of the Fc domain resulted in a decrease in the binding to low affinity canonical Fcγreceptors. However, in certain stradomers, mutation of position 299 does resulted in the expected decreased binding to FcγRs, but rather in the retention or enhancement of Fc binding to all canonical FcγRs.

In addition, a double mutation at positions 236 and 328 (Tai et al., *Blood* 119; 2074 (2012)) or a mutation at position 233 (Shields, et al. *J. Biol. Chem.*, 276(9):6591 (2001) have been shown to reduce antibody or immunoglobulin Fc binding to canonical FcγRs. The double mutation at positions 236 and 328 has further been shown to eliminate antibody or immunoglobulin binding to FcγRI (Tai et al. 2012); however, the present inventors surprisingly found that in the context of a multimerizing stradomer and a complement-enhancing mutation at position 267 and/or 268 and/or 324, FcγRI binding was retained unpredictably in certain multimerizing stradomers. In addition, the double mutation at positions 233 and 236 (E233P and G236R) is expected to reduce binding to all canonical Fc Receptors; however, the present inventors found that several combinations of mutations including mutations at these two positions resulted in binding to one or more Fc Receptor that was unpredictably retained or increased relative to the non-mutated corresponding stradomer. In addition, a mutation at position 328 (L328F) was expected to increase binding to FcγRIIb only (Chu et al., *Molecular Immunology* 45; 3926 (2008)); however, the present inventors surprisingly found that a stradomer comprising a mutation at position 328 in the context of a stradomer having additional mutations at least at positions 267, 268, and 324 resulted in increased binding to one or more other canonical FcγRs in unpredictable ways. Further, a mutation at position 238 is expected to increase binding to FcγRIIb and decrease binding to FcγRI and FcγRIIa (Mimoto et al., *Protein Engineering, Design, and Selection p.* 1-10 (2013)), while a mutation at position 265 is expected to reduce all canonical FcγR binding. However, the present inventors surprisingly found that in the context of a multimerizing stradomer and a complement-enhancing mutation at position 267 and/or 268 and/or 324, mutations at positions 238 and 265 resulted in robust binding to FcγRIIa in certain multimerizing stradomers. Thus, the inventors have surprisingly found that mutations in the literature that teach modification of antibody function, for example to reduce or eliminate canonical binding in a monoclonal antibody or to alter C1q binding, do not have the same effect in the context of a multimerizing stradomer.

Moreover, even within the context of a stradomer, the effects of mutations are similarly unpredictable. For example, as described herein, where two stradomers are identical to one another other than one or more mutations at one or more particular positions, even where the mutations are to structurally similar amino acids, the two stradomers may have vastly different functional characteristics. In addition, WO 2012/016073 discloses that surprisingly, despite the fact that GL-2045 and G019 have the exact same components, and in fact are the exact same molecule other than the position of the IgG2 Hinge region relative to the IgG1 Fc domain, these molecules exhibit vastly different activities with respect to complement binding. Both molecules multimerize and bind Fc receptors. Strikingly, GL-2045 exhibits robust binding to all Fc receptors as well as complement binding and complement-dependent cytotoxicity (CDC) inhibition, whereas G019 does not bind complement or inhibit CDC. Similarly, when the exact same mutations are made to GL-2045 and G019, the outcome may be completely different and, in fact, opposite. By way of example, compounds 996 and 999 both harbor the triple mutation disclosed in Moore, et al. that is expected to increase C1q binding (S267E/H268F/S324T), as well as an additional mutation, G236R. However, in the context of GL-2045 this mutation preferentially retains C1q binding over the canonical Fcγ receptors (G996), whereas in G019, there is no binding to C1q (G999). This dichotomy of function in what is otherwise a well characterized mutation underscores the unpredictability of mutations made in the context of a multimerizing stradomer.

Moreover, whereas monoclonal antibodies have affinity for their FcγR and complement targets, which can be up- or down-regulated by introducing mutations, stradomers present polyvalent Fc to FcγRs and complement, and therefore rely more heavily on avidity to bind their targets. In contrast, monoclonal antibodies do not have avid binding through their Fc domains. These features highlight the fact that stradomers and monoclonal antibodies are fundamentally different, not only in structure, but in function and utility.

Thus, the effect of any mutation or set of mutations within any region of the molecule on the activity of a multimerizing stradomer cannot be predicted based on literature regarding monoclonal antibodies. Accordingly, the effect of amino acid mutations that are known in the art to have particular effects on antibodies, such as mutations that will, for example, increase or decrease binding to a particular FcγR in the context of an antibody having antigen specificity, cannot be predicted in the context of stradomers. Similarly, the point mutations L234A and L235A have been described to decrease Fc binding to C1q (See WO 2015/132364; Arduin et al, Molecular Immunology, 65(2):456-463 (2015); Boyle et al, Immunity, 42(3):580-590 (2015)). However, the present inventors surprisingly found that the introduction of these mutations into the biomimetics of the present invention resulted in retention or enhancement of C1q binding (e.g. G1033 and G1032).

The present inventors set out to identify immunologically active biomimetics wherein the ratio of complement binding relative to Fc receptor binding, as compared to their parent biomimetic (e.g. GL-2045 or G019), is increased. In one embodiment, the biomimetics of the present invention exhibit retained or enhanced binding to C1q. In one embodiment, the biomimetics of the present invention bind components of the complement system, without limitation including C1q, C1r, C1s, C4, C4a, C3, C3a, C4b2a3b, C3b, C5, C5a, C5b, C6, C7, C8, and/or C9, and may thereby act as a "complement sink." "Complement sink" as used herein refers to the phenomenon of binding C1q or another upstream component of the complement cascade and preventing downstream activation of complement systems. In one embodiment, the biomimetics of the present invention bind components of the complement system upstream of C5b-9 Membrane Attack Complex. In one embodiment, the biomimetics of the present invention bind components of the complement system upstream of C5a. In one embodiment, the biomimetics of the present invention exhibit decreased C5a and Membrane Attack Complex. In one embodiment, the biomimetics of the present invention exhibit reduced FcγRI and/or FcγRIIa and/or FcγRIIb and/or FcγRIII binding and retained or enhanced complement binding. In one embodiment, the biomimetics of the present invention exhibit reduced FcRn binding and retained or enhanced complement binding. In a further embodiment, the biomimetics of the present invention exhibit retained or enhanced complement binding and reduced canonical FcγR binding as well as reduced FcRn binding. In one embodiment, the biomimetics of the present invention exhibit retained or enhanced complement binding and selective binding to one or more canonical FcγRs (e.g., binding to FcγRI, but not FcγRIIb, or binding to FcγRIIb but not FcγRI), or enhanced complement binding and selective binding to FcRn.

In some embodiments, the biomimetics and compositions of the present invention have the advantage of enhanced binding of components of the complement pathway relative to innate immunoglobulin IgG1. The degree of enhanced binding of components of the complement pathway relative to innate immunoglobulin IgG1 may, in fact be quite significant, approaching or surpassing the binding of components of the complement pathway to aggregated IgG1 that can occur in humans under certain circumstances. In some embodiments, the biomimetics and compositions of the present invention have the advantage of retained binding of components of the complement pathway relative to innate immunoglobulin IgG1 with diminished binding of Fc receptors and other ligands.

In some embodiments, the biomimetics and compositions of the present invention have the advantage of preferential complement binding relative to canonical Fc Receptor binding observed with innate immunoglobulin IgG1, Intravenous Immunoglobulin (IVIG), human plasma enriched for immunoglobulin aggregates, or to the parent biomimetic composition that does not have point mutations. Such preferential binding may be characterized, without limitation, by enhanced association, diminished dissociation, evidence of avidity, or similar binding at lower concentration. In some embodiments, the biomimetics and compositions of the present invention have the advantage of enhanced complement binding relative to canonical Fc Receptor binding observed with innate immunoglobulin IgG1, Intravenous Immunoglobulin (IVIG), human plasma enriched for immunoglobulin aggregates, or to the parent biomimetic composition that does not have point mutations. In some embodiments, the complement-binding biomimetics and compositions of the present invention inhibit Complement Dependent Cytotoxicity (CDC). In some embodiments, the complement-binding biomimetics and compositions of the present invention inhibit CDC with reduced or functionally absent binding to FcγRI and/or FcγRIIa and/or FcγRIIb and/or FcγRIII In some embodiments, the complement-binding biomimetics and compositions of the present invention bind complement component(s) C1q and/or C4 and/or C4a and/or C3 and/or C3a and/or C5 and/or C5a. In some embodiments, the complement-binding biomimetics and compositions of the present invention bind C3b. In some embodiments, the biomimetics and compositions of the present invention bind a complement molecule, for example, C1q, C3, or C3b, preventing or reducing activation of the complement system and preventing or reducing downstream complement-mediated functions such as cell lysis, inflammation, or thrombosis. In some embodiments, the biomimetics and compositions of the present invention are associated with increased levels of C4a, C3a, and/or C5a and these increased levels are associated with anti-inflammatory or anti-thrombotic clinical profiles.

In some embodiments, the complement-binding biomimetics and compositions of the present invention have the further advantage of enhanced multimerization relative to intact immunoglobulins and/or previously described complement binding compositions. In another embodiment, the biomimetics and compositions of the present invention have the additional advantage of reduced or absent binding to all or certain canonical FcγRs. In some embodiments, the complement-binding biomimetics and compositions of the present invention have the advantage of the same or enhanced complement binding as intact immunoglobulins, enhanced multimerization as well as diminished binding to one or more canonical FcγRs relative to intact immunoglobulins or the unmutated parent compound. In other embodiments, the complement-binding biomimetics and compositions of the present invention have the advantage of enhanced complement binding, enhanced multimerization as well as diminished binding to FcγRIIIa. In some embodiments, the complement-binding biomimetics and compositions of the present invention exhibit retained or enhanced complement binding and retain binding to FcγRI, FcγRIIa, FcγRIIb, or FcγRIII. In one embodiment, the complement-binding biomimetics and compositions of the present invention exhibit retained or enhanced complement binding and retain binding to neonatal Fc receptor (FcRn) but not to any other canonical low affinity FcγR to any significant degree (for example, stradomer G1033 described herein). In one embodiment, the complement-binding biomimetics and compositions of the present invention exhibit retained or enhanced complement binding and retain binding to FcRn and FcγRI but not to any activating low affinity canonical FcγR to any significant degree (for example, stradomers G994 and G998 described herein). In one embodiment, the complement-binding biomimetics and compositions of the present invention exhibit retained or enhanced complement binding and retain binding to FcγRI and/or FcγRIIb but not to any other canonical FcγR (e.g. stradomer G994 described herein). In one embodiment, the complement-binding biomimetics and compositions of the present invention exhibit retained or enhanced complement binding and retain binding to FcRn and FcγRI but have diminished binding to the low affinity activating receptors FcγRIIa and/or FcγRIIIa (for example, stradomers G997, G1003, and G1022 described herein). In another embodiment, the complement-binding biomimetics and compositions of the present invention exhibit retained or enhanced complement binding and retain binding to FcγRIIb but have diminished binding to other canonical FcγRs, comprising FcγRI, FcγRIIa, or FcγRIIIa (e.g., stradomer G996 and G1003 described herein).

In another embodiment, the complement-binding biomimetics and compositions of the present invention exhibit retained or enhanced complement binding and retain binding to FcγRIIb but not to any other canonical low affinity FcγR (e.g. G994 and G998). Thus, in one aspect, the biomimetics and compositions of the present invention have the advantage of retained or enhanced complement binding with relatively decreased or absent binding to FcγRs, or have the advantage of binding to selected activating or inhibitory FcγRs, in each case relative to native unaggregated immunoglobulin IgG1 and/or relative to the parent biomimetic. Thus, in one embodiment, the biomimetics and compositions of the present invention exhibit retained or enhanced complement binding relative to innate immunoglobulin IgG1 or the parent biomimetic.

In one embodiment, the biomimetics and compositions of the present invention may have modified effector functions, such as Complement Dependent Cytotoxicity, relative to innate immunoglobulin IgG1 or the parent biomimetic or composition. In one embodiment, the biomimetics and compositions of the present invention exhibit retained or enhanced binding to complement molecules relative to innate immunoglobulin IgG1, IVIG, or the parent biomimetic or composition. In a further embodiment, the biomimetics and compositions exhibit retained or enhanced C1q binding relative to innate immunoglobulin IgG1, IVIG, or the parent biomimetic or composition. In some embodiments, the present invention provides biomimetics that are capable of binding C1q, C4, C4a, C3, C3a, C3b, C5, or C5a to reduce or prevent downstream complement-mediated functions such as Complement Dependent Cytotoxicity or cell lysis. In other embodiments, the present invention provides biomimetics that exhibit retained or enhanced C1q binding as well as equivalent or enhanced CDC with altered canonical Fc binding relative to innate immunoglobulin IgG1, IVIG, or the parent biomimetic.

In one embodiment, the biomimetics and compositions of the present invention exhibit retained or enhanced complement binding and similar FcRn binding with decreased binding to one or more canonical Fc receptors relative to innate immunoglobulin IgG1 or the parent biomimetic. In one embodiment, the biomimetics and compositions of the present invention exhibit retained or enhanced complement binding and a longer half-life relative to innate immunoglobulin IgG1 or the parent biomimetic. In one embodiment, and without being bound by theory, the biomimetics of the present invention have a longer functional half-life relative to innate immunoglobulin IgG1 or the parent biomimetic made possible by the internalization by FcRn, which allows for later release and a delayed or prolonged biological effect of the biomimetic. In another embodiment, the biomimetics and compositions of the present invention exhibit retained or enhanced complement binding and a shorter half-life relative to innate immunoglobulin IgG1 or the parent biomimetic. In one embodiment, the biomimetics and compositions of the present invention exhibit retained or enhanced clearing of complement relative to innate immunoglobulin IgG1 or the parent biomimetic. Thus, in some embodiments, the present invention provides biomimetics with a decreased half-life relative to innate immunoglobulin IgG1, IVIG, or parent biomimetics and that are further capable of binding C1q or other complement components to reduce or prevent formation of Membrane Attack complex and downstream complement-mediated functions such as cell lysis.

There are six heads on C1q, connected by collagen-like stems to a central stalk (Reid K. B. M. & Porter, R. R. *Biochem. J.* 155, 19-23 (1976)), and the isolated heads bind to the Fc portion of antibody rather weakly, with an affinity of 100 microM (Hughes-Jones, N.C. & Gardner, B. *Molec Immun.* 16, 697-701 (1979)). Binding of antibody to multiple epitopes on an antigenic surface aggregates the antibody. This aggregation facilitates the binding of several of the C1q heads of a C1q molecule, leading to an enhanced affinity of about 10 nM (Burton, D. R. *Molec. Immun.* 22, 161-206 (1985)). In contrast, the complement-preferential binding multimerizing stradomers and generalized multimerizing stradomers of the present invention present polyvalent Fc to C1q, thereby avidly binding complement components to a stradomer unit within the multimerized stradomer, with an Fc that preferentially binds complement components over one or more canonical Fc Receptors. In this manner, the complement-preferential multimerizing stradomers and generalized stradomers of the present invention can display retained or enhanced binding affinity and/or avidity to C1q, behaving as a complement sink, even though these stradomers have no Fab (and thus no FD portion of the Fc) and cannot bind multiple epitopes on an antigenic surface as would aggregated antibodies. In one embodiment, the complement-preferential multimerizing stradomers of the current invention present 4, 5, 6, 7, 8, or more functional Fc to hexameric C1q, causing avid binding with a slow dissociation rate and functional inhibition of CDC. Similarly, the complement-preferential multimerizing stradomers and generalized stradomers of the present invention can display retained or enhanced binding affinity and/or avidity to C4, C4a, C3, C3a, C3b, C5, or C5a, behaving as a complement sink. In this manner, the biomimetics of the current invention, similar to the Fc portion of the aggregates in IVIG or to aggregated antibodies, can bind complement components C1q, C4, C4a, C3, C3a, C3b, C5, or C5a whereas the Fc portion of an intact isolated immunoglobulin has low binding affinity and no avidity for these complement components.

Specific single, double, or triple mutations at position 267, 268, and/or 324 of the Fc domain of monoclonal antibodies, and in particular the triple mutation S267E/H268F/S324T, have been reported to increase the ratio of complement binding of a monoclonal antibody relative to canonical Fcγreceptor or FcRn binding (Moore et al., *MAbs* 2; 181 (2010)), and it has been previously thought that increased complement binding is dependent on prior binding of antibody Fab to target antigen followed by C1q binding. However, the present inventors surprisingly found that a mutation at position S267E, H268F, and/or S324T, including the triple mutation S267E/H268F/S324T, in the context of a multimerizing stradomer unpredictably decreased complement binding, increased complement binding, or selectively retained complement binding, demonstrating that the described effects of these mutations in a monoclonal antibody do not at all predict the effect in the context of a multimerizing stradomer. Furthermore, where increased complement binding was surprisingly demonstrated in the multimerizing stradomers of the current invention, this occurred despite the absence of an Fab in the multimerizing stradomer. In one embodiment, the complement-preferential multimerizing stradomer of the current invention binds to C1q independent of Fab antigen targeting. In one embodiment, in contrast to a monoclonal antibody, the complement-preferential multimerizing stradomer of the current invention binds to C1q without the stradomer being cell bound. Thus, in one aspect, the present disclosure provides multimerizing stradomers comprising point mutations at positions S267E, H268F, and/or S324T. Thus, the present disclosure provides multimerizing stradomers comprising point mutations at positions S267E, H268F, and/or S324T that bind well to C1q and inhibit CDC (such as 1102). However, in contrast, the present disclosure also provides multimerizing stradomers comprising point mutations at positions S267E, H268F, and/or S324T that do not bind C1q well or inhibit CDC well (such as G1106. G999, G1024, G1030, G1031, G1040, G1044, and G1048). Thus, the point mutations S267E, H268F, and/or S324T that increase binding to C1q in a monoclonal antibody have an unpredictable effect in the context of a multimerizing stradomer, particularly in the context of additional mutations. In some embodiments, the present disclosure further provides multimerizing stradomers comprising point mutations at positions S267E, H268F, and S324T as well as point mutations at one or more of positions 233, 234, 235, 236, 238, 265, 297, 299, 328, and/or deletion of the amino acid at position 236.

In one aspect, the present invention provides biomimetics that exhibit retained or enhanced complement binding, wherein the biomimetics comprise an Fc domain comprising a point mutation at position 267 and/or 268 and/or 324. In a further embodiment, the Fc domain comprises one more of the following point mutations: S267E and/or H268F and/or S324T. In a further embodiment, the Fc domain comprises the following point mutations: S267E, H268F, and S324T.

In one embodiment, the complement-binding biomimetic comprises an Fc domain, wherein the Fc domain comprises a point mutation at position 267 and/or 268 and/or 324, and wherein the Fc domain further comprises a point mutation at position 297, 298, and/or 299. Fc domains comprising a mutation at position 297, 298, and/or 299 are referred to herein as "aglycosylated mutants" or "aglycosylation mutants" since mutations at these positions alter the normal glycosylation pattern of IgG Fc. In the context of a monoclonal antibody, where these mutations were first characterized, aglycosylated mutants decrease or eliminate the binding of normal immunoglobulin Fc to canonical FcγRs as a result of the altered glycosylation pattern. However, in the context of a multimerizing stradomer, these mutations are not predictable. In certain multimerizing stradomers, FcγR binding is decreased relative to the parent biomimetic (e.g. G998). However, in certain other multimerizing stradomers, FcγR binding is retained or enhanced in aglycosylated mutants relative to the non-mutated parent compounds (e.g. G1068).

In one embodiment, the complement-binding biomimetic comprises an Fc domain, wherein the Fc domain comprises a point mutation at position 267 and/or 268 and/or 324, and wherein the Fc domain further comprises a point mutation at position 233 and/or 234 and/or 235 and/or 236 and/or 238 and/or 265 and/or 297 and/or 299.

As used herein, the use of the word "a" or "an" when used in conjunction with the term "comprising" in the claims and/or the specification may mean "one," but it is also consistent with the meaning of "one or more," "at least one," and "one or more than one."

As used herein, the terms "biomimetic", "biomimetic molecule", "biomimetic compound", and related terms, refer to a human made compound that imitates the function of another compound, such as pooled human Intravenous Immunoglobulin ("hIVIG"), a monoclonal antibody or the Fc fragment of an antibody. "Biologically active" biomimetics are compounds which possess biological activities that are the same as or similar to their naturally occurring counterparts. By "naturally occurring" is meant a molecule or portion thereof that is normally found in an organism. By naturally occurring is also meant substantially naturally occurring. "Immunologically active" biomimetics are biomimetics which exhibit immunological activity the same as or similar to naturally occurring immunologically active molecules, such as antibodies, cytokines, interleukins and other immunological molecules known in the art. In preferred embodiments, the biomimetics of the present invention are stradomers, as defined herein. "Parent biomimetic" as used herein refers to the non-mutated biomimetics used as the basis for the compounds described herein (e.g. GL-2045 and G019).

As used herein, the term "complement" refers to any of the small proteins of the complement cascade, sometimes referred to in the literature as the complement system or complement cascade. As used herein, the terms "complement binding" or "binding to complement" refer to binding of any of the components of the complement cascade. Components of the complement cascade are known in the art and described, for example, in Janeway's Immunobiology, $8^{th}$ Ed., Murphy ed., Garland Science, 2012. There are three main complement pathways currently known: the classical pathway, the alternative pathway, and the lectin binding pathway. The classical complement pathway is activated once the protein C1q binds to one or more molecules of intact immunoglobulin IgM, or at least two molecules of intact immunoglobulin IgG1, IgG2, or IgG3. Complement activation leads to complement-dependent cytolysis. Excessive complement activation can be detrimental and is associated with several diseases including myasthenia gravis, hemolytic uremic syndrome (HUS), and paroxysmal nocturnal hemoglobinuria (PNH). "Complement-preferential," as used herein, refers to binding of one or more components of the complement cascade to a higher degree relative to binding to other receptors (e.g. FcγRs or FcRn). In some embodiments, the stradomers provided herein are complement preferential stradomers. In some embodiments, the stradomers provided herein are generalized stradomers. The term "generalized stradomers" herein refers to stradomers that bind one or more components of the complement cascade and also bind each of the canonical Fc Receptors and/or the neonatal receptor FcRn.

As used herein, the terms "complement-mediated disease" and "complement-associated disease" refer to diseases and conditions in which the complement system plays a role. For example, complement-mediated diseases include diseases involving abnormalities of the activation of the complement system. In some embodiments, the complement-mediated diseases can be treated, prevented, or reduced by inhibition of the complement cascade. Complement-associated diseases are known in the art and include, without limitation, myasthenia gravis, hemolytic uremic syndrome (HUS), atypical hemolytic uremic syndrome (aHUS), Shiga toxin E. coli-related hemolytic uremic syndrome (STEC-HUS), systemic thrombotic microangiopathy (TMA), paroxysmal nocturnal hemoglobinuria (PNH), neuromyelitis optica, relapsing neuromyelitis optica (NMO), antibody-mediated rejection of transplant allografts, Barraquer-Simons Syndrome, asthma, lupus erythematosus, autoimmune heart disease, multiple sclerosis, inflammatory bowel disease, ischemia-reperfusion injuries, Alzheimer's disease, Parkinson's disease, Amyotrophic Lateral Sclerosis, spinal cord injuries, factor H (Y402H)-associated macular degeneration, age-related macular degeneration (AMD), hereditary angioedema, and membranoproliferative glomerulonephritis (MPGN), membranous nephropathy, rheumatoid arthritis (RA), acute respiratory distress syndrome (ARDS), complement activation during cardiopulmonary bypass surgery, dermatomyositis, pemphigus, lupus nephritis, glomerulonephritis and vasculitis, IgA nephropathy, acute renal failure, cryoglobulemia, antiphospholipid antibody syndrome, uveitis, diabetic retinopathy, hemodialysis, chronic occlusive pulmonary distress syndrome (COPD), and aspiration pneumonia. Complement-associated diseases may also include various other autoimmune, inflammatory, immunological, neurological, rheumatic, or infectious agent-associated diseases.

By "directly linked" is meant two sequences connected to each other without intervening or extraneous sequences, for example, amino acid sequences derived from insertion of restriction enzyme recognition sites in the DNA or cloning fragments. One of ordinary skill in the art will understand that "directly linked" encompasses the addition or removal of amino acids so long as the multimerization capacity is substantially unaffected.

By "homologous" is meant identity over the entire sequence of a given nucleic acid or amino acid sequence. For example, by "80% homologous" is meant that a given sequence shares about 80% identity with the claimed sequence and can include insertions, deletions, substitutions, and frame shifts. One of ordinary skill in the art will understand that sequence alignments can be done to take into account insertions and deletions to determine identity over the entire length of a sequence.

Throughout the present specification, the numbering of the residues in an IgG heavy chain is that of the EU index as in Kabat et al., Sequences of Proteins of Immunological Interest, 5th Ed. Public Health Service, National Institutes of Health, Bethesda, MD (1991), expressly incorporated herein by references. The "EU index as in Kabat" refers to the numbering of the human IgG1 EU antibody. See FIGS. 36A and 36B.

There are two human polymorphs of IgG1, termed DEL and EEM polymorphs. The DEL polymorph has a D at position 356 and an L at position 358; the EEM polymorph has an E at position 356 and an M at position 358 (Kabat numbering; see FIGS. 36A and 36B). The stradomers provided herein may comprise either the DEL or the EEM IgG1 polymorph. Thus, even if a sentence for a particular mutant is explicitly produced in the context of the DEL polymorphism, one of skill in the art will understand that the same mutations may be made to the EEM polymorph to yield the same results. For example, compounds G994 and G998 were each constructed with both the DEM and EEM polymorphisms and assessed for functional difference. No functional differences were observed. Specifically, binding to C1q and inhibition of CDC were substantially the same for each polymorphism of the respective compounds.

In one embodiment, the immunologically active biomimetics of the current invention are stradomers. The immunologically active compounds of the current invention are multimers of homodimers. In one embodiment, each homodimer possesses the ability to bind to complement. Thus, when multimerized, the immunologically active biomimetics contain at least two homodimers each possessing the ability to bind to complement.

The following paragraphs define the building blocks of the biomimetics of the present invention, both structurally and functionally, and then define biomimetics themselves. However, it is first helpful to note that, as indicated above, each of the biomimetics of the present invention has at least one Fc domain and one multimerization domain. At a minimum, an each of the Fc domain and multimerization domain are dimeric polypeptides (or are dimeric regions of a larger polypeptide) that comprises two peptide chains or arms (monomers) that associate to form a functional Fc receptor or complement binding site and multimerization domain capable of multimerizing the resulting homodimer. Therefore, the functional form of the individual fragments and domains discussed herein generally exist in a dimeric (or multimeric) form. The monomers of the individual fragments and domains discussed herein are the single chains or arms that must associate with a second chain or arm to form a functional dimeric structure.

Fc Fragment

"Fc fragment" is a term of art that is used to describe the protein region or protein folded structure that is routinely found at the carboxy terminus of immunoglobulins. The Fc fragment can be isolated from the Fab fragment of a monoclonal antibody through the use of enzymatic digestion, for example papain digestion, which is an incomplete and imperfect process (see Mihaesco C and Seligmann M. Papain Digestion Fragments Of Human IgM Globulins. Journal of Experimental Medicine, Vol 127, 431-453 (1968)). In conjunction with the Fab fragment (containing the antigen binding domain) the Fc fragment constitutes the holo-antibody, meaning here the complete antibody. The Fc fragment consists of the carboxy terminal portions of the antibody heavy chains. Each of the chains in an Fc fragment is between about 220-265 amino acids in length and the chains are often linked via a disulfide bond. The Fc fragment often contains one or more independent structural folds or functional subdomains. In particular, the Fc fragment encompasses an Fc domain, defined herein as the minimum structure that binds an Fcγ receptor. An isolated Fc fragment is comprised of two Fc fragment monomers (e.g., the two carboxy terminal portions of the antibody heavy chains; further defined herein) that are dimerized. When two Fc fragment monomers associate, the resulting Fc fragment has complement and/or Fc receptor binding activity.

Fc Partial Fragment

An "Fc partial fragment" is a domain comprising less than the entire Fc fragment of an antibody, yet which retains sufficient structure to have the same activity as the Fc fragment, including Fc receptor binding activity and/or complement binding activity. An Fc partial fragment may therefore lack part or all of a hinge region, part or all of a CH2 domain, part or all of a CH3 domain, and/or part or all of a CH4 domain, depending on the isotype of the antibody from which the Fc partial domain is derived. Another example of an Fc partial fragment includes a molecule comprising the CH2 and CH3 domains of IgG1. In this example, the Fc partial fragment lacks the hinge domain present in IgG1. Fc partial fragments are comprised of two Fc partial fragment monomers. As further defined herein, when two such Fc partial fragment monomers associate, the resulting Fc partial fragment has Fc receptor binding activity and/or complement binding activity.

Fc Domain

As used herein, "Fc domain" describes the minimum region (in the context of a larger polypeptide) or smallest protein folded structure (in the context of an isolated protein) that can bind to or be bound by an Fc receptor (FcR). In both an Fc fragment and an Fc partial fragment, the Fc domain is the minimum binding region that allows binding of the molecule to an Fc receptor. While an Fc domain can be limited to a discrete homodimeric polypeptide that is bound by an Fc receptor, it will also be clear that an Fc domain can be a part or all of an Fc fragment, as well as part or all of an Fc partial fragment. When the term "Fc domains" is used in this invention it will be recognized by a skilled artisan as meaning more than one Fc domain. An Fc domain is comprised of two Fc domain monomers. As further defined herein, when two such Fc domain monomers associate, the resulting Fc domain has Fc receptor binding activity and/or complement binding activity. Thus an Fc domain is a dimeric structure that can bind complement and/or an Fc receptor. The stradomers described herein comprise an Fc domain comprising one or more mutations that alter the ability of the stradomer to bind complement and/or an Fc receptor.

Fc Partial Domain

As used herein, "Fc partial domain" describes a portion of an Fc domain. Fc partial domains include the individual heavy chain constant region domains (e.g., CH1, CH2, CH3 and CH4 domains) and hinge regions of the different immunoglobulin classes and subclasses. Thus, human Fc partial domains of the present invention include the CH1 domain of IgG1, the CH2 domain of IgG1, Ig the CH3 domain of IgG1 and the hinge regions of IgG1, and IgG2. The corresponding Fc partial domains in other species will depend on the immunoglobulins present in that species and the naming thereof. Preferably, the Fc partial domains of the current invention include CH1, CH2 and hinge domains of IgG1 and the hinge domain of IgG2. The Fc partial domain of the present invention may further comprise a combination of more than one of these domains and hinges. However, the individual Fc partial domains of the present invention and combinations thereof lack the ability to bind an FcR. Therefore, the Fc partial domains and combinations thereof comprise less than an Fc domain. Fc partial domains may be linked together to form a peptide that has complement and/or Fc receptor binding activity, thus forming an Fc domain. In the present invention, Fc partial domains are used with Fc domains as the building blocks to create the biomimetics of the present invention, as defined herein. Each Fc partial domain is comprised of two Fc partial domain monomers. When two such Fc partial domain monomers associate, an Fc partial domain is formed.

As indicated above, each of Fc fragments, Fc partial fragments, Fc domains and Fc partial domains are dimeric proteins or domains. Thus, each of these molecules is comprised of two monomers that associate to form the dimeric protein or domain. While the characteristics and activity of the homodimeric forms was discussed above the monomeric peptides are discussed as follows.

Fc Fragment Monomer

As used herein, an "Fc fragment monomer" is a single chain protein that, when associated with another Fc fragment monomer, comprises an Fc fragment. The Fc fragment monomer is thus the carboxy terminal portion of one of the antibody heavy chains that make up the Fc fragment of a holo-antibody (e.g., the contiguous portion of the heavy chain that includes the hinge region, CH2 domain and CH3 domain of IgG). In one embodiment, the Fc fragment monomer comprises, at a minimum, one chain of a hinge region (a hinge monomer), one chain of a CH2 domain (a CH2 domain monomer) and one chain of a CH3 domain (a CH3 domain monomer), contiguously linked to form a peptide. In one embodiment, the CH2, CH3 and hinge domains are from different isotypes. In a particular embodiment, the Fc fragment monomer contains an IgG2 hinge domain and IgG1 CH2 and CH3 domains.

Fc Domain Monomers

As used herein, "Fc domain monomer" describes the single chain protein that, when associated with another Fc domain monomer, comprises an Fc domain that can bind to complement. The association of two Fc domain monomers creates one Fc domain.

In one embodiment, the Fc domain monomers of the present invention do not contain extraneous sequences as did the previously described Fc domain monomers described in WO 2008/151088. Instead the Fc domain monomers of the current invention are linked directly to the leader sequence (e.g., SEQ ID NO: 1) on one terminus (for example, the N-terminus of the Fc monomer) and to the multimerization domain (e.g., SEQ ID NO: 4, 5, or 6) on the other terminus (for example, the C terminus of the Fc monomer). One of skill in the art will recognize that while constructs are produced with a leader sequence, this sequence is subsequently cleaved. Thus, in preferred embodiments, the mature protein will not contain the leader sequence.

In one embodiment, the Fc domain monomer comprises, from amino to carboxy terminus, an Fc domain comprising an IgG1 hinge, IgG1CH2, and IgG1 CH3 and an IgG2 hinge (G045c background), wherein the monomer comprises one or more point mutation in the Fc domain. In another embodiment, the Fc domain monomer comprises, from amino to carboxy terminus, an Fc domain comprising an IgG2 hinge, IgG1 hinge, IgG1 CH2, and IgG1 CH3 (G019 background), wherein the Fc monomer comprises one or more point mutation in the Fc domain. In another embodiment, the Fc domain monomer comprises, from amino to carboxy terminus, an Fc domain comprising an IgG2 hinge, IgG1 CH2, and IgG1 CH3 (G051 background), wherein the Fc monomer comprises one or more point mutation in the Fc domain.

Stradomers

In particular embodiments, the biomimetics of the present invention include stradomers. The stradomers of the present invention are biomimetic compounds capable of binding complement, preferably demonstrating significantly improved complement binding. In a preferred embodiment, the stradomers of the present invention exhibit an increased ratio of complement binding to binding of one or more canonical Fc receptor. A stradomer can have four different physical conformations: serial, cluster, core or Fc fragment. As will be evident, the Fc fragments, Fc partial fragments, Fc domains and Fc partial domains discussed above are used in the construction of the various stradomer conformations. Further, it is the individual Fc domain monomers and Fc partial domain monomers, also discussed above, that are first produced to form homodimeric stradomer units, and that then multimerize through the inclusion of a multimerization domain (e.g. an IgG2 hinge) to form the multimeric structures that are the cluster stradomers of the present invention. Specific stradomers are described in great detail in WO 2008/151088 and WO 2012/016073, the contents of both of which are herein incorporated by reference in their entireties. The ratio of complement binding to Fcγ receptor and/or FcRn binding may be further enhanced with additional mutations at one or more of positions 233 and/or 234 and/or 235 and/or 236 and/or 238 and/or 265 and/or 297 and/or 299.

Stradomer Unit Monomer

As used herein, the term "stradomer unit monomer" refers to a single, contiguous peptide molecule that, when associated with at least a second stradomer unit monomer, forms a homodimeric stradomer unit comprising at least one Fc domain. While in preferred embodiments stradomer units are comprised of two associated stradomer monomers, a stradomer may also contain three or more stradomer monomers.

A stradomer unit monomer may have an amino acid sequence that will form one, two, three, four, five, six, seven, eight, nine, ten, eleven, twelve, thirteen, fourteen or more Fc domains when associated with another stradomer unit monomer to form a "stradomer unit." A stradomer unit monomer may further have an amino acid sequence that will form one, two, three, four, five, six, seven, eight, nine, ten, eleven, twelve, thirteen, fourteen or more Fc partial domains when associated with another stradomer unit monomer to form a stradomer unit.

The regions of stradomer unit monomers that will form Fc domains and Fc partial domains in the context of a stradomer unit may simply be arranged from carboxy terminal to amino terminal of successive regions of the stradomer unit monomer molecule. The arrangement of the particular Fc domain monomers and Fc partial domain monomers comprising a stradomer unit monomer is not critical. However, the arrangement must permit formation of two functional Fc domains upon association of two stradomer unit monomers. In one embodiment, the stradomer of the current invention contains a direct linkage between the N-terminus of the IgG1 Fc monomer and the C terminus of a leader peptide (SEQ ID NO:1) and the C terminus of the IgG1 Fc and the N terminus of the multimerization domain IgG2 hinge (SEQ ID NO:4).

As a clarifying example, the skilled artisan will understand that the stradomer molecules of the present invention comprising the indicated point mutations may be constructed by preparing a polynucleotide molecule that encodes an Fc domain monomer with the desired point mutations and a multimerizing region. Such a polynucleotide molecule may be inserted into an expression vector, which can be used to transform a population of bacteria or transfect a population of mammalian cells. Stradomer unit monomers can then be produced by culturing the transformed bacteria or transfected mammalian cells under appropriate culture conditions. For example, a clonal cell line continuing a pool of stably transfected cells can be achieved by selecting cells with genetecin/G418. Alternatively, cells can be transiently transfected with DNA encoding the stradomer of the current invention (e.g. DNA encoding the stradomer according to any one of SEQ ID NOs. 10-77) under the control of the CMV promoter. The expressed stradomer monomers can then form functional stradomer units and stradomers upon either self-aggregation of the stradomer monomers or units or association of stradomer monomers using inter-stradomer monomer linkages. The expressed stradomers can then be purified from the cell culture media by affinity chromatography using, for example, Protein A or Protein G columns. One of skill in the art will understand that the leader peptide included in the nucleic acid construct is used only to facilitate production of the stradomer unit monomer peptides and is cleaved upon expression of the mature protein. Thus, the biologically active biomimetics of the present invention do not comprise a leader peptide.

Cluster Stradomer

In one embodiment the stradomer used in accordance with the present disclosure is a cluster stradomer. A "cluster stradomer" is a biomimetic that has a radial form with a central moiety "head" and two or more "legs", wherein each leg comprises one or more Fc domains that is capable of binding at least one Fc gamma receptor and/or complement.

A cluster stradomer is also known as a "multimerizing stradomer" by virtue of the presence of a multimerization domain that results in multimerization of the stradomer. Thus, serial stradomers which contain multiple Fc domains on one stradomer monomer molecule may still be classified as a cluster stradomer or multimerizing stradomer so long as the molecule also contains at least one multimerization domain. Each cluster stradomer is comprised of more than one homodimeric protein, each called a "cluster stradomer unit." Each cluster stradomer unit is comprised of at least one region that multimerizes and a "leg" region that comprises at least one functional Fc domain. The multimerizing region creates a cluster stradomer "head" once multimerized with another cluster stradomer unit. The leg region may be capable of binding as many complement molecules as there are Fc domains in each leg region. For example, the leg region may bind as many C1q molecules as there are Fc domains in each leg region. Thus a cluster stradomer is a biomimetic compound capable of binding two or more C1q molecules, thus preventing downstream complement-mediated lysis. A particularly potent biomimetic of the current invention can bind all six heads of the C1q molecule.

The multimerizing region may be a peptide sequence that causes dimeric proteins to further multimerize or alternatively the multimerizing region may be a glycosylation that enhances the multimerization of dimeric proteins. Examples of peptide multimerizing regions include IgG2 hinge, IgE CH2 domain, isoleucine zipper, collagen Glycine-Proline-Proline repeat ("GPP") and zinc fingers. Glycosylation changes, whether a result of amino acid substitutions or of culture conditions, can also affect multimerization of the biomimetics of the current invention. The influence of glycosylation on peptide multimerization is well described in the art (e.g., Role of Carbohydrate in Multimeric Structure of Factor VIII/V on Willebrand Factor Protein. Harvey R. Gralnick, Sybil B. Williams and Margaret E. Rick. Proceedings of the National Academy of Sciences of the United States of America, Vol. 80, No. 9, [Part 1: Biological Sciences] (May 1, 1983), pp. 2771-277 '4; Multimerization and collagen binding of vitronectin is modulated by its glycosylation. Kimie Asanuma, Fumio Arisaka and Haruko Ogawa. International Congress Series Volume 1223, December 2001, Pages 97-101).

The multimerizing region may be a peptide sequence that causes peptides to dimerize or multimerize and includes the IgG2 hinge, the IgE CH2 domain, an isoleucine zipper, collagen GPP, and a zinc finger. As is known in the art, the hinge region of human IgG2 can form covalent dimers (Yoo, E. M. et al. J. Immunol. 170, 3134-3138 (2003); Salfeld Nature Biotech. 25, 1369-1372 (2007)). The dimer formation of IgG2 is potentially mediated through the IgG2 hinge structure by C—C bonds (Yoo et al 2003), suggesting that the hinge structure alone can mediate dimer formation. The amount of IgG2 dimers found in human serum, however, is limited. It is estimated that the amount of IgG2 existing as a dimer of the homodimer is less than 10% of the total IgG2 (Yoo et al. 2003). Furthermore, there is no quantitative evidence of the multimerization of IgG2 beyond the dimer of the homodimer. (Yoo et al. 2003). That is, native IgG2 has not been found to form higher order multimers in human serum. The IgG2 hinge-containing stradomers (i.e. G045c and G019 as described in WO 2012/016073) are present in high order multimers and unlike native IgG2 in human serum in which the IgG2 hinge interactions are variable and dynamic, G045c has been demonstrated to form highly stable multimers evidenced on non-reducing SDS-PAGE gels, by analytical ultracentrifugation and by 3 month stability studies at 100% humidity at 37° C. Furthermore, it is also surprising that the amount of multimers in the IgG2 hinge-containing stradomer preparations are significantly higher than the approximately 10% of dimers and no multimers observed for IgG2 in human serum. For example, the percent of complement-preferential stradomers that is multimers, including dimers, trimers, tetramers and higher order multimers of the homodimer, exceeds 20% and may exceed 30%, 40%, 50%, 60%, 70%, 80% or even 90%.

The amino acid sequence of the human IgG2 hinge monomer is as follows: ERKCCVECPPCP (SEQ ID NO: 4). Mutation of any one of the 4 cysteines in SEQ ID NO: 4 may be associated with greatly diminished multimerization of the stradomer. There are two C-X-X-C portions of the IgG2 hinge monomer. Thus, stradomer monomers of the present invention may comprise either the complete 12 amino acid sequence of the IgG2 hinge monomer, or either or both of the four amino acid cores, along with Fc domain monomers. While the X-X of the core structures can be any amino acid, in a preferred embodiment the X-X sequence is V-E or P-P. The skilled artisan will understand that the IgG2 hinge monomer may be comprised of any portion of the hinge sequence in addition to the core four amino acid structures, including all of the IgG2 hinge sequence and some or all of the IgG2 CH2 and CH3 domain monomer sequences. Without being bound by theory, the IgG2 hinge multimerization domain may form multimers by interacting with any portion of the stradomer monomer. That is, the IgG2 hinge of one stradomer monomer may bind the IgG2 hinge of another stradomer monomer, thereby forming a dimer of the homodimer, or higher order multimers while retaining increased functional binding to Fc receptors relative to natural IgG1 Fc. Alternatively, the IgG2 hinge domain of one stradomer monomer may bind the IgG1 hinge of another stradomer monomer, thereby forming a dimer of the homodimer, or higher order multimers while retaining increased functional binding to Fc receptors relative to natural IgG1 Fc. It is also possible that the IgG2 hinge domain of one stradomer monomer binds to another portion of the IgG1 Fc domain, i.e. the CH2 or CH3 domain of another stradomer monomer to form the dimer of the homodimer, or higher order multimers while retaining increased functional binding to Fc receptors relative to natural IgG1 Fc.

Leucine and isoleucine zippers may also be used as the multimerizing region. Leucine and isoleucine zippers (coiled-coil domains) are known to facilitate formation of protein dimers, trimers and tetramers (Harbury et al. Science 262:1401-1407 (1993); O'Shea et al. Science 243:538 (1989)). By taking advantage of the natural tendency of an isoleucine zipper to form a trimer, cluster stradomers may be produced.

While the skilled artisan will understand that different types of leucine and isoleucine zippers may be used, in a preferred embodiment the isoleucine zipper from the GCN4 transcriptional regulator modified as described (Morris et al., Mol. Immunol. 44:3112-3121 (2007); Harbury et al. Science 262:1401-1407 (1993)) is used: GGGSIKQIEDKIEEILSKIYHIENEIARIKKLIGERGHGGG (SEQ ID NO: 5) This isoleucine zipper sequence is only one of several possible sequences that can be used for multimerization of Fc domain monomers. While the entire sequence shown in SEQ ID NO: 5 may be used, the underlined portion of the sequence represents the core sequence of the isoleucine zipper that may be used in the cluster stradomers of the present invention. Thus, stradomer monomers of the present invention may comprise either the complete amino acid sequence of the isoleucine zipper, or the 28 amino acid core, along with one or more Fc domain monomers. The skilled artisan will also understand that the isoleucine zipper may be comprised of any portion of the zipper in addition to the core 28 amino acid structure, and thus may be comprised of more than 28 amino acids but less than the entire sequence.

GPP is an amino acid sequence found in human collagen that causes collagen protein: protein binding. While the skilled artisan will understand that different types of GPP repeats may be used as a Multimerization Domain, in a preferred embodiment the Glycine—Proline-Proline repeats as described (Fan et al FASEB Journal 3796 vol. 22 2008) is used: (SEQ ID NO: 6) This Glycine-Proline-Proline repeat sequence is only one of several possible sequences that can be used for multimerization of Fc domain monomers. While the entire sequence shown in SEQ ID NO: 6 may be used, repeats of different length may also possible be used to multimerize Fc domain monomers. Likewise, repeats containing different amino acids within the GPP repeats may also be substituted.

It is understood that the stradomers and other biomimetic molecules disclosed herein can be derived from any of a variety of species including humans. Indeed, Fc domains, or Fc partial domains, in any one biomimetic molecules of the present invention can be derived from immunoglobulin from more than one (e.g., from two, three, four, five, or more) species. However, they will more commonly be derived from a single species. In addition, it will be appreciated that any of the methods disclosed herein (e.g., methods of treatment) can be applied to any species. Generally, the components of a biomimetic applied to a species of interest will all be derived from that species. However, biomimetics in which all the components are of a different species or are from more than one species (including or not including the species to which the relevant method is applied) can also be used.

The specific CH1, CH2, CH3 and CH4 domains and hinge regions that comprise the Fc domains and Fc partial domains of the stradomers and other biomimetics of the present invention may be independently selected, both in terms of the immunoglobulin subclass, as well as in the organism, from which they are derived. Accordingly, the stradomers and other biomimetics disclosed herein may comprise Fc domains and partial Fc domains that independently come from various immunoglobulin types such as human IgG1, IgG2, IgG3, IgG4, IgA, IgA1, IgD, IgE, and IgM, mouse IgG2a, or dog IgA or IgB. Similarly each Fc domain and partial Fc domain may be derived from various species, preferably a mammalian species, including non-human primates (e.g., monkeys, baboons, and chimpanzees), humans, murine, rattus, bovine, equine, feline, canine, porcine, rabbits, goats, deer, sheep, ferrets, gerbils, guinea pigs, hamsters, bats, birds (e.g., chickens, turkeys, and ducks), fish and reptiles to produce species-specific or chimeric stradomer molecules.

The individual Fc domains and partial Fc domains may also be humanized. One of skill in the art will realize that different Fc domains and partial Fc domains will provide different types of functionalities. For example, FcRn binds specifically to IgG immunoglobulins and not well other classes of immunoglobulins. One of ordinary skill in the art will also understand various deleterious consequences can be associated with the use of particular Ig domains, such as the anaphylaxis associated with IgA infusions. The biomimetics disclosed herein should generally be designed to avoid such effects, although in particular circumstances such effects may be desirable.

The present invention also encompasses stradomers comprising Fc domains and Fc partial domains having amino acids that differ from the naturally-occurring amino acid sequences of the Fc domain or Fc partial domain. Preferred Fc domains for inclusion in the biomimetic compounds of the present invention have a measurable specific binding affinity to complement. Primary amino acid sequences and X-ray crystallography structures of numerous Fc domains and Fc domain monomers are available in the art. See, e.g., Woof J M, Burton D R. Human antibody-Fc receptor interactions illuminated by crystal structures. Nat Rev Immunol. 2004 February; 4(2):89-99. Representative Fc domains with Fcγ receptor binding capacity include the Fc domains from human IgG1 (SEQ ID NO: 2 or 3). These native sequences have been subjected to extensive structure-function analysis including site directed mutagenesis mapping of functional sequences. Based on these prior structure-function studies and the available crystallography data, one of skill in the art may design functional Fc domain sequence variants while preserving complement binding capacity. For example, cysteine residues may be added to enhance disulfide bonding between monomers or deleted to alter the interaction between stradomer homodimers. Further, one of skill in the art may design functional Fc domain sequence variants while preserving the enhanced complement binding capacity or may design functional Fc domain sequence variants with even further enhanced complement binding capacity.

The amino acid changes may be found throughout the sequence of the Fc domain, or may be isolated to particular Fc partial domains that comprise the Fc domain. The functional variants of the Fc domain used in the stradomers and other biomimetics of the present invention will have at least about 50%, 60%, 70%, 80%, 90%, 95%, 96%, 97%, 98% or 99% sequence identity to a native Fc domain. Similarly, the functional variants of the Fc partial domains used in the stradomers and other biomimetics of the present invention will have at least about 50%, 60%, 70%, 80%, 90%, 95%, 96%, 97%, 98% or 99% sequence identity to a native Fc partial domain.

The skilled artisan will appreciate that the present invention further encompasses the use of functional variants of Fc domain monomers in the construction of Fc fragment monomers, Fc partial fragment monomers, stradomer monomers and the other monomers of the present invention. The functional variants of the Fc domain monomers will have at least about 50%, 60%, 70%, 80%, 90%, 95%, 96%, 97%, 98% or 99% sequence identity to a native Fc domain monomer sequence.

Similarly, the present invention also encompasses the use of functional variants of Fc partial domain monomers in the construction of Fc fragment monomers, Fc partial fragment monomers, Fc domains monomers, stradomer monomers and the other monomers of the present invention. The functional variants of the Fc partial domain monomers will have at least about 50%, 60%, 70%, 80%, 90%, 95%, 96%, 97%, 98% or 99% sequence identity to a native Fc partial domain monomer sequence.

The amino acid changes may decrease, increase, or leave unaltered the binding affinity of the stradomer to the FcRn or the canonical Fcγ receptors. Preferably such amino acid changes will be conservative amino acid substitutions, however, such changes include deletions, additions and other substitutions. Conservative amino acid substitutions typically include changes within the following groups: glycine and alanine; valine, isoleucine, and leucine; aspartic acid and glutamic acid; asparagine, glutamine, serine and threonine; lysine, histidine and arginine; and phenylalanine and tyrosine. Additionally, the amino acid change may enhance multimerization strength, for example by the addition of cysteine residues.

The term "functional variant" as used herein refers to a sequence related by homology to a reference sequence which is capable of mediating the same biological effects as the reference sequence (when a polypeptide), or which encodes a polypeptide that is capable of mediating the same biological effects as a polypeptide encoded by the reference sequence (when a polynucleotide). For example, a functional variant of any of the biomimetics herein described would have a specified homology or identity and would be capable of immune modulation of monocytes or DCs. Functional sequence variants include both polynucleotides and polypeptides. Sequence identity is assessed generally using BLAST 2.0 (Basic Local Alignment Search Tool), operating with the default parameters: Filter-On, Scoring Matrix—BLOSUM62, Word Size—3, E value—10, Gap Costs—11,1 and Alignments—50. In some embodiments, a functional variant comprises an amino acid sequence having at least 80%, at least 85%, at least 90%, at least 95%, or at least 99% sequence identity with an amino acid sequence provided herein.

In addition to the amino acid sequence composition of native Fc domains, the carbohydrate content of the Fc domain is known to play an important role on Fc domain structure. See, e.g., Robert L. Shields, et al. Lack of Fucose on Human IgG1 N-Linked Oligosaccharide Improves Binding to Human FcγRIII and Antibody-dependent Cellular Toxicity. J. Biol. Chem., July 2002; 277: 26733-26740 (doi:10.1074/jbc.M202069200); Ann Wright and Sherie L. Morrison. Effect of C2—Associated Carbohydrate Structure on Ig Effector Function: Studies with Chimeric Mouse-Human IgG1 Antibodies in Glycosylation Mutants of Chinese Hamster Ovary Cells. J. Immunol, April 1998; 160: 3393-3402. Carbohydrate content may be controlled using, for example, particular protein expression systems including particular cell lines or in vitro enzymatic modification. Thus, the present invention includes stradomers comprising Fc domains with the native carbohydrate content of holo-antibody from which the domains were obtained, as well as those biomimetic compounds with an altered carbohydrate content. In another embodiment, multimer components of the stradomer are characterized by a different glycosylation pattern compared with the homodimer component of the same stradomer. In one embodiment, the complement-binding stradomer comprises mutations that do not alter the glycosylation pattern but reduce or eliminate canonical Fc receptor binding and/or FcRn receptor binding.

Preferred Embodiments of Complement-Preferential Stradomers

The complement-preferential stradomers described herein provide an increased ratio of complement binding to Fc receptor binding. Thus, the complement-preferential stradomers provided herein are referred to in some embodiments as "complement-preferential stradomers" or "complement binding stradomers." In some embodiments, the stradomers provided herein are "generalized stradomers" that bind one or more components of the complement cascade and also bind each of the FcγRs.

A stradomer on the G045c background having point mutations at positions 267, 268, and 324 (SEQ ID NO: 13) is herein termed G997. In some embodiments, G997 surprisingly exhibits strong C1q binding and CDC inhibition with retained binding to FcγRI, inhibitory receptor FcγRII and FcRn and significantly diminished binding to activating receptors FcγRIIa and FcγRIIIa.

A stradomer on the G045c background having point mutations at positions 267, 268, 297, and 324 (SEQ ID NO: 14 or 15) is herein termed G998. A multimerizing stradomer comprising the Fc mutation N297A (but no mutation at position 267, 268, or 324) binds C1q, without high affinity and avidity, and demonstrates modest inhibition of CDC and no appreciable binding to FcγRIIa, FcγRIIb, or FcγRIIIa. In contrast, and surprisingly, the inventors have found that the further introduction of Fc mutations S267E, H268F, and/or S324T in the context of a stradomer on the GL-2045 backbone comprising the mutation N297A (stradomer designated G998) further enhances C1q binding significantly and inhibition of CDC. Even more surprisingly, the resultant compound avidly binds FcγRIIb. Thus, in some embodiments, G998 surprisingly exhibits even stronger C1q binding and CDC inhibition than the parent stradomer G045c, as well as fully retained FcRn and mostly retained FcγRI binding relative to the G045c parent, as well as partial retention of binding to the inhibitory receptor FcγRIIb with significantly diminished binding to activating receptors FcγRIIa and FcγRIIIa. To underscore the unpredictability of these mutations, when the same series of mutations is made to a stradomer with an N-terminal multimerization domain (G019) in contrast a stradomer with a C-terminal multimerization domain (GL-2045), this preferential binding to C1q is completely abrogated (see compound G999). In some embodiments, the present disclosure provides a stradomer having point mutations at positions 267, 268, 297, and 324 and further comprising mutations at positions 253, 310, and 435. In yet further embodiments, the present disclosure provide stradomers comprising mutations at positions 233, 234, 235, 253, 267, 268, 297, 299, 310, 324, and 435, and a deletion of the amino acid at position G236. Thus, in some embodiments, the present disclosure provides a stradomer comprising the following mutations: I253A, S267E, H268F, N297A, H310A, S324T, and H435A; or a stradomer comprising the following mutations: E233P, L234V, L235A, I253A, S267E, H268F, N297A, T299A, H310A, S324T, and H435A, and a deletion of G236. In some embodiments, the resulting stradomers retain C1q binding and CDC inhibition of a stradomer according to SEQ ID NO: 14 or 15, and demonstrate less binding to FcγRIIb and/or FcγRI relative to the stradomer according to SEQ ID NO: 14 or 15.

A stradomer on the G045c background having point mutations at positions 234, 235, 267, 268, 297, and 324 (SEQ ID NO: 21 or 22) is herein termed G1033. In some embodiments, G1033 surprisingly (e.g., in light of the N297A and the L234A/L235A mutations) retains some binding to FcγRI and FcγRIIa in addition to strong C1q binding and CDC inhibition.

A stradomer on the G045c background having point mutations at positions 233, 236, 267, 268, and 324 (SEQ ID NO: 10 or 11) is herein termed G994. In some embodiments, G994 retains robust binding to FcγRI and FcRn and minimal binding to FcγRIIb with no significant binding to activating receptors FcγRIIa and FcγRIIIa. These results were particularly surprising in view of Shields et al. (Shields, et al. J. Biol. Chem., 276(9):6591 (2001)), which discloses that mutations at positions 233 or 236 resulted in abrogated binding to FcγRI, FcγRIIa, FcγRIIb, FcγRIIIa, and FcRn. These results further highlight the unpredictability of a given point mutation in the context of a stradomer. A multimerizing stradomer comprising the Fc mutations E233P and G236R (but without a mutation at position 267, 268, or 324) binds C1q, without high affinity and avidity, but has no appreciable inhibition of CDC and no appreciable binding to FcγRIIa, FcγRIIb, or FcγRIIIa. In contrast, and surprisingly, the inventors found that the further introduction of Fc mutations S267E, H268F, and/or S324T in the context of a stradomer comprising E233P and G236R mutations (stradomer designated G994) further enhances C1q binding and inhibition of CDC while retaining some binding to FcγRIIb.

A stradomer on the G045c background having point mutations at positions 233, 234, 235, 267, 268, 297, and 324 and G236 deleted (SEQ ID NO: 19) is herein termed G1022. In some embodiments, G1022 surprisingly binds C1q, inhibits its CDC and retains strong binding to FcγRIIa and modest binding to FcγRIIb but very surprisingly does not retain binding to the high affinity FcγRI.

A stradomer on the G045c background having point mutations at positions 234, 235, 267, 268, and 324 (SEQ ID NO: 63) is herein termed G1032. In some embodiments, G1032 surprisingly binds C1q and inhibits CDC while also retaining robust binding to all canonical Fc receptors, and moderately robust binding to FcRn.

A stradomer on the G045c background having point mutations at positions 233, 234, 235, 267, 268, and 324 and G236 deleted (SEQ ID NO: 62) is herein termed G1023. In some embodiments, G1023 surprisingly binds C1q and inhibited CDC while retaining robust binding to all canonical Fc receptors.

A stradomer on the G045c background having point mutations at positions 265, 267, 268, and 324 (SEQ ID NO: 18) is herein termed G1006. In some embodiments, G1006 surprisingly binds C1q and inhibited CDC while retaining robust binding to FcγRI and FcRn and moderate binding to FcγRIIa despite the mutation at position 265 which would be expected to reduce binding to all canonical Fc receptors.

A stradomer on the G045c background having point mutations at positions 238, 267, 268, 297, and 324 (SEQ ID NO: 20) is herein termed G1027. In some embodiments, G1027 surprisingly binds C1q and inhibits CDC but does not eliminate canonical Fc receptor binding despite the mutations at positions 238 and 297, retaining robust binding to FcγRI and FcRn and modest binding to FcγRIIa and FcγRIIb.

A stradomer on the G045c background having point mutations at positions 236, 267, 268, and 324 (SEQ ID NO: 12) is herein termed G996. In some embodiments, G996 surprisingly binds to FcγRI, FcγRIIa and FcγRIIb in addition to C1q binding and CDC inhibition. Also surprisingly, G996 exhibited no canonical binding in a mouse, making it an ideal compound with which to assess pure CDC inhibition in rodents. In contrast to G996, a multimerizing stradomer comprising the Fc mutation G236R (but no mutation at position 267, 268, or 324) is designated G990 and binds C1q, without high affinity and avidity, but has no appreciable inhibition of CDC. G990 also has no appreciable binding to FcγRIIa, FcγRIIb, or FcγRIIIa. Surprisingly, the inventors have found that the further introduction of Fc mutations S267E, H268F, and/or S324T in the context of G990 further enhances C1q binding and inhibition of CDC. Even more surprisingly, G996 very avidly binds FcγRIIb.

A stradomer on the G045c background having point mutations at positions 233, 236, 267, 268, 324, and 328 (SEQ ID NO: 23) is herein termed G1042. In some embodiments, G1042 surprisingly robustly binds FcγRI, FcγRIIa and FcγRIIb. Thus, the addition of the mutation at position 328 (compare G1042 to G994, having point mutations at positions 233, 236, 267, 268, and 324) surprisingly resulted in robust binding to both FcγRIIa and FcγRIIb, despite the fact that the mutation at position 328 was expected to increase binding to FcγRIIb only.

A stradomer on the G045c background having point mutations P238D, D265G, S267E, H268F, and S324T (SEQ ID NO: 24) is herein termed G1043. In some embodiments, G1043 surprisingly robustly binds to FcγRIIa, FcγRIIb, and FcγRI, despite that fact that the mutations at positions 238 and 265 were expected to reduce binding to FcγRIIa and FcγRI.

A stradomer on the G045c background having point mutations P238D, D265W, S267E, H268F, and S324T (SEQ ID NO: 25) is herein termed G1046. In some embodiments, G1046 surprisingly robustly binds FcγRI and also increases binding to FcγRIIa. This result was surprising because the mutation at position 238 was expected to increase FcγRIIb binding, rather than FcγRIIa binding.

A stradomer on the G045c background having point mutations at positions 233, 234, 235, 267, 268, 297, 324, and 328, and a deletion of the amino acid at position 236, (SEQ ID NO: 26) is herein termed G1050. In some embodiments, G1050 robustly binds FcγRIIa and FcγRIIb. Surprisingly, binding to the low affinity FcγRII was retained while binding to the high affinity FcγRI was lost.

A stradomer on the G045c background having point mutations P238D, S267E, H268F, and S324T (SEQ ID NO: 27) is herein termed G1025. In some embodiments, G1025 surprisingly robustly binds FcγRI, FcγRIIa, and FcγRIIb. This result was surprising because the mutation at position 238 was expected to decrease binding to FcγRI, FcγRIIa, and FcγRIIIa, but only binding to FcγRIIIa was decreased. Even more surprisingly, when the same set of mutations is made on a stradomer with an N-linked multimerization domain (G1024) as opposed to the C-terminally linked GL-2045 stradomer, this complement preferential binding is completely abrogated. This again underscores the unpredictable nature of these mutation in the context of a multimerizing stradomer.

In some embodiments, the present disclosure provides stradomers having the backbone of G019 (IgG2 Hinge—IgG1 Hinge—IgG1 CH2 IgG1 CH3, from amino to carboxy terminus) and comprising one or more point mutation in the Fc domain. The resulting stradomer having point mutations at positions 267, 268, and 324 (SEQ ID NO: 17) is herein termed G1003. In some embodiments, G1003 surprisingly exhibited binding to C1q and robust inhibition of CDC despite the fact that the parent stradomer exhibits minimal C1q binding and no CDC inhibition, despite the parent compound G019 forming higher order multimers capable of avidity based interaction with receptors.

A stradomer on the G019 background having point mutations at positions 267, 268, 324, and 328 (SEQ ID NO: 64) is herein termed G1049. In some embodiments, G1049 surprisingly exhibits robust binding to all canonical FcγRs along with complement inhibition and C1q binding activity.

In a surprising finding, the current inventors have discovered that when certain Fc mutations that are described as increasing complement affinity to a monoclonal antibody are added to the Fc region of a multimerizing stradomer which has no appreciable binding to FcγRIIb, the resulting compound regains binding to FcγRIIb. For example, G994, G996, and G998 each binds FcγRIIb, sometimes avidly, despite the fact that the corresponding stradomers having the same mutation except for a lack of the S267E, H268F, and S324T mutations did not exhibit avid FcγRIIb binding.

Additional stradomers were generated based on either of complement-preferential stradomers G994 and G998. In a first set of stradomers derived from G994, the G994 mutations E233P, H268F, and S324T were retained, position 267 was wild type (serine), and various mutations were made at position 236: either arginine (as in G994), or an amino acid similar to arginine. These stradomers were termed G1103, G1088, G1089, G1104, G1082, G1105, and G1106. The extent to which these stradomers bind FcγRs and complement C1q varied drastically and unpredictably, indicating that a mutation at position 236 in the context of the G994 stradomer has unpredictable effects. In a second set of stradomers derived from G994, the G994 mutations E233P, H268F, and S324T were retained, position 236 was wild type (glycine), and various mutations were made at position 267: either glutamic acid (as in G994), or an amino acid similar to glutamic acid. These stradomers were termed G1102, G1100, G1101, G1125, G1108, G1109, and G1084. Again, the extent to which the stradomers bound FcγRs and complement C1q varied drastically and unpredictably, indicating that like position 236, a mutation at position 267 in the context of the G994 stradomer has unpredictable effects. In the next set of G994-based stradomers, combinations of mutations at positions 236 and 267 were tested and were termed G1110, G1111, G1112, G1114, G1115, G1116, G1117, G1118, G1119, G1120, G1121, G1122, G1123, G1124, G1128, G1129, G1130, and G1131. The FcγR and complement binding profiles of these stradomers were also unpredictable.

Derivatives of G998 were also prepared and tested. In a first set of G998 derivative, the G998 mutations H268F and S324T were retained, position 267 was either wild type (serine) or was mutated to an amino acid similar to serine, and a mutation at position 299 was added (T299A). These compounds were termed G1071d2, G1068, G1094, G1092, G1096, G1107, G1093, and G1095. The T299A mutation was designed to destroy the deglycosylation site. The extent to which this mutation reduced FcγR binding was unpredictable in the context of the stradomer structure and the other mutations. In addition, derivatives of G998 having the H268F, S324T, and N297A (for aglycosylation) mutations of G998, but different mutations at position 267, were generated. These compounds were termed G1069, G1070, G1132, G1074, and G1075, and also exhibited unpredictable FcγR and complement binding profiles. Strikingly, only one of the compounds in this group (G1069) retained complement binding while eliminating FcγR binding. This compound was therefore a complement-preferential stradomer.

In some embodiments, G994, G998, G1033, G1022, G1032, G1023, G1006, G1027, G996 or another complement-preferential multimerizing stradomer is administered to a subject that has an acute condition such as, for example, acute hemolysis (e.g., in hemolytic disease of newborns), autoimmune hemolytic anemia, drug-induced hemolytic anemia, acquired hemolytic anemias, transfusion reactions/alloimmune hemolytic anemia, infectious hemolytic anemias (e.g., those associated with tick-borne diseases including bacterial (Lyme disease, Typhus, Rocky Mountain Spotted Fever, Tularemia, Ehrlicosis), viral (meningoencephalitides and hemorrhagic fevers), and protozoal (Babesiosis) tick borne diseases; or those associated with mosquito borne diseases such as malaria including black water fever, Dengue fever Chikungunya, Zika, or Ebola virus), toxin-associated hemolytic anemias (e.g., from snake venom, toxic chemicals, or tick toxins), malignant hypertension, burns, or Reye syndrome. In some embodiments, G998, G994, G1033, G1022, G1032, G1023, G1006, G1027, G996 complement preferential multimerizing stradomer is administered to a subject in need thereof via intravenous administration.

In some embodiments, G998, G994, G1033, G1022, G1032, G1023, G1006, G1027, G996 complement preferential multimerizing stradomer is administered to a subject that has a chronic disease or condition. Chronic diseases and conditions include, for example, renal conditions, macular degeneration, chronic hemolysis (e.g., paroxysmal nocturnal hemoglobinuria), mechanical hemolysis (e.g., from an artificial heart valve, heart-lung bypass machine or other device used in blood vessels, hemodialysis with or without cellophane membranes, preeclampsia or eclampsia, or thrombotic thrombocytopenic purpura), hereditary spherocytosis, ovalocytosis, pyruvate kinase deficiency, G6PD deficiency, sickle cell anemia, thalassemias, inherited hemolytic anemias, hemolytic uremic syndrome, immune complex disorders with complement consumption (e.g., Hepatitis B, Hepatitis C, mixed cryoglobulinemia, lepromatous leprosy, and bacteremic shock), primary biliary cirrhosis, celiac disease, multiple myeloma, and urticarial vasculitis. In some embodiments, G994 is administered to a subject in need thereof via subcutaneous administration.

In some embodiments, G998, G994, G1033, G1022, G1032, G1023, G1006, G1027, G996 complement preferential multimerizing stradomer is administered to a subject that has a renal condition. Renal conditions include, without limitation, membranoproliferative glomerulonephritis, mesangioproliferative glomerulonephritis, idiopathic proliferative glomerulonephritis, focal sclerosing glomerulonephritis, focal segmental glomerulosclerosis, thin basement membrane disease, nephritis, lupus nephritis, fibrillary glomerulonephritis, immunotactoid glomerulonephritis, Bright's disease, Berger's disease/IgA nephropathy, nephrosclerosis, nephrosis, nephrotic syndrome, membranous nephropathy, membranous nephritis, postinfectious glomerulonephritis, tubular necrosis, drug-induced nephrotoxicity, and Goodpasture's syndrome.

Thus, the present inventors have found that individual stradomers may be generated that exhibit complement preferential activity by exhibiting robust C1q binding and reduced binding to FcγRs relative to a parent stradomer having a native Fc domain sequence, but that that the activity that each individual stradomer has with respect to C1q binding and to FcγR binding is entirely unpredictable based on the effect that the mutation would have in a monoclonal antibody.

The amino acid sequences of exemplary stradomers encompassed by the present disclosure are provided in Table 1. The mutated amino acids are indicated in the table (gray highlighted text).

TABLE 1

Exemplary complement-binding stradomers

| Stradomer | SEQ ID NO | Mutated Amino Acids | Amino acid sequence |
|---|---|---|---|
| G994 (DEL) | 10 | E233P G236R S267E H268F S324T | METDTLLLWVLLLWVPGSTGEPKSCDKTHTCPPCPAPPLLRGPSV FLFPPKPKDTLMISRTPEVTCVVVDVEFEDPEVKFNWYVDGVEVH NAKTKPREEQYNSTYRVVSVLTVLHQDWLNGKEYKCKVTNKALPA PIEKTISKAKGQPREPQVYTLPPSRDELTKNQVSLTCLVKGFYPS DIAVEWESNGQPENNYKTTPPVLDSDGSFFLYSKLTVDKSRWQQG NVFSCSVMHEALHNHYTQKSLSLSPGKERKCCVECPPCP |
| G994 (EEM) | 11 | E233P G236R S267E H268F S324T | METDTLLLWVLLLWVPGSTGEPKSCDKTHTCPPCPAPPLLRGPSV FLFPPKPKDTLMISRTPEVTCVVVDVEFEDPEVKFNWYVDGVEVH NAKTKPREEQYNSTYRVVSVLTVLHQDWLNGKEYKCKVTNKALPA PIEKTISKAKGQPREPQVYTLPPSREEMTKNQVSLTCLVKGFYPS DIAVEWESNGQPENNYKTTPPVLDSDGSFFLYSKLTVDKSRWQQG NVFSCSVMHEALHNHYTQKSLSLSPGKERKCCVECPPCP |
| G996 | 12 | G236R S267E H268F S324T | METDTLLLWVLLLWVPGSTGEPKSCDKTHTCPPCPAPELLRGPSV FLFPPKPKDTLMISRTPEVTCVVVDVEFEDPEVKFNWYVDGVEVH NAKTKPREEQYNSTYRVVSVLTVLHQDWLNGKEYKCKVTNKALPA PIEKTISKAKGQPREPQVYTLPPSRDELTKNQVSLTCLVKGFYPS DIAVEWESNGQPENNYKTTPPVLDSDGSFFLYSKLTVDKSRWQQG NVFSCSVMHEALHNHYTQKSLSLSPGKERKCCVECPPCP |
| G997 | 13 | S267E H268F S324T | METDTLLLWVLLLWVPGSTGEPKSCDKTHTCPPCPAPELLGGPSV FLFPPKPKDTLMISRTPEVTCVVVDVEFEDPEVKFNWYVDGVEVH NAKTKPREEQYNSTYRVVSVLTVLHQDWLNGKEYKCKVTNKALPA PIEKTISKAKGQPREPQVYTLPPSRDELTKNQVSLTCLVKGFYPS DIAVEWESNGQPENNYKTTPPVLDSDGSFFLYSKLTVDKSRWQQG NVFSCSVMHEALHNHYTQKSLSLSPGKERKCCVECPPCP |
| G998 (DEL) | 14 | S267E H268F N297A S324T | METDTLLLWVLLLWVPGSTGEPKSCDKTHTCPPCPAPELLGGPSV FLFPPKPKDTLMISRTPEVTCVVVDVEFEDPEVKFNWYVDGVEVH NAKTKPREEQYASTYRVVSVLTVLHQDWLNGKEYKCKVTNKALPA PIEKTISKAKGQPREPQVYTLPPSRDELTKNQVSLTCLVKGFYPS DIAVEWESNGQPENNYKTTPPVLDSDGSFFLYSKLTVDKSRWQQG NVFSCSVMHEALHNHYTQKSLSLSPGKERKCCVECPPCP |
| G998 (EEM) | 15 | S267E H268F N297A S324T | METDTLLLWVLLLWVPGSTGEPKSCDKTHTCPPCPAPELLGGPSV FLFPPKPKDTLMISRTPEVTCVVVDVEFEDPEVKFNWYVDGVEVH NAKTKPREEQYASTYRVVSVLTVLHQDWLNGKEYKCKVTNKALPA PIEKTISKAKGQPREPQVYTLPPSREEMTKNQVSLTCLVKGFYPS DIAVEWESNGQPENNYKTTPPVLDSDGSFFLYSKLTVDKSRWQQG NVFSCSVMHEALHNHYTQKSLSLSPGKERKCCVECPPCP |
| G989 | 16 | E233P G236R | METDTLLLWVLLLWVPGSTGEPKSCDKTHTCPPCPAPPLLRGPSV FLFPPKPKDTLMISRTPEVTCVVVDVSHEDPEVKFNWYVDGVEVH NAKTKPREEQYNSTYRVVSVLTVLHQDWLNGKEYKCKVSNKALPA PIEKTISKAKGQPREPQVYTLPPSRDELTKNQVSLTCLVKGFYPS DIAVEWESNGQPENNYKTTPPVLDSDGSFFLYSKLTVDKSRWQQG NVFSCSVMHEALHNHYTQKSLSLSPGKERKCCVECPPCP |
| G1003 | 17 | S267E H268F S324T | METDTLLLWVLLLWVPGSTGERKCCVECPPCPEPKSCDKTHTCPP CPAPELLGGPSVFLFPPKPKDTLMISRTPEVTCVVVDVEFEDPEV KFNWYVDGVEVHNAKTKPREEQYNSTYRVVSVLTVLHQDWLNGKE YKCKVTNKALPAPIEKTISKAKGQPREPQVYTLPPSREEMTKNQV SLTCLVKGFYPSDIAVEWESNGQPENNYKTTPPVLDSDGSFFLYS KLTVDKSRWQQGNVFSCSVMHEALHNHYTQKSLSLSPGK |

TABLE 1-continued

Exemplary complement-binding stradomers

| Stradomer | SEQ ID NO | Mutated Amino Acids | Amino acid sequence |
|---|---|---|---|
| G1006 | 18 | D265A<br>S267E<br>H268F<br>S324T | METDTLLLWVLLLWVPGSTGEPKSCDKTHTCPPCPAPELLGGPSV<br>FLFPPKPKDTLMISRTPEVTCVVVAVEFEDPEVKFNWYVDGVEVH<br>NAKTKPREEQYNSTYRVVSVLTVLHQDWLNGKEYKCKVTNKALPA<br>PIEKTISKAKGQPREPQVYTLPPSRDELTKNQVSLTCLVKGFYPS<br>DIAVEWESNGQPENNYKTTPPVLDSDGSFFLYSKLTVDKSRWQQG<br>NVFSCSVMHEALHNHYTQKSLSLSPGKERKCCVECPPCP |
| G1022* | 19 | E233P<br>L234V<br>L235A<br>S267E<br>H268F<br>N297A<br>S324T<br>Deletion of G236 | METDTLLLWVLLLWVPGSTGEPKSCDKTHTCPPCPAPPVAGGPSV<br>FLFPPKPKDTLMISRTPEVTCVVVDVEFEDPEVKFNWYVDGVEVH<br>NAKTKPREEQYASTYRVVSVLTVLHQDWLNGKEYKCKVTNKALPA<br>PIEKTISKAKGQPREPQVYTLPPSRDELTKNQVSLTCLVKGFYPS<br>DIAVEWESNGQPENNYKTTPPVLDSDGSFFLYSKLTVDKSRWQQG<br>NVFSCSVMHEALHNHYTQKSLSLSPGKERKCCVECPPCP |
| G1027 | 20 | P238D<br>S267E<br>H268F<br>N297A<br>S324T | METDTLLLWVLLLWVPGSTGEPKSCDKTHTCPPCPAPELLGGDSV<br>FLFPPKPKDTLMISRTPEVTCVVVDVEFEDPEVKFNWYVDGVEVH<br>NAKTKPREEQYASTYRVVSVLTVLHQDWLNGKEYKCKVTNKALPA<br>PIEKTISKAKGQPREPQVYTLPPSRDELTKNQVSLTCLVKGFYPS<br>DIAVEWESNGQPENNYKTTPPVLDSDGSFFLYSKLTVDKSRWQQG<br>NVFSCSVMHEALHNHYTQKSLSLSPGKERKCCVECPPCP |
| G1033 (DEL) | 21 | L234A<br>L235A<br>S267E<br>H268F<br>N297A<br>S324T | METDTLLLWVLLLWVPGSTGEPKSCDKTHTCPPCPAPEAAGGPSV<br>FLFPPKPKDTLMISRTPEVTCVVVDVEFEDPEVKFNWYVDGVEVH<br>NAKTKPREEQYASTYRVVSVLTVLHQDWLNGKEYKCKVTNKALPA<br>PIEKTISKAKGQPREPQVYTLPPSRDELTKNQVSLTCLVKGFYPS<br>DIAVEWESNGQPENNYKTTPPVLDSDGSFFLYSKLTVDKSRWQQG<br>NVFSCSVMHEALHNHYTQKSLSLSPGKERKCCVECPPCP |
| G1033 (EEM) | 22 | L234A<br>L235A<br>S267E<br>H268F<br>N297A<br>S324T | METDTLLLWVLLLWVPGSTGEPKSCDKTHTCPPCPAPEAAGGPSV<br>FLFPPKPKDTLMISRTPEVTCVVVDVEFEDPEVKFNWYVDGVEVH<br>NAKTKPREEQYASTYRVVSVLTVLHQDWLNGKEYKCKVTNKALPA<br>PIEKTISKAKGQPREPQVYTLPPSREEMTKNQVSLTCLVKGFYPS<br>DIAVEWESNGQPENNYKTTPPVLDSDGSFFLYSKLTVDKSRWQQG<br>NVFSCSVMHEALHNHYTQKSLSLSPGKERKCCVECPPCP |
| G1042 | 23 | E233P<br>G236R<br>S267E<br>H268F<br>S324T<br>L328F | METDTLLLWVLLLWVPGSTGEPKSCDKTHTCPPCPAPPLLRGPSV<br>FLFPPKPKDTLMISRTPEVTCVVVDVEFEDPEVKFNWYVDGVEVH<br>NAKTKPREEQYNSTYRVVSVLTVLHQDWLNGKEYKCKVTNKAFPA<br>PIEKTISKAKGQPREPQVYTLPPSRDELTKNQVSLTCLVKGFYPS<br>DIAVEWESNGQPENNYKTTPPVLDSDGSFFLYSKLTVDKSRWQQG<br>NVFSCSVMHEALHNHYTQKSLSLSPGKERKCCVECPPCP |
| G1043 | 24 | P238D<br>D265G<br>S267E<br>H268F<br>S324T | METDTLLLWVLLLWVPGSTGEPKSCDKTHTCPPCPAPELLDGPSV<br>FLFPPKPKDTLMISRTPEVTCVVVGVEFEDPEVKFNWYVDGVEVH<br>NAKTKPREEQYNSTYRVVSVLTVLHQDWLNGKEYKCKVTNKALPA<br>PIEKTISKAKGQPREPQVYTLPPSREEMTKNQVSLTCLVKGFYPS<br>DIAVEWESNGQPENNYKTTPPVLDSDGSFFLYSKLTVDKSRWQQG<br>NVFSCSVMHEALHNHYTQKSLSLSPGKERKCCVECPPCP |

TABLE 1-continued

Exemplary complement-binding stradomers

| Stradomer | SEQ ID NO | Mutated Amino Acids | Amino acid sequence |
|---|---|---|---|
| G1046 | 25 | P238D<br>D265W<br>S267E<br>H268F<br>S324T | METDTLLLWVLLLWVPGSTGEPKSCDKTHTCPPCPAPELLDGPSV<br>FLFPPKPKDTLMISRTPEVTCVVVWVEFEDPEVKFNWYVDGVEVH<br>NAKTKPREEQYNSTYRVVSVLTVLHQDWLNGKEYKCKVTNKALPA<br>PIEKTISKAKGQPREPQVYTLPPSREEMTKNQVSLTCLVKGFYPS<br>DIAVEWESNGQPENNYKTTPPVLDSDGSFFLYSKLTVDKSRWQQG<br>NVFSCSVMHEALHNHYTQKSLSLSPGKERKCCVECPPCP |
| G1050 | 26 | E233P<br>L234V<br>L235A<br>S267E<br>H268F<br>N297A<br>S324T<br>L328F<br>Deletion of G236 | METDTLLLWVLLLWVPGSTGEPKSCDKTHTCPPCPAPPVAGPSVF<br>LFPPKPKDTLMISRTPEVTCVVVDVEFEDPEVKFNWYVDGVEVHN<br>AKTKPREEQYASTYRVVSVLTVLHQDWLNGKEYKCKVTNKAFPAP<br>IEKTISKAKGQPREPQVYTLPPSRDELTKNQVSLTCLVKGFYPSD<br>IAVEWESNGQPENNYKTTPPVLDSDGSFFLYSKLTVDKSRWQQGN<br>VFSCSVMHEALHNHYTQKSLSLSPGKERKCCVECPPCP |
| G1025 | 27 | P238D<br>S267E<br>H268F<br>S324T | METDTLLLWVLLLWVPGSTGEPKSCDKTHTCPPCPAPELLGGPSV<br>FLFPPKPKDTLMISRTPEVTCVVVDVEFEDPEVKFNWYVDGVEVH<br>NAKTKPREEQYNSTYRVVSVLTVLHQDWLNGKEYKCKVTNKALPA<br>PIEKTISKAKGQPREPQVYTLPPSRDELTKNQVSLTCLVKGFYPS<br>DIAVEWESNGQPENNYKTTPPVLDSDGSFFLYSKLTVDKSRWQQG<br>NVFSCSVMHEALHNHYTQKSLSLSPGKERKCCVECPPCP |
| G1088 | 28 | E233P<br>G236Q<br>H268F<br>S324T | METDTLLLWVLLLWVPGSTGEPKSCDKTHTCPPCPAPPLLQGPSV<br>FLFPPKPKDTLMISRTPEVTCVVVDVSFEDPEVKFNWYVDGVEVH<br>NAKTKPREEQYNSTYRVVSVLTVLHQDWLNGKEYKCKVTNKALPA<br>PIEKTISKAKGQPREPQVYTLPPSRDELTKNQVSLTCLVKGFYPS<br>DIAVEWESNGQPENNYKTTPPVLDSDGSFFLYSKLTVDKSRWQQG<br>NVFSCSVMHEALHNHYTQKSLSLSPGKERKCCVECPPCP |
| G1089 | 29 | E233P<br>G236R<br>H268F<br>S324T | METDTLLLWVLLLWVPGSTGEPKSCDKTHTCPPCPAPPLLRGPSV<br>FLFPPKPKDTLMISRTPEVTCVVVDVSREDPEVKFNWYVDGVEVH<br>NAKTKPREEQYNSTYRVVSVLTVLHQDWLNGKEYKCKVTNKALPA<br>PIEKTISKAKGQPREPQVYTLPPSRDELTKNQVSLTCLVKGFYPS<br>DIAVEWESNGQPENNYKTTPPVLDSDGSFFLYSKLTVDKSRWQQG<br>NVFSCSVMHEALHNHYTQKSLSLSPGKERKCCVECPPCP |
| G1082 | 30 | E233P<br>G236H<br>H268F<br>S324T | METDTLLLWVLLLWVPGSTGEPKSCDKTHTCPPCPAPPLLHGPSV<br>FLFPPKPKDTLMISRTPEVTCVVVDVSFEDPEVKFNWYVDGVEVH<br>NAKTKPREEQYNSTYRVVSVLTVLHQDWLNGKEYKCKVTNKALPA<br>PIEKTISKAKGQPREPQVYTLPPSRDELTKNQVSLTCLVKGFYPS<br>DIAVEWESNGQPENNYKTTPPVLDSDGSFFLYSKLTVDKSRWQQG<br>NVFSCSVMHEALHNHYTQKSLSLSPGKERKCCVECPPCP |
| G1105 | 31 | E233P<br>G236N<br>H268F<br>S324T | METDTLLLWVLLLWVPGSTGEPKSCDKTHTCPPCPAPPLLNGPSV<br>FLFPPKPKDTLMISRTPEVTCVVVDVSFEDPEVKFNWYVDGVEVH<br>NAKTKPREEQYNSTYRVVSVLTVLHQDWLNGKEYKCKVTNKALPA<br>PIEKTISKAKGQPREPQVYTLPPSRDELTKNQVSLTCLVKGFYPS<br>DIAVEWESNGQPENNYKTTPPVLDSDGSFFLYSKLTVDKSRWQQG<br>NVFSCSVMHEALHNHYTQKSLSLSPGKERKCCVECPPCP |

TABLE 1-continued

Exemplary complement-binding stradomers

| Stradomer | SEQ ID NO | Mutated Amino Acids | Amino acid sequence |
|---|---|---|---|
| G1106 | 32 | E233P G236K H268F S324T | METDTLLLWVLLLWVPGSTGEPKSCDKTHTCPPCPAPPLLKGPSV<br>FLFPPKPKDTLMISRTPEVTCVVVDVSFEDPEVKFNWYVDGVEVH<br>NAKTKPREEQYNSTYRVVSVLTVLHQDWLNGKEYKCKVTNKALPA<br>PIEKTISKAKGQPREPQVYTLPPSRDELTKNQVSLTCLVKGFYPS<br>DIAVEWESNGQPENNYKTTPPVLDSDGSFFLYSKLTVDKSRWQQG<br>NVFSCSVMHEALHNHYTQKSLSLSPGKERKCCVECPPCP |
| G1100 | 33 | E233P S267R H268F S324T | METDTLLLWVLLLWVPGSTGEPKSCDKTHTCPPCPAPPLLGGPSV<br>FLFPPKPKDTLMISRTPEVTCVVVDVRFEDPEVKFNWYVDGVEVH<br>NAKTKPREEQYNSTYRVVSVLTVLHQDWLNGKEYKCKVTNKALPA<br>PIEKTISKAKGQPREPQVYTLPPSRDELTKNQVSLTCLVKGFYPS<br>DIAVEWESNGQPENNYKTTPPVLDSDGSFFLYSKLTVDKSRWQQG<br>NVFSCSVMHEALHNHYTQKSLSLSPGKERKCCVECPPCP |
| G1108 | 34 | E233P, S267N H268F S324T | METDTLLLWVLLLWVPGSTGEPKSCDKTHTCPPCPAPPLLGGPSV<br>FLFPPKPKDTLMISRTPEVTCVVVDVNFEDPEVKFNWYVDGVEVH<br>NAKTKPREEQYNSTYRVVSVLTVLHQDWLNGKEYKCKVTNKALPA<br>PIEKTISKAKGQPREPQVYTLPPSRDELTKNQVSLTCLVKGFYPS<br>DIAVEWESNGQPENNYKTTPPVLDSDGSFFLYSKLTVDKSRWQQG<br>NVFSCSVMHEALHNHYTQKSLSLSPGKERKCCVECPPCP |
| G1084 | 35 | E233P S267K H268F S324T | METDTLLLWVLLLWVPGSTGEPKSCDKTHTCPPCPAPPLLGGPSV<br>FLFPPKPKDTLMISRTPEVTCVVVDVKFEDPEVKFNWYVDGVEVH<br>NAKTKPREEQYNSTYRVVSVLTVLHQDWLNGKEYKCKVTNKALPA<br>PIEKTISKAKGQPREPQVYTLPPSRDELTKNQVSLTCLVKGFYPS<br>DIAVEWESNGQPENNYKTTPPVLDSDGSFFLYSKLTVDKSRWQQG<br>NVFSCSVMHEALHNHYTQKSLSLSPGKERKCCVECPPCP |
| G1110 | 36 | E233P G236D S267R H268F S324T | METDTLLLWVLLLWVPGSTGEPKSCDKTHTCPPCPAPPLLRGPSV<br>FLFPPKPKDTLMISRTPEVTCVVVDVRFEDPEVKFNWYVDGVEVH<br>NAKTKPREEQYNSTYRVVSVLTVLHQDWLNGKEYKCKVTNKALPA<br>PIEKTISKAKGQPREPQVYTLPPSRDELTKNQVSLTCLVKGFYPS<br>DIAVEWESNGQPENNYKTTPPVLDSDGSFFLYSKLTVDKSRWQQG<br>NVFSCSVMHEALHNHYTQKSLSLSPGKERKCCVECPPCP |
| G1112 | 37 | E233P G236R S267R H268F S324T | METDTLLLWVLLLWVPGSTGEPKSCDKTHTCPPCPAPPLLRGPSV<br>FLFPPKPKDTLMISRTPEVTCVVVDVRFEDPEVKFNWYVDGVEVH<br>NAKTKPREEQYNSTYRVVSVLTVLHQDWLNGKEYKCKVTNKALPA<br>PIEKTISKAKGQPREPQVYTLPPSRDELTKNQVSLTCLVKGFYPS<br>DIAVEWESNGQPENNYKTTPPVLDSDGSFFLYSKLTVDKSRWQQG<br>NVFSCSVMHEALHNHYTQKSLSLSPGKERKCCVECPPCP |
| G1113 | 38 | E233P G236R S267D H268F S324T | METDTLLLWVLLLWVPGSTGEPKSCDKTHTCPPCPAPPLLRGPSV<br>FLFPPKPKDTLMISRTPEVTCVVVDVDFEDPEVKFNWYVDGVEVH<br>NAKTKPREEQYNSTYRVVSVLTVLHQDWLNGKEYKCKVTNKALPA<br>PIEKTISKAKGQPREPQVYTLPPSRDELTKNQVSLTCLVKGFYPS<br>DIAVEWESNGQPENNYKTTPPVLDSDGSFFLYSKLTVDKSRWQQG<br>NVFSCSVMHEALHNHYTQKSLSLSPGKERKCCVECPPCP |

TABLE 1-continued

Exemplary complement-binding stradomers

| Stradomer | SEQ ID NO | Mutated Amino Acids | Amino acid sequence |
|---|---|---|---|
| G1115 | 39 | E233P<br>G236E<br>S267R<br>H268F<br>S324T | METDTLLLWVLLLWVPGSTGEPKSCDKTHTCPPCPAPPLLEGPSV<br>FLFPPKPKDTLMISRTPEVTCVVVDVREEDPEVKFNWYVDGVEVH<br>NAKTKPREEQYNSTYRVVSVLTVLHQDWLNGKEYKCKVTNKALPA<br>PIEKTISKAKGQPREPQVYTLPPSRDELTKNQVSLTCLVKGFYPS<br>DIAVEWESNGQPENNYKTTPPVLDSDGSFFLYSKLTVDKSRWQQG<br>NVFSCSVMHEALHNHYTQKSLSLSPGKERKCCVECPPCP |
| G1116 | 40 | E233P<br>G236H<br>S267K<br>H268F<br>S324T | METDTLLLWVLLLWVPGSTGEPKSCDKTHTCPPCPAPPLLHGPSV<br>FLFPPKPKDTLMISRTPEVTCVVVDVKFEDPEVKFNWYVDGVEVH<br>NAKTKPREEQYNSTYRVVSVLTVLHQDWLNGKEYKCKVTNKALPA<br>PIEKTISKAKGQPREPQVYTLPPSRDELTKNQVSLTCLVKGFYPS<br>DIAVEWESNGQPENNYKTTPPVLDSDGSFFLYSKLTVDKSRWQQG<br>NVFSCSVMHEALHNHYTQKSLSLSPGKERKCCVECPPCP |
| G1118 | 41 | E233P<br>G236Q<br>S267Q<br>H268F<br>S324T | METDTLLLWVLLLWVPGSTGEPKSCDKTHTCPPCPAPPLLQGPSV<br>FLFPPKPKDTLMISRTPEVTCVVVDVQFEDPEVKFNWYVDGVEVH<br>NAKTKPREEQYNSTYRVVSVLTVLHQDWLNGKEYKCKVTNKALPA<br>PIEKTISKAKGQPREPQVYTLPPSRDELTKNQVSLTCLVKGFYPS<br>DIAVEWESNGQPENNYKTTPPVLDSDGSFFLYSKLTVDKSRWQQG<br>NVFSCSVMHEALHNHYTQKSLSLSPGKERKCCVECPPCP |
| G1119 | 42 | E233P<br>G236R<br>S267K<br>H268F<br>S324T | METDTLLLWVLLLWVPGSTGEPKSCDKTHTCPPCPAPPLLRGPSV<br>FLFPPKPKDTLMISRTPEVTCVVVDVKFEDPEVKFNWYVDGVEVH<br>NAKTKPREEQYNSTYRVVSVLTVLHQDWLNGKEYKCKVTNKALPA<br>PIEKTISKAKGQPREPQVYTLPPSRDELTKNQVSLTCLVKGFYPS<br>DIAVEWESNGQPENNYKTTPPVLDSDGSFFLYSKLTVDKSRWQQG<br>NVFSCSVMHEALHNHYTQKSLSLSPGKERKCCVECPPCP |
| G1120 | 43 | E233P<br>G236R<br>S267Q<br>H268F<br>S324T | METDTLLLWVLLLWVPGSTGEPKSCDKTHTCPPCPAPPLLRGPSV<br>FLFPPKPKDTLMISRTPEVTCVVVDVQFEDPEVKFNWYVDGVEVH<br>NAKTKPREEQYNSTYRVVSVLTVLHQDWLNGKEYKCKVTNKALPA<br>PIEKTISKAKGQPREPQVYTLPPSRDELTKNQVSLTCLVKGFYPS<br>DIAVEWESNGQPENNYKTTPPVLDSDGSFFLYSKLTVDKSRWQQG<br>NVFSCSVMHEALHNHYTQKSLSLSPGKERKCCVECPPCP |
| G1121 | 44 | E233P<br>G236D<br>S267K<br>H268F<br>S324T | METDTLLLWVLLLWVPGSTGEPKSCDKTHTCPPCPAPPLLKDPSV<br>FLFPPKPKDTLMISRTPEVTCVVVDVKFEDPEVKFNWYVDGVEVH<br>NAKTKPREEQYNSTYRVVSVLTVLHQDWLNGKEYKCKVTNKALPA<br>PIEKTISKAKGQPREPQVYTLPPSRDELTKNQVSLTCLVKGFYPS<br>DIAVEWESNGQPENNYKTTPPVLDSDGSFFLYSKLTVDKSRWQQG<br>NVFSCSVMHEALHNHYTQKSLSLSPGKERKCCVECPPCP |
| G1122 | 45 | E233P<br>G236H<br>S267Q<br>H268F<br>S324T | METDTLLLWVLLLWVPGSTGEPKSCDKTHTCPPCPAPPLLHGPSV<br>FLFPPKPKDTLMISRTPEVTCVVVDVQFEDPEVKFNWYVDGVEVH<br>NAKTKPREEQYNSTYRVVSVLTVLHQDWLNGKEYKCKVTNKALPA<br>PIEKTISKAKGQPREPQVYTLPPSRDELTKNQVSLTCLVKGFYPS<br>DIAVEWESNGQPENNYKTTPPVLDSDGSFFLYSKLTVDKSRWQQG<br>NVFSCSVMHEALHNHYTQKSLSLSPGKERKCCVECPPCP |

TABLE 1-continued

Exemplary complement-binding stradomers

| Stradomer | SEQ ID NO | Mutated Amino Acids | Amino acid sequence |
|---|---|---|---|
| G1123 | 46 | E233P | METDTLLLWVLLLWVPGSTGEPKSCDKTHTCPPCPAPPLLQGPSV |
| | | G236Q | FLFPPKPKDTLMISRTPEVTCVVVDVRPEDPEVKFNWYVDGVEVH |
| | | S267R | NAKTKPREEQYNSTYRVVSVLTVLHQDWLNGKEYKCKVTNKALPA |
| | | H268F S324T | PIEKTISKAKGQPREPQVYTLPPSRDELTKNQVSLTCLVKGFYPS DIAVEWESNGQPENNYKTTPPVLDSDGSFFLYSKLTVDKSRWQQG NVFSCSVMHEALHNHYTQKSLSLSPGKERKCCVECPPCP |
| G1124 | 47 | E233P | METDTLLLWVLLLWVPGSTGEPKSCDKTHTCPPCPAPPLLKGPSV |
| | | G236K | FLFPPKPKDTLMISRTPEVTCVVVDVKPEDPEVKFNWYVDGVEVH |
| | | S267K | NAKTKPREEQYNSTYRVVSVLTVLHQDWLNGKEYKCKVTNKALPA |
| | | H268F S324T | PIEKTISKAKGQPREPQVYTLPPSRDELTKNQVSLTCLVKGFYPS DIAVEWESNGQPENNYKTTPPVLDSDGSFFLYSKLTVDKSRWQQG NVFSCSVMHEALHNHYTQKSLSLSPGKERKCCVECPPCP |
| G1128 | 48 | E233P | METDTLLLWVLLLWVPGSTGEPKSCDKTHTCPPCPAPPLLKGPSV |
| | | G236K | FLFPPKPKDTLMISRTPEVTCVVVDVNPEDPEVKFNWYVDGVEVH |
| | | S267N | NAKTKPREEQYNSTYRVVSVLTVLHQDWLNGKEYKCKVTNKALPA |
| | | H268F S324T | PIEKTISKAKGQPREPQVYTLPPSRDELTKNQVSLTCLVKGFYPS DIAVEWESNGQPENNYKTTPPVLDSDGSFFLYSKLTVDKSRWQQG NVFSCSVMHEALHNHYTQKSLSLSPGKERKCCVECPPCP |
| G1129 | 49 | E233P | METDTLLLWVLLLWVPGSTGEPKSCDKTHTCPPCPAPPLLNGPSV |
| | | G236N | FLFPPKPKDTLMISRTPEVTCVVVDVEPEDPEVKFNWYVDGVEVH |
| | | S267E | NAKTKPREEQYNSTYRVVSVLTVLHQDWLNGKEYKCKVTNKALPA |
| | | H268F S324T | PIEKTISKAKGQPREPQVYTLPPSRDELTKNQVSLTCLVKGFYPS DIAVEWESNGQPENNYKTTPPVLDSDGSFFLYSKLTVDKSRWQQG NVFSCSVMHEALHNHYTQKSLSLSPGKERKCCVECPPCP |
| G1130 | 50 | E233P | METDTLLLWVLLLWVPGSTGEPKSCDKTHTCPPCPAPPLLNGPSV |
| | | G236N | FLFPPKPKDTLMISRTPEVTCVVVDVKPEDPEVKFNWYVDGVEVH |
| | | S267K | NAKTKPREEQYNSTYRVVSVLTVLHQDWLNGKEYKCKVTNKALPA |
| | | H268F S324T | PIEKTISKAKGQPREPQVYTLPPSRDELTKNQVSLTCLVKGFYPS DIAVEWESNGQPENNYKTTPPVLDSDGSFFLYSKLTVDKSRWQQG NVFSCSVMHEALHNHYTQKSLSLSPGKERKCCVECPPCP |
| G1131 | 51 | E233P | METDTLLLWVLLLWVPGSTGEPKSCDKTHTCPPCPAPPLLRGPSV |
| | | G236R | FLFPPKPKDTLMISRTPEVTCVVVDVNPEDPEVKFNWYVDGVEVH |
| | | S267N | NAKTKPREEQYNSTYRVVSVLTVLHQDWLNGKEYKCKVTNKALPA |
| | | H268F S324T | PIEKTISKAKGQPREPQVYTLPPSRDELTKNQVSLTCLVKGFYPS DIAVEWESNGQPENNYKTTPPVLDSDGSFFLYSKLTVDKSRWQQG NVFSCSVMHEALHNHYTQKSLSLSPGKERKCCVECPPCP |
| G1071d2 | 52 | H268F | METDTLLLWVLLLWVPGSTGEPKSCDKTHTCPPCPAPELLGGPSV |
| | | S324T | FLFPPKPKDTLMISRTPEVTCVVVDVSPEDPEVKFNWYVDGVEVH |
| | | T299A | NAKTKPREEQYNSAYRVVSVLTVLHQDWLNGKEYKCKVTNKALPA |
| | | | PIEKTISKAKGQPREPQVYTLPPSRDELTKNQVSLTCLVKGFYPS DIAVEWESNGQPENNYKTTPPVLDSDGSFFLYSKLTVDKSRWQQG NVFSCSVMHEALHNHYTQKSLSLSPGKERKCCVECPPCP |
| G1096 | 53 | S267R H268F | METDTLLLWVLLLWVPGSTGEPKSCDKTHTCPPCPAPELLGGPSV FLFPPKPKDTLMISRTPEVTCVVVDVRPEDPEVKFNWYVDGVEVH |
| | | S324T | NAKTKPREEQYNSAYRVVSVLTVLHQDWLNGKEYKCKVTNKALPA |
| | | T299A | PIEKTISKAKGQPREPQVYTLPPSRDELTKNQVSLTCLVKGFYPS DIAVEWESNGQPENNYKTTPPVLDSDGSFFLYSKLTVDKSRWQQG NVFSCSVMHEALHNHYTQKSLSLSPGKERKCCVECPPCP |

TABLE 1-continued

Exemplary complement-binding stradomers

| Stradomer | SEQ ID NO | Mutated Amino Acids | Amino acid sequence |
|---|---|---|---|
| G1093 | 54 | S267K H268F | METDTLLLWVLLLWVPGSTGEPKSCDKTHTCPPCPAPELLGGPSV FLFPPKPKDTLMISRTPEVTCVVVDVKFEDPEVKFNWYVDGVEVH |
| | | S324T | NAKTKPREEQYNSAYRVVSVLTVLHQDWLNGKEYKCKVTNKALPA |
| | | T299A | PIEKTISKAKGQPREPQVYTLPPSRDELTKNQVSLTCLVKGFYPS DIAVEWESNGQPENNYKTTPPVLDSDGSFFLYSKLTVDKSRWQQG NVFSCSVMHEALHNHYTQKSLSLSPGKERKCCVECPPCP |
| G1095 | 55 | S267N H268F | METDTLLLWVLLLWVPGSTGEPKSCDKTHTCPPCPAPELLGGPSV FLFPPKPKDTLMISRTPEVTCVVVDVNFEDPEVKFNWYVDGVEVH |
| | | S324T | NAKTKPREEQYNSAYRVVSVLTVLHQDWLNGKEYKCKVTNKALPA |
| | | T299A | PIEKTISKAKGQPREPQVYTLPPSRDELTKNQVSLTCLVKGFYPS DIAVEWESNGQPENNYKTTPPVLDSDGSFFLYSKLTVDKSRWQQG NVFSCSVMHEALHNHYTQKSLSLSPGKERKCCVECPPCP |
| G1069 | 56 | H268F S324T | METDTLLLWVLLLWVPGSTGEPKSCDKTHTCPPCPAPELLGGPSV FLFPPKPKDTLMISRTPEVTCVVVDVSFEDPEVKFNWYVDGVEVH |
| | | N297A | NAKTKPREEQYASTYRVVSVLTVLHQDWLNGKEYKCKVTNKALPA PIEKTISKAKGQPREPQVYTLPPSRDELTKNQVSLTCLVKGFYPS DIAVEWESNGQPENNYKTTPPVLDSDGSFFLYSKLTVDKSRWQQG NVFSCSVMHEALHNHYTQKSLSLSPGKERKCCVECPPCP |
| G1070 | 57 | S267K H268F | METDTLLLWVLLLWVPGSTGEPKSCDKTHTCPPCPAPELLGGPSV FLFPPKPKDTLMISRTPEVTCVVVDVKFEDPEVKFNWYVDGVEVH |
| | | S324T | NAKTKPREEQYASTYRVVSVLTVLHQDWLNGKEYKCKVTNKALPA |
| | | N297A | PIEKTISKAKGQPREPQVYTLPPSRDELTKNQVSLTCLVKGFYPS DIAVEWESNGQPENNYKTTPPVLDSDGSFFLYSKLTVDKSRWQQG NVFSCSVMHEALHNHYTQKSLSLSPGKERKCCVECPPCP |
| G1132 | 58 | S267R H268F | METDTLLLWVLLLWVPGSTGEPKSCDKTHTCPPCPAPELLGGPSV FLFPPKPKDTLMISRTPEVTCVVVDVRFEDPEVKFNWYVDGVEVH |
| | | S324T | NAKTKPREEQYASTYRVVSVLTVLHQDWLNGKEYKCKVTNKALPA |
| | | N297A | PIEKTISKAKGQPREPQVYTLPPSRDELTKNQVSLTCLVKGFYPS DIAVEWESNGQPENNYKTTPPVLDSDGSFFLYSKLTVDKSRWQQG NVFSCSVMHEALHNHYTQKSLSLSPGKERKCCVECPPCP |
| G1074 | 59 | S267D H268F | METDTLLLWVLLLWVPGSTGEPKSCDKTHTCPPCPAPELLGGPSV FLFPPKPKDTLMISRTPEVTCVVVDVDFEDPEVKFNWYVDGVEVH |
| | | S324T | NAKTKPREEQYASTYRVVSVLTVLHQDWLNGKEYKCKVTNKALPA |
| | | N297A | PIEKTISKAKGQPREPQVYTLPPSRDELTKNQVSLTCLVKGFYPS DIAVEWESNGQPENNYKTTPPVLDSDGSFFLYSKLTVDKSRWQQG NVFSCSVMHEALHNHYTQKSLSLSPGKERKCCVECPPCP |
| G1075 | 60 | S267Q H268F | METDTLLLWVLLLWVPGSTGEPKSCDKTHTCPPCPAPELLGGPSV FLFPPKPKDTLMISRTPEVTCVVVDVQFEDPEVKFNWYVDGVEVH |
| | | S324T | NAKTKPREEQYASTYRVVSVLTVLHQDWLNGKEYKCKVTNKALPA |
| | | N297A | PIEKTISKAKGQPREPQVYTLPPSRDELTKNQVSLTCLVKGFYPS DIAVEWESNGQPENNYKTTPPVLDSDGSFFLYSKLTVDKSRWQQG NVFSCSVMHEALHNHYTQKSLSLSPGKERKCCVECPPCP |

*For stradomers G1022, G1023, and G1050, the deletion of the G at position 236 is shown as strikethrough/bold text.

TABLE 2

General Stradomers

| Stradomer | SEQ ID NO | Mutated Amino Acids | Amino acid sequence |
|---|---|---|---|
| G990 | 61 | G236R | METDTLLLWVLLLWVPGSTGEPKSCDKTHTCPPCPAPELLRGPSV FLFPPKPKDTLMISRTPEVTCVVVDVSHEDPEVKFNWYVDGVEVH NAKTKPREEQYNSTYRVVSVLTVLHQDWLNGKEYKCKVSNKALPA PIEKTISKAKGQPREPQVYTLPPSRDELTKNQVSLTCLVKGFYPS DIAVEWESNGQPENNYKTTPPVLDSDGSFFLYSKLTVDKSRWQQG NVFSCSVMHEALHNHYTQKSLSLSPGKERKCCVECPPCP |
| G1023* | 62 | E233P L234V L235A S267E H268F S324T Deletion of G236 | METDTLLLWVLLLWVPGSTGEPKSCDKTHTCPPCPAPPVAGGPSV FLFPPKPKDTLMISRTPEVTCVVVDVEFEDPEVKFNWYVDGVEVH NAKTKPREEQYNSTYRVVSVLTVLHQDWLNGKEYKCKVTNKALPA PIEKTISKAKGQPREPQVYTLPPSRDELTKNQVSLTCLVKGFYPS DIAVEWESNGQPENNYKTTPPVLDSDGSFFLYSKLTVDKSRWQQG NVFSCSVMHEALHNHYTQKSLSLSPGKERKCCVECPPCP |
| G1032 | 63 | L234A L235A S267E H268F S324T | METDTLLLWVLLLWVPGSTGEPKSCDKTHTCPPCPAPEAAGGPSV FLFPPKPKDTLMISRTPEVTCVVVDVEFEDPEVKFNWYVDGVEVH NAKTKPREEQYNSTYRVVSVLTVLHQDWLNGKEYKCKVTNKALPA PIEKTISKAKGQPREPQVYTLPPSRDELTKNQVSLTCLVKGFYPS DIAVEWESNGQPENNYKTTPPVLDSDGSFFLYSKLTVDKSRWQQG NVFSCSVMHEALHNHYTQKSLSLSPGKERKCCVECPPCP |
| G1049 | 64 | S267E H268F S324T L328F | METDTLLLWVLLLWVPGSTGERKCCVECPPCPEPKSCDKTHTCPP CPAPELLGGPSVFLFPPKPKDTLMISRTPEVTCVVVDVEFEDPEV KFNWYVDGVEVHNAKTKPREEQYNSTYRVVSVLTVLHQDWLNGKE YKCKVTNKAFPAPIEKTISKAKGQPREPQVYTLPPSRDELTKNQV SLTCLVKGFYPSDIAVEWESNGQPENNYKTTPPVLDSDGSFFLYS KLTVDKSRWQQGNVFSCSVMHEALHNHYTQKSLSLSPGK |
| G1103 | 65 | E233P G236E H268F S324T | METDTLLLWVLLLWVPGSTGEPKSCDKTHTCPPCPAPPLLEGPSV FLFPPKPKDTLMISRTPEVTCVVVDVSFEDPEVKFNWYVDGVEVH NAKTKPREEQYNSTYRVVSVLTVLHQDWLNGKEYKCKVTNKALPA PIEKTISKAKGQPREPQVYTLPPSRDELTKNQVSLTCLVKGFYPS DIAVEWESNGQPENNYKTTPPVLDSDGSFFLYSKLTVDKSRWQQG NVFSCSVMHEALHNHYTQKSLSLSPGKERKCCVECPPCP |
| G1104 | 66 | E233P G236D H268F S324T | METDTLLLWVLLLWVPGSTGEPKSCDKTHTCPPCPAPPLLDGPSV FLFPPKPKDTLMISRTPEVTCVVVDVSFEDPEVKFNWYVDGVEVH NAKTKPREEQYNSTYRVVSVLTVLHQDWLNGKEYKCKVTNKALPA PIEKTISKAKGQPREPQVYTLPPSRDELTKNQVSLTCLVKGFYPS DIAVEWESNGQPENNYKTTPPVLDSDGSFFLYSKLTVDKSRWQQG NVFSCSVMHEALHNHYTQKSLSLSPGKERKCCVECPPCP |
| G1102 | 67 | E233P S267Q H268F S324T | METDTLLLWVLLLWVPGSTGEPKSCDKTHTCPPCPAPPLLGGPSV FLFPPKPKDTLMISRTPEVTCVVVDVQFEDPEVKFNWYVDGVEVH NAKTKPREEQYNSTYRVVSVLTVLHQDWLNGKEYKCKVTNKALPA PIEKTISKAKGQPREPQVYTLPPSRDELTKNQVSLTCLVKGFYPS DIAVEWESNGQPENNYKTTPPVLDSDGSFFLYSKLTVDKSRWQQG NVFSCSVMHEALHNHYTQKSLSLSPGKERKCCVECPPCP |

TABLE 2-continued

General Stradomers

| Stradomer | SEQ ID NO | Mutated Amino Acids | Amino acid sequence |
|---|---|---|---|
| G1101 | 68 | E233P | METDTLLLWVLLLWVPGSTGEPKSCDKTHTCPPCPAPPLLGGPSV |
| | | S267D | FLFPPKPKDTLMISRTPEVTCVVVDVDFEDPEVKFNWYVDGVEVH |
| | | H268F | NAKTKPREEQYNSTYRVVSVLTVLHQDWLNGKEYKCKVTNKALPA |
| | | S324T | PIEKTISKAKGQPREPQVYTLPPSRDELTKNQVSLTCLVKGFYPS |
| | | | DIAVEWESNGQPENNYKTTPPVLDSDGSFFLYSKLTVDKSRWQQG |
| | | | NVFSCSVMHEALHNHYTQKSLSLSPGKERKCCVECPPCP |
| G1125 | 69 | E233P | METDTLLLWVLLLWVPGSTGEPKSCDKTHTCPPCPAPPLLGGPSV |
| | | S267H | FLFPPKPKDTLMISRTPEVTCVVVDVHFEDPEVKFNWYVDGVEVH |
| | | H268F | NAKTKPREEQYNSTYRVVSVLTVLHQDWLNGKEYKCKVTNKALPA |
| | | S324T | PIEKTISKAKGQPREPQVYTLPPSRDELTKNQVSLTCLVKGFYPS |
| | | | DIAVEWESNGQPENNYKTTPPVLDSDGSFFLYSKLTVDKSRWQQG |
| | | | NVFSCSVMHEALHNHYTQKSLSLSPGKERKCCVECPPCP |
| G1109 | 70 | E233P | METDTLLLWVLLLWVPGSTGEPKSCDKTHTCPPCPAPPLLGGPSV |
| | | S267E | FLFPPKPKDTLMISRTPEVTCVVVDVEFEDPEVKFNWYVDGVEVH |
| | | H268F | NAKTKPREEQYNSTYRVVSVLTVLHQDWLNGKEYKCKVTNKALPA |
| | | S324T | PIEKTISKAKGQPREPQVYTLPPSRDELTKNQVSLTCLVKGFYPS |
| | | | DIAVEWESNGQPENNYKTTPPVLDSDGSFFLYSKLTVDKSRWQQG |
| | | | NVFSCSVMHEALHNHYTQKSLSLSPGKERKCCVECPPCP |
| G1111 | 71 | E233P | METDTLLLWVLLLWVPGSTGEPKSCDKTHTCPPCPAPPLLDGPSV |
| | | G236D | FLFPPKPKDTLMISRTPEVTCVVVDVQFEDPEVKFNWYVDGVEVH |
| | | S267Q | NAKTKPREEQYNSTYRVVSVLTVLHQDWLNGKEYKCKVTNKALPA |
| | | H268F | PIEKTISKAKGQPREPQVYTLPPSRDELTKNQVSLTCLVKGFYPS |
| | | S324T | DIAVEWESNGQPENNYKTTPPVLDSDGSFFLYSKLTVDKSRWQQG |
| | | | NVFSCSVMHEALHNHYTQKSLSLSPGKERKCCVECPPCP |
| G1114 | 72 | E233P | METDTLLLWVLLLWVPGSTGEPKSCDKTHTCPPCPAPPLLQGPSV |
| | | G236Q | FLFPPKPKDTLMISRTPEVTCVVVDVDFEDPEVKFNWYVDGVEVH |
| | | S267D | NAKTKPREEQYNSTYRVVSVLTVLHQDWLNGKEYKCKVTNKALPA |
| | | H268F | PIEKTISKAKGQPREPQVYTLPPSRDELTKNQVSLTCLVKGFYPS |
| | | S324T | DIAVEWESNGQPENNYKTTPPVLDSDGSFFLYSKLTVDKSRWQQG |
| | | | NVFSCSVMHEALHNHYTQKSLSLSPGKERKCCVECPPCP |
| G1117 | 73 | E233P | METDTLLLWVLLLWVPGSTGEPKSCDKTHTCPPCPAPPLLDGPSV |
| | | G236D | FLFPPKPKDTLMISRTPEVTCVVVDVDFEDPEVKFNWYVDGVEVH |
| | | S267D | NAKTKPREEQYNSTYRVVSVLTVLHQDWLNGKEYKCKVTNKALPA |
| | | H268F | PIEKTISKAKGQPREPQVYTLPPSRDELTKNQVSLTCLVKGFYPS |
| | | S324T | DIAVEWESNGQPENNYKTTPPVLDSDGSFFLYSKLTVDKSRWQQG |
| | | | NVFSCSVMHEALHNHYTQKSLSLSPGKERKCCVECPPCP |
| G1068 | 74 | S267E | METDTLLLWVLLLWVPGSTGEPKSCDKTHTCPPCPAPELLGGPSV |
| | | H268F | FLFPPKPKDTLMISRTPEVTCVVVDVEFEDPEVKFNWYVDGVEVH |
| | | S324T | NAKTKPREEQYASTYRVVSVLTVLHQDWLNGKEYKCKVTNKALPA |
| | | T299A | PIEKTISKAKGQPREPQVYTLPPSRDELTKNQVSLTCLVKGFYPS |
| | | | DIAVEWESNGQPENNYKTTPPVLDSDGSFFLYSKLTVDKSRWQQG |
| | | | NVFSCSVMHEALHNHYTQKSLSLSPGKERKCCVECPPCP |
| G1094 | 75 | S267Q | METDTLLLWVLLLWVPGSTGEPKSCDKTHTCPPCPAPELLGGPSV |
| | | H268F | FLFPPKPKDTLMISRTPEVTCVVVDVQFEDPEVKFNWYVDGVEVH |
| | | S324T | NAKTKPREEQYASTYRVVSVLTVLHQDWLNGKEYKCKVTNKALPA |
| | | T299A | PIEKTISKAKGQPREPQVYTLPPSRDELTKNQVSLTCLVKGFYPS |
| | | | DIAVEWESNGQPENNYKTTPPVLDSDGSFFLYSKLTVDKSRWQQG |
| | | | NVFSCSVMHEALHNHYTQKSLSLSPGKERKCCVECPPCP |

TABLE 2-continued

General Stradomers

| Stradomer | SEQ ID NO | Mutated Amino Acids | Amino acid sequence |
|---|---|---|---|
| G1092 | 76 | S267D H268F | METDTLLLWVLLLWVPGSTGEPKSCDKTHTCPPCPAPELLGGPSV FLFPPKPKDTLMISRTPEVTCVVVDVDFEDPEVKFNWYVDGVEVH |
| | | S324T | NAKTKPREEQYASTYRVVSVLTVLHQDWLNGKEYKCKVTNKALPA |
| | | T299A | PIEKTISKAKGQPREPQVYTLPPSRDELTKNQVSLTCLVKGFYPS DIAVEWESNGQPENNYKTTPPVLDSDGSFFLYSKLTVDKSRWQQG NVFSCSVMHEALHNHYTQKSLSLSPGKERKCCVECPPCP |
| G1107 | 77 | S267H H268F | METDTLLLWVLLLWVPGSTGEPKSCDKTHTCPPCPAPELLGGPSV FLFPPKPKDTLMISRTPEVTCVVVDVHFEDPEVKFNWYVDGVEVH |
| | | S324T | NAKTKPREEQYASTYRVVSVLTVLHQDWLNGKEYKCKVTNKALPA |
| | | T299A | PIEKTISKAKGQPREPQVYTLPPSRDELTKNQVSLTCLVKGFYPS DIAVEWESNGQPENNYKTTPPVLDSDGSFFLYSKLTVDKSRWQQG NVFSCSVMHEALHNHYTQKSLSLSPGKERKCCVECPPCP |

Complement-binding proteins such as the monoclonal antibody eculizumab (anti-C5 antibody) have been used in the art in attempts to block the complement pathway as a treatment for complement-mediated diseases. The biomimetics of the present invention achieve increased binding to complement components, e.g., C1q, through particular Fc domain mutations. For example, the biomimetics of the present invention comprise a point mutation at position 267 and/or 268 and/or 324 of the IgG1 Fc domain. The complement-binding biomimetics of the present invention further exhibit altered binding to FcRn, FcγRI, FcγRII, and/or FcγRIII compared to wild type IgG1 Fc domains, often in ways that would not be predicted by the literature describing the mutations comprised in the biomimetics of the current invention. Thus, in one embodiment, the biomimetics of the present invention are complement-preferential stradomers that are capable of multimerization and exhibit an increased ratio of complement binding to one or more canonical FcγRs and/or FcRn binding compared with a normal non-aggregated immunoglobulin. In a further embodiment, the biomimetics of the present invention are complement-preferential stradomers that are capable of multimerization and exhibit an increased ratio of complement binding to one or more canonical FcγRs and/or FcRn binding compared with a normal aggregated immunoglobulin. In a further embodiment, the biomimetics of the present invention are complement-preferential stradomers that are capable of multimerization and exhibit an increased ratio of complement binding to one or more canonical FcγRs and/or FcRn binding compared with a monoclonal antibody comprising the same mutations within its Fc domain. In a further embodiment, the biomimetics of the present invention have an altered half-life relative to native IgG, IVIG, or a parent stradomer.

The terms "FcγR" and "Fcγreceptor" as used herein encompass all members of the Fc gamma RI, RII, and RIII families. Fcγreceptor includes low affinity and high affinity Fcγ receptors, including but not limited in humans to FcγRI (CD64); FcγRII (CD32) and its isotypes and allotypes FcγRIIa LR, FcγRIIa HR, FcγRIIb, and FcγRIIc; FcγRIII (CD 16) and its isotypes FcγRIIIa and FcγRIIIb. A skilled artisan will recognize that the disclosure provided herein regarding FcγR and FcγR homologues such as those described in Davis, et al. (2004) "Differential B cell expression of mouse Fc receptor homologs," Int. Immunol., 16(9): 1343-1353, will apply to future FcγRs and associated isotypes and allotypes that may not yet have been discovered.

Specific binding is generally defined as the amount of labeled ligand which is displaceable by a subsequent excess of unlabeled ligand in a binding assay. However, this does not exclude other means of assessing specific binding which are well established in the art (e.g., Mendel C M, Mendel D B, 'Non-specific' binding. The problem, and a solution. Biochem J. 1985 May 15; 228(1):269-72). Specific binding may be measured in a variety of ways well known in the art such as surface plasmon resonance (SPR) technology (commercially available through BIACORE®) or biolayer interferometry (commercially available through ForteBio®) to characterize both association and dissociation constants of the immunologically active biomimetics (Asian K, Lakowicz J R, Geddes C. Plasmon light scattering in biology and medicine: new sensing approaches, visions and perspectives. Current Opinion in Chemical Biology 2005, 9:538-544).

"Immunological activity of aggregated native IgG" refers to the properties of multimerized IgG which impact the functioning of an immune system upon exposure of the immune system to the IgG aggregates. Specific properties of native multimerized IgG includes altered specific binding to FcγRs, cross-linking of FcγRs on the surfaces of immune cells, or an effector functionality of multimerized IgG such as antibody dependent cell-mediated cytotoxicity (ADCC), phagocytosis (ADCP), or complement fixation (See, e.g., Nimmerjahn F, Ravetch J V. The anti-inflammatory activity of IgG: the intravenous IgG paradox. J Exp Med. 2007; 204:11-15; Augener W, Friedman B, Brittinger G. Are aggregates of IgG the effective part of high-dose immunoglobulin therapy in adult idiopathic thrombocytopenic purpura (ITP) Blut. 1985; 50:249-252; Arase N, Arase H, Park S Y, Ohno H, Ra C, Saito T. Association with FcRgamma is essential for activation signal through NKR-P1 (CD161) in natural killer (NK) cells and NK1.1+ T cells. J Exp Med. 1997; 186:1957-1963; Teeling J L, Jansen-Hendriks T, Kuijpers T W, et al. Therapeutic efficacy of intravenous immunoglobulin preparations depends on the immunoglobulin G dimers: studies in experimental immune thrombocytopenia. Blood. 2001; 98: 1095-1099; Anderson C F, Mosser D M. Cutting edge: biasing immune responses by directing antigen to macrophage Fc gamma receptors. J Immunol. 2002; 168:3697-3701; Jefferis R, Lund J. Interaction sites on human IgG-Fc for FcγR: current models. Immunology Letters. 2002; 82:57; Banki Z, Kacani L, Mullauer B, et al. Cross-Linking of CD32 Induces Maturation of Human Monocyte—Derived Dendritic Cells Via NF—{kappa} B Signaling Pathway. J Immunol. 2003; 170: 3963-3970; Siragam V, Brine D, Crow A R, Song S, Freedman J, Lazarus A H. Can antibodies with specificity for soluble antigens mimic the therapeutic effects of intravenous IgG in the treatment of autoimmune disease? J Clin Invest. 2005; 115:155-160). These properties are generally evaluated by comparison to the properties of homodimeric IgG.

While higher order multimers have been found to be effective in altering the immune response, as described herein, homodimers were also effective immune modulators. Without being bound by theory, it is believed that homodimers modulate the avid binding of the higher order multimers over time and may be able to form higher ordered multimers in vivo. Without being bound by theory, it is also believed that the multimers of the present invention dissociate slowly from bound target and are internalized in immune cells expressing those targets, possibly altering the activation status or maturation rate of that immune cell for a prolonged period or possibly forever. The multimerization experiments described herein show that an otherwise pure population of homodimers is able to multimerize in the presence of low levels of blood or fetal bovine serum. Therefore, while higher ordered multimers are more effective than the homodimer fraction in modulating the immune response, the homodimer fraction of the naturally linked stradomers of the current invention may also be effective immune modulators, in part through multimerization of the homodimer in the presence of low levels of blood or serum. Therefore, by "higher order multimers" we mean multimers beyond the homodimer that are formed in solution prior to injection into a subject as well as multimers beyond the homodimer that are formed in vivo.

"Immune modulating activities," "modulating immune response," "modulating the immune system," and "immune modulation" mean altering immune systems by changing the activities, capacities, and relative numbers of one or more immune cells, including maturation of a cell type within its cell type or into other cell types. For example, immune modulation may be suppression or an activation of an immune response. For example, in one aspect, immune modulation may mean the induction of non-responsiveness or tolerance in a T cell or a B cell. The term "tolerance," as used herein, refers to a state in a T cell or a B cell, or in the immune response as a whole, wherein the T cell or B cell or other immune cell does not respond to its cognate antigen or to an antigen, epitope, or other signal to which it would normally respond. As another example, immune modulation of memory B cells may lead to selective apoptosis of certain memory B cells with concomitant decreases in production of particular antibodies. As another example, immune modulating activities may lead to decreases of proinflammatory cytokines or cytokines that are commonly elevated in autoimmune diseases such as IL-6 and IL-8. As another example, immune modulating activities may lead to activation of NKT cells with subsequent secretion and cleavage of TGF-beta. Blockading immune cell receptors to prevent receptor activation is also encompassed within "immune modulation" and may be separately referred to as "inhibitory immune modulation." In another aspect, immune modulation may be an enhancement or activation of an immune response. For example, immune modulation may mean the activation of T cells or B cells. As another example, immune modulation of immature monocytes may lead to greater populations of more mature monocytes, dendritic cells, macrophages, or osteoclasts, all of which are derived from immature monocytes. As another example, immune modulation of NK cells may lead to enhanced Antibody Dependent Cell Cytotoxicity (ADCC). As another example, immune modulating activities may lead to increased populations of cells with phenotypes that may otherwise not be expressed at high levels, such as $CD8\beta^+/CD11c^+$ cells. For example, immune cell receptors may be bound by immunologically active biomimetics and activate intracellular signaling to induce various immune cell changes, referred to separately as "activating immune modulation."

Modulation of dendritic cells may promote or inhibit antigen presentation to T cells for example by the induction of expression of CD86 and/or CD1a on the surface of dendritic cells. CD1a is an MHC-class I-related glycoprotein that is expressed on the surface of antigen presenting cells, particularly dendritic cells. CD1a is involved in the presentation of lipid antigens to T cells. CD86 is also expressed on the surface of antigen presenting cells and provides costimulation to T cells. CD86 is a ligand to both CD28 and CTLA-4 on the surface of T cells to send activating and inhibitory signals, respectively. Therefore, the level of expression of CD86 and its cognate receptors, determines whether tolerance or a specific immune response will be induced. In a preferred embodiment, the stradomers of the current invention are capable of modulating the immune response, in part by inducing the expression of CD86 and CD1a on the surface of antigen presenting cells, particularly dendritic cells. In one embodiment, the modulated dendritic cell interacts with immune cells specific for the antigen of the antigen-specific stradomer.

Modulation of maturation of a monocyte refers to the differentiation of a monocyte into a mature DC, a macrophage, or an osteoclast. Differentiation may be modulated to accelerate the rate or direction of maturation and/or to increase the number of monocytes undergoing differentiation. Alternatively, differentiation may be reduced in terms of rate of differentiation and/or number of cells undergoing differentiation.

The term "isolated" polypeptide or peptide as used herein refers to a polypeptide or a peptide which either has no naturally-occurring counterpart or has been separated or purified from components which naturally accompany it, e.g., in tissues such as pancreas, liver, spleen, ovary, testis, muscle, joint tissue, neural tissue, gastrointestinal tissue, or breast tissue or tumor tissue (e.g., breast cancer tissue), or body fluids such as blood, serum, or urine. Typically, the polypeptide or peptide is considered "isolated" when it is at least 70%, by dry weight, free from the proteins and other naturally-occurring organic molecules with which it is naturally associated. Preferably, a preparation of a polypeptide (or peptide) of the invention is at least 80%, more preferably at least 90%, and most preferably at least 99%, by dry weight, the polypeptide (peptide), respectively, of the invention. Since a polypeptide or peptide that is chemically synthesized is, by its nature, separated from the components that naturally accompany it, the synthetic polypeptide or peptide is "isolated."

An isolated polypeptide (or peptide) of the invention can be obtained, for example, by extraction from a natural source (e.g., from tissues or bodily fluids); by expression of a recombinant nucleic acid encoding the polypeptide or peptide; or by chemical synthesis. A polypeptide or peptide that is produced in a cellular system different from the source from which it naturally originates is "isolated," because it will necessarily be free of components which naturally accompany it. In a preferred embodiment, the isolated polypeptide of the current invention contains only the sequences corresponding to the IgG1 Fc monomer and the IgG2 hinge multimerization domain (SEQ ID NO: 4), the isoleucine multimerization domain (SEQ ID NO: 5) or the GPP multimerization domain (SEQ ID NO: 6) and no further sequences that may aid in the cloning or purification of the protein (i.e. introduced restriction enzyme recognition sites or purification tags). The degree of isolation or purity can be measured by any appropriate method, e.g., column chromatography, polyacrylamide gel electrophoresis, or HPLC analysis.

Pharmaceutical Compositions

Administration of the stradomer compositions described herein will be via any common route, orally, parenterally, or topically. Exemplary routes include, but are not limited to oral, nasal, buccal, rectal, vaginal, ophthalmic, subcutaneous, intramuscular, intraperitoneal, intravenous, intraarterial, intratumoral, spinal, intrathecal, intra-articular, intraarterial, sub-arachnoid, sublingual, oral mucosal, bronchial, lymphatic, intra-uterine, subcutaneous, intratumor, integrated on an implantable device such as a suture or in an implantable device such as an implantable polymer, intradural, intracortical, or dermal. Such compositions would normally be administered as pharmaceutically acceptable compositions as described herein. In a preferred embodiment the isolated stradomer is administered intravenously or subcutaneously.

The term "pharmaceutically acceptable carrier" as used herein includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the vectors or cells of the present invention, its use in therapeutic compositions is contemplated. Supplementary active ingredients also can be incorporated into the compositions.

The stradomer compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Sterile injectable solutions are prepared by incorporating the stradomer in the required amount in the appropriate solvent with various of the other ingredients enumerated above, as required, followed by filtered sterilization. In some embodiments, the sterile injectable solutions are formulated for intramuscular, subcutaneous, or intravenous administration. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Further, one embodiment is a stradomer composition suitable for oral administration and is provided in a pharmaceutically acceptable carrier with or without an inert diluent. The carrier should be assimilable or edible and includes liquid, semi-solid, i.e., pastes, or solid carriers. Except insofar as any conventional media, agent, diluent or carrier is detrimental to the recipient or to the therapeutic effectiveness of a stradomer preparation contained therein, its use in an orally administrable a stradomer composition for use in practicing the methods of the present invention is appropriate. Examples of carriers or diluents include fats, oils, water, saline solutions, lipids, liposomes, resins, binders, fillers and the like, or combinations thereof. The term "oral administration" as used herein includes oral, buccal, enteral or intragastric administration.

In one embodiment, the stradomer composition is combined with the carrier in any convenient and practical manner, i.e., by solution, suspension, emulsification, admixture, encapsulation, microencapsulation, absorption and the like. Such procedures are routine for those skilled in the art.

In a specific embodiment, the stradomer composition in powder form is combined or mixed thoroughly with a semi-solid or solid carrier. The mixing can be carried out in any convenient manner such as grinding. Stabilizing agents can be also added in the mixing process in order to protect the composition from loss of therapeutic activity through, i.e., denaturation in the stomach. Examples of stabilizers for use in an orally administrable composition include buffers, antagonists to the secretion of stomach acids, amino acids such as glycine and lysine, carbohydrates such as dextrose, mannose, galactose, fructose, lactose, sucrose, maltose, sorbitol, mannitol, etc., proteolytic enzyme inhibitors, and the like. More preferably, for an orally administered composition, the stabilizer can also include antagonists to the secretion of stomach acids.

Further, the stradomer composition for oral administration which is combined with a semi-solid or solid carrier can be further formulated into hard or soft shell gelatin capsules, tablets, or pills. More preferably, gelatin capsules, tablets, or pills are enterically coated. Enteric coatings prevent denaturation of the composition in the stomach or upper bowel where the pH is acidic. See, i.e., U.S. Pat. No. 5,629,001. Upon reaching the small intestines, the basic pH therein dissolves the coating and permits the composition to be released to interact with intestinal cells, e.g., Peyer's patch M cells.

In another embodiment, the stradomer composition in powder form is combined or mixed thoroughly with materials that create a nanoparticle encapsulating the immunologically active biomimetic or to which the immunologically active biomimetic is attached. Each nanoparticle will have a size of less than or equal to 100 microns. The nanoparticle may have mucoadhesive properties that allow for gastrointestinal absorption of an immunologically active biomimetic that would otherwise not be orally bioavailable.

In another embodiment, a powdered composition is combined with a liquid carrier such as, i.e., water or a saline solution, with or without a stabilizing agent.

A specific stradomer formulation that may be used is a solution of immunologically active biomimetic protein in a hypotonic phosphate based buffer that is free of potassium where the composition of the buffer is as follows: 6 mM sodium phosphate monobasic monohydrate, 9 mM sodium phosphate dibasic heptahydrate, 50 mM sodium chloride, pH 7.0+/−0.1. The concentration of immunologically active biomimetic protein in a hypotonic buffer may range from 10 microgram/ml to 100 milligram/ml. This formulation may be administered via any route of administration, for example, but not limited to intravenous administration.

Further, a stradomer composition for topical administration which is combined with a semi-solid carrier can be further formulated into a cream or gel ointment. A preferred carrier for the formation of a gel ointment is a gel polymer. Preferred polymers that are used to manufacture a gel composition of the present invention include, but are not limited to carbopol, carboxymethyl-cellulose, and pluronic polymers. Specifically, a powdered Fc multimer composition is combined with an aqueous gel containing an polymerization agent such as Carbopol 980 at strengths between 0.5% and 5% wt/volume for application to the skin for treatment of disease on or beneath the skin. The term "topical administration" as used herein includes application to a dermal, epidermal, subcutaneous or mucosal surface.

Further, a stradomer composition can be formulated into a polymer for subcutaneous or subdermal implantation. A preferred formulation for the implantable drug-infused polymer is an agent Generally Regarded as Safe and may include, for example, cross-linked dextran (Samantha Hart, Master of Science Thesis, "Elution of Antibiotics from a Novel Cross-Linked Dextran Gel: Quantification" Virginia Polytechnic Institute and State University, Jun. 8, 2009) dextran-tyramine (Jin, et al. (2010) Tissue Eng. Part A. 16(8):2429-40), dextran-polyethylene glycol (Jukes, et al. (2010) Tissue Eng. Part A., 16(2):565-73), or dextran-gluteraldehyde (Brondsted, et al. (1998) J. Controlled Release, 53:7-13). One skilled in the art will know that many similar polymers and hydrogels can be formed incorporating the stradomer fixed within the polymer or hydrogel and controlling the pore size to the desired diameter.

Upon formulation, solutions are administered in a manner compatible with the dosage formulation and in such amount as is therapeutically effective to result in an improvement or remediation of the symptoms. The formulations are easily administered in a variety of dosage forms such as ingestible solutions, drug release capsules and the like. Some variation in dosage can occur depending on the condition of the subject being treated. The person responsible for administration can, in any event, determine the appropriate dose for the individual subject. Moreover, for human administration, preparations meet sterility, general safety and purity standards as required by FDA Center for Biologics Evaluation and Research standards.

The route of administration will vary, naturally, with the location and nature of the disease being treated, and may include, for example intradermal, transdermal, subdermal, parenteral, nasal, intravenous, intramuscular, intranasal, subcutaneous, percutaneous, intratracheal, intraperitoneal, intratumoral, perfusion, lavage, direct injection, and oral administration.

In one embodiment, the stradomer is administered intravenously, subcutaneously, orally, intraperitoneally, sublingually, buccally, transdermally, rectally, by subdermal implant, or intramuscularly. In particular embodiments, the stradomer is administered intravenously, subcutaneously, or intramuscularly. In one embodiment, the stradomer is administered at a dose of about 0.01 mg/Kg to about 1000 mg/Kg. In a further embodiment, the stradomer is administered at about 0.1 mg/Kg to about 100 mg/Kg. In yet a further embodiment, the stradomer is administered at about 0.5 mg/Kg to about 50 mg/Kg. In still a further embodiment, the stradomer is administered at about 1 mg/Kg to about 25 mg/Kg. In still a further embodiment, the stradomer is administered at about 5 mg/Kg to about 15 mg/Kg. The stradomer may be administered at least once daily, weekly, biweekly or monthly. A biphasic dosage regimen may be used wherein the first dosage phase comprises about 0.1% to about 300% of the second dosage phase.

In a further embodiment, the stradomer is administered before, during or after administration of one or more additional pharmaceutical and/or therapeutic agents. In a further embodiment the additional pharmaceutically active agent comprises a steroid; a biologic anti-autoimmune drug such as a monoclonal antibody, a fusion protein, or an anti-cytokine; a non-biologic anti-autoimmune drug; an immunosuppressant; an antibiotic; and anti-viral agent; a cytokine; or an agent otherwise capable of acting as an immune-modulator. In still a further embodiment, the steroid is prednisone, prednisolone, cortisone, dexamethasone, mometasone testosterone, estrogen, oxandrolone, fluticasone, budesonide, beclamethasone, albuterol, or levalbuterol. In still a further embodiment, the monoclonal antibody is eculizumab, infliximab, adalimumab, rituximab, tocilizumab, golimumab, ofatumumab, LY2127399, belimumab, veltuzumab, mepolizumab, necitumumab, nivolumab, dinutuximab, secukinumab, evolocumab, blinatumomab, pembrolizumab, ramucirumab, vedolizumab, siltuximab, obinutuzumab, adotrastuzumab, raxibacumab, pertuzumab, brentuximab, ipilumumab, denosumab, canakinumab, ustekinumab, catumaxomab, ranibizumab, panitumumab, natalizumab, bevacizumab, cetuximab, efalizumab, omalizumab, toitumomab-I131, alemtuzumab, gemtuzumab, trastuzumab, palivizumab, basilixumab, daclizumab, abciximab, murononomab or certolizumab. In still a further embodiment, the fusion protein is etanercept or abatacept. In still a further embodiment, the anti-cytokine biologic is anakinra. In still a further embodiment, the anti-rheumatic non-biologic drug is cyclophosphamide, methotrexate, azathioprine, hydroxychloroquine, leflunomide, minocycline, organic gold compounds, fostamatinib, tofacitinib, etoricoxib, or sulfasalazine. In still a further embodiment, the immunosuppressant is cyclosporine A, tacrolimus, sirolimus, mycophenolate mofetil, everolimus, OKT3, antithymocyte globulin, basiliximab, daclizumumab, or alemtuzumab. In still a further embodiment, the stradomer is administered before, during or after administration of a chemotherapeutic agent. In still a further embodiment, the stradomer and the additional therapeutic agent display therapeutic synergy when administered together. In one embodiment, the stradomer is administered prior to the administration of the additional therapeutic against. In another embodiment, the stradomer is administered at the same time as the administration of the additional therapeutic agent. In still another embodiment, the stradomer is administered after the administration with the additional therapeutic agent.

In one embodiment, the stradomer is administered covalently fixed to an implantable device. In one embodiment the stradomer is fixed to a suture. In another embodiment the stradomer is fixed to a graft or stent. In another embodiment the stradomer is fixed to a heart valve, an orthopedic joint replacement, or implanted electronic lead. In another embodiment the stradomer is fixed to and embedded within an implantable matrix. In a preferred embodiment the stradomer is fixed to and embedded within an implantable hydrogel. In one embodiment the hydrogel is comprised of dextran, polyvinyl alcohol, sodium polyacrylate, or acrylate polymers. In a further embodiment, the stradomer is administered fixed in a hydrogel with pore sizes large enough to allow entry of immune cells to interact with the fixed stradomer and then return to circulation. In a further embodiment, the pore size of the hydrogel is 5 to 50 microns. In a preferred embodiment, the pore size of the hydrogel is 25-30 microns.

In another embodiment, the stradomer is administered to treat humans, non-human primates (e.g., monkeys, baboons, and chimpanzees), mice, rats, bovines, horses, cats, dogs, pigs, rabbits, goats, deer, sheep, ferrets, gerbils, guinea pigs, hamsters, bats, birds (e.g., chickens, turkeys, and ducks), fish and reptiles with species-specific or chimeric stradomer molecules. In another embodiment, the human is an adult or a child. In still another embodiment, the stradomer is administered to prevent a complement-mediated disease. In a further embodiment the stradomer is administered to prevent vaccine-associated autoimmune conditions in companion animals and livestock.

The term "parenteral administration" as used herein includes any form of administration in which the compound is absorbed into the subject without involving absorption via the intestines. Exemplary parenteral administrations that are used in the present invention include, but are not limited to intramuscular, intravenous, intraperitoneal, intratumoral, intraocular, nasal or intraarticular administration.

In addition, the stradomer of the current invention may optionally be administered before, during or after another pharmaceutical agent. For example, it has been surprisingly found that concomitant administration of the stradomer of the current invention and prednisolone achieves synergistically superior results than that observed with either the stradomer composition or the prednisolone alone (WO 2012/016073).

Below are specific examples of various pharmaceutical formulation categories and preferred routes of administration, as indicated, for specific exemplary diseases:

Buccal or sub-lingual dissolvable tablet: angina, polyarteritis nodosa.

Intravenous, intramuscular, or subcutaneous: myasthenia gravis, hemolytic uremic syndrome (HUS), atypical hemolytic uremic syndrome (aHUS), paroxysmal nocturnal hemoglobinuria (PNH), membranous nephropathy, neuromyelitis optica, antibody-mediated rejection of allografts, membranoproliferative glomerulonephritis (MPGN), lupus nephritis, Idiopathic Thrombocytopenic Purpura, Inclusion Body Myositis, Paraproteinemic IgM demyelinating Polyneuropathy, Necrotizing fasciitis, Pemphigus, Gangrene, Dermatomyositis, Granuloma, Lymphoma, Sepsis, Aplastic anemia, Multisystem organ failure, Multiple Myeloma and Monoclonal Gammopathy of Unknown Significance, Chronic Inflammatory Demyelinating Polyradiculoneuropathy, Inflammatory Myopathies, Thrombotic thrombocytopenic purpura, Myositis, Anemia, Neoplasia, Hemolytic anemia, Encephalitis, Myelitis, Myelopathy especially associated with Human T-cell lymphotropic virus-1, Leukemia, Multiple sclerosis and optic neuritis, Asthma, Epidermal necrolysis, Lambert-Eaton myasthenic syndrome, Myasthenia gravis, Neuropathy, Uveitis, Guillain-Barré syndrome, Graft Versus Host Disease, Stiff Man Syndrome, Paraneoplastic cerebellar degeneration with anti-Yo antibodies, paraneoplastic encephalomyelitis and sensory neuropathy with anti-Hu antibodies, systemic vasculitis, Systemic Lupus Erythematosus, autoimmune diabetic neuropathy, acute idiopathic dysautonomic neuropathy, Vogt-Koyanagi-Harada Syndrome, Multifocal Motor Neuropathy, Lower Motor Neuron Syndrome associated with anti-/GM1, Demyelination, Membranoproliferative glomerulonephritis, Cardiomyopathy, Kawasaki's disease, Rheumatoid arthritis, and Evan's syndrome IM-ITP, CIDP, MS, dermatomyositis, myasthenia gravis, muscular dystrophy. The term "intravenous administration" as used herein includes all techniques to deliver a compound or composition of the present invention to the systemic circulation via an intravenous injection or infusion.

Dermal gel, lotion, cream or patch: vitiligo, Herpes zoster, acne, chelitis.

Rectal suppository, gel, or infusion: ulcerative colitis, hemorrhoidal inflammation.

Oral as pill, troche, encapsulated, or with enteric coating: Crohn's disease, celiac sprue, irritable bowel syndrome, inflammatory liver disease, Barrett's esophagus.

Intra-cortical: epilepsy, Alzheimer's, multiple sclerosis, Parkinson's Disease, Huntingdon's Disease.

Intra-abdominal infusion or implant: endometriosis.

Intra-vaginal gel or suppository: bacterial, trichomonal, or fungal vaginitis.

Medical devices: coated on coronary artery stent, prosthetic joints.

Therapeutic Applications of Complement-Preferential Stradomers

In one embodiment, a method for treating or preventing a disease or condition such as a complement-mediated disease or condition is provided, comprising administering to a subject in need thereof a stradomer comprising an IgG1 Fc domain and a multimerization domain, wherein the stradomer exhibits an increased ratio of complement binding to Fc receptor binding. In a further embodiment, the stradomer exhibits reduced or absent binding to FcγR and/or reduced or absent binding to FcRn binding and exhibits enhanced or preferential binding to complement. In a further embodiment, the stradomer exhibits enhanced or preferential binding to C1q.

Based on rational design and in vitro and in vivo validations, the stradomers of the present invention will serve as important biopharmaceuticals for treating inflammatory diseases and disorders, particularly complement-mediated diseases and disorders; as well as for altering immune function in a variety of other contexts such as bioimmunotherapy for allergies, cancer, autoimmune diseases, infectious diseases, and inflammatory diseases. Medical conditions suitable for treatment with the immunologically active complement-preferential biomimetics disclosed herein include any disease caused by or associated with complement activation or complement-mediated effector functions, including increased or inappropriate complement activity. Such medical conditions include those that are currently or have previously been treated with complement binding drugs such as eculizumab. Eculizumab binds to complement protein C5 (a complement protein that is downstream of C1 and C1q in the classical complement pathway), inhibiting its cleavage and subsequent complement-mediated cell lysis. The biomimetics of the present invention provide a safe and effective alternative to other complement-binding drugs known in the art. For example, in some embodiments, the biomimetics of the present invention bind C1q, the first subunit in the C1 complex of the classical complement pathway. Medical conditions suitable for treatment with the immunologically active complement-preferential biomimetics include, but are not limited to, myasthenia gravis, hemolytic uremic syndrome (HUS), atypical hemolytic uremic syndrome (aHUS), paroxysmal nocturnal hemoglobinuria (PNH), neuromyelitis optica, antibody-mediated rejection of allografts, macular degeneration, sickle cell disease, and membranoproliferative glomerulonephritis (MPGN). Additional medical conditions suitable for treatment with the immunologically active complement-preferential biomimetics described herein include those currently routinely treated with broadly immune suppressive therapies including hIVIG, or in which hIVIG has been found to be clinically useful such as autoimmune cytopenias, chronic inflammatory demyelinating polyneuropathy, Guillain-Barre' syndrome, myasthenia gravis, anti-Factor VIII autoimmune disease, dermatomyositis, vasculitis, and uveitis (See, F. G. van der Meche, P. I. Schmitz, N. Engl. J. Med. 326, G1123 (1992); P. Gajdos et al, Lancet i, 406 (1984); Y. Sultan, M. D. Kazatchkine, P. Maisonneuve, U. E. Nydegger, Lancet ii, 765 (1984); M. C. Dalakas et al., N. Engl. J. Med. 329, 1993 (1993); D. R. Jayne, M. J. Davies, C. J. Fox, C. M. Black, C. M. Lockwood, Lancet 337, 1137 (1991); P. LeHoang, N. Cassoux, F. George, N. Kullmann, M. D. Kazatchkine, Ocul. Immunol. Inflamm. 8, 49 (2000)) and those cancers or inflammatory disease conditions in which a monoclonal antibody may be used or is already in clinical use. Conditions included among those that may be effectively treated by the compounds that are the subject of this invention include an inflammatory disease with an imbalance in cytokine networks, an autoimmune disorder mediated by pathogenic autoantibodies or autoaggressive T cells, or an acute or chronic phase of a chronic relapsing autoimmune, inflammatory, or infectious disease or process.

In addition, other medical conditions having an inflammatory component involving complement will benefit from treatment with stradomers such as Amyotrophic Lateral Sclerosis, Huntington's Disease, Alzheimer's Disease, Parkinson's Disease, Myocardial Infarction, Stroke, Hepatitis B, Hepatitis C, Human Immunodeficiency Virus associated inflammation, adrenoleukodystrophy, and epileptic disorders especially those believed to be associated with postviral encephalitis including Rasmussen Syndrome, West Syndrome, and Lennox-Gastaut Syndrome.

The general approach to therapy using the isolated stradomers described herein is to administer to a subject having a disease or condition, a therapeutically effective amount of the isolated immunologically active biomimetic to effect a treatment. In some embodiments, diseases or conditions may be broadly categorized as inflammatory diseases with an imbalance in cytokine networks, an autoimmune disorder mediated by pathogenic autoantibodies or autoaggressive T cells, or an acute or chronic phase of a chronic relapsing disease or process.

The term "treating" and "treatment" as used herein refers to administering to a subject a therapeutically effective amount of a stradomer of the present invention so that the subject has an improvement in a disease or condition, or a symptom of the disease or condition. The improvement is any improvement or remediation of the disease or condition, or symptom of the disease or condition. The improvement is an observable or measurable improvement, or may be an improvement in the general feeling of well-being of the subject. Thus, one of skill in the art realizes that a treatment may improve the disease condition, but may not be a complete cure for the disease. Specifically, improvements in subjects may include one or more of: decreased inflammation; decreased inflammatory laboratory markers such as C-reactive protein; decreased autoimmunity as evidenced by one or more of: improvements in autoimmune markers such as autoantibodies or in platelet count, white cell count, or red cell count, decreased rash or purpura, decrease in weakness, numbness, or tingling, increased glucose levels in patients with hyperglycemia, decreased joint pain, inflammation, swelling, or degradation, decrease in cramping and diarrhea frequency and volume, decreased angina, decreased tissue inflammation, or decrease in seizure frequency; decreases in cancer tumor burden, increased time to tumor progression, decreased cancer pain, increased survival or improvements in the quality of life; or delay of progression or improvement of osteoporosis.

The term "therapeutically effective amount" as used herein refers to an amount that results in an improvement or remediation of the symptoms of the disease or condition.

As used herein, "prophylaxis" can mean complete prevention of the symptoms of a disease, a delay in onset of the symptoms of a disease, or a lessening in the severity of subsequently developed disease symptoms.

The term "subject" as used herein, is taken to mean any mammalian subject to which stradomers of the present invention are administered according to the methods described herein. In a specific embodiment, the methods of the present disclosure are employed to treat a human subject. The methods of the present disclosure may also be employed to treat non-human primates (e.g., monkeys, baboons, and chimpanzees), mice, rats, bovines, horses, cats, dogs, pigs, rabbits, goats, deer, sheep, ferrets, gerbils, guinea pigs, hamsters, bats, birds (e.g., chickens, turkeys, and ducks), fish and reptiles to produce species-specific or chimeric stradomer molecules.

In one embodiment, the stradomers of the present invention provide superior safety and efficacy relative to other complement-binding molecules. In a further embodiment, the stradomers of the present invention exhibit superior safety and efficacy relative to the anti-C5 antibody eculizumab.

Complement inhibition has been demonstrated to decrease antibody-mediated diseases (See for example Stegall et al. Terminal Complement Inhibition Decreases Antibody-Mediated Rejection in Sensitized Renal Transplant Recipients. American Journal of Transplantation 2011 November; 11(1):2405-2413-Epub 2011 Sep. 22; DOI: 10.1111/j.1600-6143.2011.03757.x). The stradomers of the present invention may also be used to treat a disease or condition that is antibody-mediated. Auto-antibodies mediate many known autoimmune diseases and likely play a role in numerous other autoimmune diseases. Recognized antibody mediated diseases in which the stradomers of the present invention may be used include, but are not limited to, anti-glomerular basement membrane antibody mediated nephritis including Goodpasture's; anti-donor antibodies (Donor Specific Alloantibodies) in solid organ transplantation; anti-Aquaporin-4 Antibody in Neuromyelitis Optica; anti-VGKC antibody in neuromyotonia, limbic encephalitis, and Morvan's syndrome; anti-nicotinic acetylcholine receptor and anti-MuSK antibodies in Myasthenia gravis; anti-VGCC antibodies in Lambert Eaton myasthenic syndrome; anti-AMPAR and anti-GABA(B)R antibodies in limbic encephalitis often associated with tumors; anti-GlyR antibodies in stiff person syndrome or hyperekplexia; anti-phospholipid, anti-cardiolipin, and anti-$\beta_2$ glycoprotein I antibodies in recurrent spontaneous abortion, Hughes syndrome, and Systemic Lupus Erythematosus; anti-Glutamic acid decarboxylase antibodies in stiff person syndrome, autoimmune cerebellar ataxia or limbic encephalitis; anti-NMDA receptor antibodies in a newly-described syndrome including both limbic and subcortical features with prominent movement disorders often in young adults and children that is often associated with ovarian teratoma but can be non-paraneoplastic; anti-double stranded DNA, anti-single stranded DNA, anti-RNA, anti-SM, and anti-C1q antibodies in Systemic Lupus Erythematosus; anti-nuclear and anti-nucleolar antibodies in Connective Tissue Diseases including scleroderma, Sjogren's syndrome, and Polymyositis including anti-Ro, anti-La, anti-Scl 70, anti-Jo-1; anti-Rheumatoid Factor antibodies in rheumatoid arthritis; anti-Hepatitis B Surface Antigen antibodies in Polyarteritis Nodosa; anti-Centromere antibodies in CREST syndrome; anti-streptococcal antibodies in or as a risk for endocarditis; anti-thyroglobulin, anti-thyroid peroxidase, and anti-TSH receptor antibodies in Hashimoto's thyroiditis; anti-U1 RNP antibodies in Mixed Connective Tissue Disease and Systemic Lupus Erythematosus; and anti-desmoglein and anti-keratinocyte antibodies in pemphigus.

The stradomers of the present invention may be used to treat conditions including but not limited to congestive heart failure (CHF), vasculitis, rosacea, acne, eczema, myocarditis and other conditions of the myocardium, systemic lupus erythematosus, diabetes, spondylopathies, synovial fibroblasts, and bone marrow stroma; bone loss; Paget's disease, osteoclastoma; multiple myeloma; breast cancer; disuse osteopenia; malnutrition, periodontal disease, Gaucher's disease, Langerhans' cell histiocytosis, spinal cord injury, acute septic arthritis, osteomalacia, Cushing's syndrome, monoostotic fibrous dysplasia, polyostotic fibrous dysplasia, periodontal reconstruction, and bone fractures; sarcoidosis; osteolytic bone cancers, lung cancer, kidney cancer and rectal cancer; bone metastasis, bone pain management, and humoral malignant hypercalcemia, ankylosing spondylitis and other spondyloarthropathies; transplantation rejection, viral infections, hematologic neoplasias and neoplastic-like conditions for example, Hodgkin's lymphoma; non-Hodgkin's lymphomas (Burkitt's lymphoma, small lymphocytic lymphoma/chronic lymphocytic leukemia, mycosis fungoides, mantle cell lymphoma, follicular lymphoma, diffuse large B-cell lymphoma, marginal zone lymphoma, hairy cell leukemia and lymphoplasmacytic leukemia), tumors of lymphocyte precursor cells, including B-cell acute lymphoblastic leukemia/lymphoma, and T-cell acute lymphoblastic leukemia/lymphoma, thymoma, tumors of the mature T and NK cells, including peripheral T-cell leukemias, adult T-cell leukemia/T-cell lymphomas and large granular lymphocytic leukemia, Langerhans cell histiocytosis, myeloid neoplasias such as acute myelogenous leukemias, including AML with maturation, AML without differentiation, acute promyelocytic leukemia, acute myelomonocytic leukemia, and acute monocytic leukemias, myelodysplastic syndromes, and chronic myeloproliferative disorders, including chronic myelogenous leukemia, tumors of the central nervous system, e.g., brain tumors (glioma, neuroblastoma, astrocytoma, medulloblastoma, ependymoma, and retinoblastoma), solid tumors (nasopharyngeal cancer, basal cell carcinoma, pancreatic cancer, cancer of the bile duct, Kaposi's sarcoma, testicular cancer, uterine, vaginal or cervical cancers, ovarian cancer, primary liver cancer or endometrial cancer, tumors of the vascular system (angiosarcoma and hemangiopericytoma)) or other cancer.

"Cancer" herein refers to or describes the physiological condition in mammals that is typically characterized by unregulated cell growth. Examples of cancer include but are not limited to carcinoma, lymphoma, blastoma, sarcoma (including liposarcoma, osteogenic sarcoma, angiosarcoma, endotheliosarcoma, leiomyosarcoma, chordoma, lymphangiosarcoma, lymphangioendotheliosarcoma, rhabdomyosarcoma, fibrosarcoma, myxosarcoma, chondrosarcoma), neuroendocrine tumors, mesothelioma, synovioma, schwannoma, meningioma, adenocarcinoma, melanoma, and leukemia or lymphoid malignancies. More particular examples of such cancers include squamous cell cancer (e.g. epithelial squamous cell cancer), lung cancer including small-cell lung cancer, non-small cell lung cancer, adenocarcinoma of the lung and squamous carcinoma of the lung, small cell lung carcinoma, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulvar cancer, thyroid cancer, hepatic carcinoma, anal carcinoma, penile carcinoma, testicular cancer, esophageal cancer, tumors of the biliary tract, Ewing's tumor, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, testicular tumor, lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemia, lymphoma, multiple myeloma, Waldenstrom's macroglobulinemia, myelodysplastic disease, heavy chain disease, neuroendocrine tumors, Schwannoma, and other carcinomas, as well as head and neck cancer.

The stradomers of the present invention may be used to treat autoimmune diseases. The term "autoimmune disease" as used herein refers to a varied group of more than 80 diseases and conditions. In all of these diseases and conditions, the underlying problem is that the body's immune system attacks the body itself. Autoimmune diseases affect all major body systems including connective tissue, nerves, muscles, the endocrine system, skin, blood, and the respiratory and gastrointestinal systems. Autoimmune diseases include, for example, systemic lupus erythematosus, rheumatoid arthritis, multiple sclerosis, myasthenia gravis, and type 1 diabetes.

The disease or condition treatable using the compositions and methods of the present invention may be a hematoimmunological process, including but not limited to Sickle Cell Disease, Idiopathic Thrombocytopenic Purpura, alloimmune/autoimmune thrombocytopenia, Acquired immune thrombocytopenia, Autoimmune neutropenia, Autoimmune hemolytic anemia, Parvovirus B19-associated red cell aplasia, Acquired antifactor VIII autoimmunity, acquired von Willebrand disease, Multiple Myeloma and Monoclonal Gammopathy of Unknown Significance, Sepsis, Aplastic anemia, pure red cell aplasia, Diamond-Blackfan anemia, hemolytic disease of the newborn, Immune-mediated neutropenia, refractoriness to platelet transfusion, neonatal, post-transfusion purpura, hemolytic uremic syndrome, systemic Vasculitis, Thrombotic thrombocytopenic purpura, or Evan's syndrome.

The disease or condition may also be a neuroimmunological process, including but not limited to Guillain-Barre syndrome, Chronic Inflammatory Demyelinating Polyradiculoneuropathy, Paraproteinemic IgM demyelinating Polyneuropathy, Lambert-Eaton myasthenic syndrome, Myasthenia gravis, Multifocal Motor Neuropathy, Lower Motor Neuron Syndrome associated with anti-/GM1, Demyelination, Multiple Sclerosis and optic neuritis, Stiff Man Syndrome, Paraneoplastic cerebellar degeneration with anti-Yo antibodies, paraneoplastic encephalomyelitis, sensory neuropathy with anti-Hu antibodies, epilepsy, Encephalitis, Myelitis, Myelopathy especially associated with Human T-cell lymphotropic virus-1, Autoimmune Diabetic Neuropathy, Alzheimer's disease, Parkinson's disease, Huntingdon's disease, or Acute Idiopathic Dysautonomic Neuropathy.

The disease or condition may also be inflammation or autoimmunity associated with hearing loss or vision loss. For example, the disease or condition may be autoimmune-related hearing loss such as noise-induced hearing loss or age-related hearing loss, or may be associated with implantation of devices such as hearing devices (e.g., cochlear implants). In some embodiment, the compositions provided herein may be administered to a subject prior to, concurrently with, or subsequent to the implantation of a device.

The disease or condition may also be a Rheumatic disease process, including but not limited to Kawasaki's disease, Rheumatoid arthritis, Felty's syndrome, ANCA-positive Vasculitis, Spontaneous Polymyositis, Dermatomyositis, Antiphospholipid syndromes, Recurrent spontaneous abortions, Systemic Lupus Erythematosus, Juvenile idiopathic arthritis, Raynaud's, CREST syndrome, or Uveitis.

The disease or condition may also be a dermatoimmunological disease process, including but not limited to Toxic Epidermal Necrolysis, Gangrene, Granuloma, Autoimmune skin blistering diseases including Pemphigus vulgaris, Bullous Pemphigoid, Pemphigus foliaceus, Vitiligo, Streptococcal toxic shock syndrome, Scleroderma, systemic sclerosis including diffuse and limited cutaneous systemic sclerosis, or Atopic dermatitis (especially steroid dependent).

The disease or condition may also be a musculoskeletal immunological disease process, including but not limited to Inclusion Body Myositis, Necrotizing fasciitis, Inflammatory Myopathies, Myositis, Anti-Decorin (BJ antigen) Myopathy, Paraneoplastic Necrotic Myopathy, X-linked Vacuolated Myopathy, Penacillamine-induced Polymyositis, Atherosclerosis, Coronary Artery Disease, or Cardiomyopathy.

The disease or condition may also be a gastrointestinal immunological disease process, including but not limited to pernicious anemia, autoimmune chronic active hepatitis, primary biliary cirrhosis, Celiac disease, dermatitis herpetiformis, cryptogenic cirrhosis, Reactive arthritis, Crohn's disease, Whipple's disease, ulcerative colitis, or sclerosing cholangitis.

The disease or condition may also be Graft Versus Host Disease, Antibody-mediated rejection of the graft, Post-bone marrow transplant rejection, Postinfectious disease inflammation, Lymphoma, Leukemia, Neoplasia, Asthma, Type 1 Diabetes mellitus with anti-beta cell antibodies, Sjogren's syndrome, Mixed Connective Tissue Disease, Addison's disease, Vogt-Koyanagi-Harada Syndrome, Membranoproliferative glomerulonephritis, Goodpasture's syndrome, Graves' disease, Hashimoto's thyroiditis, Wegener's granulomatosis, micropolyarterits, Churg-Strauss syndrome, Polyarteritis nodosa or Multisystem organ failure.

"Allergy, as used herein, includes all immune reactions mediated by IgE as well as those reactions that mimic IgE-mediated reactions. Allergies are induced by allergens, including proteins, peptides, carbohydrates, and combinations thereof, that trigger an IgE or IgE-like immune response. Exemplary allergies include nut allergies, pollen allergies, and insect sting allergies. Exemplary allergens include urushiol in poison ivy and oak; house dust antigen; birch pollen components Bet v 1 and Bet v 2; the 15 kd antigen in celery; apple antigen Mal d 1; Pm p3 in peach; Timothy grass pollen allergen Phl p 1; Lol p 3, Lol p I, or Lol p V in Rye grass; Cyn d 1 in Bermuda grass; dust mite allergens dust mite der p1, der p2, or der f1; α-gliadin and γ-gliadin epitopes in gluten; bee venom phospholipase A2; Ara h 1, Ara h 2, and Ara h 3 epitopes in peanuts.

The disease or condition may be a glomerular disease and/or nephritis. Mesangial proliferation is a common feature of many human glomerular diseases including IgA nephropathy, resolving post-infectious glomerulonephritis and a number of secondary glomerular diseases such as lupus nephritis, Schonlein-Henoch purpura, rheumatoid arthritis, liver cirrhosis, Alport's syndrome, and diabetic nephropathy. The disease is characterized by varying degrees of mesangial hyper-cellularity and mesangial matrix expansion. In progressive cases these cellular changes may lead to glomerular capillary narrowing, sclerosis and capsular adhesions as a result of injury by a variety of immunologic, toxic, metabolic, mechanical, and inflammatory mediators. Although several experimental models have been developed, the most widely used model for the study of mesangial proliferation has been the anti-thymocyte (anti-Thy-1) model (Yamamoto and Wilson, "Quantitative and qualitative studies of antibody-induced mesangial cell damage in the rat." *Kidney International* 32; 514-24 (1987); Jefferson J A et al, "Experimental mesangial proliferative glomerulonephritis (the anti Thy-1.1 model)." *J. Nephrol* 12; 297-307 (1999)). Another model on nephropathy involves immunization of animals with a proximal tubular epithelial fraction (Fx1A) (Probetex, San Antonio Texas). Immunization of rats with Fx1A induces an immune complex "membranous" nephritis characterized by subepithelial immune deposits and proteinuria with clear resemblance to human disease (Heymann W. et al., *Proc Soc. Exp. Biol. Med.* 100:660-64 (1959); Edgington T S et al., *J Exp. Med.* 127; 555 (1968)). Fx1A contains a large glycoprotein gp330 (megalin) a nephritogenic antigen produced by glomerular epithelial cells. Administration of anti-Fx1A antibody produces a nephritis defined by two phases: 1) a heterologous phase representing an acute nephritis induced by exogenously administered antibody, and 2) a chronic autologous phase characterized by the production of the hosts own response to the exogenous (heterologous) sheep immunoglobulin planted within glomerular structures. The anti Fx1A membranous nephropathy model produces sub-epithelial deposits and proteinuria. The Passive Heymann Nephritis model and complement involvement in this model has been reviewed elsewhere (Jefferson et al. "Experimental Models of Membranous Nephropathy," *Drug Discov. Today Dis. Models* 7(1-2): 27-33 (2010).

The present invention further comprises methods and compositions effective for the treatment of diseases caused by infectious agents. Infectious agents include, but are not limited to, bacterial, mycological, parasitic, and viral agents. Examples of such infectious agents include the following: *Staphylococcus*, methicillin-resistant *Staphylococcus aureus*, *Escherichia coli*, streptococcaceae, neisseriaaceae, *Cocci*, enterobacteriaceae, *Enterococcus*, vancomycin-resistant *Enterococcus*, *Cryptococcus*, histoplasmosis, *Aspergillus*, pseudomonadaceae, vibrionaceae, *Campylobacter*, pasteurellaceae, *Bordetella*, *Francisella*, *Brucella*, legionellaceae, bacteroidaceae, gram-negative bacilli, *Clostridium*, *Corynebacterium*, *Propionibacterium*, gram-positive bacilli, *Anthrax*, *Actinomyces*, *Nocardia*, *Mycobacterium*, *Treponema*, *Borrelia*, *Leptospira*, *Mycoplasma*, *Ureaplasma*, *Rickettsia*, chlamydiae, *Candida*, systemic mycoses, opportunistic mycoses, protozoa, nematodes, trematodes, cestodes, adenoviruses, herpesviruses (including, for example, herpes simplex virus and Epstein Barr virus, and herpes zoster virus), poxviruses, papovaviruses, hepatitis viruses, (including, for example, hepatitis B virus and hepatitis C virus), papilloma viruses, orthomyxoviruses (including, for example, influenza A, influenza B, and influenza C), paramyxoviruses, coronaviruses, picornaviruses, reoviruses, togaviruses, flaviviruses, bunyaviridae, rhabdoviruses, rotavirus, respiratory syncitial virus, human immunodeficiency virus and retroviruses. Exemplary infectious diseases include but are not limited to candidiasis, candidemia, aspergillosis, streptococcal pneumonia, streptococcal skin and oropharyngeal conditions, gram negative sepsis, tuberculosis, mononucleosis, influenza, respiratory illness caused by Respiratory Syncytial Virus, malaria, schistosomiasis, and trypanosomiasis. The present invention comprises methods and compositions effective for the treatment of infectious disease, including but not limited to those caused by bacterial, mycological, parasitic, and viral agents. Exemplary infectious diseases include but are not limited to candidiasis, candidemia, aspergillosis, streptococcal pneumonia, streptococcal skin and oropharyngeal conditions, gram negative sepsis, tuberculosis, mononucleosis, influenza, respiratory illness caused by Respiratory Syncytial Virus, malaria, schistosomiasis, and trypanosomiasis.

In another embodiment, the stradomers herein described could be utilized in a priming system wherein blood is drawn from a patient and transiently contacted with the stradomer(s) for a period of time from about one half hour to about three hours prior to being introduced back into the patient. In this form of cell therapy, the patient's own effector cells are exposed to stradomer that is fixed on a matrix ex vivo in order to modulate the effector cells through exposure of the effector cells to stradomer. The blood including the modulated effector cells are then infused back into the patient. Such a priming system could have numerous clinical and therapeutic applications.

The stradomers disclosed herein may also be readily applied to alter immune system responses in a variety of contexts to affect specific changes in immune response profiles. Altering or modulating an immune response in a subject refers to increasing, decreasing or changing the ratio or components of an immune response. For example, cytokine production or secretion levels may be increased or decreased as desired by targeting complement along with the appropriate combination of FcγRs with a stradomer designed to bind complement and interact with those receptors. Antibody production may also be increased or decreased; the ratio of two or more cytokines or immune cell receptors may be changed; or additional types of cytokines or antibodies may be caused to be produced.

In a preferred embodiment, a subject with an autoimmune or inflammatory disease has their immune response altered comprising the step of administering a therapeutically effective amount of a stradomer described herein to a subject, wherein the therapeutically effective amount of the stradomer alters the immune response in the subject. Ideally this intervention treats the disease or condition in the subject. The altered immune response may be an increased or a decreased response and may involve altered cytokine levels including the levels of any of IL-6, IL-10, IL-8, IL-23, IL-7, IL-4, IL-12, IL-13, IL-17, TNF-alpha and IFN-alpha. In a preferred embodiment, 11-6 or IL-8 is decreased in response to therapy. In an especially preferred embodiment, IL-6 and IL-8 are decreased in response to therapy. The invention is however not limited by any particular mechanism of action of the described biomimetics. The altered immune response may be an altered autoantibody level in the subject. The altered immune response may be an altered autoaggressive T-cell level in the subject.

For example, reducing the amount of TNF-alpha production in autoimmune diseases can have therapeutic effects. A practical application of this is anti-TNF-alpha antibody therapy (e.g. REMICADE®) which is clinically proven to treat Plaque Psoriasis, Rheumatoid Arthritis, Psoriatic Arthritis, Crohn's Disease, Ulcerative Colitis and Ankylosing Spondylitis. These autoimmune diseases have distinct etiologies but share key immunological components of the disease processes related to inflammation and immune cell activity. A stradomer designed to reduce TNF-alpha production will likewise be effective in these and many other autoimmune diseases. The altered immune response profile may also be direct or indirect modulation to effect a reduction in antibody production, for example autoantibodies targeting a subject's own tissues, or altered autoaggressive T-cell levels in the subject. For example, Multiple Sclerosis is an autoimmune disorder involving autoreactive T-cells which may be treated by interferon beta therapy. See, e.g., Zafranskaya M, et al., Interferon-beta therapy reduces CD4+ and CD8+ T-cell reactivity in multiple sclerosis, Immunology 2007 May; 121(1):29-39-Epub 2006 Dec. 18. A stradomer design to reduce autoreactive T-cell levels will likewise be effective in Multiple Sclerosis and may other autoimmune diseases involving autoreactive T-cells.

The stradomers described herein may be used to modulate expression of co-stimulatory molecules from an immune cell, including a dendritic cell, a macrophage, an osteoclast, a monocyte, or an NK cell or to inhibit in these same immune cells' differentiation, maturation, or cytokine secretion, including interleukin-12 (IL-12), or of increasing cytokine secretion, including interleukin-10 (IL-10), or interleukin-6 (IL-6), or IL1-RA. A skilled artisan may also validate the efficacy of an immunologically active biomimetic by exposing an immune cell to the immunologically active biomimetic and measuring modulation of the immune cell function, wherein the immune cell is a dendritic cell, a macrophage, an osteoclast, or a monocyte. In one embodiment the immune cell is exposed to the immunologically active biomimetic in vitro and further comprising the step of determining an amount of a cell surface receptor or of a cytokine production, wherein a change in the amount of the cell surface receptor or the cytokine production indicates a modulation of the immune cell function. In another embodiment the immune cell is exposed to the immunologically active biomimetic in vivo in a model animal for an autoimmune disease further comprising a step of assessing a degree of improvement in the autoimmune disease.

The stradomers described herein may also be used as a component of a device. For example, in some embodiments, the stradomers provided herein may be coated on a device, such as a medical implant. For example, the stradomers may be coated on a coronary stent or as part of nanoparticle therapy to enhance penetration and prolong drug release, for example for intra-ophthalmic use in uveitis or macular degeneration. The stradomers described herein may also be used as a component of a diagnostic. In some embodiments, a skilled artisan may personalize therapy by determining in which patients use of a stradomer may be particularly beneficial. For example, the skilled artisan may expose a patient's immune cells to the immunologically active biomimetic and measuring modulation of the immune cell's activation or maturation by flow cytometry or cytokine profile in order to identify high responders.

All references cited herein are incorporated by reference in their entireties.

EXAMPLES

Example 1

Complement-Preferential Stradomers

Various approaches were taken to generate complement-preferential binding stradomers. Stradomers were generated in which at least one point mutation was introduced into the Fc domain, wherein the mutation enhanced complement binding. Specifically, the following mutations were made at positions 267, 268, and 324 of the Fc domain of the GL-2045 stradomer described in WO 2012/016073: S267E, H268F, and S324T. In some stradomers, additional mutations were made to further increase the ratio of complement binding to canonical FcγR binding by altering FcγR binding and/or FcRn binding. The amino acid sequences of the exemplary stradomers are shown above in Table 1 and Table 2.

For each stradomer generated, the level of canonical FcγR binding, FcRn binding at pH 7.4, complement C1q binding, and CDC inhibition were determined and compared to the parent stradomer, G045c (IgG1 Hinge—IgG1CH2 IgG1 CH3—IgG2 Hinge). In addition, some compounds were assessed for binding to other complement cascade components.

Binding of complement-preferential stradomers or parent stradomer G045c to FcγRT, FcγRIIb, FcγRIIIa, FcγRIIa, or FcRn was assessed. RU values of dissociation were measured by biolayer interferometry using a ForteBio Octet instrument. His-tagged receptor proteins were bound to the sensor tip in 1× kinetic analysis buffer from ForteBio after which the on rate of the receptor/protein was measured by transferring the sensor tip to a 1× kinetics buffer containing the purified stradomer of choice. Off rate was measured by transferring the sensor tip to a 1× kinetics buffer, and RU value was calculated from the measured maximum binding using the ForteBio software. Biolayer interferometry detects the binding between a ligand immobilized on the biosensor tip surface and an analyte in solution. When binding occurs it produces an increase in optical thickness at the biosensor tip, which results in a wavelength shift (detected as a response unit of "RU"). The maximum binding level (RU max) is the maximum possible amount of sample binding at equilibrium that saturates the amount of ligand on the sensor surface. The RU 300 is the residual sample binding after 300 seconds of dissociation and is useful to characterize the rate of dissociation of the test article from the test ligand.

To characterize the compounds, the maximum binding by biolayer interferometry (RU max) against the 5 Fc receptors, the ELISA binding to C1q, and the inhibition of CDC are presented in the data provided herein. To present differences in dissociation rate, the RU at 300 seconds is also provided for the compounds against the 5 Fc receptors. For both the RU max and the RU 300, in each case a visual reading of the absolute value was made from a ForteBio-generated plot of association and dissociation and then the Response was normalized on a 0-10 scale where 0 is no Response and 10 is the maximum Response observed for that receptor or ligand across all tested compounds at that time point, RU max or RU 300 respectively.

For C1q binding, 96 well plates were coated with C1q (Sigma Cat #: C1740 1 µg/ml) overnight in PBS. After coating, plates were washed 3 times with standard wash buffer (1× PBS+0.05% Tween 20) and blocked with blocking buffer (1% BSA+1× PBS+0.05% Tween 20) for 2 hours at RT. Following blocking, plates were incubated with compound diluted in blocking buffer 100 µL/well and washed 3 times with standard washing buffer. C1q-bound compound was detected by incubation with 1:5000 biotinylated mouse anti-human IgG1(Cat #555869, BD Biosciences) and Streptavidin-HRP (Cat #: 7100-05 Southern Biotech) (100 µl/well) for 1 hour at room temperature followed by washing 3 times with washing buffer, after which color was developed using the standard TMB method according to manufacturer's protocol for 15 minutes. Absorbance was read at 450 nm.

Exemplary Fc receptor binding data for G045c are provided in FIG. 1.

Figure 2:
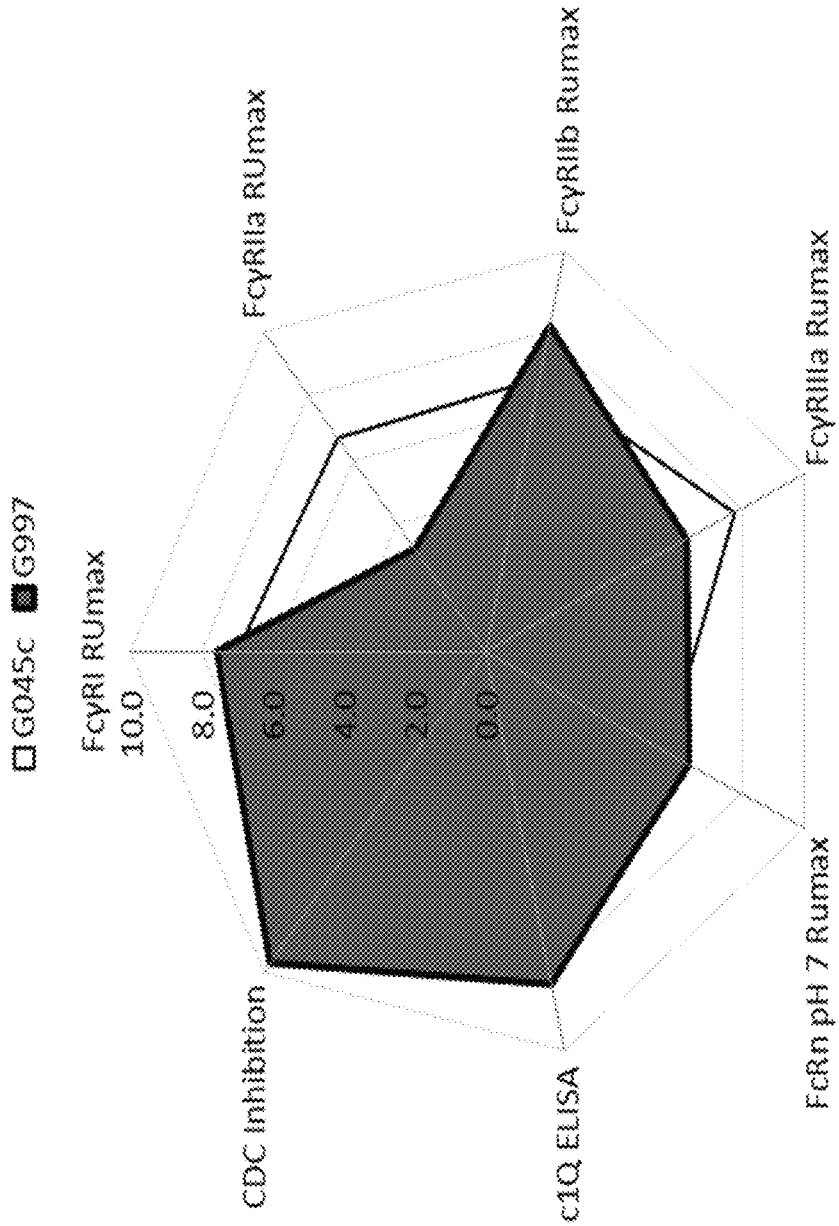
FIG. 2 is a radar graph of the maximum Response Units (RUmax) for each Fc receptor, C1q ELISA, and CDC inhibition data for G045c and complement-preferential stradomer G997. Each radar graph in these descriptions has been generated from a visual reading of the binding curves resulting from the output of the Octet biolayer interferometry.
Figure 3:
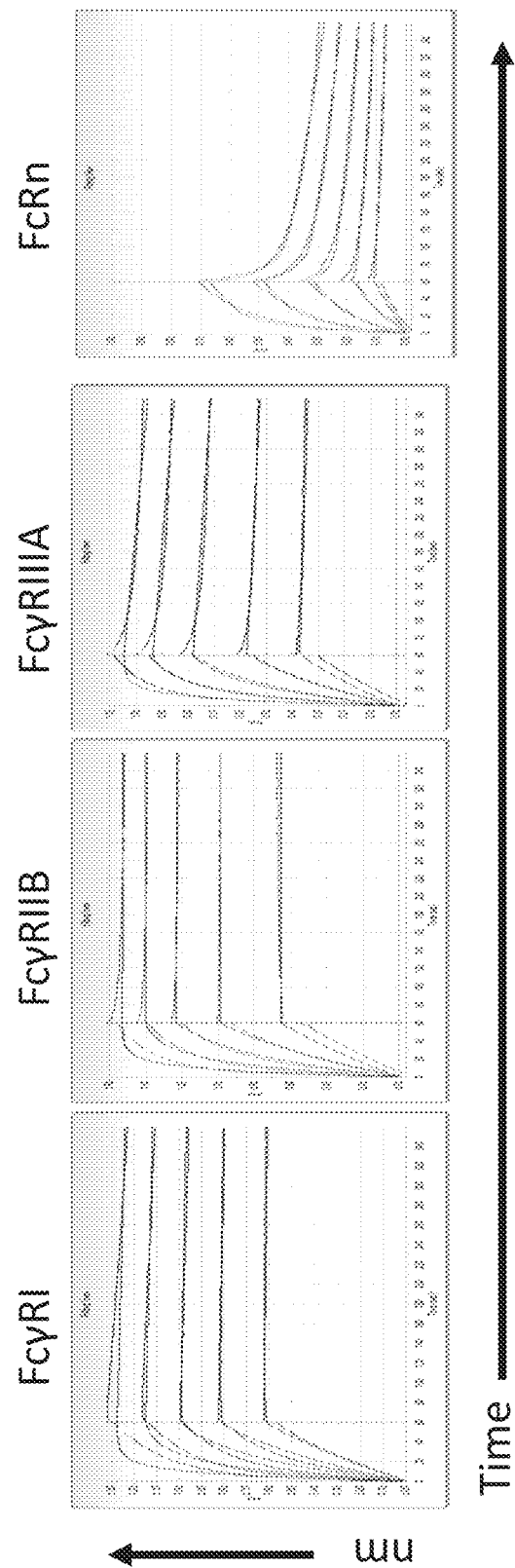
FIG. 3 shows the binding of stradomer G997 to FcγRI, FcγRIIb, FcγRIIIa, FcγRIIa, and FcRn, as measured by biolayer interferometry.

G997 is a stradomer having three mutations (S267E/H268F/S324T) inserted into the G045c backbone. As shown in FIG. 2, the resulting stradomer exhibited increased C1q binding relative to the parent G045c, as well as slightly diminished FcγRIIa and FcγRIIIa binding relative to G045c, and no effect on CDC inhibition. Fc receptor binding data for G997 are also provided in FIG. 3.

Figure 4B:
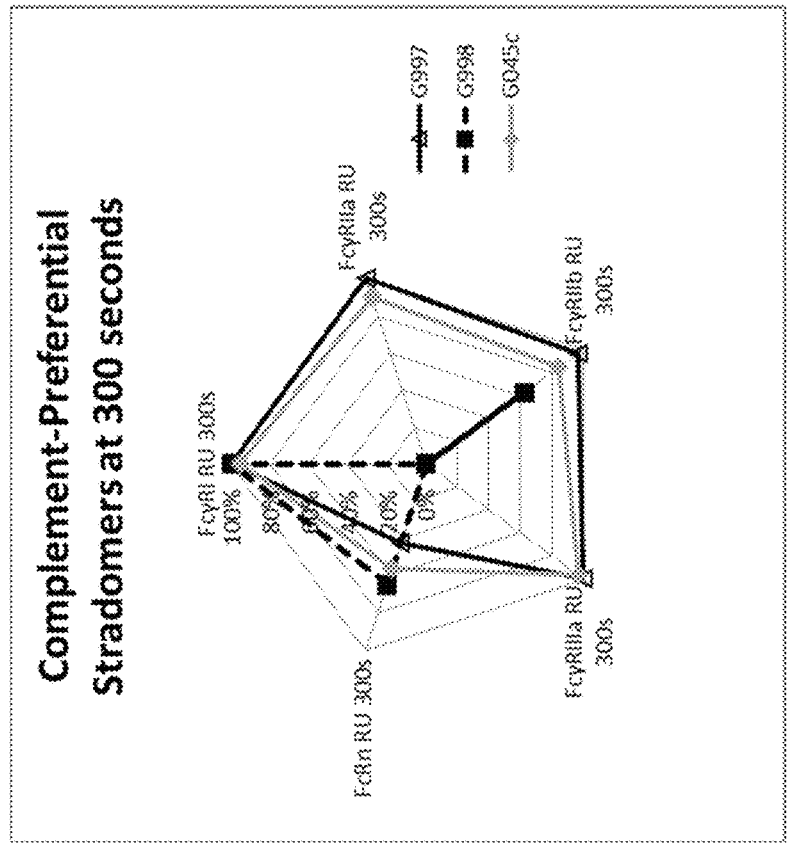
FIG. 4A-FIG. 4B provide a radar graph of the RUmax for each Fc receptor, C1q ELISA, and CDC inhibition data for G045c and complement-preferential stradomer G998 (FIG. 4A) and a radar graph of the RU at 300 seconds (RU300s) for each Fc receptor for G045c and complement-preferential stradomers G997 and G998 (FIG. 4B).
Figure 4A:
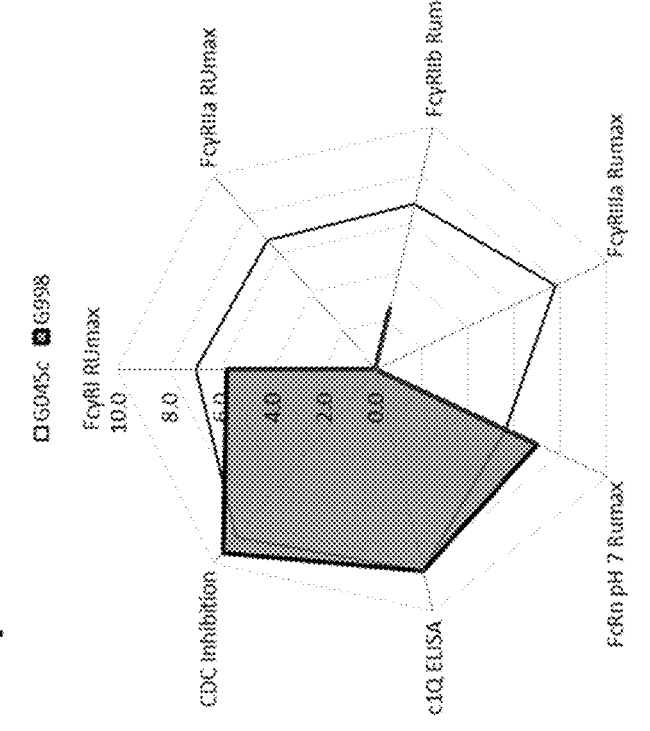
Figure 5:
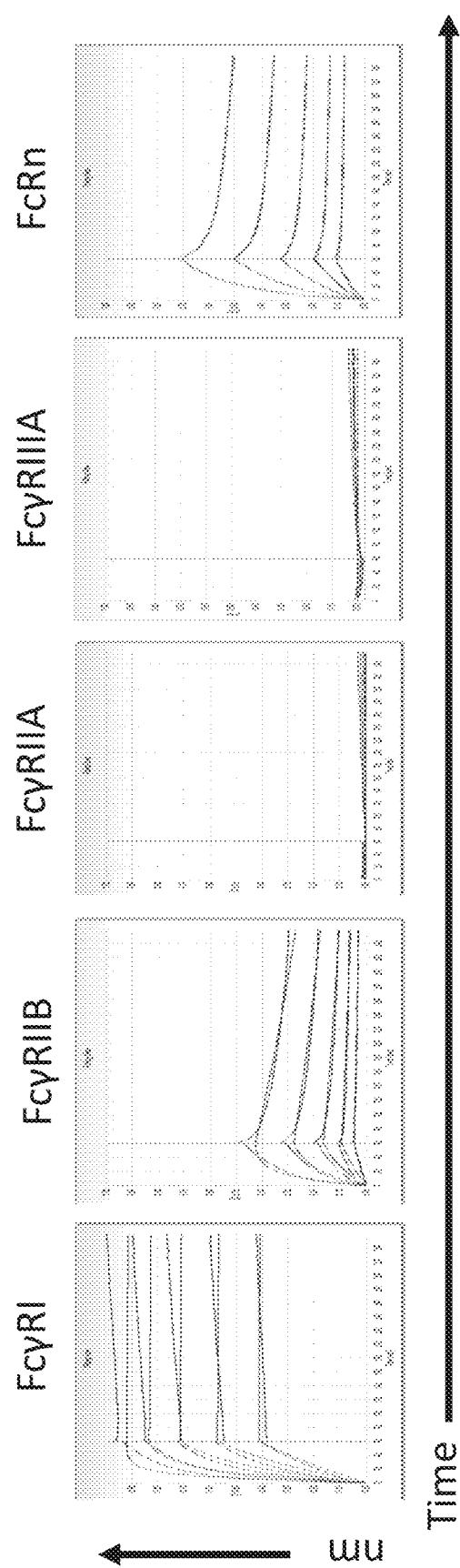
FIG. 5 shows the binding of stradomer G998 to FcγRI, FcγRIIb, FcγRIIIa, FcγRIIa, and FcRn, as measured by biolayer interferometry.

Next, G998 was constructed. G998 contains an additional mutation at amino acid position 297 relative to G997. Specifically, G998 has four mutations (S267E/H268F/S324T/N297A) inserted into the G045c backbone. The triple mutation in G998 restored strong C1q binding and CDC inhibition; binding to activating receptors FcγRIIa and FcγRIIIa was eliminated and FcγRIIb was diminished, while FcRn binding was not diminished relative to the parent stradomer G045c (FIG. 4A). Also, surprisingly, binding to FcγRT was fully retained in G998 despite the N297A mutation. A comparison of the RU300 for canonical FcγR and FcRn binding of G997, G998, and G045c is provided in FIG. 4B. Given the aglycosylation that occurs with the N297A mutation, the retention of binding to the inhibitory receptor FcγRIIb by G997 was surprising. Though FcγRIIb binding was significantly diminished at RU max for G998 relative to G997, G998 dissociates very slowly from FcγRIIb, as shown in the RU300 data (FIG. 4B). Fc receptor binding data for G998 are also provided in FIG. 5.

Specific compounds G1033 and G1022 were also generated. Specifically, G1033 has 6 mutations (S267E/H268F/S324T/N297A/L234A/L235A) inserted into the G045c backbone; and G1022 has 7 mutations (S267E/H268F/S324T/N297A/E233P/L234V/L235A and G236 deleted) inserted into the G045c backbone. The canonical FcγR and FcRn RUmax data, C1q binding, and CDC inhibition for G1033 and G1022 are provided in FIG. 6A. G1033 binds C1q and FcRn, and inhibits CDC, without appreciable binding to FcγRIIb or FcγRIIIa. Surprisingly, despite the deglycosylation of this compound due to the N297A mutation, some binding is retained to FcγRT and FcγRIIa. G1022 binds C1q and inhibits CDC without any appreciable binding to FcγRI or FcγRIIIa; slight binding is retained to FcγRIIb and modest binding is retained to FcγRIIa and FcRn in this compound. The elimination of FcγRT binding in G1022 was surprising because of the inherent avidity, even at low affinity, of stradomers to the high affinity FcγRI receptor. Thus, the elimination of FcγRT binding through the combination of mutations in G1022 was unexpected based on the retained FcγRT binding in other stradomers that contain these mutations. For example, the combination of mutations in G998 (S267E/H268F/S324T/N297A) did not result in a loss of FcγRT binding. It was particularly surprising binding to FcγRI could be eliminated in a stradomer in which binding to low affinity Fc receptors and CDC inhibition was retained. A comparison of the canonical FcγR and FcRn RU300 data for G045c, G1022, and G1033 is provided in FIG. 6B.

Figure 7A:
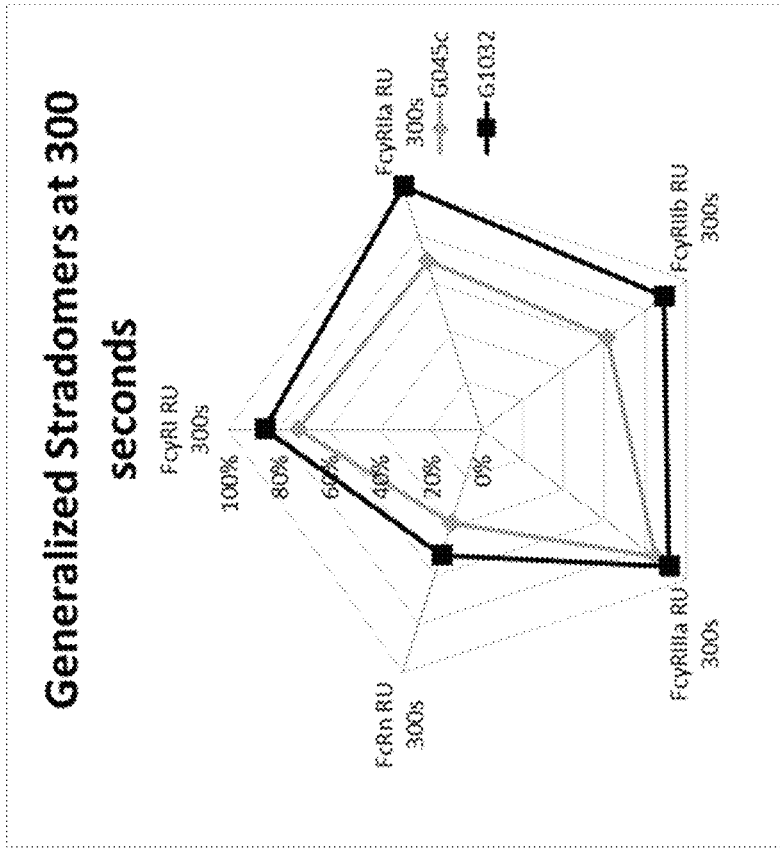
FIG. 7A-FIG. 7B provide a radar graph of the RUmax for each Fc receptor, C1q ELISA, and CDC inhibition data for G045c and generalized stradomer G1032 (FIG. 7A) and a radar graph of the RU at 300 seconds (RU300s) for each Fc receptor for G045c and generalized stradomer G1032 (FIG. 7B).
Figure 7B:
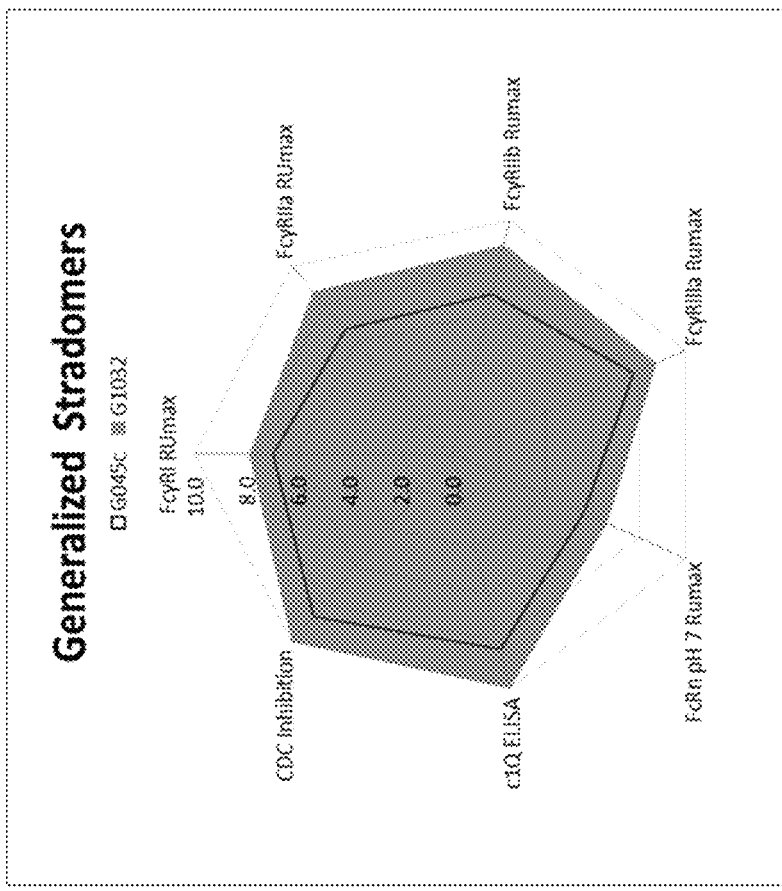

G1032 has 5 mutations (S267E/H268F/S324T/L234A/L235A) inserted into the G045c backbone. FcγR binding RUmax, FcRn binding RUmax, C1q binding, and CDC inhibition are shown in FIG. 7A, and FcR RU300 data are shown in FIG. 7B. Surprisingly, while G1032 bound C1q and inhibited CDC, robust binding was retained to all canonical Fc receptors, despite the L234A and L235A mutations; moderately robust binding was retained to FcRn.

Figure 8B:
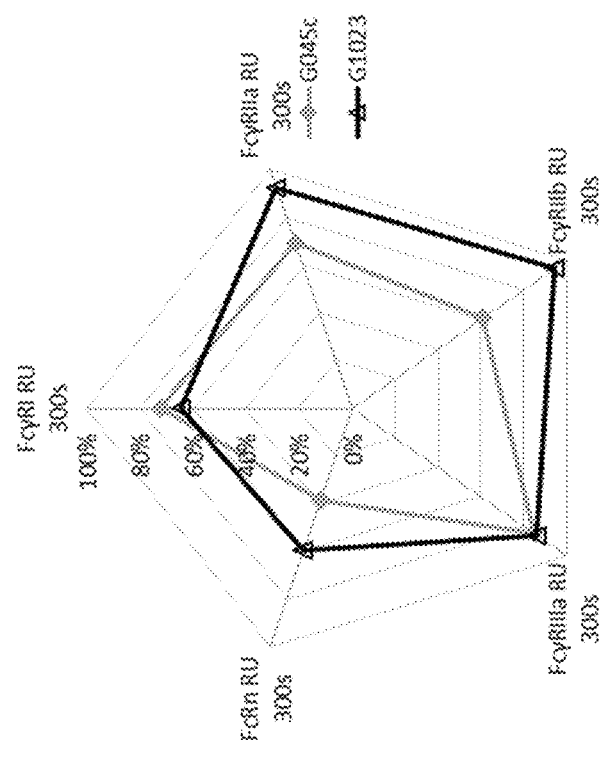
FIG. 8A-FIG. 8B provide a radar graph of the RUmax for each Fc receptor, C1q ELISA, and CDC inhibition data for G045c and generalized stradomer G1023 (FIG. 8A) and a radar graph of the RU at 300 seconds (RU300s) for each Fc receptor for G045c and generalized stradomer G1023 (FIG. 8B).
Figure 8A:
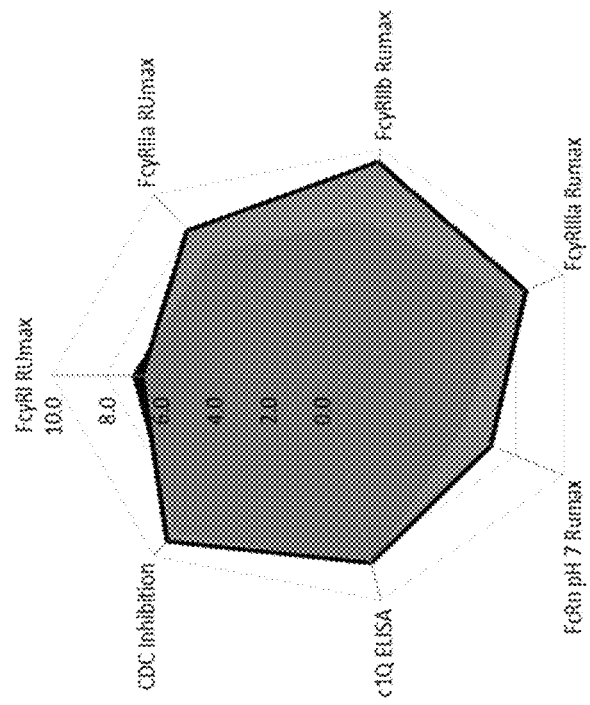

G1023 has 6 mutations (S267E/H268F/S324T/E233P/L234V/L235A) and a deletion of the G at position 236. FcγR binding RUmax, FcRn binding RUmax, C1q binding, and CDC inhibition are shown in FIG. 8A, and FcR RU300 data are shown in FIG. 8B. G1023 bound C1q and inhibited CDC with robust binding retained to all canonical Fc Receptors, and moderately robust binding retained to FcRn. Surprisingly, while G1023 bound C1q and inhibited CDC, despite the E223, L234V, and L235A mutations and the deletion of G236 (and in the absence of deglycosylation via a N297A mutation), robust binding was retained to all canonical Fc receptors.

Figure 9A:
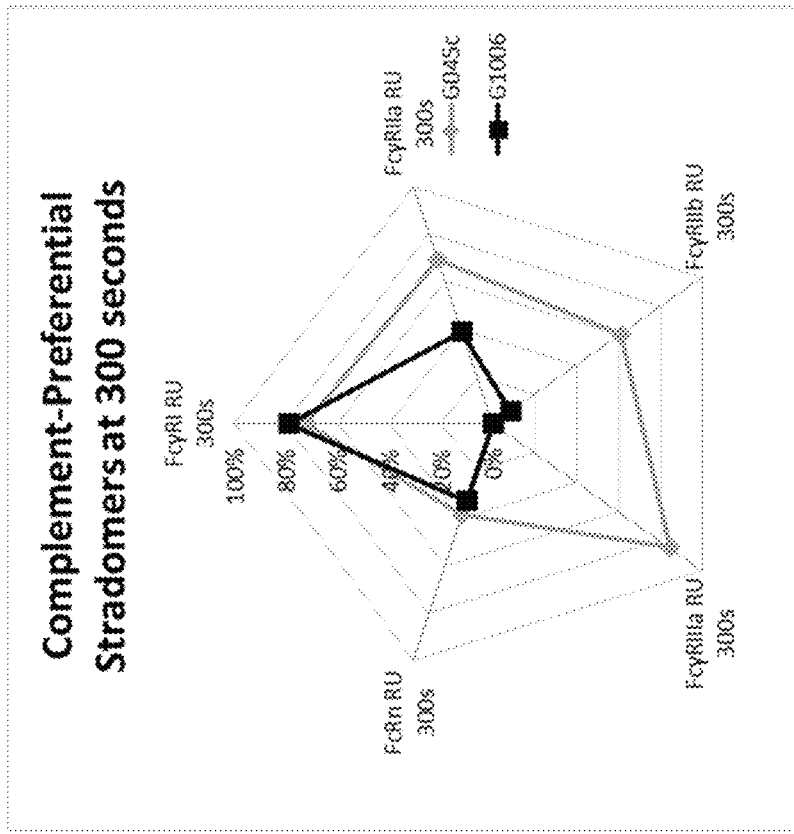
FIG. 9A-FIG. 9B provide a radar graph of the RUmax for each Fc receptor, C1q ELISA, and CDC inhibition data for G045c and complement-preferential stradomer G1006 (FIG. 9A) and a radar graph of the RU at 300 seconds (RU300s) for each Fc receptor for G045c and complement-preferential stradomer G1006 (FIG. 9B).
Figure 9B:
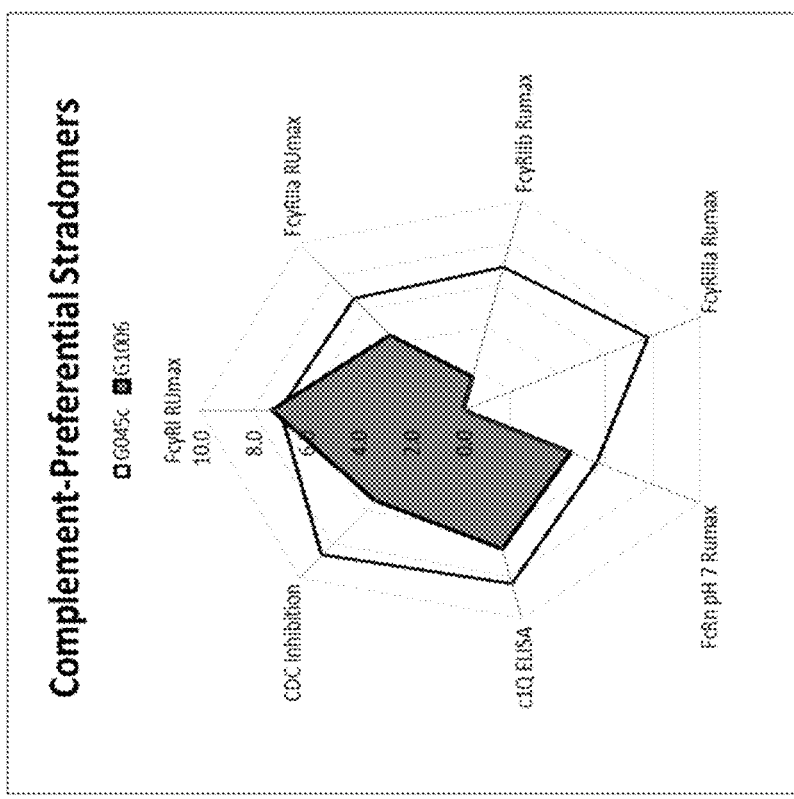

G1006 has 4 mutations (S267E/H268F/S324T/D265A). FcγR binding RUmax, FcRn binding RUmax, C1q binding, and CDC inhibition are shown in FIG. 9A, and FcR RU300 data are shown in FIG. 9B. This stradomer bound C1q and inhibited CDC, with binding retained to FcγRI, FcγRIIa and, to a lesser degree, FcγRIIb. The results were surprising because though D265A is described as reducing binding to all canonical Fc receptors, robust binding was retained to FcγRI and moderate binding was retained to FcγRIIa. FcγRIIIa binding was eliminated, and moderately robust binding was retained to FcRn (FIG. 9A).

Figure 10B:
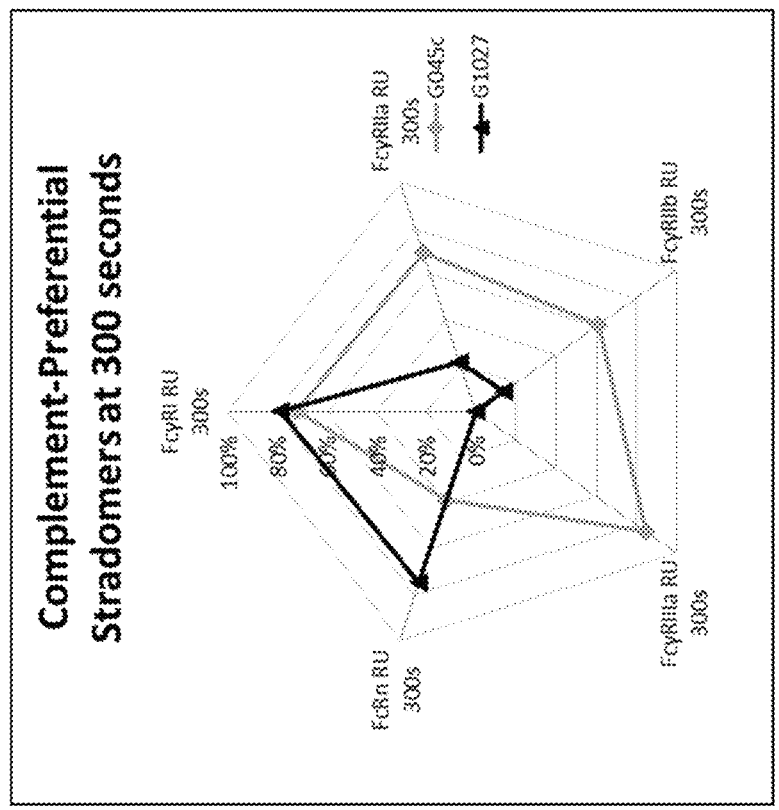
FIG. 10A-FIG. 10B provide a radar graph of the RUmax for each Fc receptor, C1q ELISA, and CDC inhibition data for G045c and complement-preferential stradomer G1027 (FIG. 10A) and a radar graph of the RU at 300 seconds (RU300s) for each Fc receptor for G045c and complement-preferential stradomer G1027 (FIG. 10B).
Figure 10A:
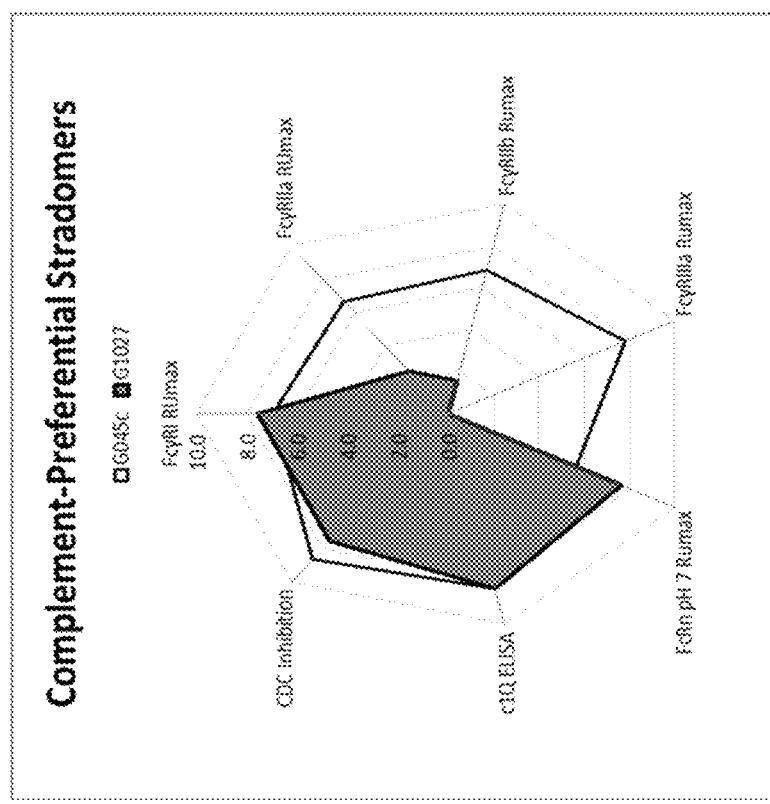

G1027 has 5 mutations (P238D/S267E/H268F/S324T/N297A). FcγR binding RUmax, FcRn binding RUmax, C1q binding, and CDC inhibition are shown in FIG. 10A, and FcR RU300 data are shown in FIG. 10B for G1027. This stradomer bound C1q and inhibited CDC, retained robust binding to FcγRI, exhibited diminished binding to FcγRIIa and FcγRIIb and moderate binding to FcRn, and eliminated FcγRIIIa binding. The fact that the canonical Fc receptor binding was not eliminated in this stradomer despite the P238D and N297A mutations was a surprising result.

Figure 11B:
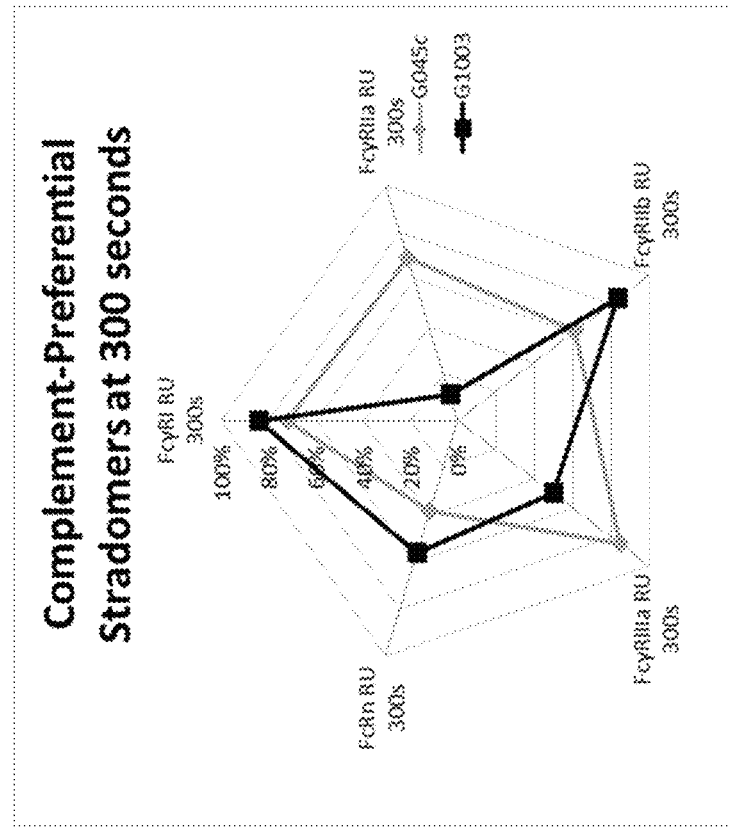
FIG. 11A-FIG. 11B provide a radar graph of the RUmax for each Fc receptor, C1q ELISA, and CDC inhibition data for G045c and complement-preferential stradomer G1003 (FIG. 11A) and a radar graph of the RU at 300 seconds (RU300s) for each Fc receptor for G045c and complement-preferential stradomer G1003 (FIG. 11B).
Figure 11A:
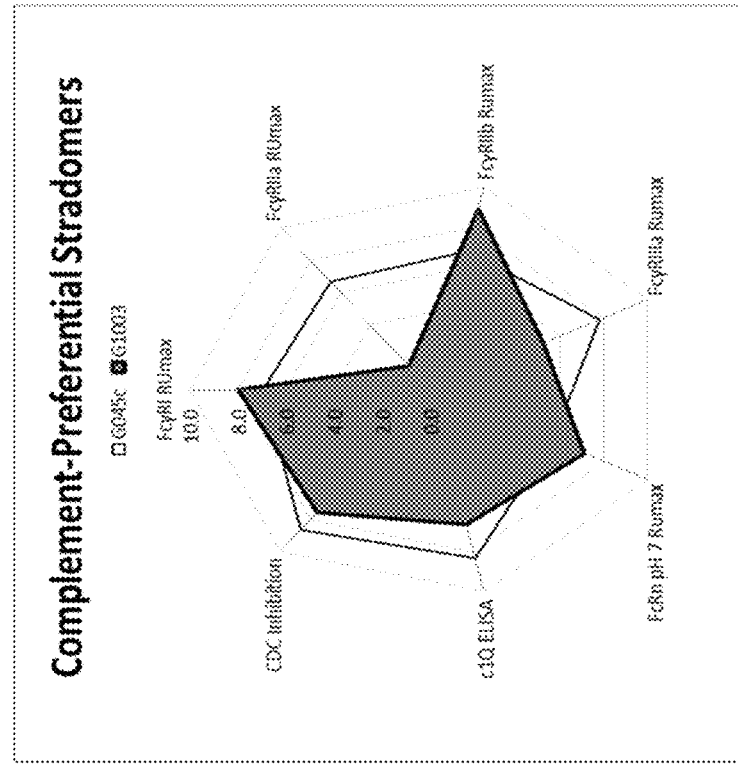

G1003 was constructed on the G019 background (IgG2 Hinge—IgG1 Hinge—IgG1 CH2 IgG1 CH3) and has 3 mutations: S267E/H268F/S324T. The results for this stradomer are provided in FIGS. 11A and 11B. This stradomer bound C1q and inhibited CDC. In addition, the stradomer exhibited robust binding to FcγRI and FcγRIIb; diminished binding to FcγRIIa; and moderately robust binding to FcRn. The G019 parent stradomer exhibits minimal C1q binding and no significant inhibition of CDC. Thus, the fact that incorporation of the triple mutation into this parent stradomer resulted in a compound with the same general structure and multimerization pattern as the parent G019, but with binding to C1q and robust inhibition of CDC, was particularly surprising. Even more surprising is the fact that the same mutations (S267E/H268F/S324T) incorporated into the GL-2045 backbone (yielding G998) demonstrated substantially different binding activity. G997 and G1003 possess the same domains with the identical mutations and present generally the same binding attributes even though the parent compounds (G045c and G019 respectively) differ significantly in C1q binding and CDC inhibition. These comparisons further highlight the unpredictability of a given set of mutations in the context of a multimerizing stradomer.

Figure 12A:
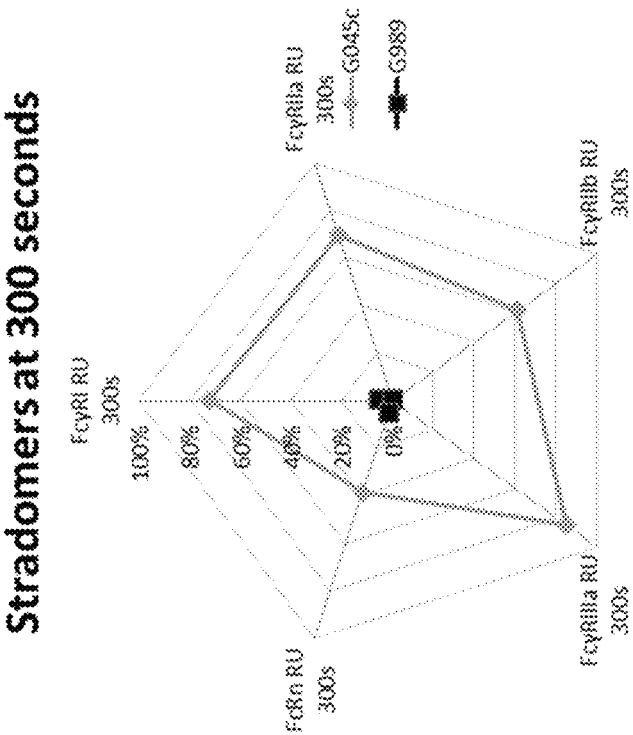
FIG. 12A-FIG. 12B provide a radar graph of the RUmax for each Fc receptor, C1q ELISA, and CDC inhibition data for G045c and complement-preferential stradomer G989 (FIG. 12A) and a radar graph of the RU at 300 seconds (RU300s) for each Fc receptor for G045c and complement-preferential stradomer G989 (FIG. 12B).
Figure 12B:
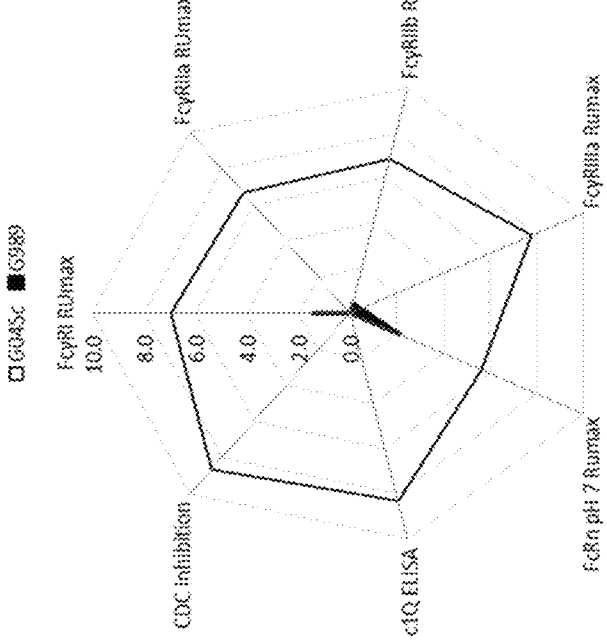

G989 is on the G045c background and contains 2 mutations (E233P/G236R), and was generated to reduce canonical binding. However, surprisingly, this stradomer exhibited not only reduced canonical binding but also a loss of C1q binding and CDC (FIGS. 12A, 12B, and 13).

Figure 14B:
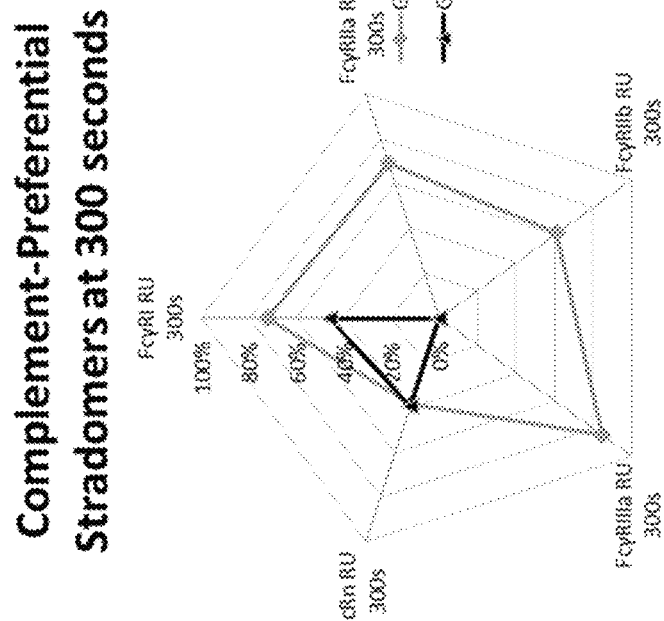
FIG. 14A-FIG. 14B provide a radar graph of the RUmax for each Fc receptor, C1q ELISA, and CDC inhibition data for G045c and complement-preferential stradomer G990 (FIG. 14A) and a radar graph of the RU at 300 seconds (RU300s) for each Fc receptor for G045c and complement-preferential stradomer G990 (FIG. 14B).
Figure 14A:
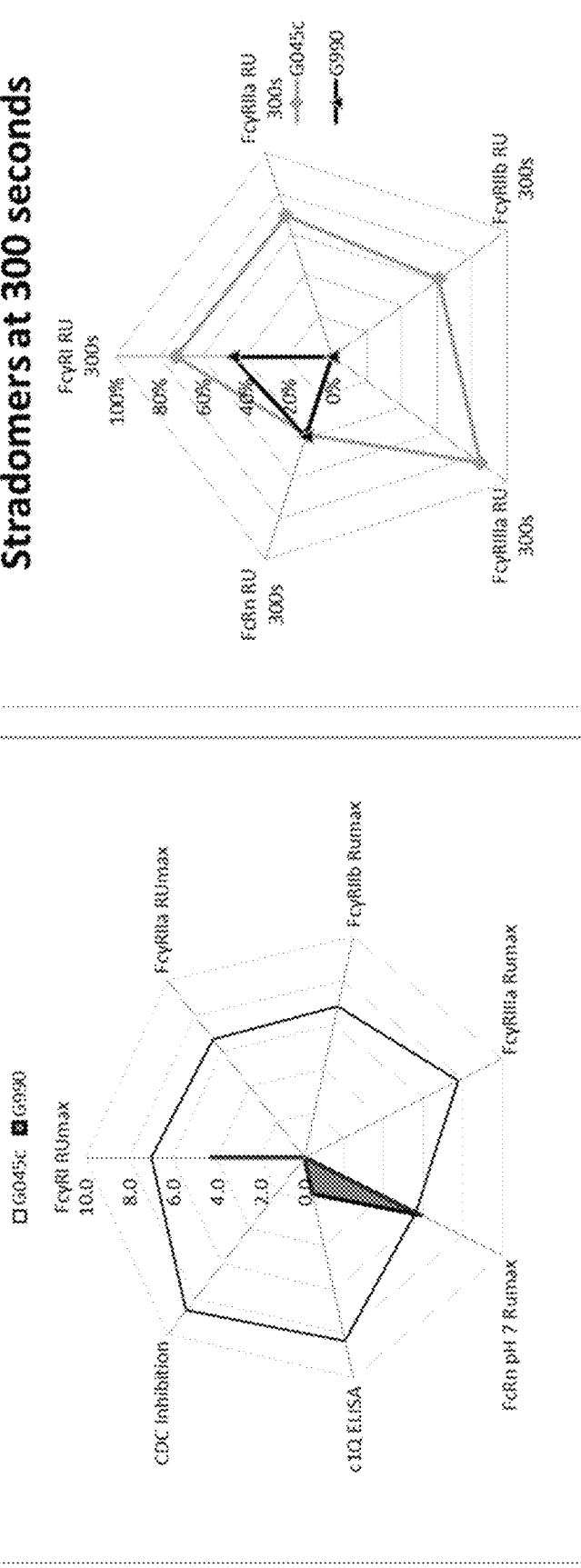
Figure 15:
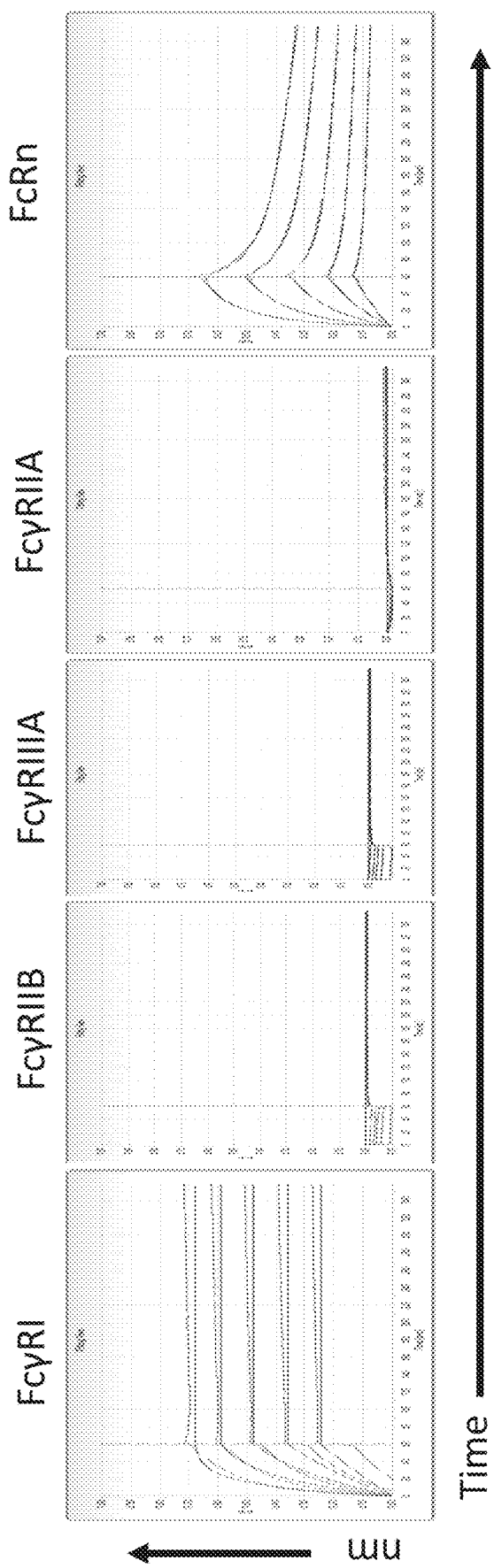
FIG. 15 shows the binding of stradomer G990 to FcγRI, FcγRIIb, FcγRIIIa, FcγRIIa, and FcRn, as measured by biolayer interferometry.
Figure 16A:
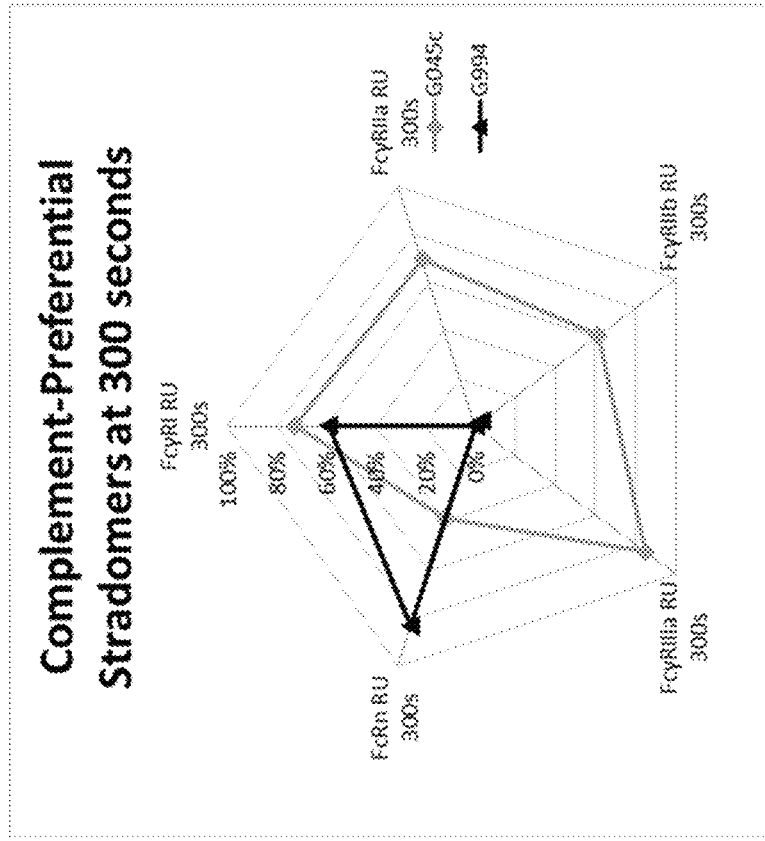
FIG. 16A-FIG. 16B provide a radar graph of the RUmax for each Fc receptor, C1q ELISA, and CDC inhibition data for G045c and complement-preferential stradomer G994 (FIG. 16A) and a radar graph of the RU at 300 seconds (RU300s) for each Fc receptor for G045c and complement-preferential stradomer G994 (FIG. 16B).
Figure 16B:
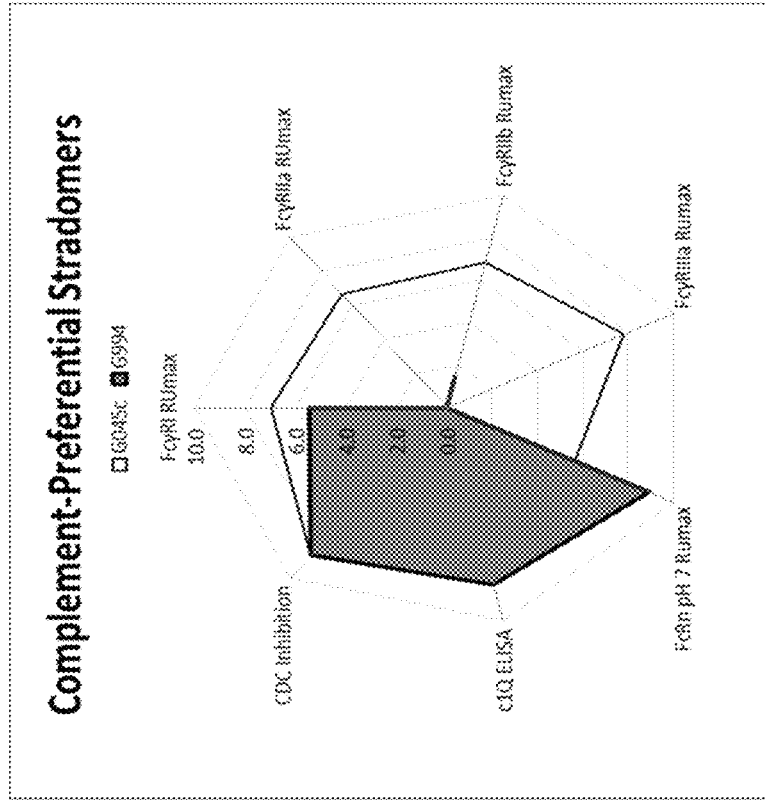
Figure 17:
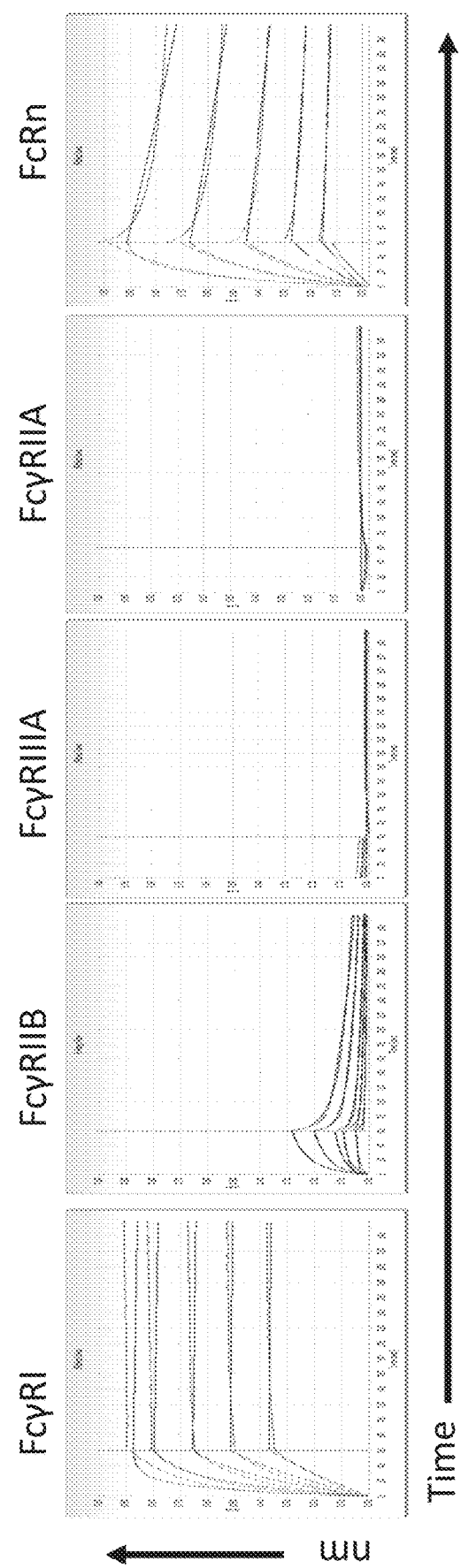
FIG. 17 shows the binding of stradomer G994 to FcγRI, FcγRIIb, FcγRIIIa, FcγRIIa, and FcRn, as measured by biolayer interferometry.
Figure 18A:
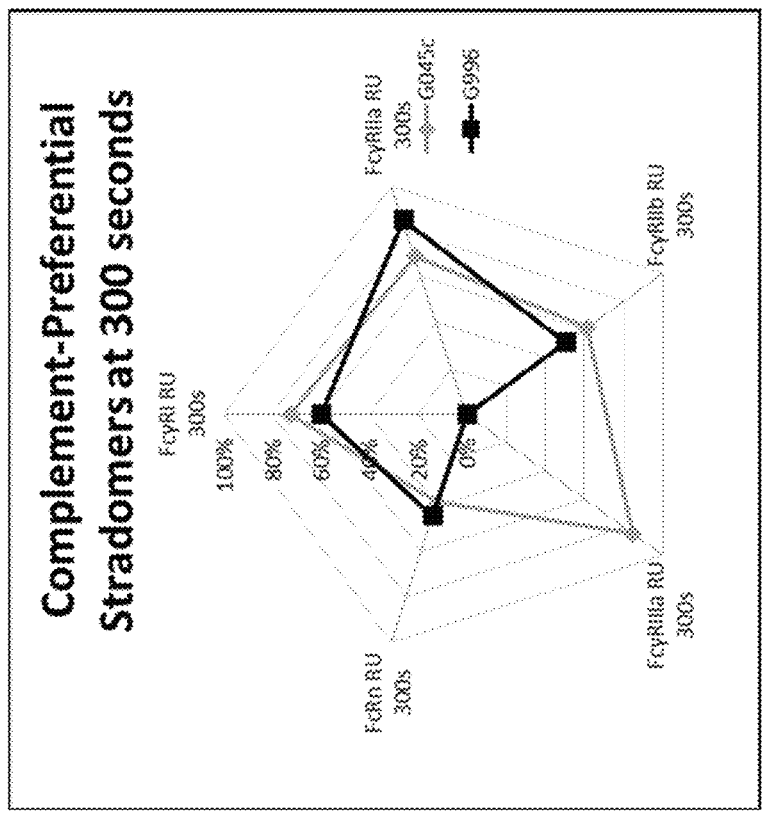
FIG. 18A-FIG. 18B provide a radar graph of the RUmax for each Fc receptor, C1q ELISA, and CDC inhibition data for G045c and complement-preferential stradomer G996 (FIG. 18A) and a radar graph of the RU at 300 seconds (RU300s) for each Fc receptor for G045c and complement-preferential stradomer G996 (FIG. 18A).
Figure 18B:
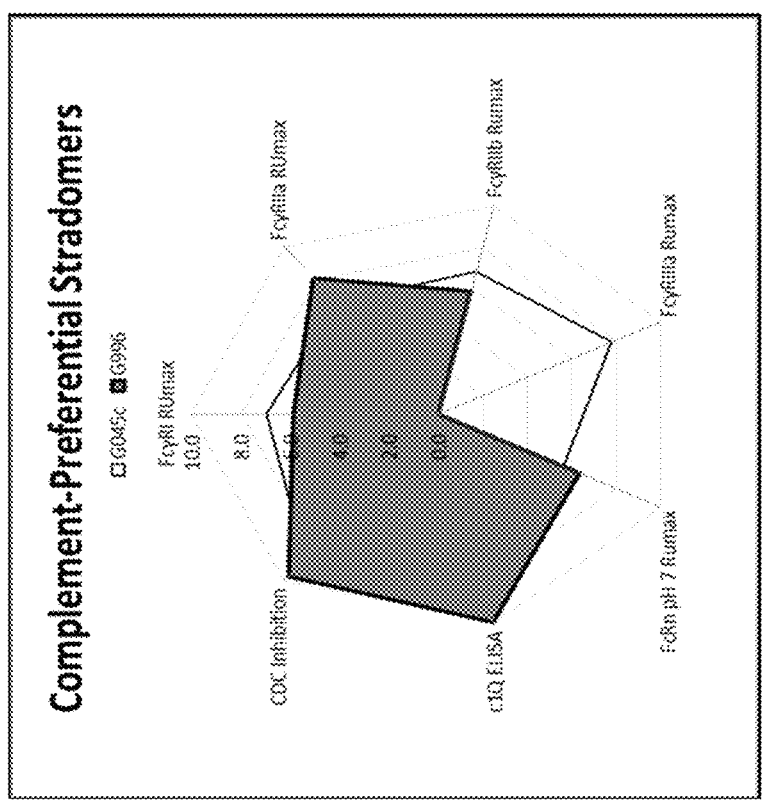
Figure 19:
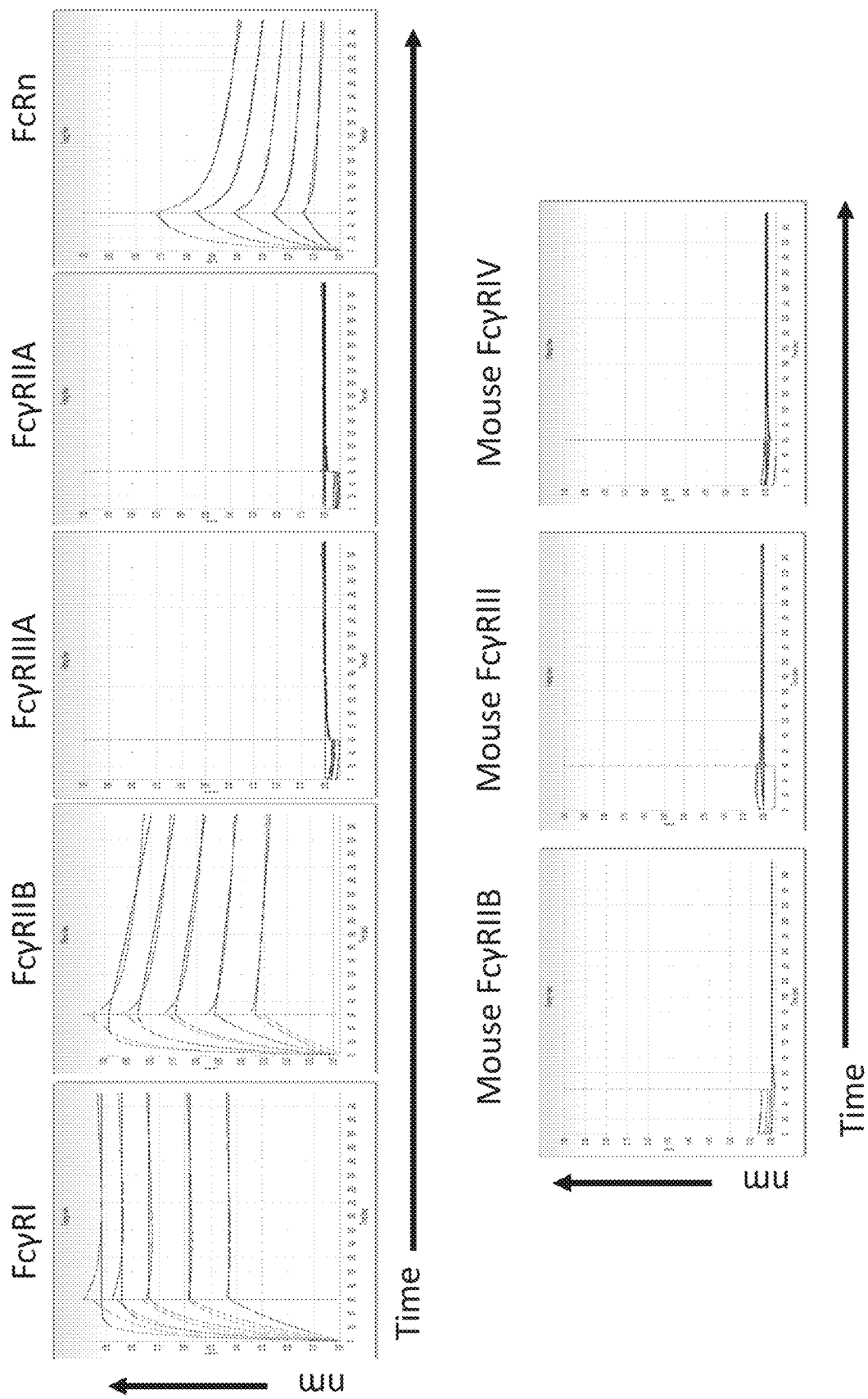
FIG. 19 (top row of panels) shows the binding of stradomer G996 to FcγRI, FcγRIIb, FcγRIIIa, FcγRIIa, or FcRn, as measured by biolayer interferometry.
Figure 20B:
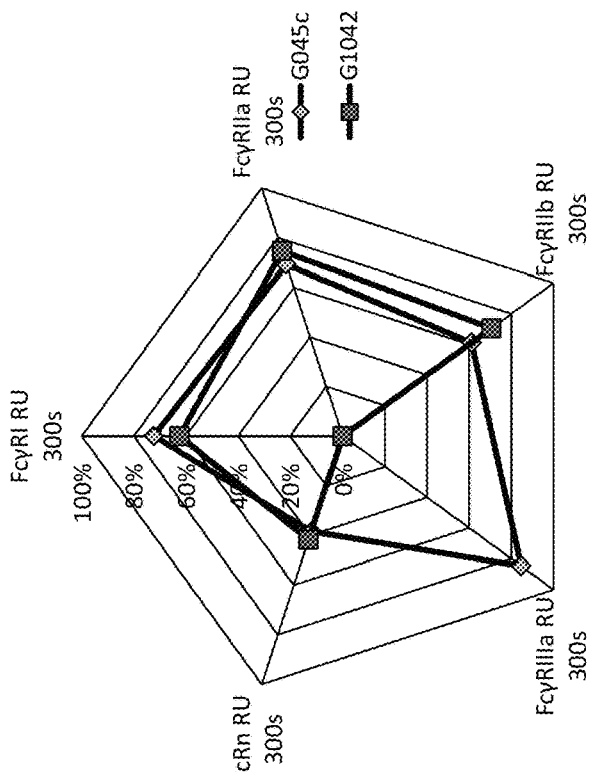
FIG. 20A-FIG. 20B provide a radar graph of the RUmax for each Fc receptor, C1q ELISA, and CDC inhibition data for G045c and complement-preferential stradomer G1042 (FIG. 20A) and a radar graph of the RU at 300 seconds (RU300s) for each Fc receptor for G045c and complement-preferential stradomer G1042 (FIG. 20B).
Figure 20A:
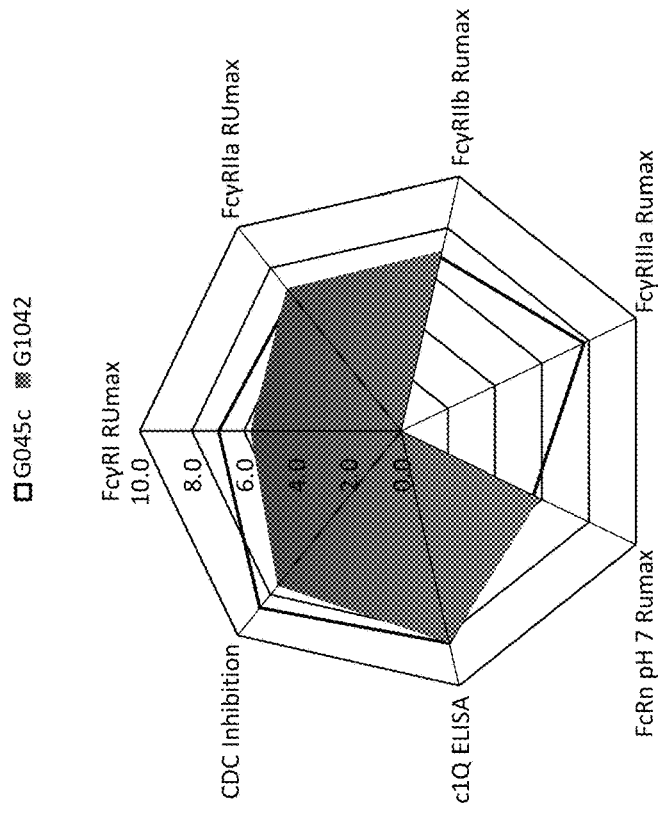
Figure 21:
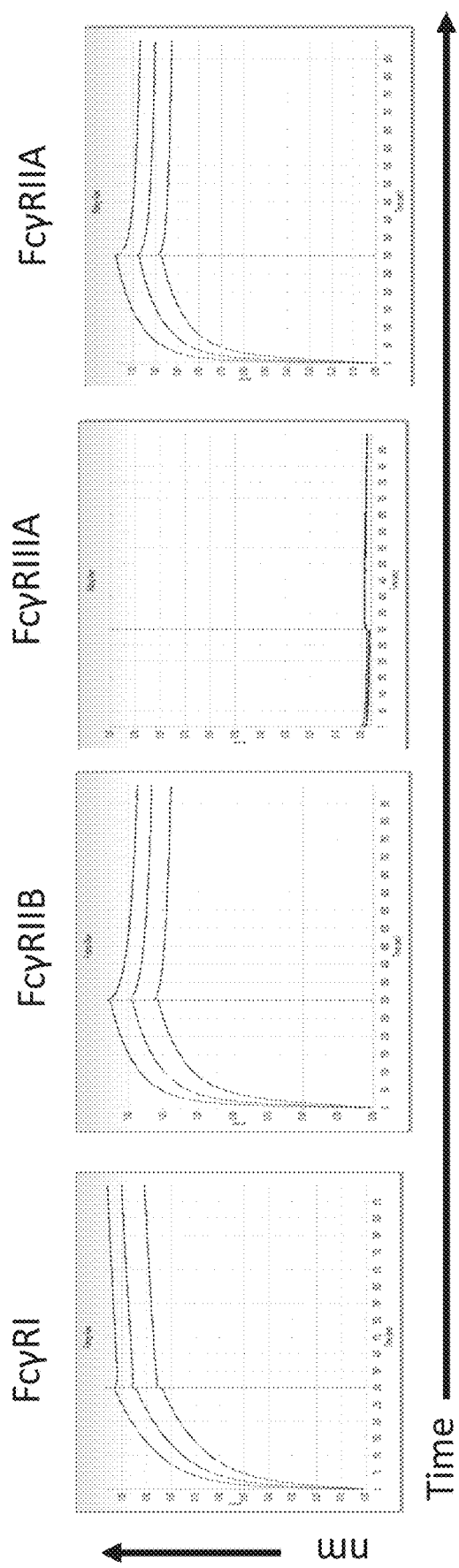
FIG. 21 shows the binding of stradomer G1042 to FcγRT, FcγRIIb, FcγRIIIa, and FcγRIIa, as measured by biolayer interferometry.
Figure 22B:
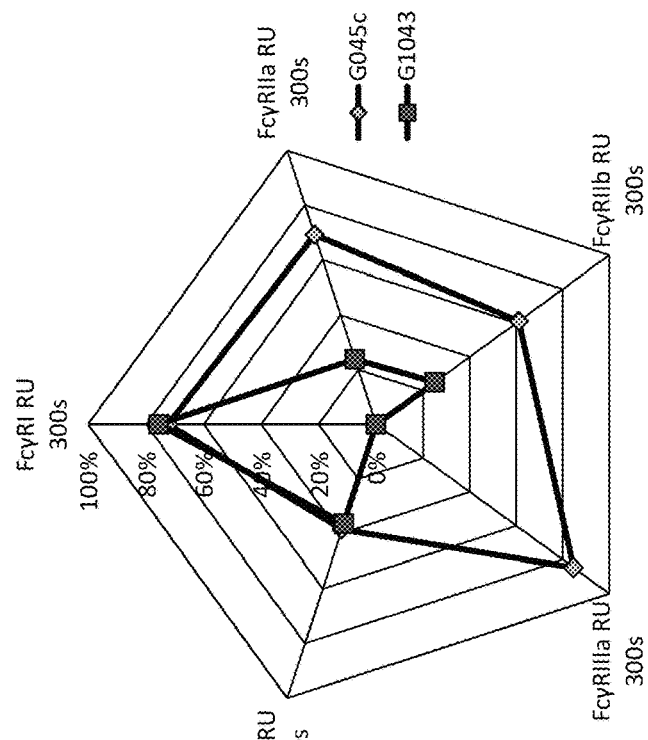
FIG. 22A-FIG. 22B provide a radar graph of the RUmax for each Fc receptor, C1q ELISA, and CDC inhibition data for G045c and complement-preferential stradomer G1043 (FIG. 22A) and a radar graph of the RU at 300 seconds (RU300s) for each Fc receptor for G045c and complement-preferential stradomer G1043 (FIG. 22B).
Figure 22A:
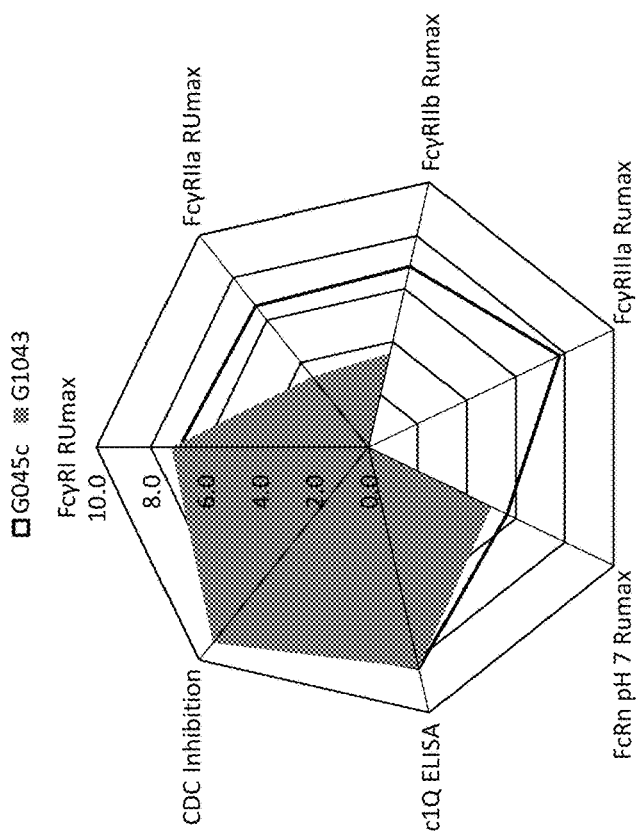
Figure 24B:
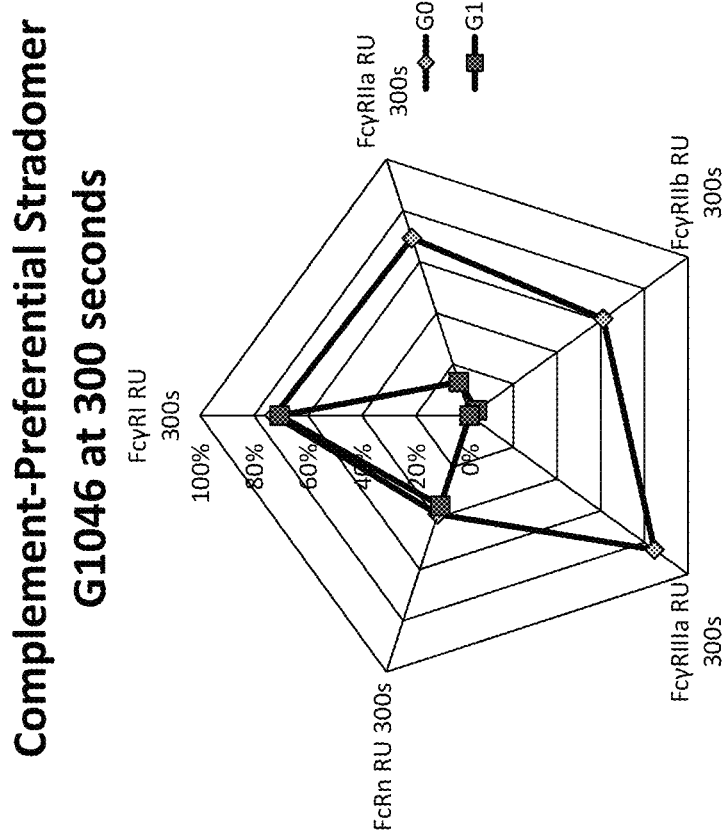
FIG. 24A-FIG. 24B provide a radar graph of the RUmax for each Fc receptor, C1q ELISA, and CDC inhibition data for G045c and complement-preferential stradomer G1046 (FIG. 24A) and a radar graph of the RU at 300 seconds (RU300s) for each Fc receptor for G045c and complement-preferential stradomer G1046 (FIG. 24B).
Figure 24A:
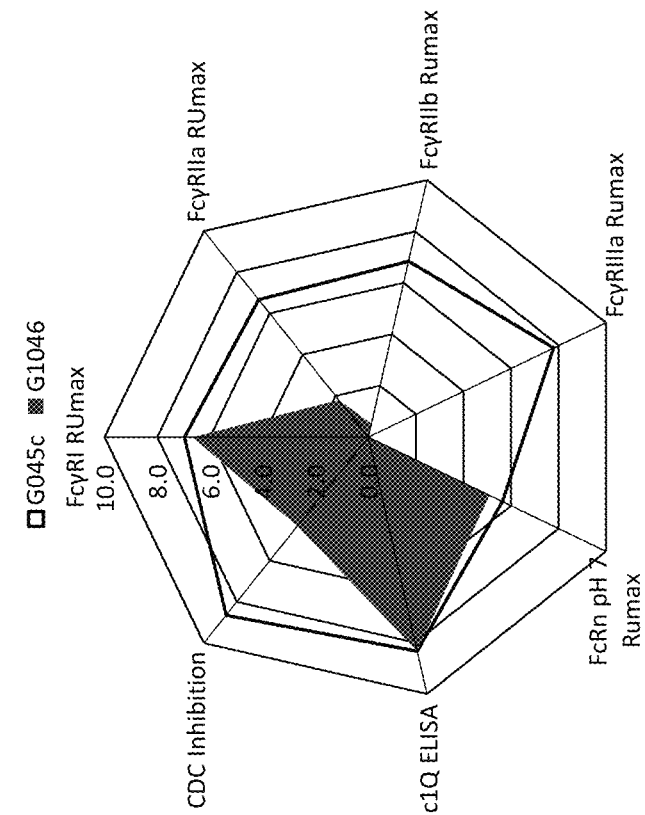
Figure 25:
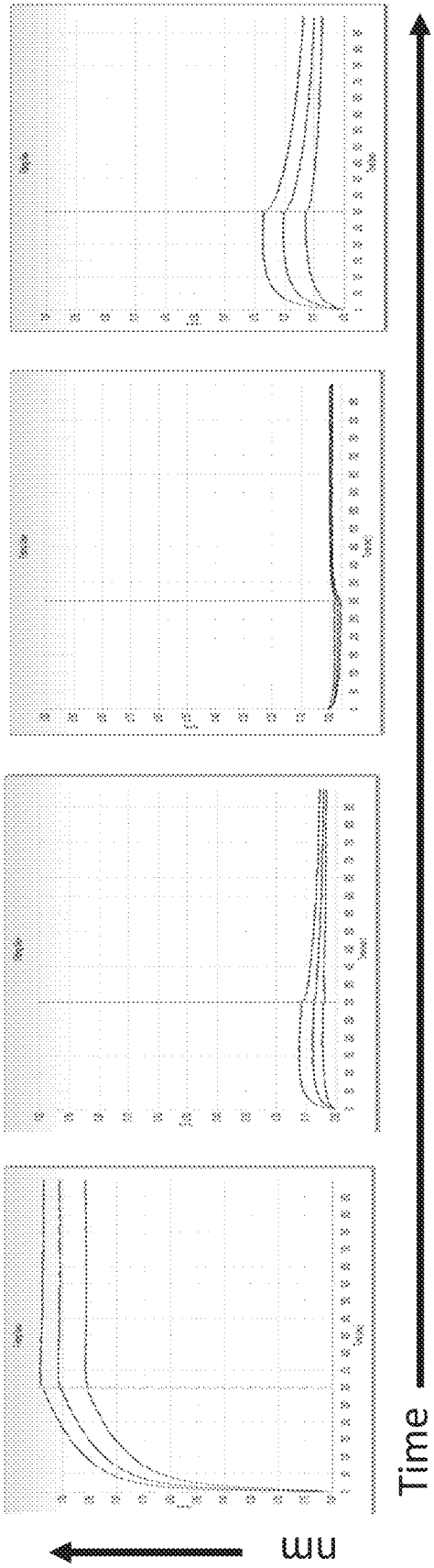
FIG. 25 shows the binding of stradomer G1046 to FcγRT, FcγRIIb, FcγRIIIa, or FcγRIIa, as measured by biolayer interferometry.
Figure 26B:
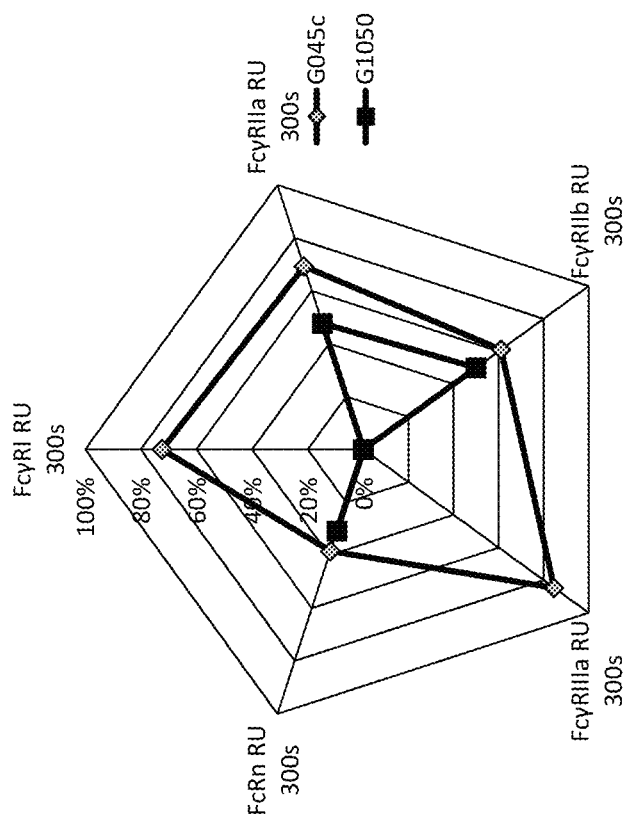
FIG. 26A-FIG. 26B provide a radar graph of the RUmax for each Fc receptor, C1q ELISA, and CDC inhibition data for G045c and complement-preferential stradomer G1050 (FIG. 26A) and a radar graph of the RU at 300 seconds (RU300s) for each Fc receptor for G045c and complement-preferential stradomer G1050 (FIG. 26B).
Figure 26A:
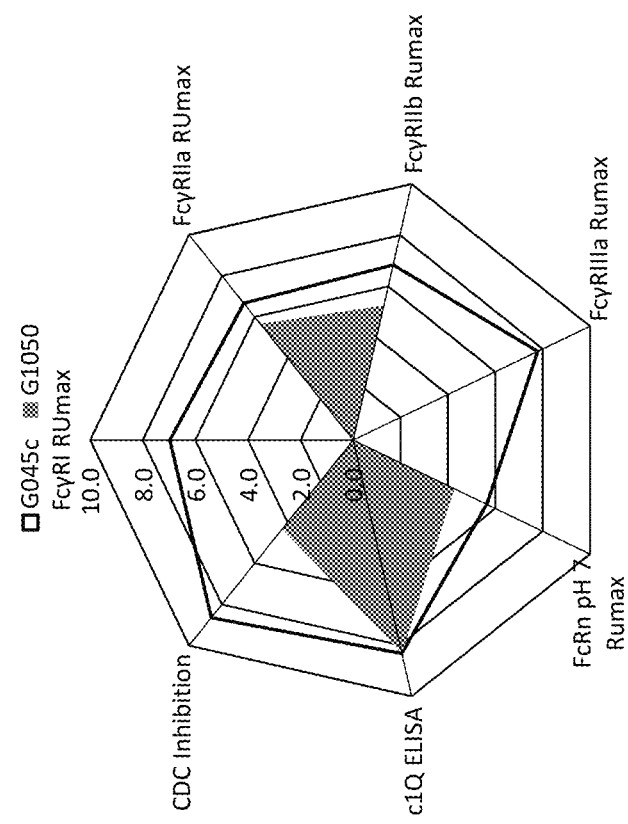
Figure 27:
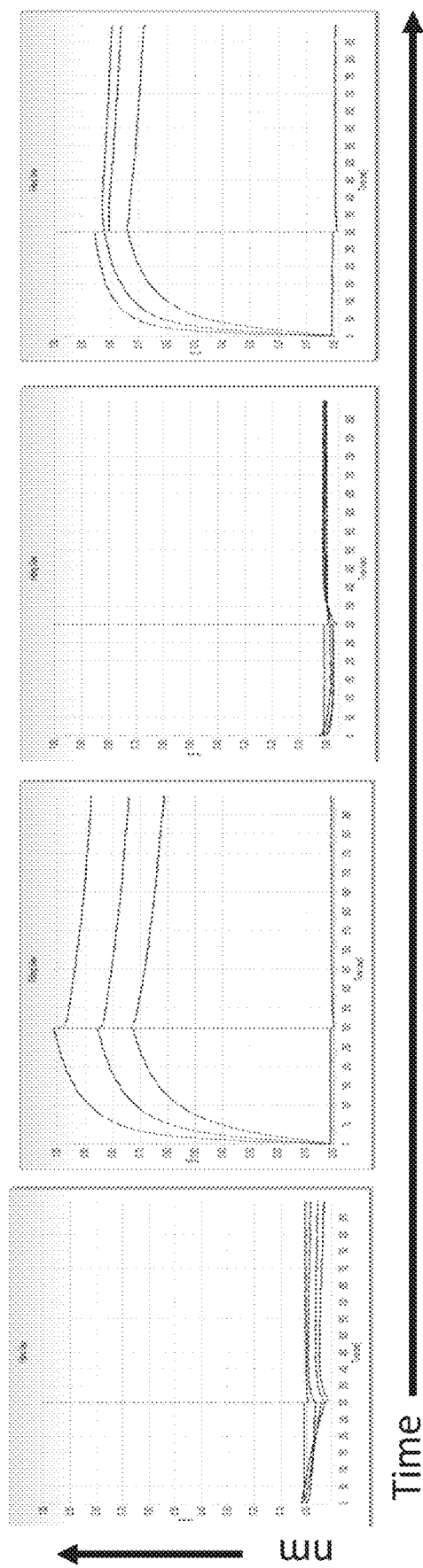
FIG. 27 shows the binding of stradomer G1050 to FcγRT, FcγRIIb, FcγRIIIa, and FcγRIIa, as measured by biolayer interferometry.
Figure 28A:
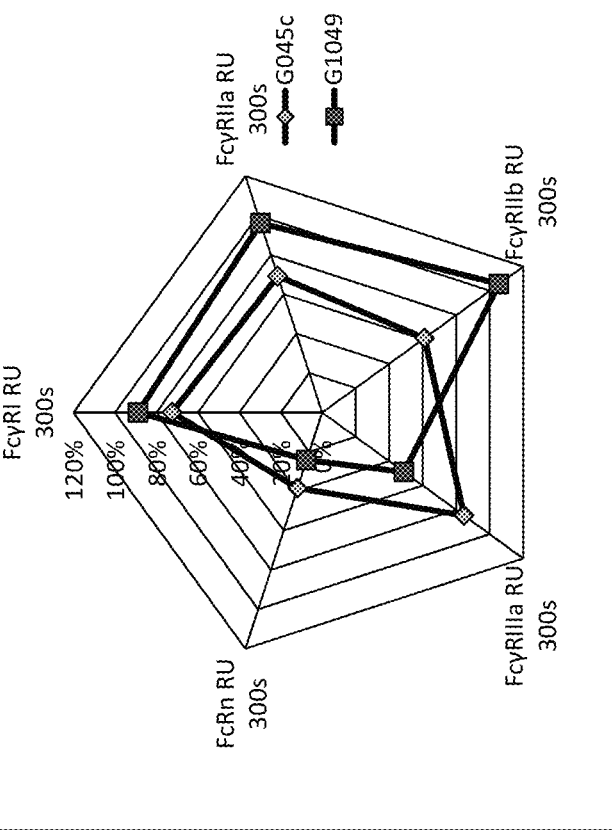
FIG. 28A-FIG. 28B provide a radar graph of the RUmax for each Fc receptor, C1q ELISA, and CDC inhibition data for G045c and generalized stradomer G1049 (FIG. 28A) and a radar graph of the RU at 300 seconds (RU300s) for each Fc receptor for G045c and generalized stradomer G1049 (FIG. 28B).
Figure 28B:
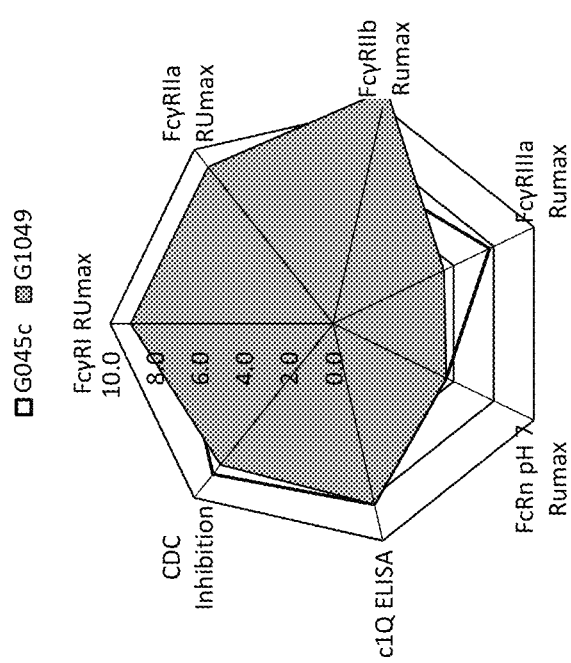
Figure 29:
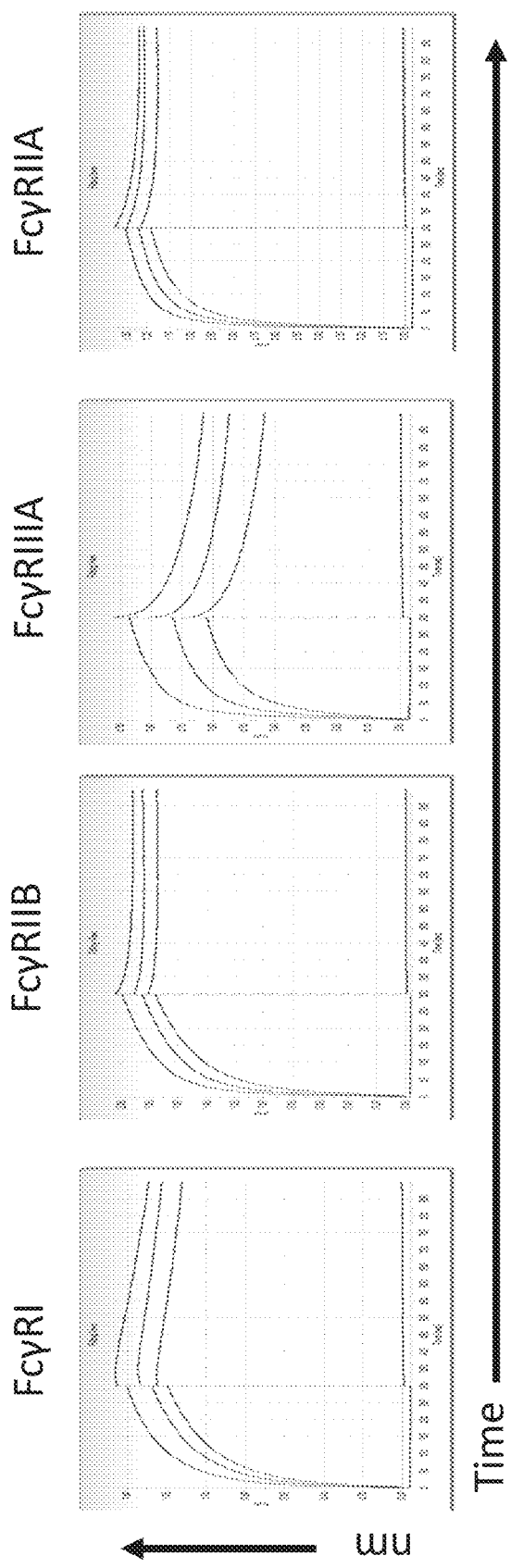
FIG. 29 shows the binding of stradomer G1049 to FcγRT, FcγRIIb, FcγRIIIa, and FcγRIIa, as measured by biolayer interferometry.

Therefore, G990, which is also on the G045c background but contains only a single mutation (G236R) was generated. Surprisingly, the G236R mutation alone decreased canonical binding and retained minimal C1q binding (FIGS. 14A, 14B, and 15).

Based on these surprising results, in order to attempt to further increase C1q binding, G994 was generated. G994 was made on the G045c background and has 5 mutations: E233P/G236R/S267E/H268F/S324T. However, surprisingly, while G994 regained the lost complement binding and CDC inhibition of the G989 stradomer on which it was based, the addition of the S267E/H268F/S324T triple mutation resulted in recovered binding of FcγRI and FcγRIIb (FIGS. 16A, 16B, and 17). Thus, the addition of the triple mutation reported to increase complement binding also resulted in an increase in canonical Fc receptor binding in the context of a stradomer.

Therefore, G994 was next used as a platform in an attempt to retain C1q binding and CDC inhibition, and gain specificity for complement binding over canonical binding. Specifically, G996, which is on the G045c background and has 4 mutations (G236R/S267E/H268F/S324T), was generated. Unexpectedly, G996 gained further binding to FcγRIIa and FcγRIIb but did not gain binding to activating receptor FcγRIIIa. Thus, G996 binds C1q, inhibits CDC, and binds all Fc receptors except FcγRIIIa (FIGS. 18A, 18B, and 19, top panels). However, also surprisingly, G996 exhibited no canonical binding in a mouse, making it an ideal compound with which to assess pure CDC inhibition in rodents (FIG. 19, bottom three panels).

G1042 is on the G045c background and has 6 mutations (E233P, G236R, S267E, H268F, S324T, and L328F). Thus, G1042 differs from G994 in that it includes the mutation L328F, which is expected to increase binding to FcγRIIb. Surprisingly, G1042 resulted in not only strong binding to FcγRIIb but also to FcγRI and FcγRIIa (FIGS. 20A, 20B, and 21).

G1043 and G1046 each are on the G045c background and each have 5 mutations: P238D/D265G/S267E/H268F/S324T and P238D/D265W/S267E/H268F/S324T, respectively. For both of these stradomers, the addition of the P238D mutation to the other mutations surprisingly resulted in binding to FcγRIIa (FIGS. 22-25). Both stradomers were expected to have increased binding to FcγRIIb and decreased binding to FcγRIIa due to the mutation at position 238; however, surprisingly, G1043 exhibited binding to both FcγRIIa and FcγRIIb (FIGS. 22A, 22B, and 23), and G1046 exhibited binding to FcγRIIa but not to FcγRIIb (FIGS. 24A, 24B, and 25).

G1050 is on the G045c background and has 8 mutations and a deletion at position 236 (E233P/L234V/L235A/S267E/H268F/N297A/S324T/S328F, and a deletion at position 236). These mutations were expected to reduce or eliminate binding to FcγRIIa and FcγRIII (due to the mutations at E233P/L234V/L235A and the deletion at 236) but retain binding to FcγRIIb (due to the mutation at position 328); however, surprisingly, G1050 exhibits binding to FcγRIIa and FcγRIIb, but no binding to FcγRI or FcγRIII (FIGS. 26A, 26B, and 27).

G1049 is on the G019 background and has 4 mutations (S267E/H268F/S324T/L328F). Thus, relative to G1003, G1049 has an additional mutation at L328F, which was expected to increase binding to FcγRIIb only. However, surprisingly, G1049 exhibits strong binding to all canonical FcγRs (FIGS. 28A, 28B, and 29) and very surprisingly demonstrates strong binding to C1q and inhibition of CDC whereas G019 does not. Thus, it was particularly surprising that strong binding to C1q and inhibition of CDC could be achieved via point mutations in a stradomer having the G019 background structure.

Figure 30B:
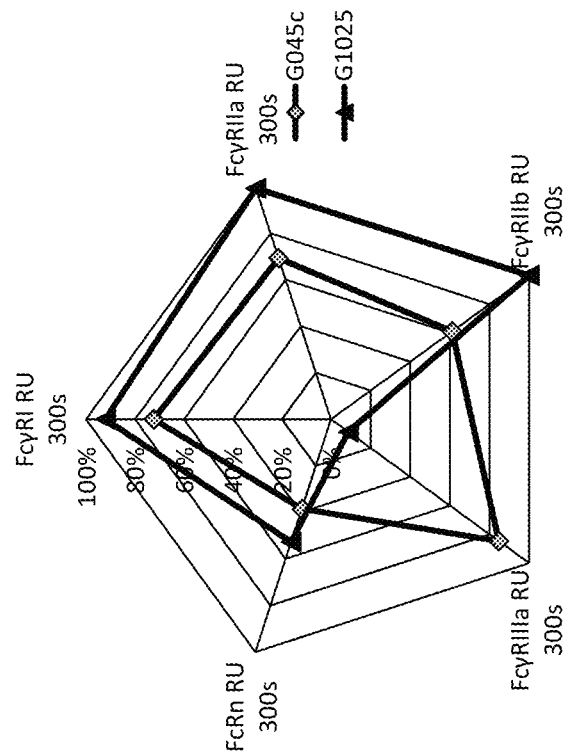
FIG. 30A-FIG. 30B provide a radar graph of the RUmax for each Fc receptor, C1q ELISA, and CDC inhibition data for G045c and complement-preferential stradomer G1025 (FIG. 30A) and a radar graph of the RU at 300 seconds (RU300s) for each Fc receptor for G045c and complement-preferential stradomer G1025 (FIG. 30B).
Figure 30A:
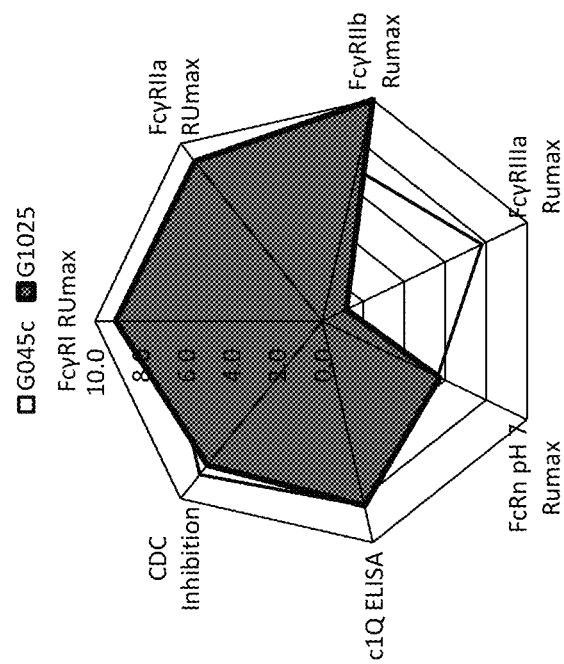

G1025 is on the G045c background and has 4 mutations (P238D/S267E/H268F/S324T). The mutation at positon 238 was expected to increase binding to FγRIIb and decrease binding to FcγRT, FcγRIIa, and FcγRIIIa; however, surprisingly, only binding to FcγRIIIa was decreased, and the stradomer retained robust binding to FcγRIIb, FcγRT, and FcγRIIa (FIGS. 30A and 30B).

An overall summary of the results of the study is provided in Table 3.

TABLE 3

Summary of complement-preferential stradomer activity

| | FcγRI binding | FcγRIIa binding | FcγRIIb binding | FcγRIIIa binding | FcRn binding | C1q binding | CDC inhibition |
|---|---|---|---|---|---|---|---|
| G994  | *** | —   | *   | —   | *** | *** | *   |
| G996  | *** | *** | *** | —   | *** | *** | *   |
| G997  | *** | **  | *** | *** | *** | *** | *   |
| G998  | *** | —   | *   | —   | *** | *** | *   |
| G1003 | *** | *   | *** | **  | *** | *** | *   |
| G1006 | *** | **  | *   | —   | *** | *** | *   |
| G1023 | *** | *** | *** | *** | *** | *** | *   |
| G1022 | —   | **  | *   | —   | *** | *** | *   |
| G1025 | *** | *** | *** | —   | *** | *** | *   |
| G1027 | *** | *   | *   | —   | *** | *** | *   |
| G1032 | *** | *** | *** | *** | *** | *** | *   |
| G1033 | *   | *   | —   | —   | *** | *** | *   |
| G1042 | *** | *** | *** | —   | *** | *** | *   |
| G1043 | *** | *   | **  | —   | *** | *** | *   |
| G1046 | *** | *   | *   | —   | *** | *** | (*) |
| G1049 | *** | *** | *** | **  | *** | *** | *   |
| G1050 | —   | *** | *** | —   | *** | *** | *   |

(*) indicates marginal activity
— indicates no binding

Example 2

Complement-Preferential Stradomers Exhibit Retained or Enhanced Binding to C1q

A comparison of C1q binding among stradomers G994, G996, G997, and G998, in comparison to parent GL-2045 or to Fc negative control G001 is provided in FIG. 31. FIG. 31A shows the absorbance at increasing concentrations of the indicated stradomers, and FIG. 31B shows the log-transformed data and the EC50 values for each of the tested stradomers. Ec50 values are shown in µg/mL. Together, the data demonstrate that the stradomers G997, G998, G996, and G994 exhibit superior C1q binding relative to G001 (IgG1 Fc control), as well as superior C1q binding relative to the parent stradomer GL-2045.

Taken together, the results of the study demonstrate that the stradomers provided herein exhibit binding to C1q and minimal or absent binding to FcγRT, FcγRII, and/or FcγRIII.

Example 3

C3 Binding of Complement-Preferential Stradomers

A study was conducted to assess the binding of complement-preferential stradomers to C3.

96 well plates were coated with C3 complement component (Quidel, #A401; 1 µg/ml in PBS) overnight at 4° C., followed by washing 3x with 300 µl PBS 1x0.1% Tween 20. Plates were blocked with PBS 1x+2% BSA+0.05% Tween 20, for 2 hours at room temperature. The compound to be tested (GL-2045, G001, G997, G998, G994, or G996) was incubated with bound C3, starting at 100 µg/ml and 1:1 down to 0.78125 µg/ml in blocking buffer) for 2 hr at RT followed by wash 3x (300 µl PBS 1x0.1% Tween 20). Compound interacting with C3 was detected by Biotin Mouse anti-Human IgG1, (BD# 555 869)+Streptavidin-HRP (Cat #: 7100-05 Southern Biotech) 1/5000 (ea.) in PBS-BSA-T 1:10 and 1:50 100 µl/well 1H at RT followed by wash 4x (300 µl PBS 1x0.1% Tween 20). Color was developed with TMB Substrate reagent 100 µl per well for 20 minutes and reaction is stopped with 50 µl H2SO4 1M and absorbance is read at 450/650 nm.

Figure 32:
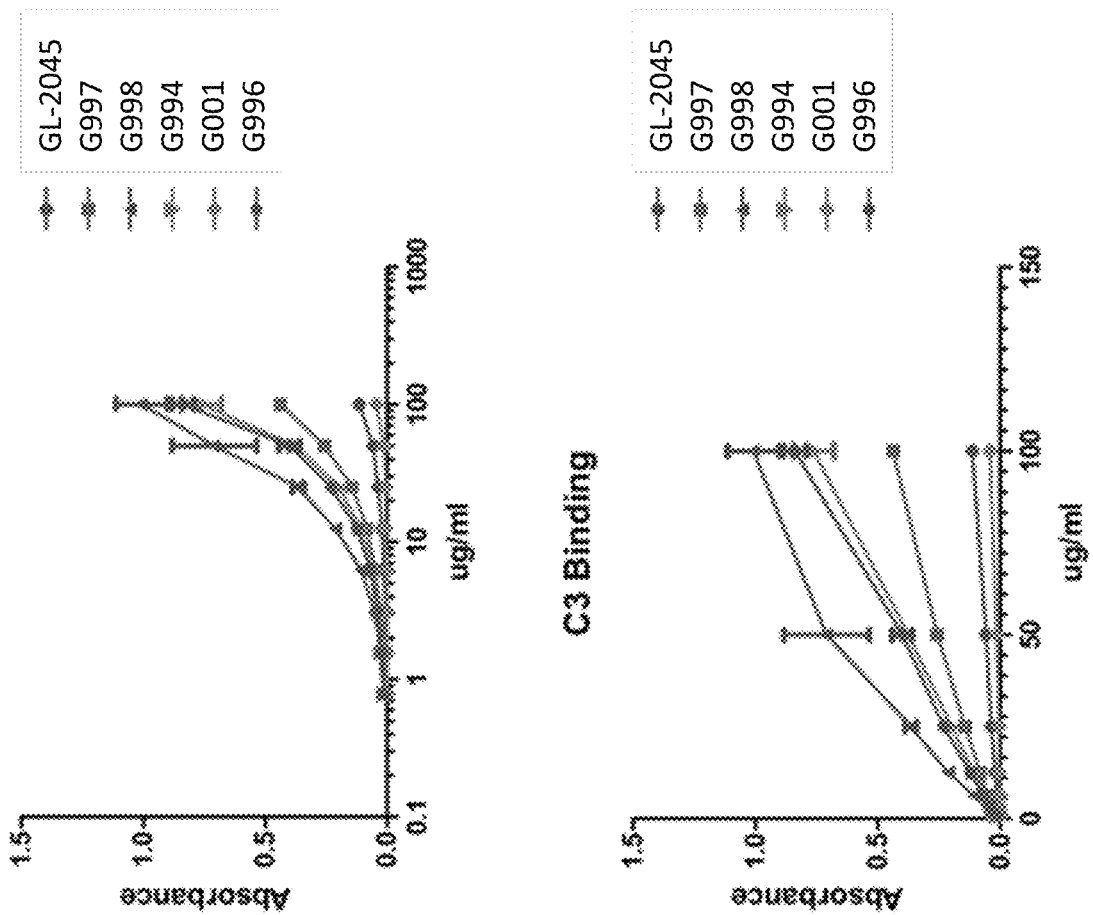
FIG. 32 shows the binding of negative control G001, parent stradomer GL-2045, G994, G996, G997, and G998 to complement component C3 as measured by absorbance at increasing concentrations of stradomer in an ELISA assay. The top panel shows the log-transformed absorbance data and the bottom panel shows the non-log transformed absorbance data.

The results of the study are shown in FIG. 32. Negative control G001 and stradomer G996 did not bind C3. G997 exhibited an intermediate level of C3 binding relative to the negative control and the parent GL-2045 stradomer. G994, GL-2045, and G998 exhibited the highest C3 binding.

Example 4

C3b, C4, and C5 Binding of Complement-Preferential Stradomers

Studies were conducted to assess binding of complement-preferential stradomers to C3b, C4, and C5.

For C3b binding, 96 well plates were coated with C3b complement component (GenWay Biotech #GWB-8BA994; 1 µg/ml in PBS). 100 µl C3b complement component was added per well and incubated overnight at 4° C. followed by washing 3x (300 µl PBS 1x0.1% Tween 20). Plates were blocked in blocking buffer (PBS 1x+2% BSA+0.05% tween 20) 2H at room temperature, followed by washing 3x (300 µl PBS 1x0.1% Tween 20). The compound to be tested (G001, GL-2045, G997, G998, or G994) was reacted to C3b for 4 hr at room temperature, with dilutions starting at 100 µg/ml and diluted 1:1 down to 0.78125 µg/ml in blocking buffer followed by washing 3x (300 µl PBS 1x0.1% Tween 20). Bound compound was detected with biotinylated Mouse anti-Human IgG1 (BD# 555 869)+Streptavidin-HRP (Cat #: 7100-05 Southern Biotech) 1/5000 (ea.) in blocking buffer 100 µl for 1 hr at room temperature. Color was developed with TMB substrate reagent for 20 min at room temperature, and the reaction was stopped with 50 µl H2SO4 1M. Absorbance was read at 450/650 nm.

For C4 binding, 96 well plates were coated with C4 complement component (Quidel #A402, 1 µg/ml in PBS). 100 µl C4 complement component was added per well and incubated overnight at 4° C. followed by washing 3× (300 µl PBS 1×0.1% Tween 20). Plates were blocked in blocking buffer (PBS 1×+2% BSA+0.05% tween 20) 2H at room temperature, followed by washing 3× (300 µl PBS 1×0.1% Tween 20). The compound to be tested (G001, GL-2045, G996, G997, G998, or G994) was reacted to C4 for 4 hr at room temperature, with dilutions starting at 100 µg/ml and diluted 1:1 down to 0.78125 µg/ml in blocking buffer followed by washing 3× (300 µl PBS 1×0.1% Tween 20). Bound compound was detected with biotinylated Mouse anti-Human IgG1 (BD# 555 869)+Streptavidin-HRP (Cat #: 7100-05 Southern Biotech) 1/5000 (ea.) in blocking buffer 100 µl for 1 hr at room temperature. Color was developed with TMB substrate reagent for 20 min at room temperature, and the reaction was stopped with 50 µl H2SO4 1M. Absorbance was read at 450/650 nm.

For C5 binding, 96 well plates were coated with C5 complement component (Quidel #A403, 1 µg/ml in PBS). 100 µl C5 complement component was added per well and incubated overnight at 4° C. followed by washing 3× (300 µl PBS 1×0.1% Tween 20). Plates were blocked in blocking buffer (PBS 1×+2% BSA+0.05% tween 20) 2H at room temperature, followed by washing 3×(300 µl PBS 1×0.1% Tween 20). The compound to be tested (G001, GL-2045, G996, G997, G998, or G994) was reacted to C5 for 4 hr at room temperature, with dilutions starting at 100 µg/ml and diluted 1:1 down to 0.78125 µg/ml in blocking buffer followed by washing 3× (300 µl PBS 1×0.1% Tween 20). Bound compound was detected with biotinylated Mouse anti-Human IgG1 (BD# 555 869)+Streptavidin-HRP (Cat #: 7100-05 Southern Biotech) 1/5000 (ea.) in blocking buffer 100 µl for 1 hr at room temperature. Color was developed with TMB substrate reagent for 20 min at room temperature, and the reaction was stopped with 50 µl H2SO4 1M. Absorbance was read at 450/650 nm.

Figure 33:
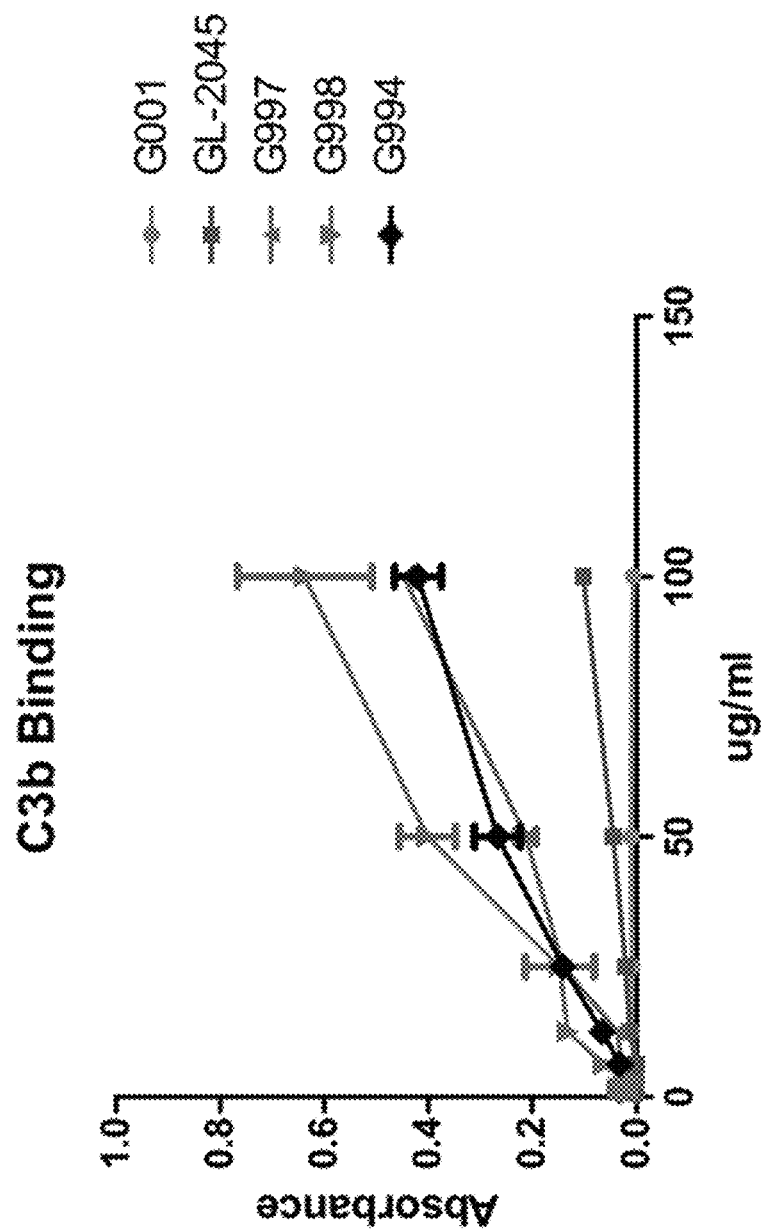
FIG. 33 shows the binding of negative control G001, parent stradomer GL-2045, G997, G998, and G994 to complement component C3b as measured by absorbance at increasing concentrations of stradomer in an ELISA assay.
Figure 34:
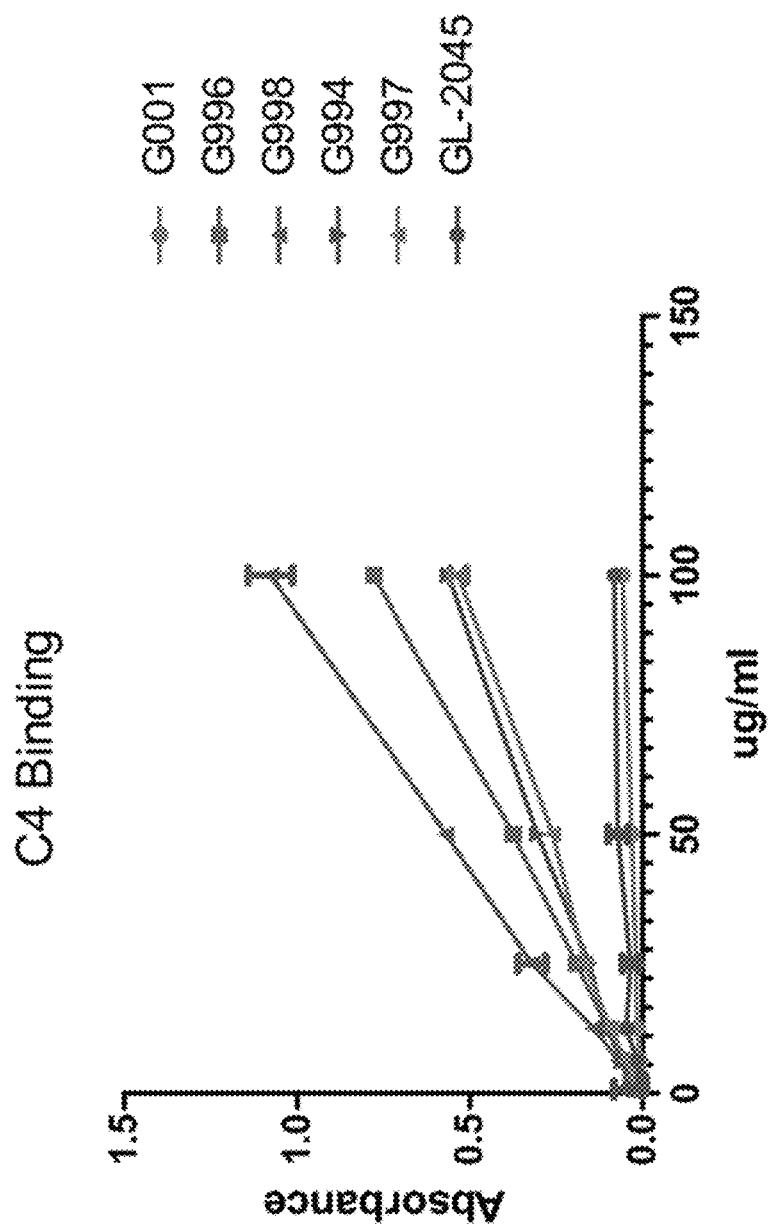
FIG. 34 shows the binding of negative control G001, parent stradomer GL-2045, G996, G997, G998, and G994 to complement component C4 as measured by absorbance at increasing concentrations of stradomer in an ELISA assay
Figure 35:
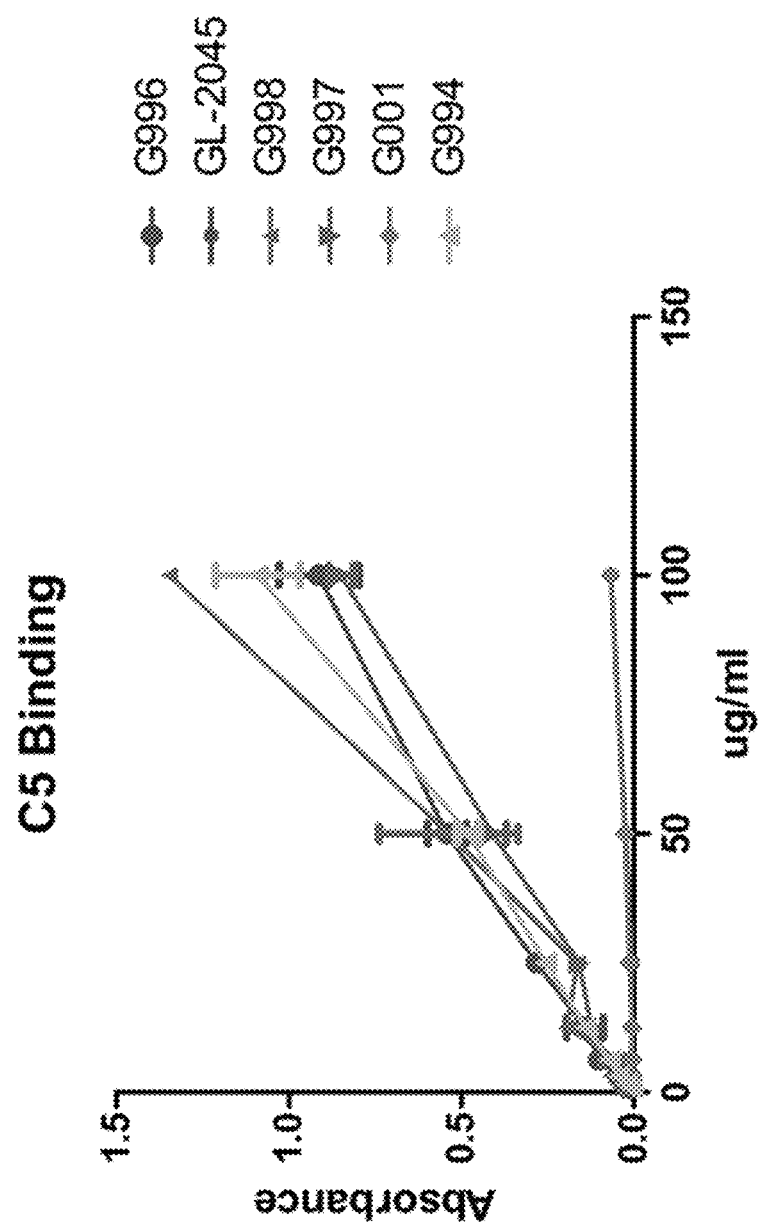
FIG. 35 shows the binding of negative control G001, parent stradomer GL-2045, G996, G997, G998, and G994 to complement component C5 as measured by absorbance at increasing concentrations of stradomer in an ELISA assay.

The results of the studies are shown in FIG. 33 (C3b complement component), FIG. 34 (C4 complement component) and FIG. 35 (C5 complement component). Negative control G001 did not bind to C3b, C4, or C5. Parent stradomer GL-2045 bound to C5, but did not exhibit binding to C3b or C4. In contrast, complement-preferential stradomers G994, G997, and G998 each bound to C4 as well as C5.

Example 5

Complement Preferential Stradomer Treatment for Nephritis in Anti-Thy 1 Model

Complement preferential stradomers were assessed in the Thy-1 nephritis model (anti Thy-1 induced mesangioproliferative glomerulonephritis). In this model, antibody to thymocytes (ATS) is reactive to surface Thy-1 antigen present on rat mesangial cells (Yamamoto 1987 and Jefferson 1999). Administration of ATS induces a complement-dependent mesangiolysis followed by a rapid mesangial proliferative glomerulonephritis that peaks within 5 days after injection, and then resolves over time.

Disease was induced at day 0 by injection of mouse anti-rat CD90 (Thy1.1) (Cedar Lane) in Wistar rats (n=8) to induce glomerulonephritis. On days 0, 2, 4, and 6, animals were administered 40 mg/kg G998, 80 mg/kg G998, 80 mg/kg G994, or 80 mg/kg G1033. Control, non-diseased animals did not receive anti-Thy 1 antibody or other treatment. Positive control Tacrolimus was dosed at 1 mg/kg intramuscular dosed daily starting at day −9 before antisera injection. Day 0 dosing was 4 hours before antisera injection. Urine was collected before dosing and at day 3, 5, 7 and 9 following antisera injection. Kidneys were collected from rats at end of study and fixed in 10% formalin for histology analysis. Serum was collected for serum BUN analysis.

Figure 37:
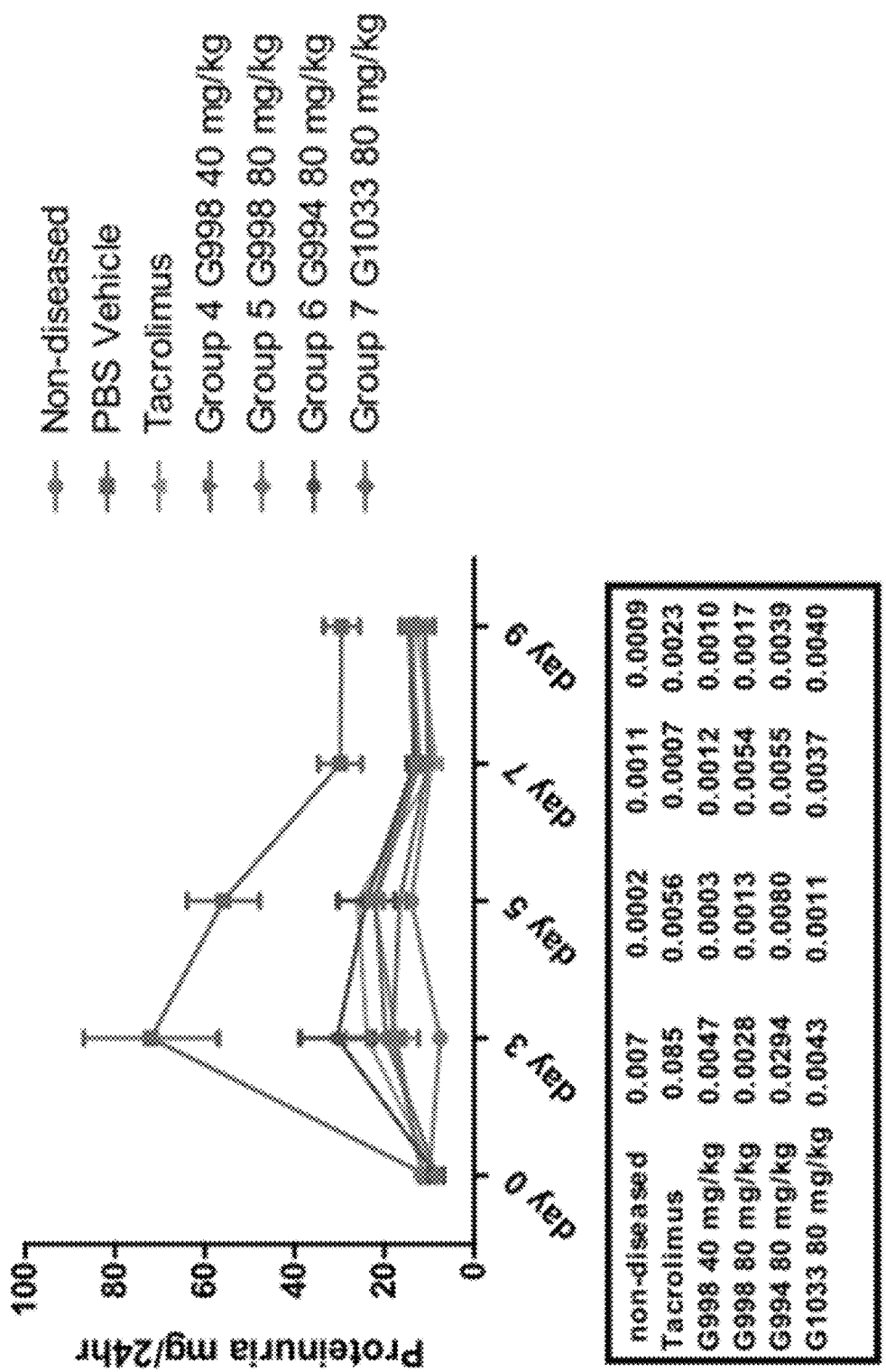
FIG. 37 shows a significant decrease in proteinuria in animals administered test stradomers, in an animal model of nephritis.
Figure 38B:
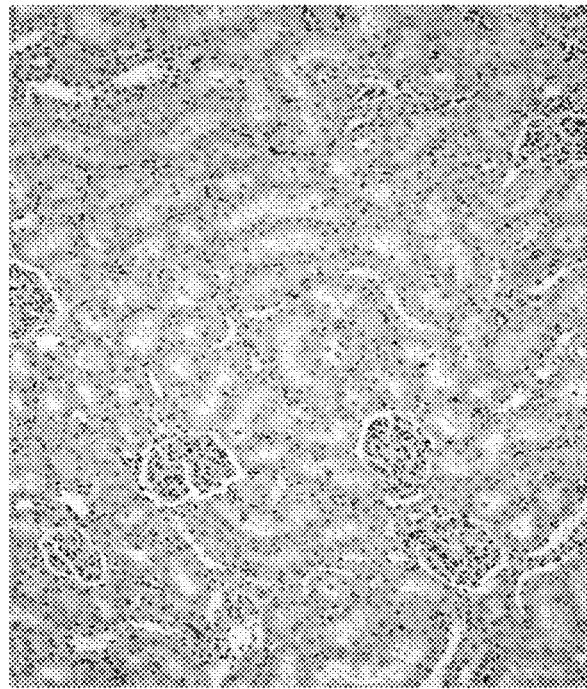
FIG. 38A-FIG. 38B show the histological analysis of a diseased PBS control animal following induction of glomerulonephritis via anti-Thy 1 antibody (FIG. 38A) and an animal that received 40 mg/kg G998 (FIG. 36B).
Figure 38A:
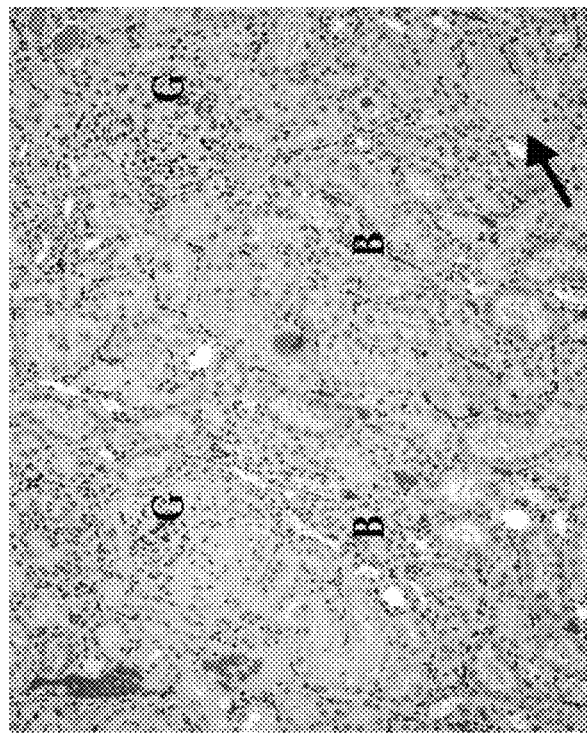
Figure 39:
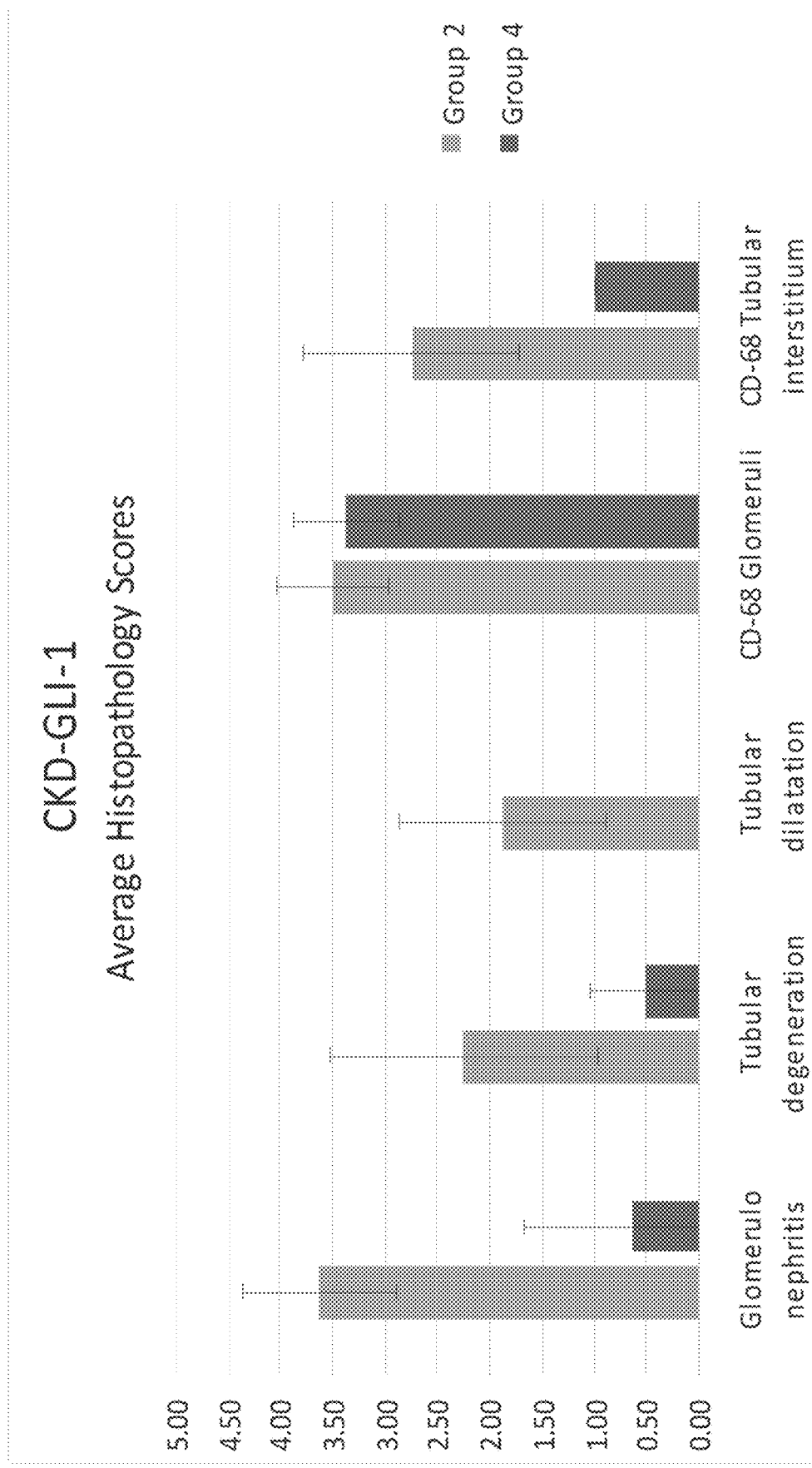
FIG. 39 provides a graphical representation of the histological analysis of the kidney tissues in animals that received PBS as a control treatment (Group 2) or 40 mg/kg G0998 (Group 4).

The results of the study are provided in FIGS. 37, 38A, 38B, 39, and 40; and Table 4. In FIG. 37, the table below the graph provides the P values relative to PBS control mice. Each of the three test compounds G994, G998, and G1033 significantly decreased proteinuria. FIGS. 38A and 38B show the histological analysis of a diseased PBS control mouse (FIG. 38A) and a mouse treated with 40 mg/kg G998 (FIG. 38B). Table 4 and FIG. 39 provide quantitation of the histological analyses of each of the animals in the PBS control group (presented as Group 2 in Table 3) and the 40 mg/kg G998 group (presented at Group 4 in Table 3). The results presented in Table 4 are provided graphically in FIG. 39.

TABLE 4

Quantitative histological results from Thy-1 nephritis model CKD-GLI-1

| Group | Animal | Kidney | | | | |
| --- | --- | --- | --- | --- | --- | --- |
| | | Glomerulo nephritis | Tubular degeneration | Tubular dilatation | CD-68 Glomeruli | CD-68 Tubular interstitium |
| 2 | 2-9 | 4 | 3 | 3 | 3 | 3 |
| | 2-10 | 4 | 2 | 2 | 3 | 2 |
| | 2-11 | 2 | 0 | 0 | 3 | 1 |
| | 2-12 | 3 | 2 | 2 | 3 | 3 |
| | 2-13 | 4 | 3 | 2 | 4 | 4 |
| | 2-14 | 4 | 1 | 1 | 4 | 2 |
| | 2-15 | 4 | 4 | 3 | 4 | 4 |
| | 2-16 | 4 | 3 | 2 | 4 | 3 |
| | AVERAGE | 3.63 | 2.25 | 1.88 | 3.50 | 2.75 |
| | SD | 0.74 | 1.28 | 0.99 | 0.53 | 1.04 |
| 4 | 4-25 | 1 | 0 | 0 | 3 | 1 |
| | 4-26 | 1 | 1 | 0 | 4 | 1 |
| | 4-27 | 0 | 1 | 0 | 3 | 1 |
| | 4-28 | 0 | 1 | 0 | 4 | 1 |
| | 4-29 | 0 | 0 | 0 | 3 | 1 |
| | 4-30 | 0 | 0 | 0 | 4 | 1 |

TABLE 4-continued

Quantitative histological results from Thy-1 nephritis model CKD-GLI-1

| Group | Animal | Kidney | | | | |
|---|---|---|---|---|---|---|
| | | Glomerulo nephritis | Tubular degeneration | Tubular dilatation | CD-68 Glomeruli | CD-68 Tubular interstitium |
| | 4-31 | 0 | 0 | 0 | 3 | 1 |
| | 4-32 | 3 | 1 | 0 | 3 | 1 |
| | AVERAGE | 0.63 | 0.50 | 0.00 | 3.38 | 1.00 |
| | SD | 1.06 | 0.53 | 0.00 | 0.52 | 0.00 |
| t-test | | 2.20447E−05 | 0.00570721 | 0.00106271 | 0.641986775 | 0.002007834 |

0 = examined, no finding,
1 = minimal,
2 = mild,
3 = moderate,
4 = Marked,
P = present,
— = not present.

Figure 40:
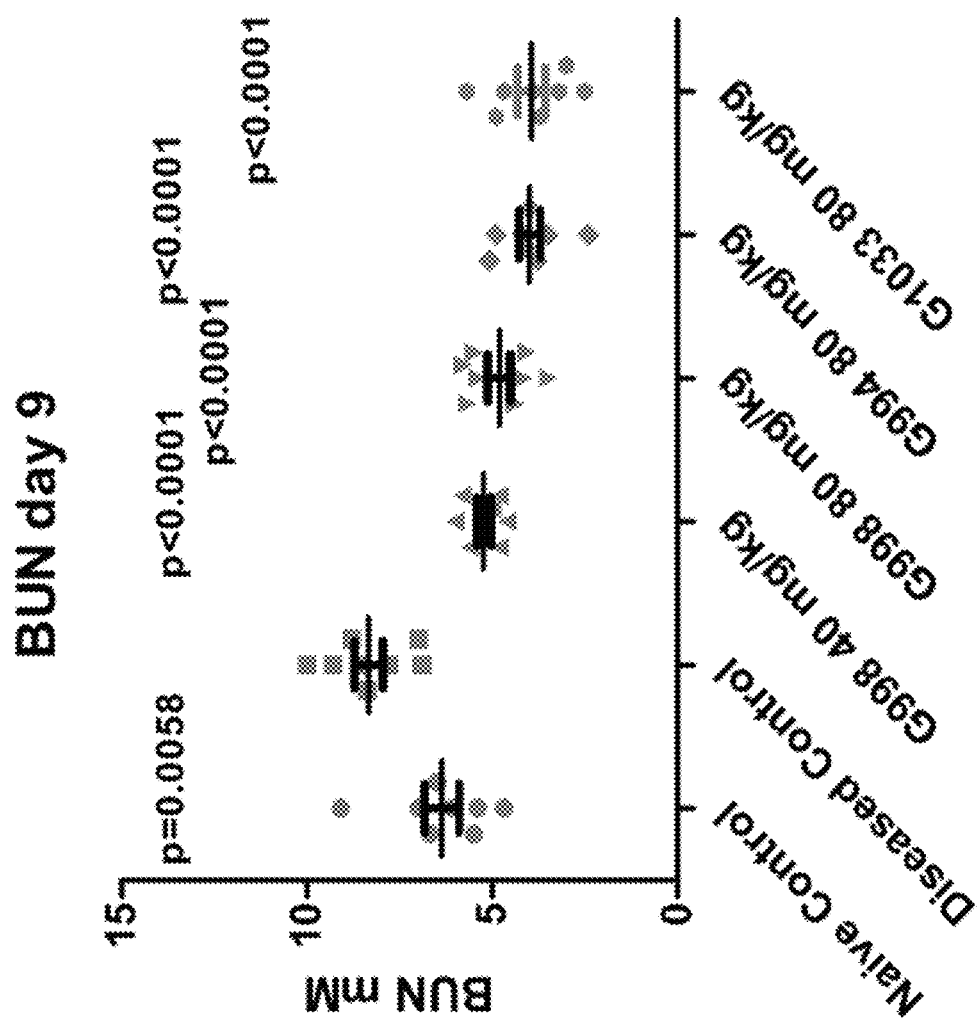
FIG. 40 provides the blood urea nitrogen (BUN) levels in PBS control animals, non-diseased control animals that did not receive anti-Thy 1 antibody, and animals that received G994 (40 mg/kg), G998 (40 mg/kg or 80 mg/kg), or G1033 (40 mg/kg). P values provided on the graph are relative to the control diseased PBS animals.

On day 9, serum was collected from each animal and analyzed for blood urea nitrogen (BUN). In each of the animals that received treatment with complement preferential stradomers, BUN was significantly decreased relative to diseased PBS control animals, indicating an improved glomerular filtration rate and therefore improved disease (FIG. 40).

Example 6

Complement Preferential Stradomer Treatment for Nephritis in the Passive Heymann Nephritis Model Disease was induced in rats at day 0 by injection of anti Fx1a serum (Probetex cat #PTX-002S). G998 was dosed at 60 mg/kg day 0 two hours before antisera injection (dose day 0) or at day 1 one day after antisera injection (dose day 1) and dosing continued 2 times/week for 3 weeks. Vehicle control mice received anti Fx1a serum only. Urine was collected before dosing and at week 1, 2 and 3 following antisera injection and assessed for proteinuria.

Figure 41:
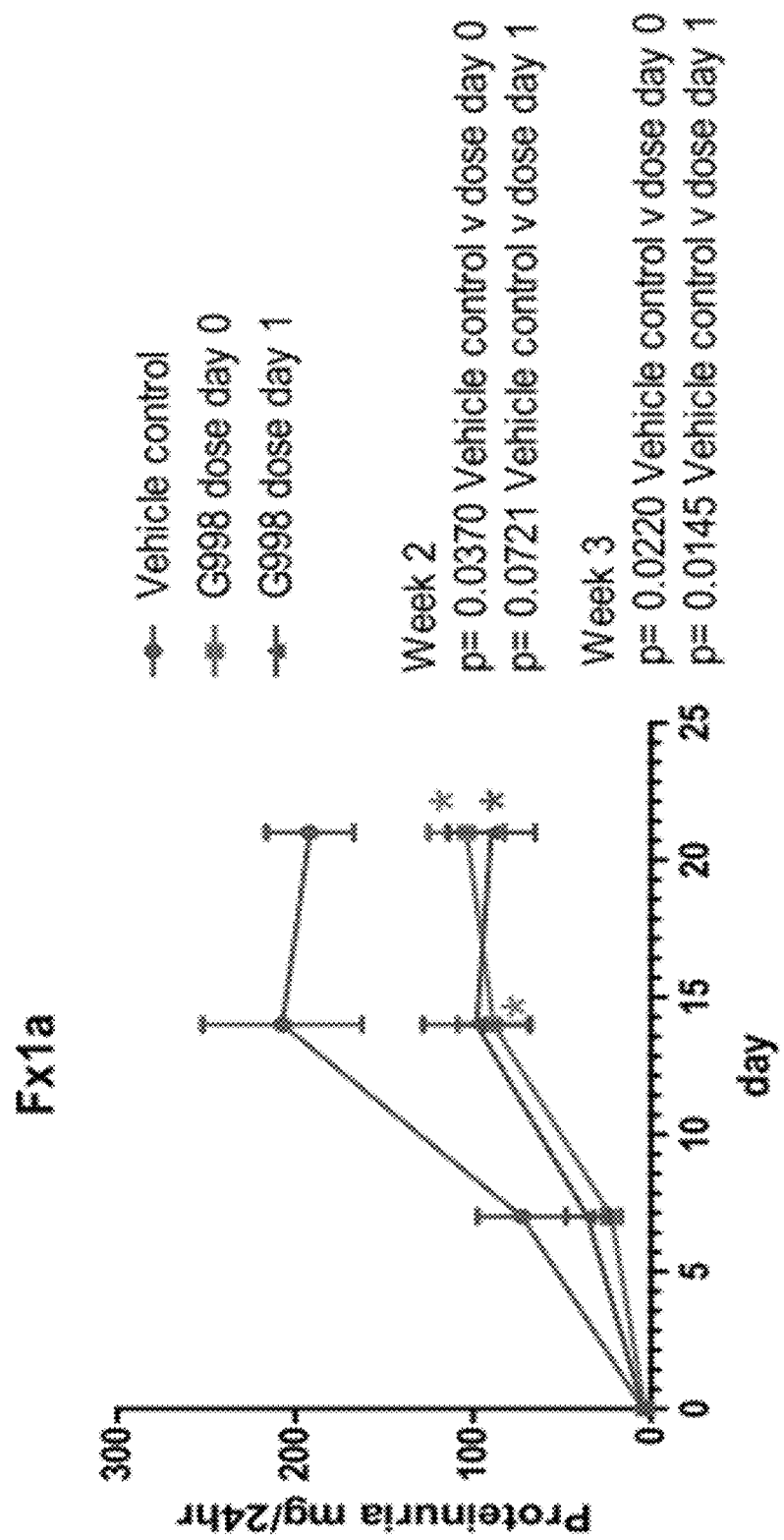
FIG. 41 shows the proteinuria (mg/24 hr) in control animals that received anti Fx1a only, animals that received anti Fx1a and G998 on day 0, and animals that received anti Fx1a on day 0 and G998 on day 1.

The results of the study are provided in FIG. 41. By day 21, both G998 groups exhibited significant reductions in proteinuria relative to the control animals (p=0.0220 for the day 0 G998 group and p=0.0145 for the day 1 G998 group).

Example 7

Drug Levels and Functional Half-Life of Complement Preferential Compounds in Rats A study was undertaken to measure the half-life of complement preferential stradomers G994, G998, and G1033 in rats after a single dose. Functional half-life was measured by assessing the complement activity in blood samples taken at different time points. Blood samples were also measured for levels of the drug target, complement factor c1q, and to assess what fraction of the drug and C1q is bound.

Sprague-Dawley rats (4 animals per group) were given a single dose intravenously of compound G994, G998, or G1033 at 60 mg/kg. Blood samples (1.2-1.4 ml) were collected from each animal by retro-orbital bleed in pre-chilled heparinized tubes at pre-dose, 1, 4, and 8 hours after test compound administration. Blood samples were also collected at days 1, 2, 4, 7 and 10.

Drug levels were measured in plasma samples by ELISA. In this ELISA assay the IgG1 Fc in compounds G994, G998, G1033 reacted with the anti-human IgG Fc antibody (Thermo #MA1-83240) which had been adsorbed to the surface of the plate. After removal of unbound sample proteins by washing, biotinylated anti-human IgG1 (BD #555869) conjugated with streptavidin horseradish peroxidase (HRP, Southern Biotech #7100-05) was added. The HRP-conjugated antibody forms a complex with the previously bound IgG1. The complex was assayed by the addition of a chromogenic substrate (TMB, BD #555214). The quantity of G994, G998 and G1033 in serum samples was interpolated from a standard curve made from the same compound mixed in monkey serum and corrected for sample dilution.

Complement activity was measured in rat plasma samples using an in vitro complement dependent cell killing assay. Briefly CD-20 expressing Will2 cells were incubated at 37C with CD-20 monoclonal antibody for 20 minutes in cell media after which the cells are spun down and re-suspended in fresh media. Cells were distributed into 96 well plates after which rat plasma from different time points was added to cell suspension and plates were incubated at 37° C. for 3 hours. Cytotox Assay Reagent (Promega) was added to each well and plates were incubated in the dark for 15 minutes at room temp. Luminescence was read on a Promega GloMax luminometer and cell death calculated. Complement activity was measured at different plasma levels in the assay, and values for 2% and 4% plasma were used for analysis.

Percent complement activity in each sample was calculated relative to complement activity in predose samples after subtraction of no antibody control sample.

Figure 42:
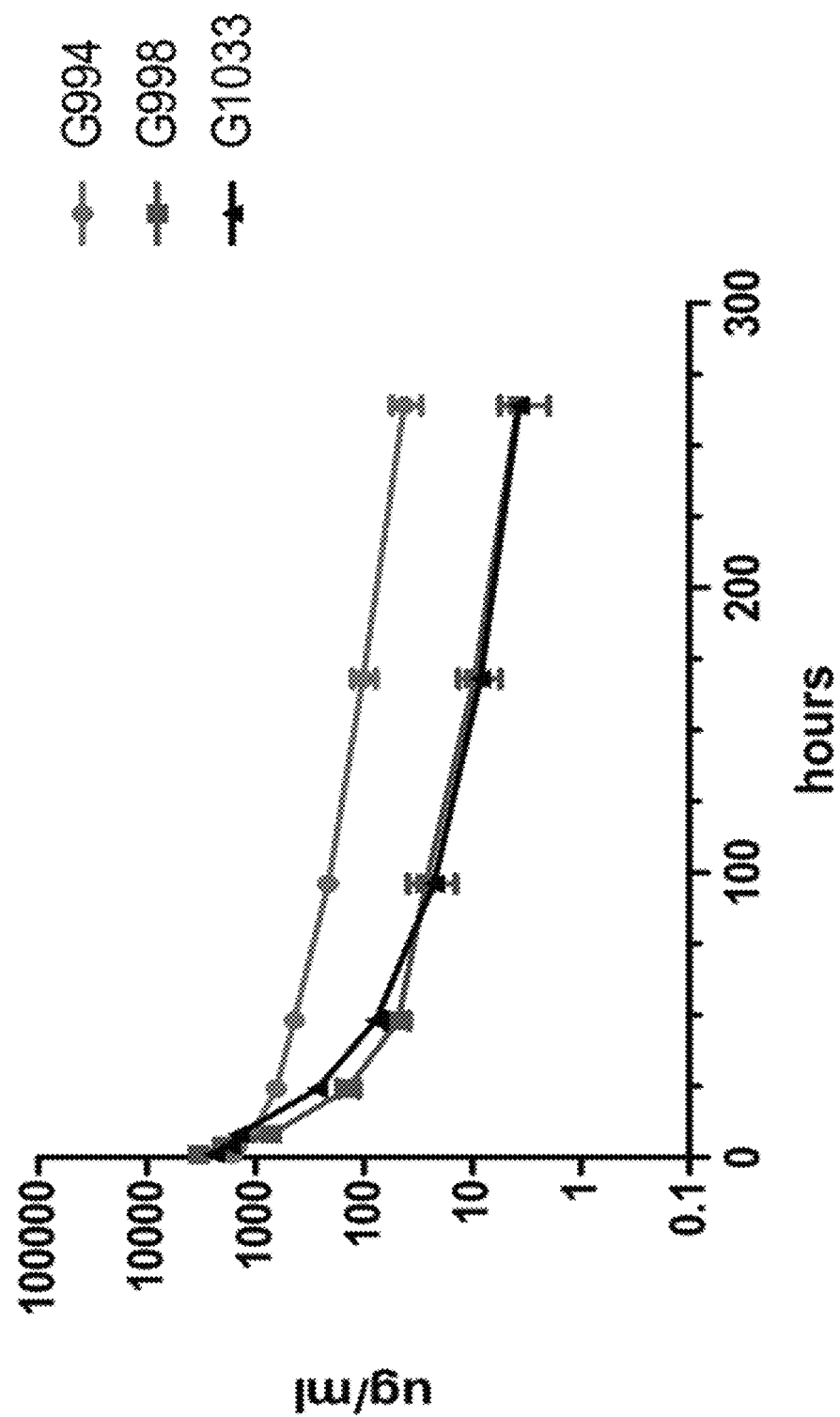
FIG. 42 shows the levels (µg/mL) of G994, G998, or G1033 in rats following a single dose of the indicated compound at time.

The results of the study are provided in FIGS. 42-45. FIG. 42 provides the half lives of G994, G998, and G1033. G994 had a significantly longer half life than the other two compounds tested in this experiment. Compound G994 eliminated complement activity in rat blood for an extended time period. Complement activity after dosing with G994 remained low until 96 hours (4 days) and was at approximately 50% of normal levels at day 10. Compound G998 and G1033 exhibited a somewhat shorter half-life in rat. For compound G998, approximately 50% of pre-dose complement levels were present at day 2. For compound G1033, functional half-life was between 2 and 4 days.

Figure 43:
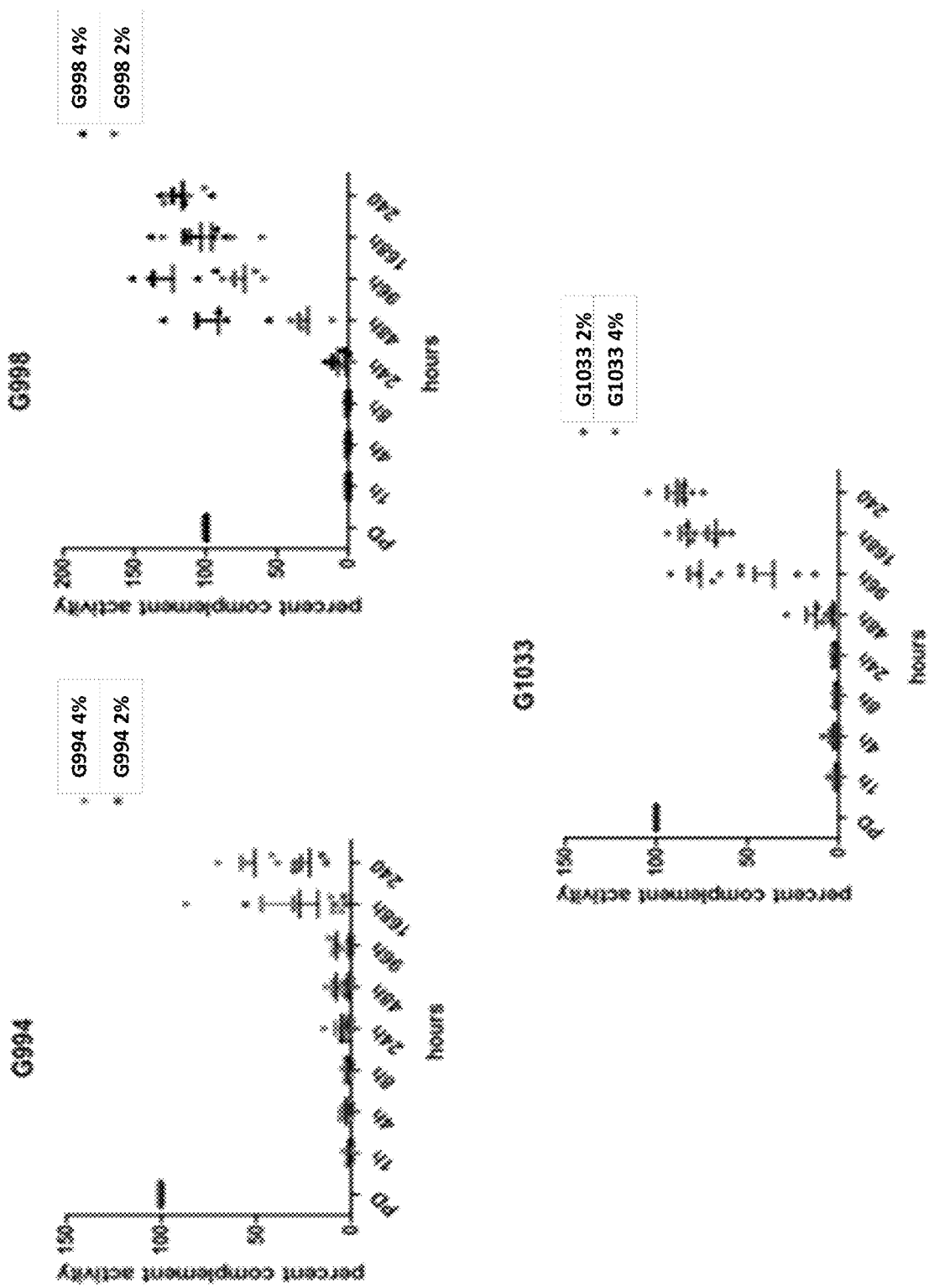
FIG. 43 shows the complement activity in rat blood following the single dose of G994 (top left panel), G998 (top right panel), or G1033 (bottom panel).

FIG. 43 provides the complement activity in rat blood following the single dose of G994, G998, or G1033.

Figure 44A:
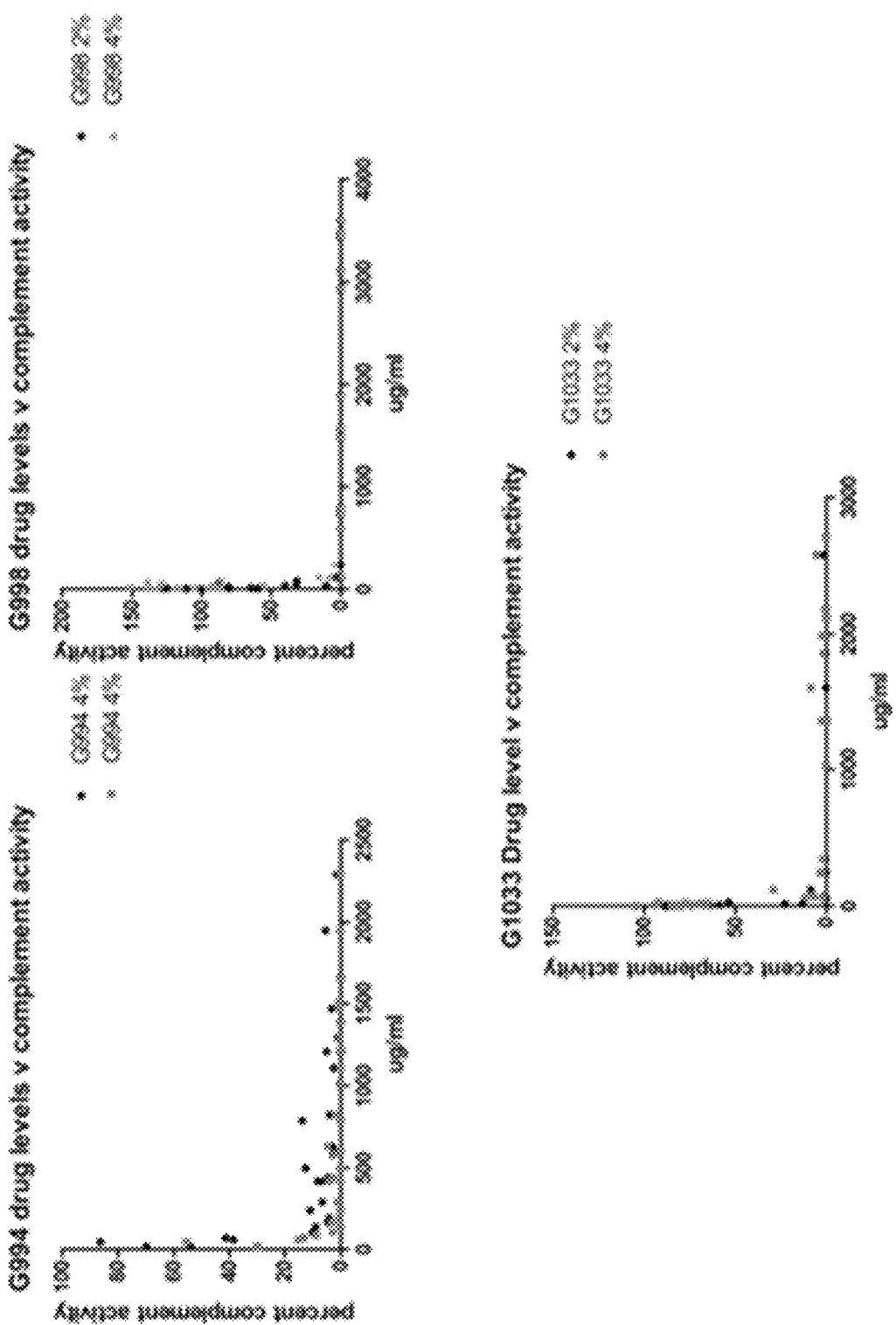
FIG. 44A-FIG. 44B provide the correlation between drug levels (μg/mL on x axes) and complement activity (% on y axis) for each of G994 (top left panels), G998 (top right panels), and G1033 (bottom panels).
Figure 44B:
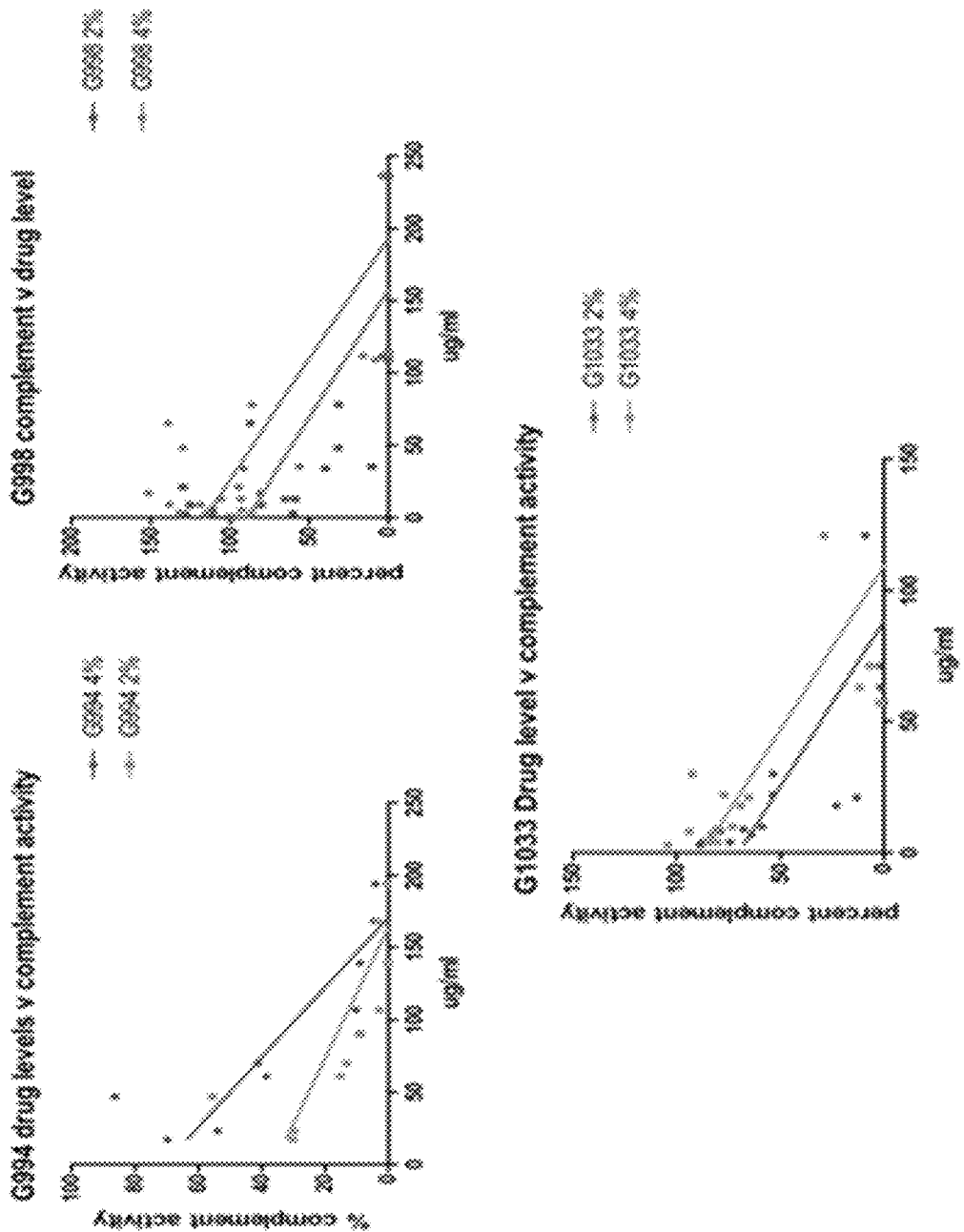

Complement activity is expressed as the percent of cell death as measured at 2% or at 4% plasma levels in the assay. FIGS. 44A and 44B provide the correlation between drug levels and complement activity for each of the complement preferential compounds G994, G998, and G1033. FIG. 44A provides all data points collected in the study, and FIG. 44B focuses on the lower drug concentration data points (0-250 µg/ml for G994 and G998, and 0-150 µg/ml for G1033). Drug levels needed to eliminate complement activity in rat blood were estimated from the estimated×interception levels. For G994 the x interception value is 164 and 170 µg/ml for 2% and 4% serum. $R^2$ values for the correlation is 0.696 and 0.558. For G998 the x-intercept value is 158 and 193 µg/ml with $R^2$ values of 0.519 and 0.560 for 2% and 4% serum. For G1033 the x-intercept is 88 and 109 µg/ml with R2 values of 0.612 and 0.648.

From the estimated x-interception levels, approximately 100-200 µg/ml of compound G994 and G998 is needed to eliminate complement activity. For compound G1033 the approximate amount needed to eliminate complement activity is 100 µg/ml.

Example 8

Pharmacokinetic Study in Cynomolgus Monkeys

A study was undertaken to measure the half-life of G994, G998, or G1033 in cynomolgus monkeys after a single dose of the complement preferential compound.

Cynomolgus monkeys (3 animals per group) were given a single dose subcutaneously of compound G994 G998 or G1033 at a dose of 28 mg/kg. Blood samples (approximately 3 ml) were collected to serum separator tubes from each animal at predose and at 1, 2, 4, 12, 24, 48, 72, 144, 216, and 312 hours post-dose. Drug levels were measured in serum samples by ELISA. In this ELISA assay the IgG1 Fc in compounds G994, G998, G1033 reacts with the anti-human IgG Fc antibody (Thermo #MA1-83240) which has been adsorbed to the surface of the plate. After removal of unbound sample proteins by washing, biotinylated anti-human IgG1 (BD #555869) conjugated with streptavidin horseradish peroxidase (HRP, Southern Biotech #7100-05) was added. The HRP-conjugated antibody forms a complex with the previously bound IgG1. The complex was assayed by the addition of a chromogenic substrate (TMB, BD #555214). The quantity of G994, G998 and G1033 in serum samples was interpolated from a standard curve made from the same compound mixed in monkey serum and corrected for sample dilution.

Complement activity was measured in cynomolgus serum samples using an in-vitro complement dependent cell killing assay. Briefly, CD-20 expressing Will2 cells were incubated at 37C with CD-20 monoclonal antibody for 20 minutes in cell media after which the cells were spun down and re-suspended in fresh media. Cells were distributed into 96 well plates after which serum from different time points was added to cell suspension and plates were incubated at 37° C. for 3 hours. Cytotox Assay Reagent (Promega) was added to each well and plates were incubated in the dark for 15 minutes at room temp. Luminescence was read on a Promega GloMax luminometer and cell death was calculated. Complement activity was measured at different serum levels in the assay, and values for 2% and 4% plasma were used for analysis.

Percent complement activity in sample was calculated relative to complement activity in predose samples after subtraction of no antibody control sample.

Figure 45:
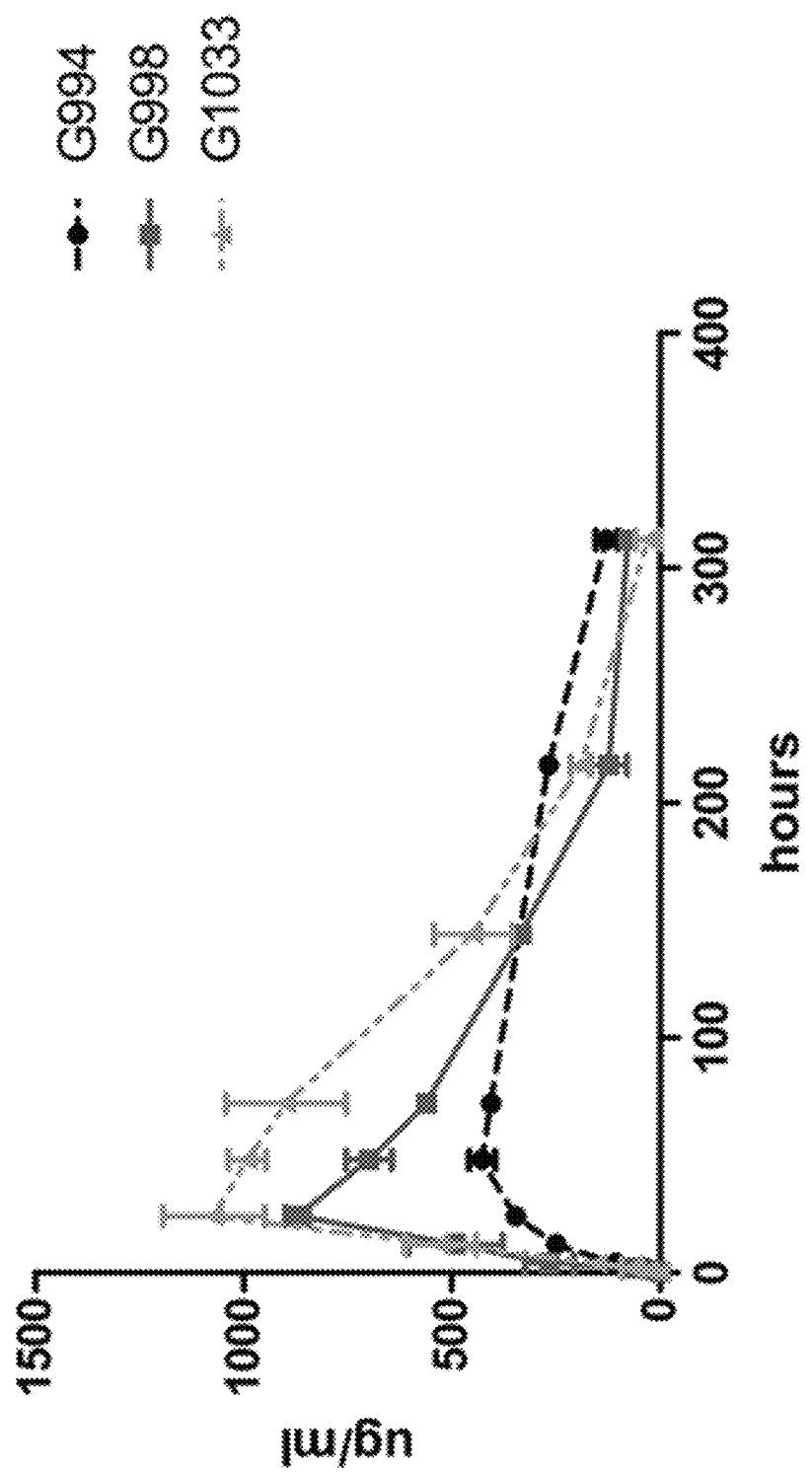
FIG. 45 shows the drug levels (μg/mL) of G994, G998, or G1033 in cynomolgus monkeys after a single dose of complement preferential compound at time 0, as measured at 0, 1, 2, 4, 12, 24, 48, 72, 144, 216, and 312 hours post-dose.
Figure 46:
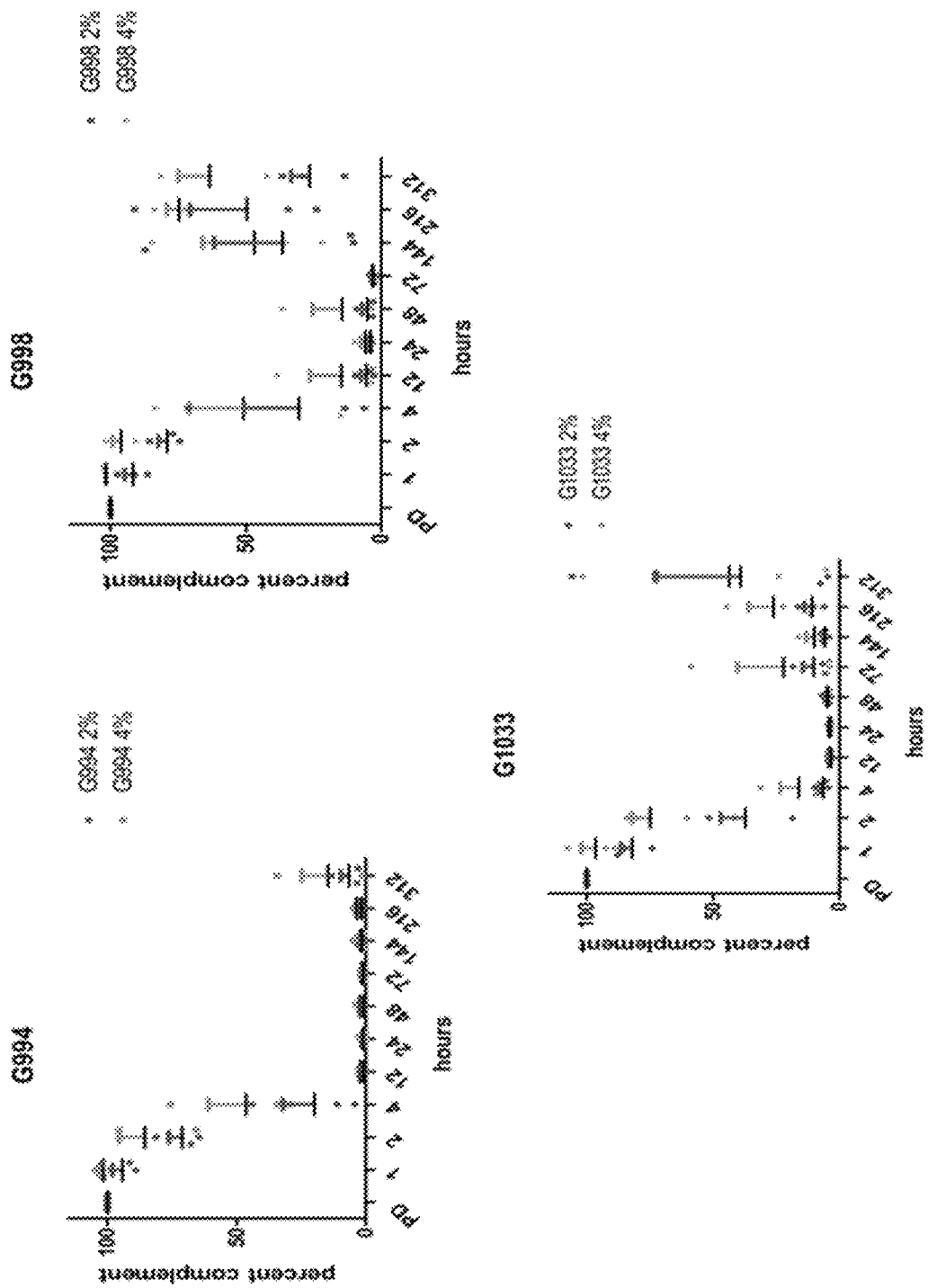
FIG. 46 shows the complement activity (% cell death) over time following the single dose of G994 (top left panel), G998 (top right panel), or G1033 (bottom panel).
Figure 47A:
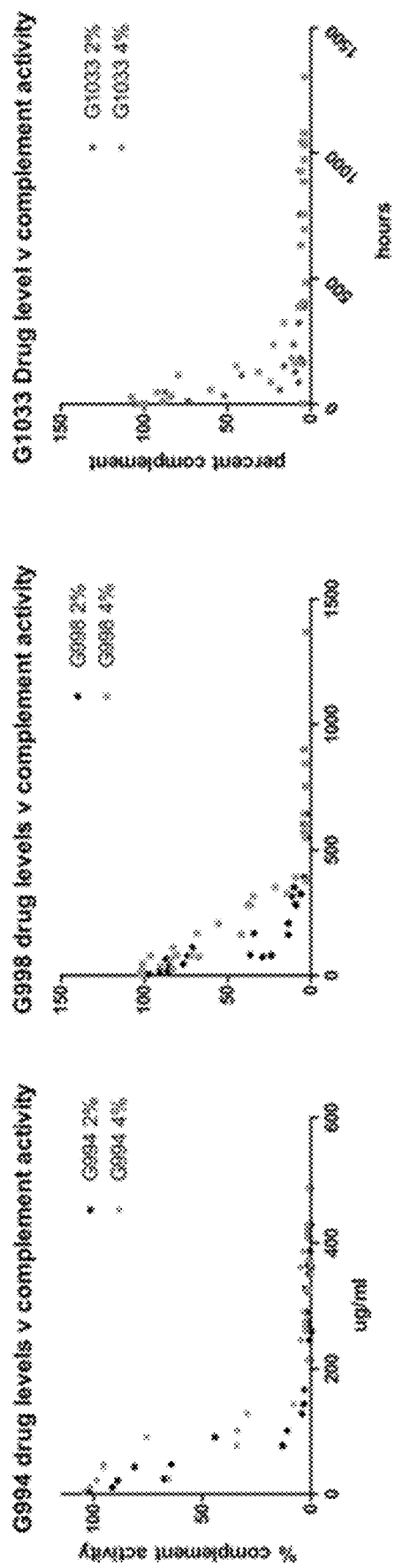
Figure 48B:
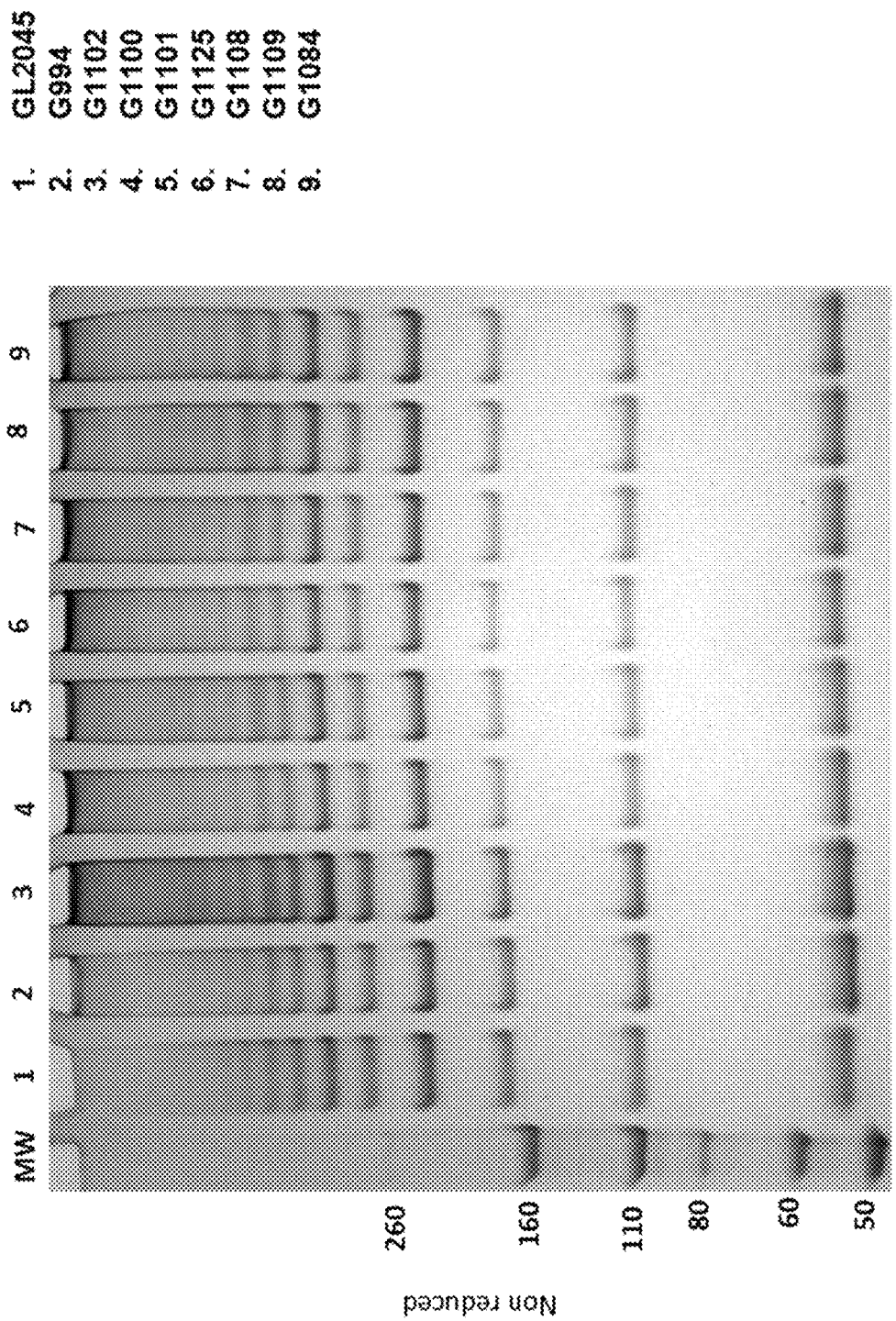
Figure 48D:
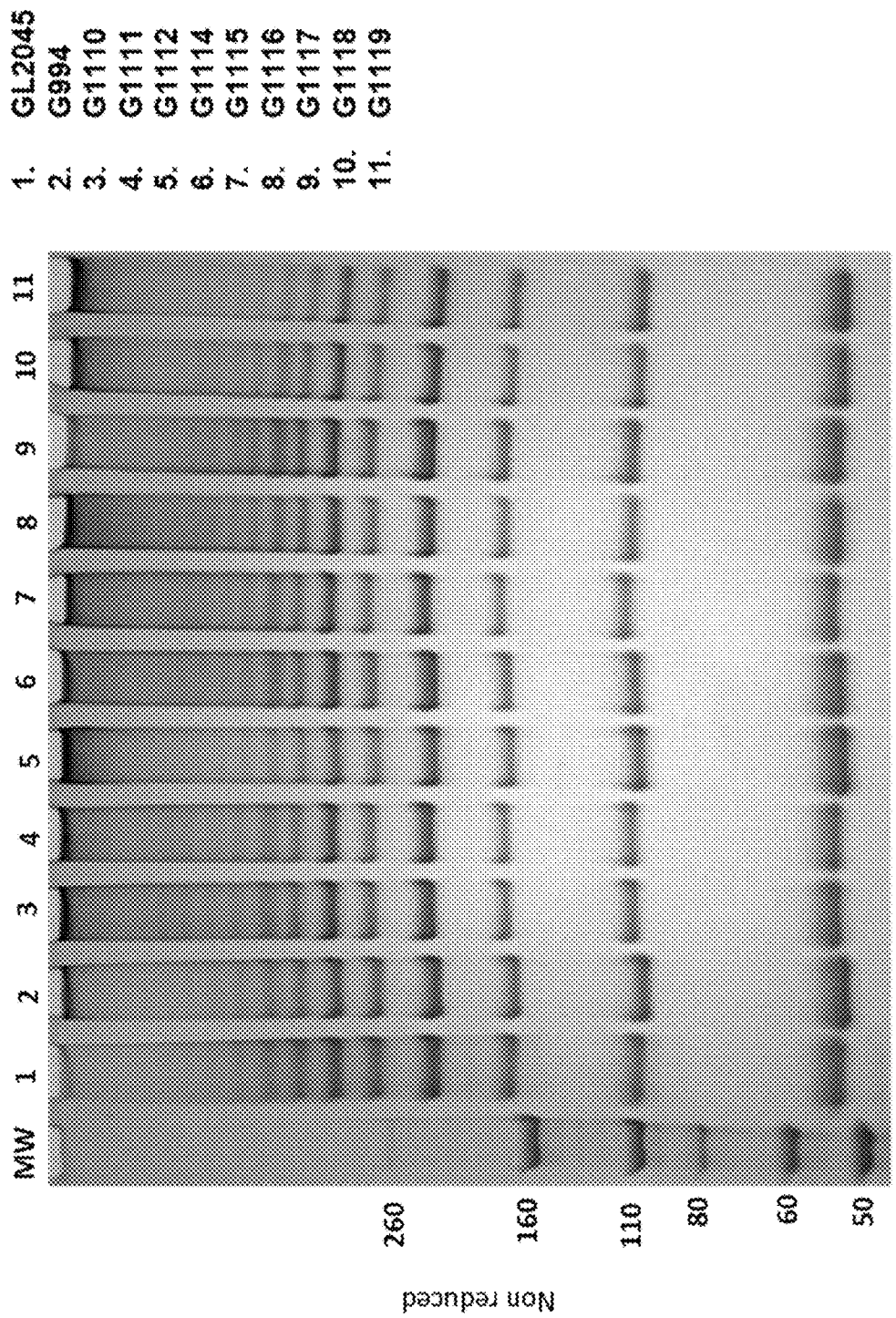
Figure 48G:
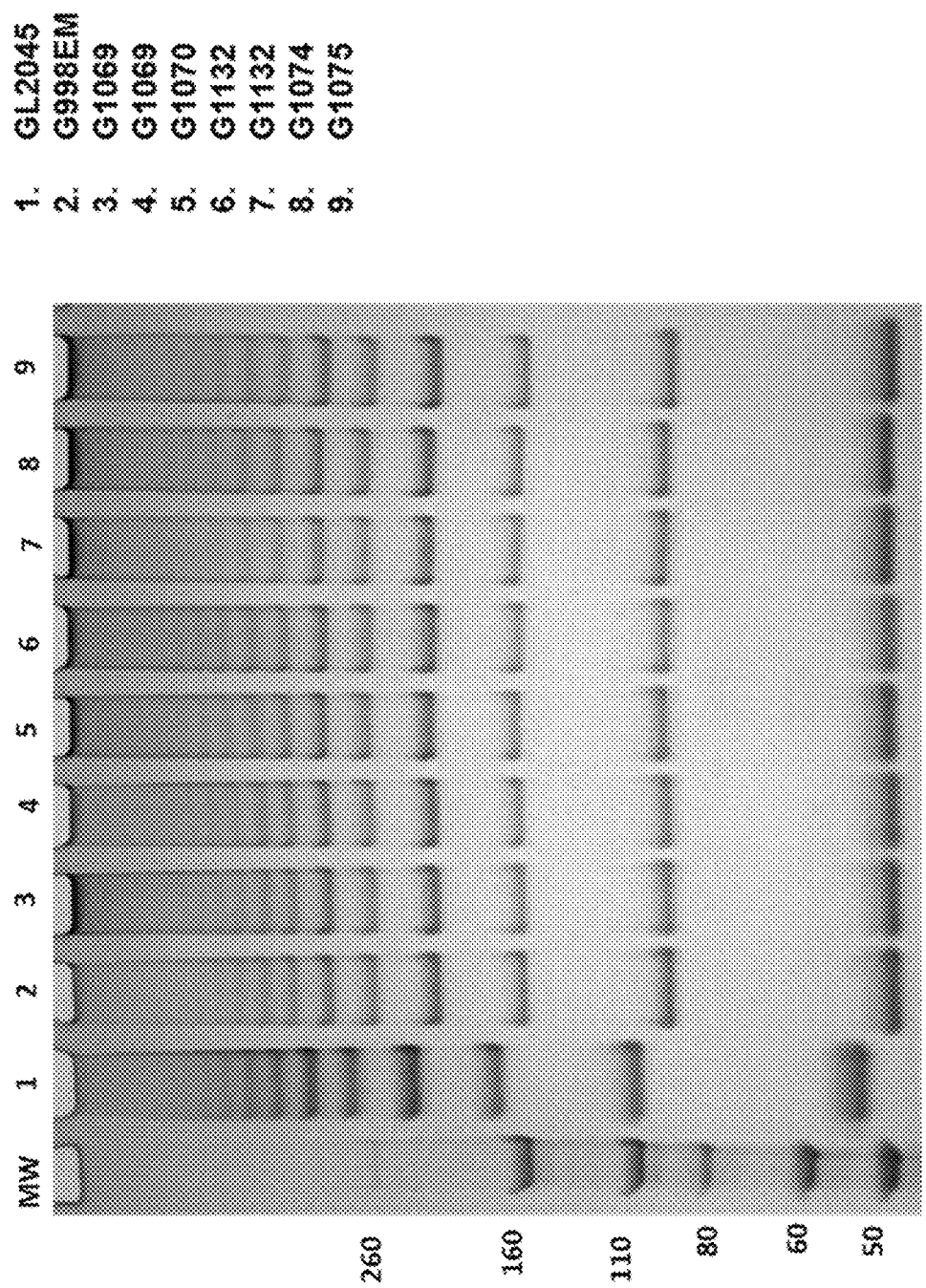

The results of the study are provided in FIGS. 45-47. FIG. 45 shows the drug level of each of the complement preferential stradomers tested after a single dose of the compound. G994 reached significantly lower peak concentrations than, but had a significantly longer half-life than, compounds G998 and G1033. FIG. 46 shows the complement activity (% cell death) over time following the single dose of G994 (top left panel), G998 (top right panel), or G1033 (bottom panel). FIGS. 47A and 47B show the correlation between drug levels and complement activity for each of the compounds tested in the study. FIG. 47A shows all data points collected in the experiment, and FIG. 47B shows the first part of the curve, with lower drug concentrations.

Studies are also performed to determine the levels of C4a, C3a, and C5a, indicative of complement activation, after a single dose of the compounds G994, G998, and G1033. Concentrations of each of C4a, C3a, and C5a will be determined from serum samples collected as described above using commercially available ELISAs. The results of these studies will show a decrease in complement activation overtime after a single administration of either G994, G998, or G1033, determined by a decrease in the concentration of C4a, C3a, and/or C5a.

Analysis of complement activity remaining after single dose of complement preferential compound indicated that compound G994 eliminates complement activity in cynomolgus blood for an extended time period. Complement activity after dosing with G994 remained low until 312 hours (13 days). Compound G998 and G1033 exhibited a somewhat shorter half-life in cynomolgus monkeys. For compound G998, approximately 50% of pre-dose complement levels were present at day 6. For compound G1033, functional half-life seemed to be between 9 and 13 days. For all compounds, complement activity remained in the blood for approximately 4 hours. Without wishing to be bound by theory, this may be due to relatively slow absorption of the subcutaneously dosed compounds.

Analysis of the correlation between drug levels and complement activity (FIG. 47B) was used to estimate drug levels needed to eliminate complement activity in cynomolgus blood. From the estimated x-interception levels approximately 150 µg/ml of compound G994 is needed to eliminate complement activity. For compound G998 and G1033, the approximate value is 300-400 µg/ml.

C1q levels are measured in serum samples from cynomolgus monkeys treated with G994, G998, or G1033 as described above. Quantitative measurements are assessed via a C1q ELISA. Serum samples are also analyzed via co-immunoprecipitation to determine the fraction of C1q that is bound by the compounds. To determine the fraction of C1q bound to drug, a C1q ELISA was performed using a capture antibody to C1q followed by a detecting antibody binding to the human IgG1 part of the complement preferential drugs. This will capture and quantitate the drug-C1q complex. This will be followed by testing the supernatant from the same ELISA above in a C1q ELISA using a C1q antibody as both capturing and detecting antibody to quantitate the unbound C1q in the samples.

Example 9

C3, C3b, C4, and C5 Binding of Complement-Preferential Stradomers G994, G996, and G1033

Additional studies were conducted to assess binding of complement-preferential stradomers to C3, C3b, C4, and C5. Ninety-six well plates were coated with complement component (Quidel #A401, 1 µg/ml for C3; GenWay Biotech #GWB-8BA994, 1 µg/ml for C3b; Quidel #A402, 1 µg/ml for C4; and Quidel A403, 1 µg/ml for C5) in PBS 100 µl per well overnight at 4C followed by washing 3× (300 µl PBS 1×0.1% Tween 20). Plates were blocked in blocking buffer (PBS 1×+2% BSA+0.05% tween 20) 2 hr at RT followed by washing 3× (300 µl PBS 1×0.1% Tween 20). Compound was reacted to complement component for 2 hr at RT starting at 100 µg/ml and diluted down 1:1 down in blocking buffer followed by washing 3× (300 µl PBS 1×0.1% Tween 20). Bound compound was detected with biotinylated mouse anti-Human IgG1 (BD# 555 869)+ Streptavidin-HRP(Cat #: 7100-05 Southern Biotech) 1/5000 each in blocking buffer 100 µl for 1 hr at RT. Color was developed with TMB substrate reagent for 20 min at RT, reaction was stopped with 50 µl H2SO4 1M and absorbance reading was at 450/650 nm.

Figure 49:
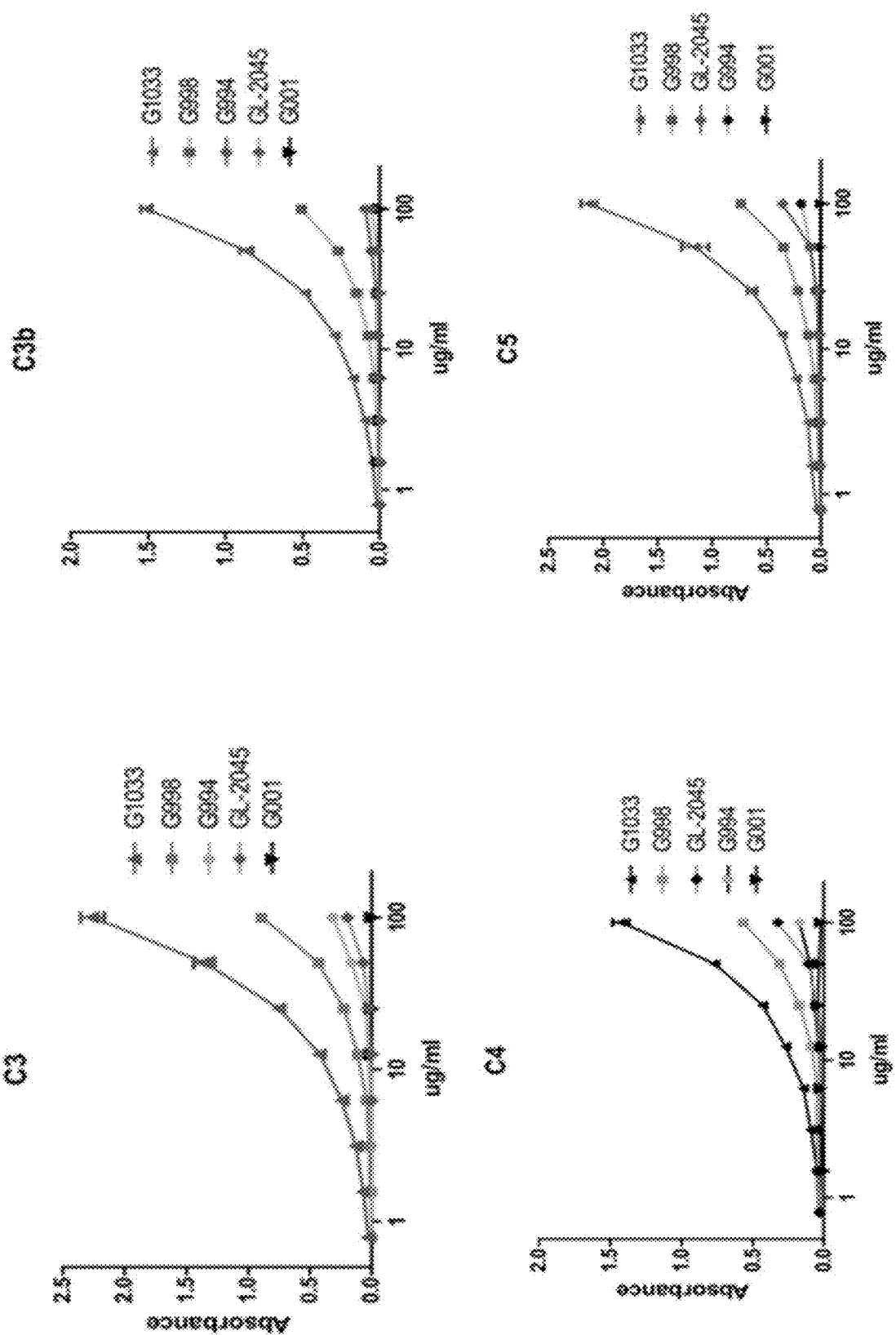
FIG. 49 shows the binding of negative control G001, which is IgG1 Fc, stradomer GL-2045, or complement preferential stradomer G994, G998, or G1033 to complement component C3 (top left panel), C3b (top right panel), C5 (bottom left panel), or C4 (bottom right panel) as measured by absorbance at increasing concentrations of stradomer in an ELISA assay FIG. 50A
Figure 52G:
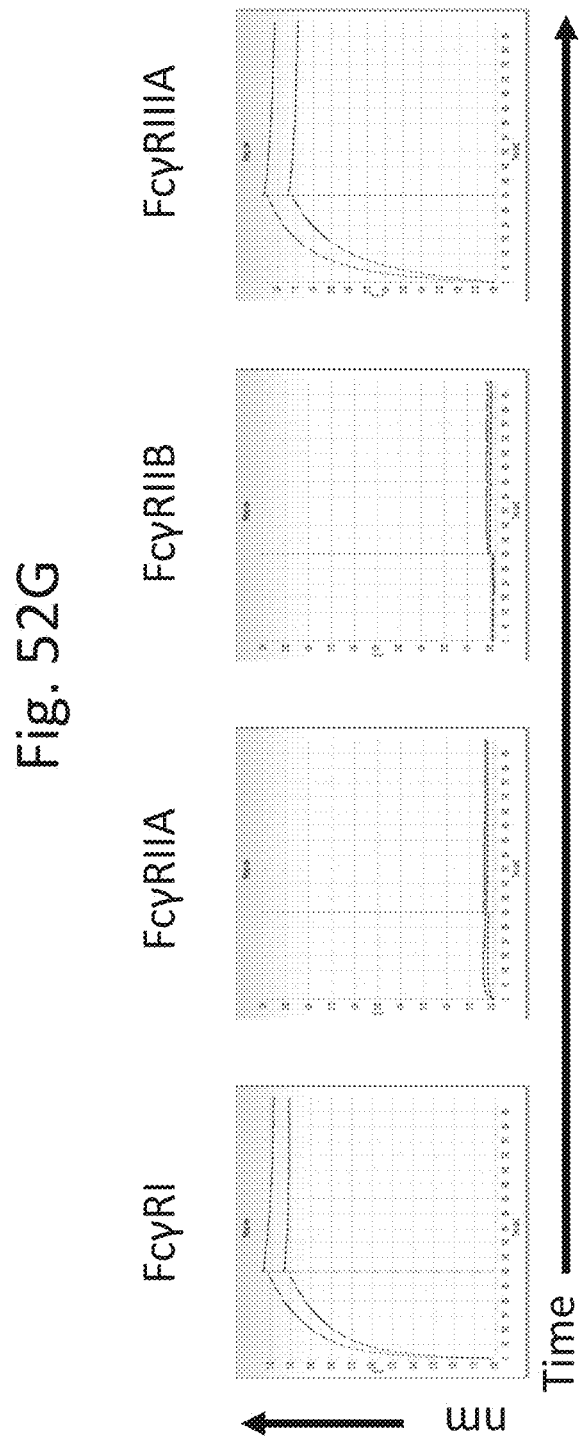
Figure 53A:
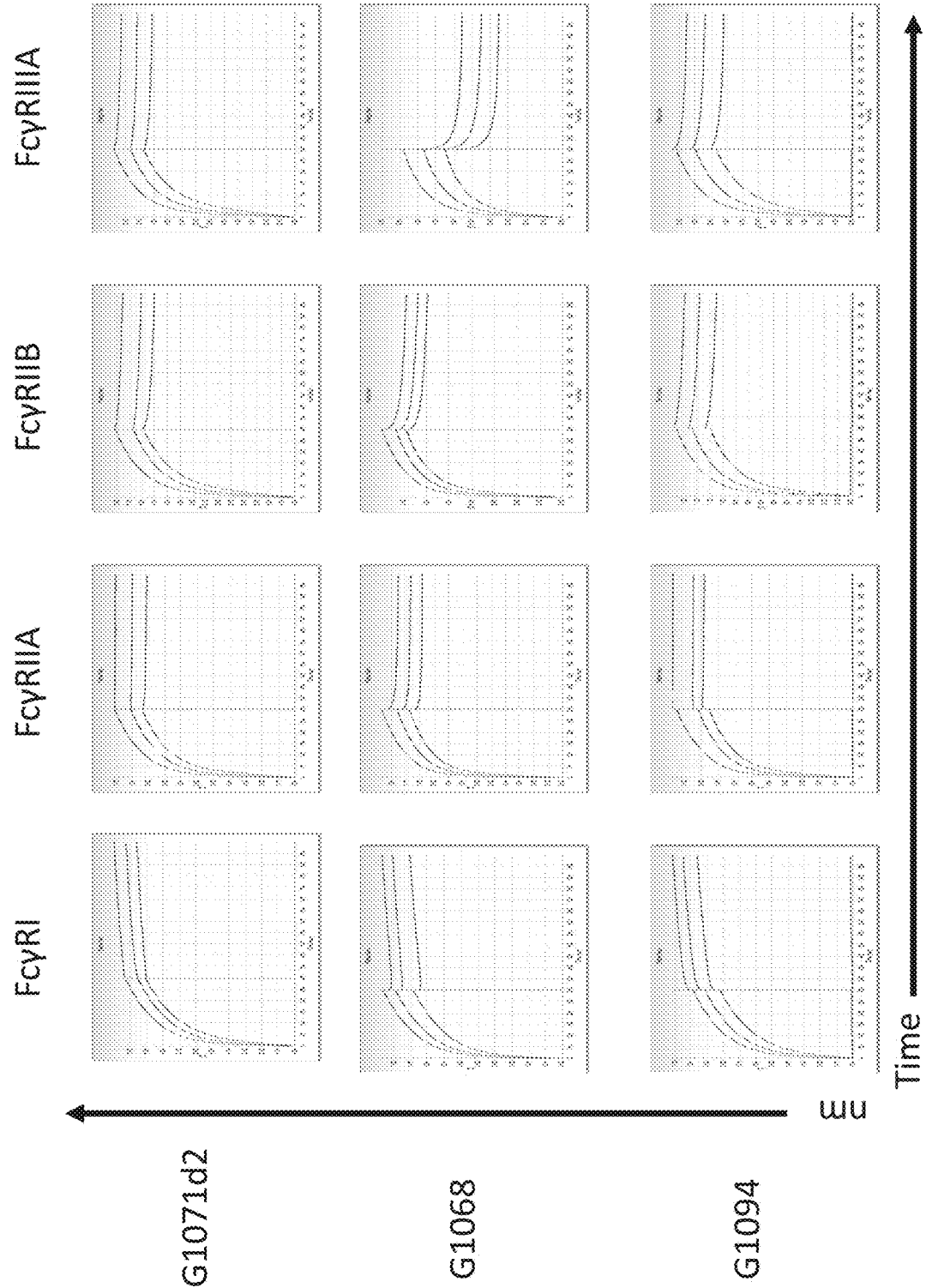
Figure 54A:
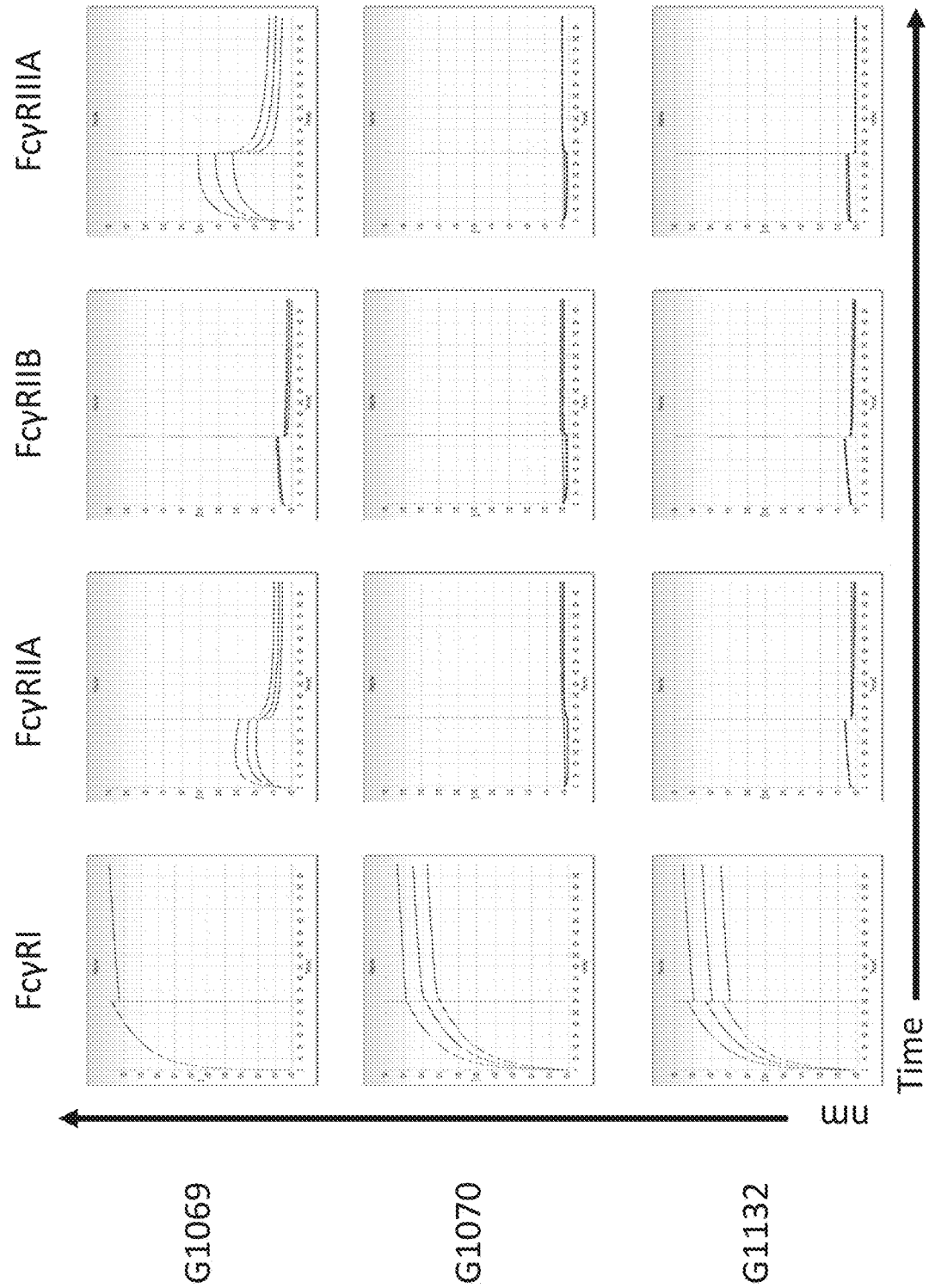

The results of the study are provided in FIG. 49. All of the complement-preferential stradomers G994, G998, and G1033 bound each of complement factors C3, C3b, C4, and C5. In addition, G1033 exhibited significantly higher binding to these complement factors in a direct binding assay, relative to GL-2045 or the other complement-preferential stradomers G994 and G998.

Example 10

Cytokine Induction of Complement-Preferential Stradomers G994, G996, and G1033

Additional studies were conducted to assess the cytokine induction of the G994 and G1033 from isolated peripheral blood mononuclear cells (PMBCs). 100 mL of human blood was collected in heparin-coated blood collection tubes. 10 mL aliquots of blood were transferred into 50 mL conical tubes and diluted with 10 mL PBS followed by gentle mixing. The 20 mL sample of diluted blood was layered onto 15 mL Ficoll-Paque PLUS in 50 mL conical tubes and centrifuges at 400×g for 30-40 minutes at 18-20° C. After centrifugation, the top layer was removed using a Pasteur pipette, leaving the lymphocyte layer undisturbed at the interface. The lymphocyte layer was transferred to a clean 50 mL conical tube and 30 mL of PBS was added. The diluted lymphocyte layer was centrifuged at 60-100×g for 10 minutes at 18-20° C. After centrifugation, the supernatant is removed and the cells were washed in 30 mL of PBS and centrifuged again. The cell pellet was resuspended in 1-2 mL of RPMI media supplemented with 10% fetal bovine serum (FBS). Cells were counted and aliquoted into tubes at $5\times10^6$ cells/tube and incubated with test material (G019, G994, or G1033) for 4 or 24 hours. Cytokine levels at 4 and 20 hours were determined by commercial ELISA kits.

Figure 55A:
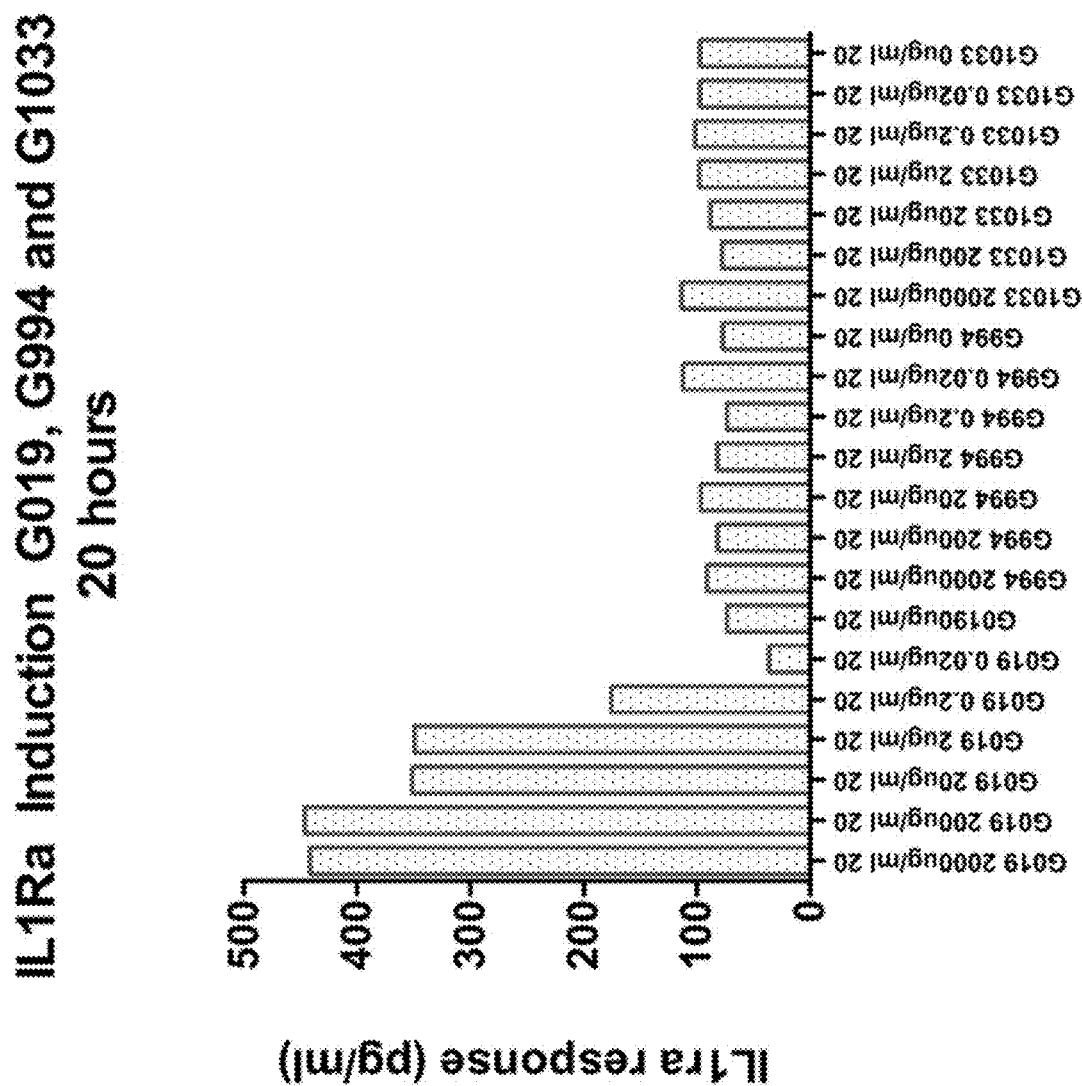
FIG. 55A shows IL1Rα induction from isolated PBMC after 20 hours of treatment with vehicle controls (0 μg/mL of G019, G994, or G1033) or doses of G019, G994, and G1033 ranging from 0.02 μg/mL to 2000 μg/μL. G019, which binds all canonical receptors, was used as a positive control.
Figure 55B:
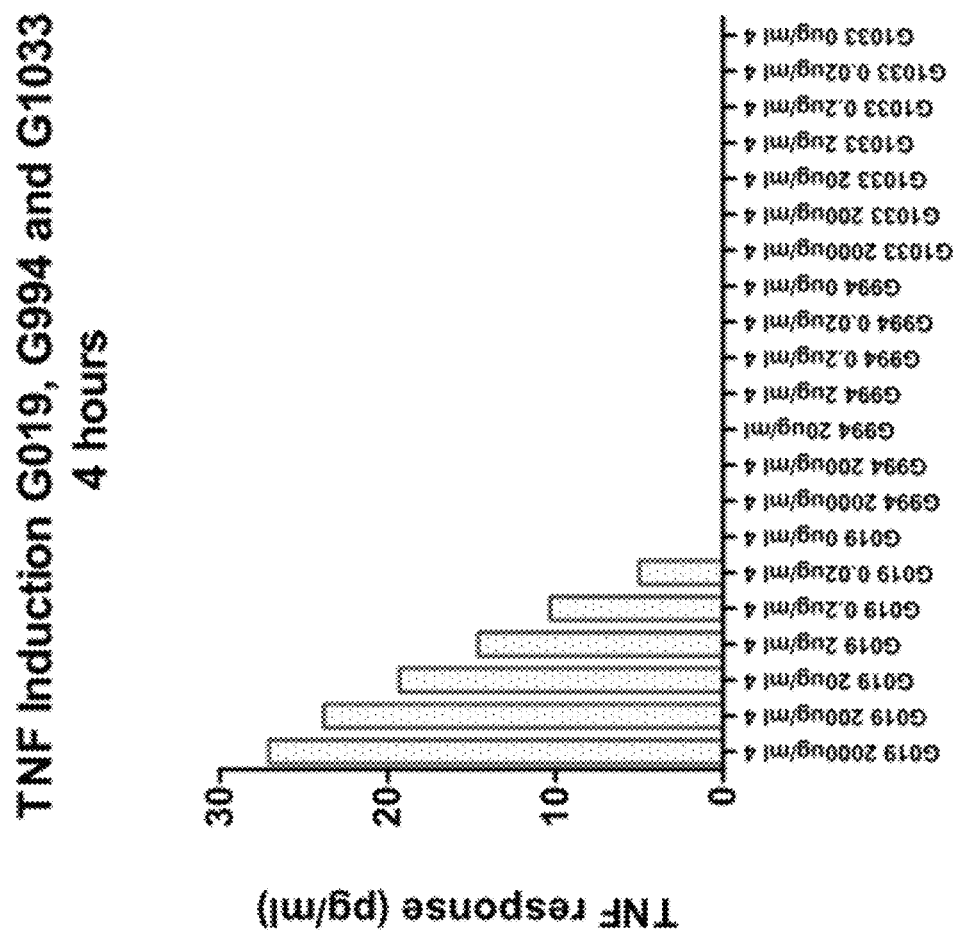
FIG. 55B shows TNFα induction from isolated PBMC after 4 hours of treatment with vehicle controls (0 μg/mL of G019, G994, or G1033) or doses of G019, G994, and G1033 ranging from 0.02 μg/mL to 2000 μg/μL. G019, which binds all canonical receptors, was used as a positive control.
Figure 56:
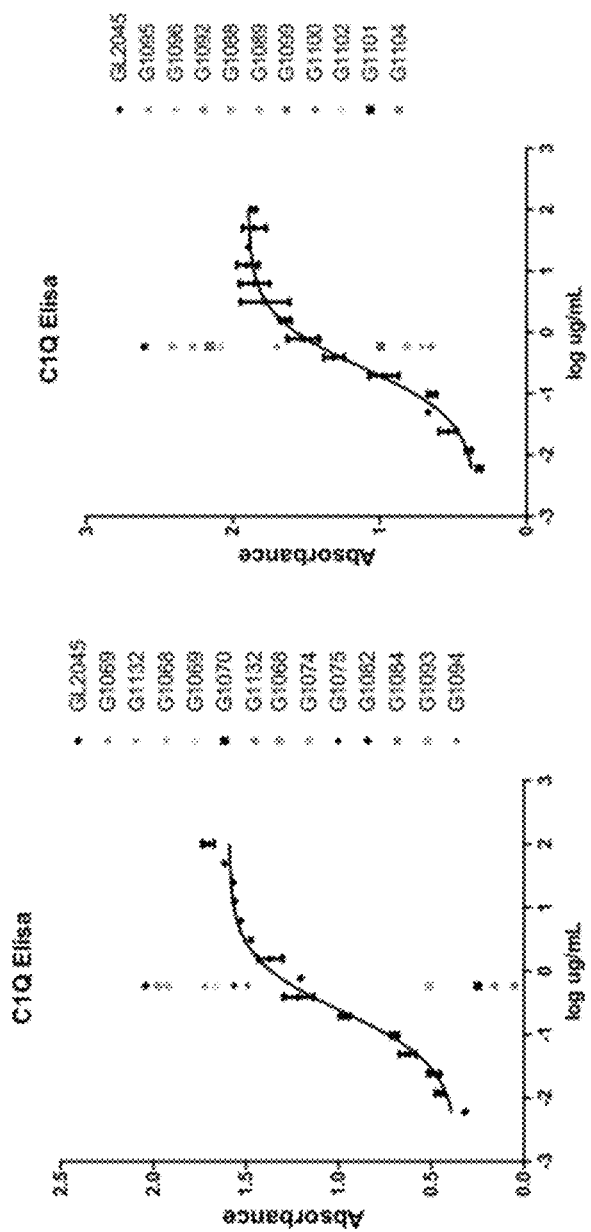
FIG. 56 shows C1q binding of complement-preferential stradomers as measured by ELISA.

The results of this study are shown in FIGS. 55A and 55B. Neither G1033 nor G994 induced the proinflammatory cytokine, TNFα (FIG. 55B). Similarly, neither of the two compounds induced the anti-inflammatory cytokine, IL-1Rα (FIG. 55A). This is likely due to the inability of G1033 and G994 to bind canonical FcγRs, as G019 (which binds canonical receptors but not complement) induced both cytokines.

Example 11

Complement-Preferential Stradomers for Treatment of Established Arthritis

Figure 57:
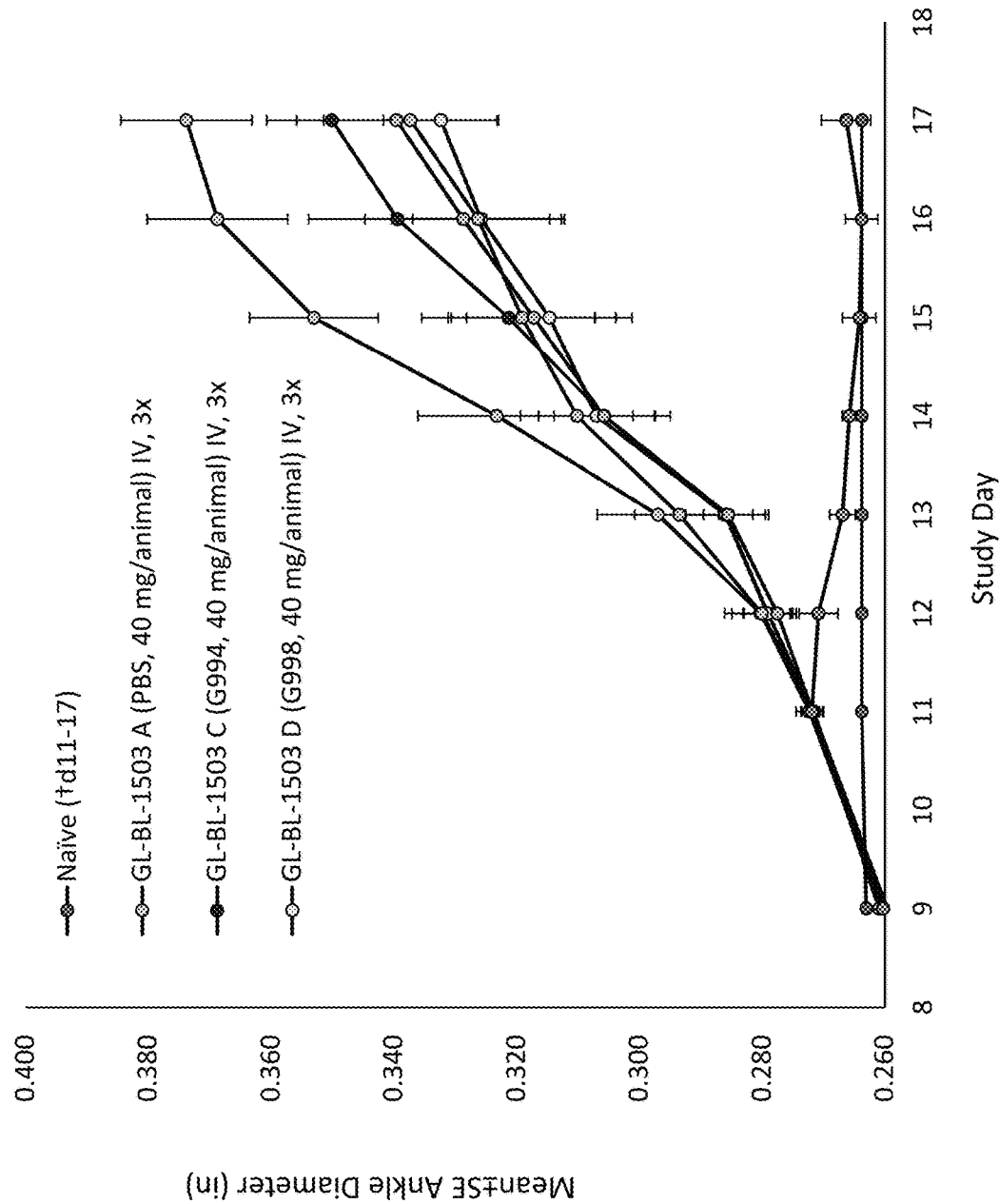
FIG. 57 shows mean ankle diameter of Lewis rats in a CIA model of arthritis treated with G994, G998, G1033, PBS controls, dexamethasone, or untreated controls.
Figure 58A:
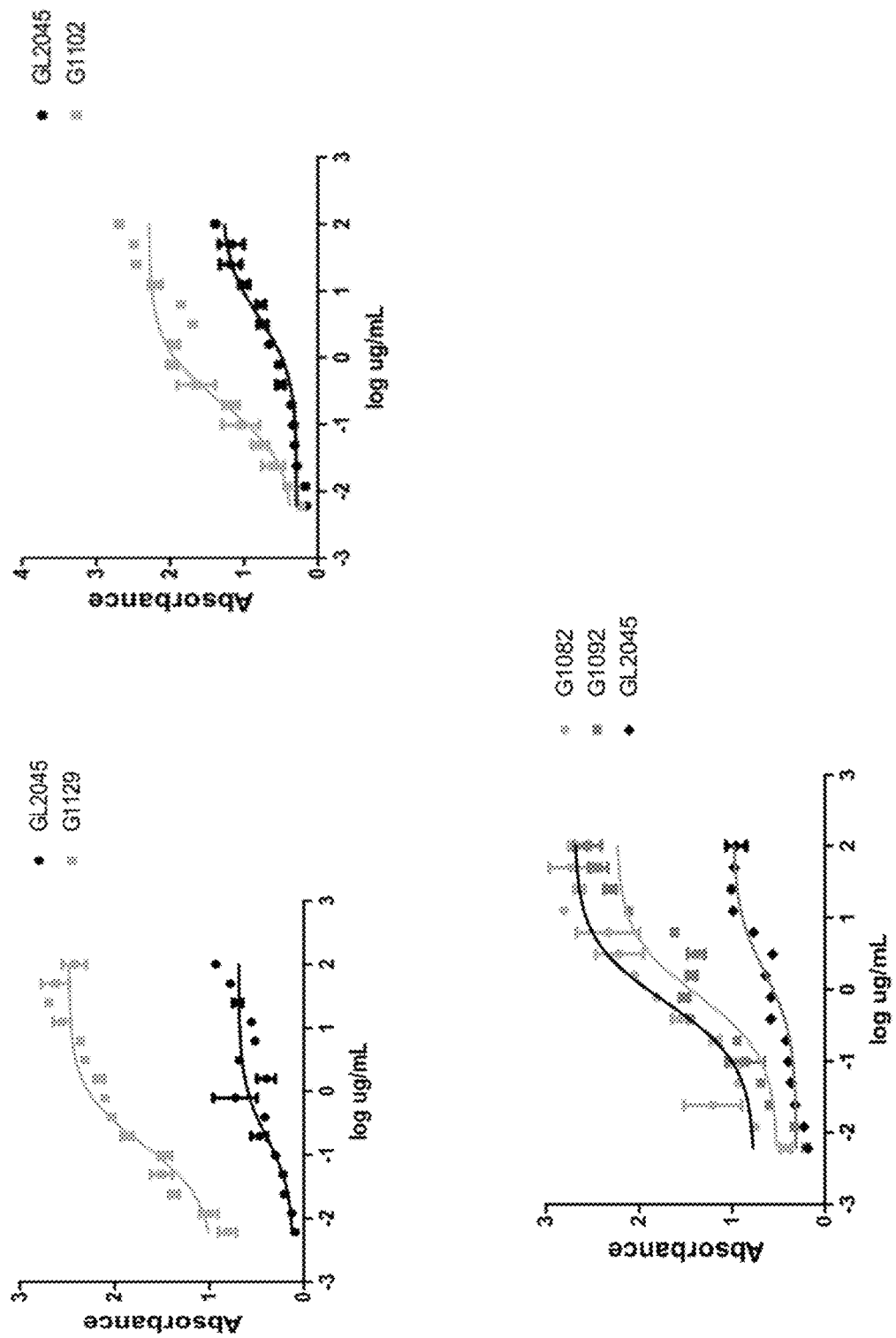
FIG. 58A-FIG. 58B shows C1q binding data for select complement preferential compounds shown in FIGS. 56, G1088, G1129, G1082, G1092, and G1102 (FIG. 58A), and G1069, G1114, and G1075 (FIG. 58B).
Figure 58B:
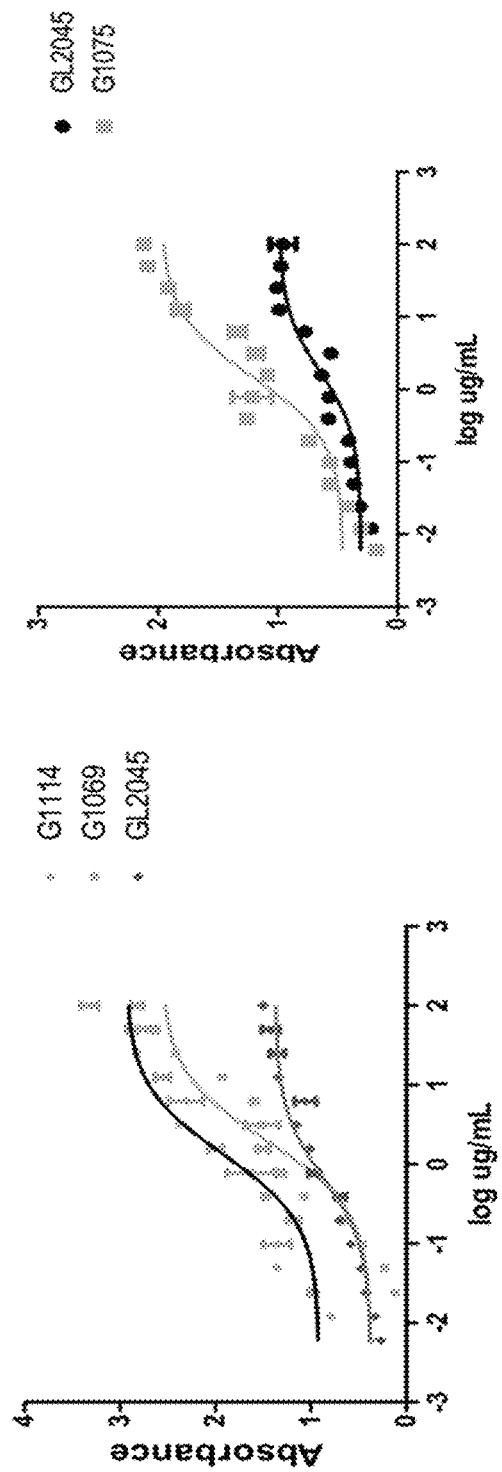
Figure 59:
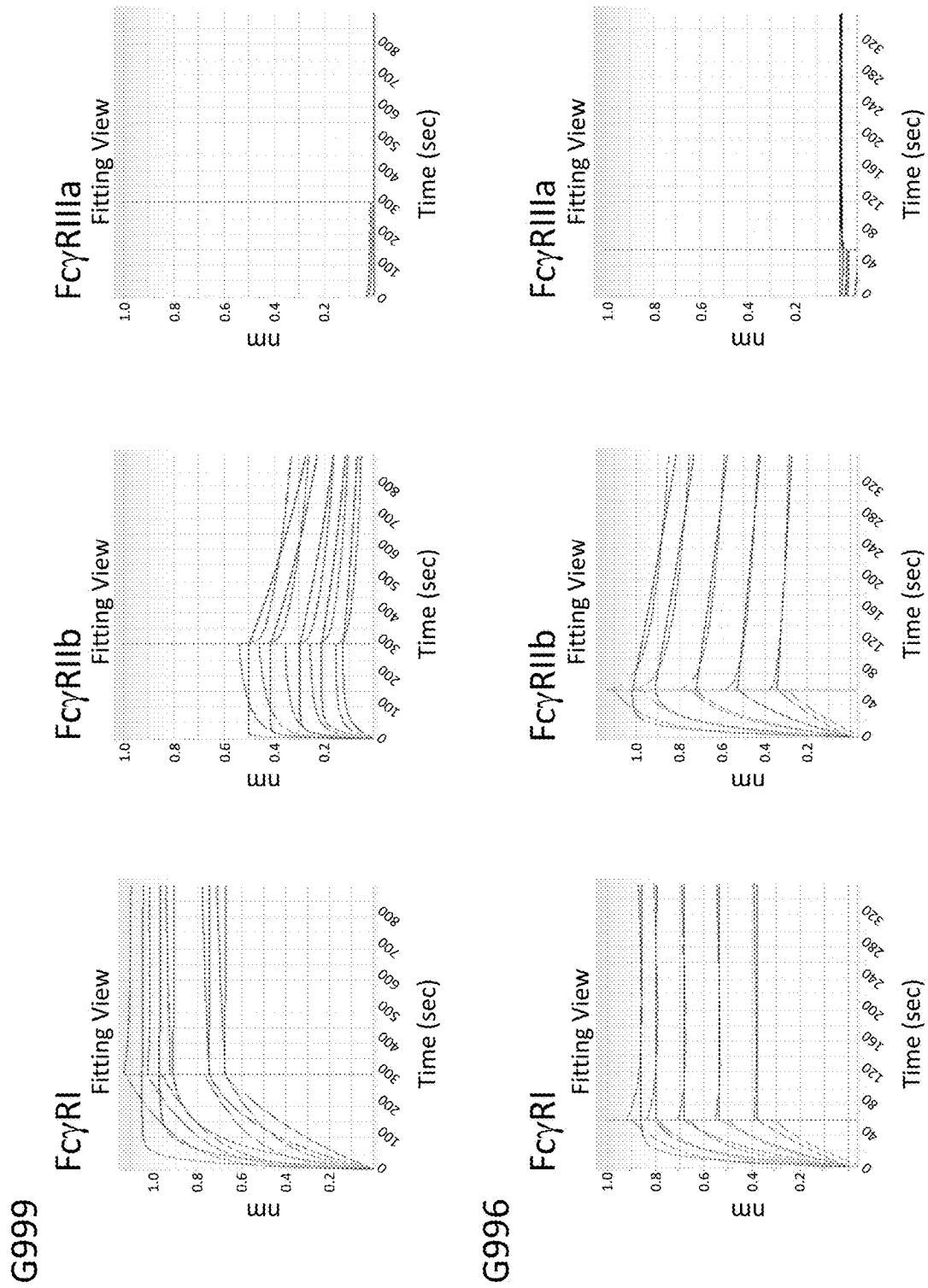
FIG. 59 shows the binding of stradomer G999 and G996 to FcγRI, FcγRIIb, and FcγRIIIa, as measured by biolayer interferometry.
Figure 60:
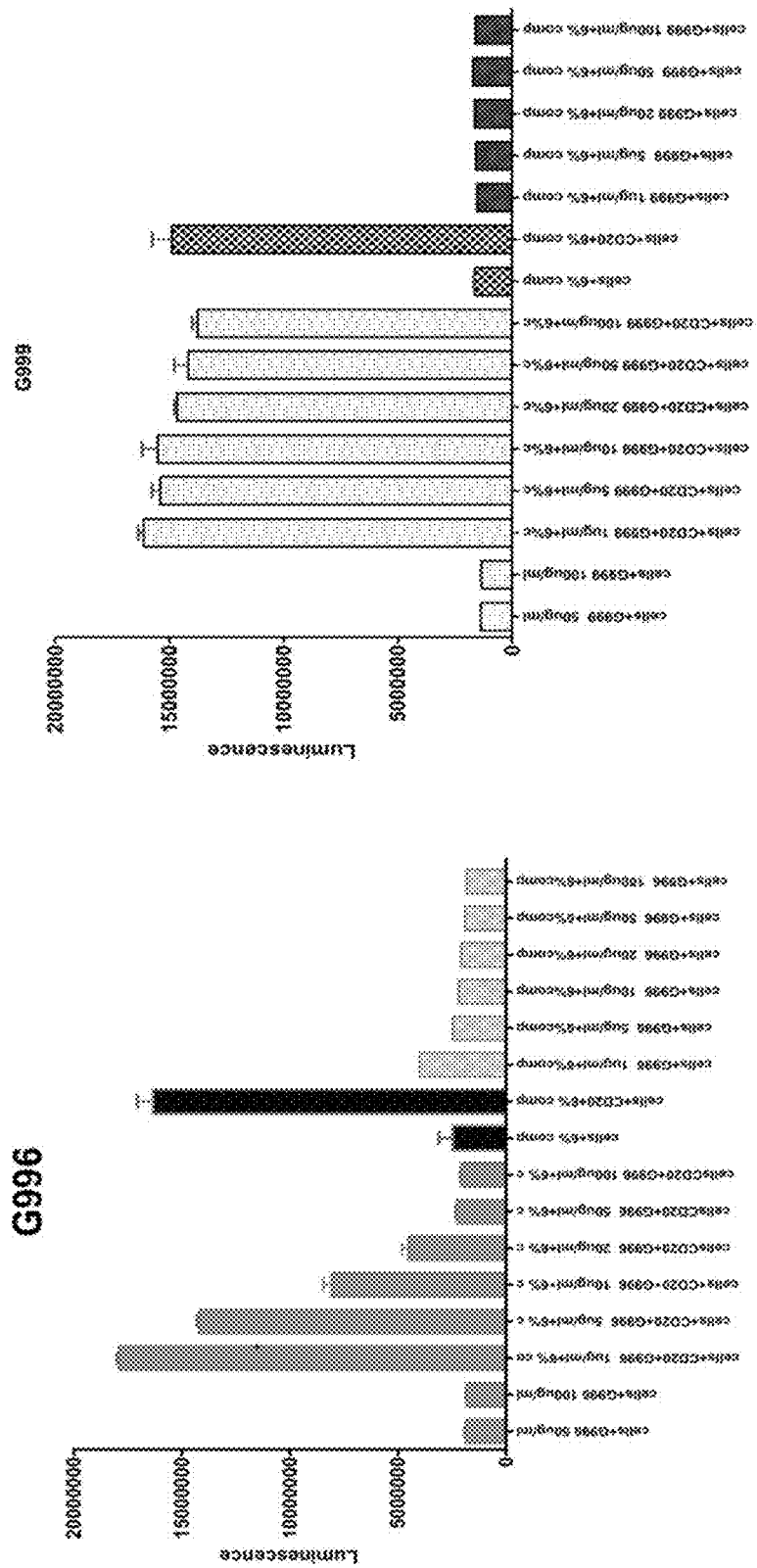
FIG. 60 shows CDC inhibition data for G999 and G996. CD20 denotes addition of the CD20 antibody. "6%" denotes addition of 6% serum complement. Controls includes cells plus addition of G996 only (50 and 100 μg/ml), cells plus serum ("+6%"), and cells plus serum plus antibody ("cells+CD20+6%").

A collagen-induced arthritis (CIA) study was conducted to determine the efficacy of G994, G998, and G1033 in the inhibition of swelling that occurs in established type II collagen arthritis in female Lewis rats. Rats were injected intradermally/subcutaneously (ID/SC) with porcine type II collagen to induce arthritis. Rats were then dosed intravenously (IV) on Days 11, 13, and 14 with phosphate buffered saline (PBS control), G994 (40 mg/rat), G998 (40 mg/rat), or G1033 (40 mg/rat). Positive controls were treated daily (QD) by the oral (PO) route on Days 11-16 with the reference compound dexamethasone (Dex, 0.075 mg/kg). The treatments were blinded until after study completion. Efficacy evaluation was based on ankle caliper measurements (FIG. 57).

These studies show that the complement-preferential compounds, G994, G998, and G1033 reduce inflammation in a Lewis rat CIA model of arthritis.

Example 12

Stradomers Derived from G994 or G998

Additional stradomers were generated using the sequence of G994 as a base sequence in order to assess the function of mutations at particular residues as well as identify and test additional complement preferential stradomers. G994 (SEQ ID NO: 10 or 11) is a stradomer having a G045c background and point mutations at positions 233, 236, 267, 268, and 324. Specifically, G994 has the following mutations: E223P, G236R, S267E, H268F, and S324T.

To analyze the function of mutations at the 236 position, stradomers were generated in which the wild type amino acid (serine) was present at the 267 position, the 236 position was mutated to either arginine (as in G994) or to a residue similar to arginine, and the remaining G994 mutations (E233P, H268F, and S324T) were present. The compounds generated are provided below in Table 5:

TABLE 5

Complement preferential stradomers having a G994 base and further mutations at position 236

| Stradomer | SEQ ID NO | Mutated Amino Acids |
| --- | --- | --- |
| 1103 | 65 | E233P, G236E, 267S, H268F, S324T |
| 1088 | 28 | E233P, G236Q, 267S, H268F, S324T |
| 1089 | 29 | E233P, G236R, 267S, H268F, S324T |
| 1104 | 66 | E233P, G236D, 267S, H268F, S324T |
| 1082 | 30 | E233P, G236H, 267S, H268F, S324T |
| 1105 | 31 | E233P, G236N, 267S, H268F, S324T |
| 1106 | 32 | E233P, G236K, 267S, H268F, S324T |

Surprisingly, the mutation of position 236 to arginine, or an amino acid similar to arginine, altered canonical binding and complement binding relative to G994. Mutation of position 236 to glutamic acid or aspartic acid (G1103 and 1104, respectively) resulted in high binding to canonical FcγRs, retained high binding to C1q, and inhibited CDC. The compound G1103 and G1104 can therefore be considered general stradomers, with increased canonical and C1q binding compared to the parent stradomer (G045c). Conversely, mutation of position 236 to glutamine, histidine, or asparagine (G1088, 1082, and 1105, respectively) resulted in reduced canonical binding, while retaining high C1q binding and inhibition of CDC. Compounds 1088, 1082, and 1105 can therefore be considered complement-preferential stradomers with similar therapeutic applicability as G994, G998, and G1033. Mutation of position 236 to lysine (G1106) ablated both C1q and canonical except FcγRI binding and resulted in an inability to inhibit CDC.

To analyze the function of mutations at the 267 position, stradomers were generated in which the wild type amino acid (glycine) was present at the 236 position, the 236 position was mutated to either glutamic acid (as in G994) or a residue similar to glutamic acid, and the remaining G994 mutations (E233P, H268F, and S324T) were present. The compounds generated are provided below in Table 6:

TABLE 6

Complement preferential stradomers having a G994 base and further mutations at position 267

| Stradomer | SEQ ID NO | Mutated Amino Acids |
|---|---|---|
| 1102 | 67 | E233P 236G, S267Q, H268F, S324T |
| 1100 | 33 | E233P 236G, S267R, H268F, S324T |
| 1101 | 68 | E233P 236G, S267D, H268F, S324T |
| 1125 | 69 | E233P 236G, S267H, H268F, S324T |
| 1108 | 34 | E233P 236G, S267N, H268F, S324T |
| 1109 | 70 | E233P 236G, S267E, H268F, S324T |
| 1084 | 35 | E233P 236G, S267K, H268F, S324T |

Mutation of position 267 to asparagine (G1108) resulted in decreased canonical binding while maintaining a high degree of C1q binding and CDC inhibition. G1108 can therefore be considered a complement-preferential stradomer with similar therapeutic applicability as G994, G998, and G1033. However, mutation of position 267 to glutamine, aspartic acid, histidine, or glutamic acid (G1102, 1101, 1125, and 1109, respectively) resulted in enhanced canonical binding while retaining high C1q binding and CDC inhibition. G1102, 1101, 1125, and 1109 can therefore be considered general stradomers, with increased C1q binding compared to the parent. Alternatively, mutation of position 267 to arginine or lysine (1100 and 1084 respectively) resulted in both reduced canonical binding, reduced C1q binding, and an inability to inhibit CDC.

To analyze the function of mutations at the 236 and 267 positions in combination, stradomers were generated in which the 236 position was mutated into arginine (as in G994) or an amino acid structurally similar to arginine and the 267 position was mutated into glutamic acid (as in G994) or an amino acid structurally similar to glutamic acid, and the remaining G994 mutations (E233P, H268F, and S324T) were present. The compounds generated are provided below in Table 7:

TABLE 7

Complement preferential stradomers having a G994 base and further mutations at positions 236 and 267

| Stradomer | SEQ ID NO | Mutated Amino Acids |
|---|---|---|
| G1110 | 36 | E233P, G236D, S267R, H268F, S324T |
| G1111 | 71 | E233P, G236D, S267Q, H268F, S324T |
| G1112 | 37 | E233P, G236R, S267R, H268F, S324T |
| G1113 | 38 | E233P, G236R, S267D, H268F, S324T |
| G1114 | 72 | E233P, G236Q, S267D, H268F, S324T |
| G1115 | 39 | E233P, G236E, S267R, H268F, S324T |
| G1116 | 40 | E233P, G236H, S267K, H268F, S324T |
| G1117 | 73 | E233P, G236D, S267D, H268F, S324T |
| G1118 | 41 | E233P, G236Q, S267Q, H268F, S324T |
| G1119 | 42 | E233P, G236R, S267K, H268F, S324T |
| G1120 | 43 | E233P, G236R, S267Q, H268F, S324T |
| G1121 | 44 | E233P, G236D, S267K, H268F, S324T |
| G1122 | 45 | E233P, G236H, S267Q, H268F, S324T |

TABLE 7-continued

Complement preferential stradomers having a G994 base and further mutations at positions 236 and 267

| Stradomer | SEQ ID NO | Mutated Amino Acids |
|---|---|---|
| G1123 | 46 | E233P, G236Q, S267R, H268F, S324T |
| G1124 | 47 | E233P, G236K, S267K, H268F, S324T |
| G1128 | 48 | E233P, G236K, S267N, H268F, S324T |
| G1129 | 49 | E233P, G236N, S267E, H268F, S324T |
| G1130 | 50 | E233P, G236N, S267K, H268F, S324T |
| G1131 | 51 | E233P, G236R, S267N, H268F, S324T |

Surprisingly, simultaneous mutations at both positions 236 and 267 had distinct effects compared to mutations of either position independently. The combination of G263N/S267E in the context of E233P/H268F/S324T (G1129) resulted in reduced binding to FcγRIIIa and retention or enhancement of binding to FcγRI, FcγRIIa, and FcγRIIb. G1129 can therefore be considered a complement-preferential stradomer. The combination of G236D/S267Q, G236Q/S267D, and G236D/S267D point mutations (G1111, G1114, and G1117, respectively) resulted in increased canonical binding relative to the parent stradomer or G994, and also resulted in the maintenance of high C1q binding and CDC inhibition. G1111, G1114, and G1117 can therefore be considered general stradomers with the potential for enhanced therapeutic efficacy compared to the parent stradomer, G045c. Alternatively, the combination of G236D/S267R, G236R/S267R, G236E/S267R, G236H/S267K, G236R/S267K, G236R/S267Q, G236D/S267K, G236H/S267Q, G236Q/S267R, G236N/S267K, or G236R/S267N (G1110, G1112, G1115, G1116, G1119, G1120, G1121, G1122, G1123, G1130, and G1131, respectively) all resulted in both decreased canonical binding and decreased binding to C1q and reduced CDC inhibition. In some instances, such as the combination of G236K/S267K and G236K/S267N (G1124 and G1128, respectively), the point mutations resulted in enhanced canonical binding and decreased binding to C1q.

Additional stradomers were also generated using the sequence of G998 as a base sequence and a mutation at position 299 (T299A) in order to assess the function of mutations at particular residues in this context. G998 (SEQ ID NO: 14 or 15) is a stradomer having a G045c background and point mutations at positions 267, 268, 297, and 324. Specifically, G998 has the following mutations: S267E, H268F, N297A, and S324T. The consensus glycosylation site is NXT, wherein N is residue 297. The 297 residue covalently links the sugar residues. The T299A mutation of the additional stradomers described herein was intended to provide an aglycosylated protein; the amino acid mutation at position 299 is designed to destroy the consensus glycosylation site such that the protein will not be glycosylated, but leave the 297 linking residue intact. Accordingly, the compounds provided in Table 8 below (in which the amino acid at position 267 was mutated to glutamic acid (as in G998) or an amino acid sequence similar to glutamic acid or was not mutated from the wild type serine residue; the amino acids at positions 268 and 324 were mutated as in G998; the amino acid at position 297 was not mutated; and a mutation from threonine to alanine was added at position 299) were generated and tested.

TABLE 8

Stradomers having a G998 base, a mutation at position 299, and further mutations at position 267.

| Stradomer | SEQ ID NO | Mutated Amino Acids |
|---|---|---|
| 1071d2 | 52 | 267S, H268F, S324T, T299A |
| 1068 | 74 | S267E, H268F, S324T, T299A |
| 1094 | 75 | S267Q, H268F, S324T, T299A |
| 1092 | 76 | S267D, H268F, S324T, T299A |
| 1096 | 53 | S267R, H268F, S324T, T299A |
| 1107 | 77 | S267H, H268F, S324T, T299A |
| 1093 | 54 | S267K, H268F, S324T, T299A |
| 1095 | 55 | S267N, H268F, S324T, T299A |

Surprisingly, the inclusion of the T299A mutation, which should result in abrogated canonical binding, only affected the FcγR binding the context of either the S267R (G1096) or S267K (G1093) mutation. In both G1096 and G1093, binding to C1q was also reduced and neither compound was able to inhibit CDC, likely due to a lack of C1q binding. Other compounds containing the T299A mutation (1071d2, G1068, G1094, G1092 and G1107) demonstrated enhanced binding to both FcγRs and C1q. G1068, G1094, G1092 and G1107 can therefore be considered general stradomers with the potential for enhanced therapeutic efficacy compared to the parent stradomer, G045c. Surprisingly, strong binding to C1q did not necessarily correlate with inhibition of CDC, as 1712d2 was unable to inhibit CDC. G1095 contains the T299A and the S267N mutations, the combination of which resulted in slightly decreased canonical binding, while retaining C1q binding and CDC inhibition. G1095 can therefore be considered a complement-preferential stradomer with similar therapeutic applicability as G994, G998, and G1033.

Additional G998-based stradomers were generated and tested to further assess the function of the 267 mutations in this context. These mutants contain the mutations at positions 268, 324, and 297, as in G998, and have either wild type serine or an amino acid substitution at position 267, as shown in Table 9 below. These stradomers do not have a mutation at position 299.

TABLE 9

Stradomers having a G998 base, a mutation at position 299, and further mutations at position 267

| Stradomer | SEQ ID NO | Mutated Amino Acids |
|---|---|---|
| 1069 | 56 | S267S, H268F, S324T, N297A |
| 1070 | 57 | S267K, H268F, S324T, N297A |
| 1132 | 58 | S267R, H268F, S324T, N297A |
| 1074 | 59 | S267D, H268F, S324T, N297A |
| 1075 | 60 | S267Q, H268F, S324T, N297A |

As expected, the stradomers in Table 9 demonstrated reduced canonical binding, due to the N297A aglycosylation mutation. Surprisingly, the wild type serine at position 267 (G1069), the S267D or the S267Q point mutations (G1074 and G1075 respectively) also resulted in enhanced C1q binding and reduced canonical binding. G1069, G1074, and G1075 can therefore be considered complement-preferential stradomers with similar therapeutic applicability as G994, G998, and G1033. The S267K (G1070) and S267R (1132) mutations resulted in not only reduced FcγR binding, but also reduced C1q binding and an inability to inhibit CDC.

The compounds derived from G994 and G998 were run on a gel to assess multimerization. 3 µg of each of the samples was run at 150V for approximately 1.2 hours. 20 mM iodoacetamide was added, and then samples were incubated for 10 minutes prior to loading on the gel. The results are provided in FIGS. 48A-G, which show that like G994 and G998, compounds G1103, G1088, G1089, G1104, G1082, G1105, G1106, G1102, G1100, G1101, G1125, G1108, G1109, G1084, G1107, G1110, G1111, G1112, G1114, G1115, G1116, G1117, G1118, G1119, G1120, G1121, G1122, G1123, G1124, G1128, G1129, G1130, G1131, G1071d2, G1068, G1094, G1092, G1096, G1093, G1095, G1069, G1070, G1132, G1075, and G1075 form multimers.

For each stradomer in Tables 5-9, the level of canonical FcγR binding, complement C1q binding, and CDC inhibition were determined according to the methods described in Example 1. These results are summarized in Table 10.

TABLE 10

Activity summary of stradomers derived from G994 or G998

| | FcγRI Binding | FcγRIIa Binding | FcγRIIb Binding | FcγRIIIa Binding | C1q Binding | CDC Inhibition (EC50, µg/mL) |
|---|---|---|---|---|---|---|
| G1103 | *** | *** | *** | *** | High | 5 |
| G1088 | *** | ** | * | ** | High | 5 |
| G1089 | ** | — | * | — | Low | 100 |
| G1104 | *** | *** | *** | *** | High | 5 |
| G1082 | *** | ** | — | *** | High | 5 |
| G1105 | *** | ** | ** | ** | High | 5 |
| G1106 | *** | — | — | — | Low | 100 |
| G1102 | *** | *** | *** | *** | High | 7.5 |
| G1100 | *** | — | — | *** | Low | NI |
| G1101 | *** | *** | *** | *** | High | 5 |
| G1125 | *** | ** | ** | ** | High | 5 |
| G1108 | *** | * | * | *** | High | 5 |
| G1109 | *** | *** | *** | *** | High | ND |
| G1084 | *** | — | — | * | Low | NI |
| G1110 | *** | — | — | — | Low | 25 |
| G1111 | *** | *** | *** | *** | High | 5 |
| G1112 | * | — | — | — | Low | NI |
| G1113 | ND | ND | ND | ND | ND | ND |
| G1114 | *** | *** | *** | *** | High | 5 |
| G1115 | *** | — | — | *** | Low | 50 |
| G1116 | ** | — | — | — | Low | NI |
| G1117 | *** | *** | *** | *** | High | 5 |
| G1118 | *** | ** | ** | ** | Low | 10 |
| G1119 | * | — | — | — | Low | NI |
| G1120 | ** | — | — | — | Low | 100 |
| G1121 | ** | — | — | — | Low | 100 |
| G1122 | *** | *** | ** | ** | Low | 5 |
| G1123 | ** | — | — | * | Low | NI |
| G1124 | *** | *** | *** | *** | Low | 10 |
| G1128 | *** | *** | *** | *** | Low | 10 |
| G1129 | *** | *** | *** | * | High | 5 |
| G1130 | *** | *** | *** | — | Low | 10 |
| G1131 | *** | — | — | *** | Low | 15 |
| G1071d2 | *** | *** | *** | *** | High | NI |
| G1068 | *** | *** | *** | * | High | 10 |
| G1094 | *** | *** | *** | *** | High | 12.5 |
| G1092 | *** | *** | *** | *** | High | 10 |
| G1096 | ** | — | — | ** | Low | NI |
| G1107 | *** | *** | *** | ** | High | 12.5 |
| G1093 | *** | — | — | — | Low | NI |
| G1095 | *** | ** | ** | ** | High | 15 |
| G1069 | *** | — | — | * | High | 10 |
| G1070 | *** | — | — | — | Low | NI |
| G1132 | *** | — | — | — | Low | NI |
| G1074 | *** | ** | ** | * | High | 10 |
| G1075 | *** | — | — | — | High | 15 |

NI = No Inhibition
ND = No Data

Example 13

Stradomers with Decreased C1q and Canonical FcγR Binding

Additional compounds were generated comprising the S267E/H268F/S324T triple mutation in order to generate additional complement-preferential mutants.

G1001 (SEQ ID: 78) is on the G019 background and contains four mutations (S267E/H268F/S324T/N297A). Surprisingly, in the context of the G019 parent compound, removal of glycosylation by introducing the N297A mutation to G1003 to arrive at G1001 is unexpectedly associated with loss of C1q binding in addition to the expected loss of canonical binding, even in the presence of the triple mutation S267E/H268F/S324T (Moore et. al.). This surprising finding is not replicated in the context of the G045c parent compound, whereby removal of glycosylation by introducing the N297A mutation to G997 to arrive at G998 is associated with the expected loss of canonical binding but full C1q binding and CDC inhibition are retained. Therefore, although G998 and G1001 possess the same domains with the identical mutations and differ only in the position of the IgG2 hinge, they demonstrate substantially the same canonical Fc receptor binding but significantly different C1q binding and CDC inhibition. These comparisons further highlight the unpredictability of a given set of mutations in the context of a multimerizing stradomer.

G999 (SEQ ID NO: 79) is a stradomer on the G019 background comprising four point mutations (G236R, S267E, H268F, and S324T) and demonstrated reduced C1q binding and an inability to inhibit CDC. This is surprising in that, as described above, G999 differs from G996 only in the location of the IgG2 hinge relative to the Fc domain. Yet, these two compounds exhibit opposing abilities to bind C1q and inhibit CDC (G999 can do neither, while G996 exhibits high C1q binding and inhibits CDC). This comparison further underscores the unpredictability of a given set of mutations in the context of a multimerizing stradomer.

G1024 (SEQ ID NO: 80) is a stradomer on the G019 background comprising 4 point mutations (P238D, S267E, H268F, S324T).

G1030 (SEQ ID NO: 81) is a stradomer on the GL-2045 background comprising 7 point mutations and a deletion at 236 (E233P, L234V, L235A, G236Del, N297A, S267E, H268F, S324T).

G1031 (SEQ ID NO: 82) is a stradomer on the GL-2045 background comprising 6 point mutations (E233P, G236R, D265A, S267E, H268F, S324T, N297A).

G1040 (SEQ ID NO:83) is a stradomer on the GL-2045 background comprising 8 point mutations and a deletion at position 236 (E233P, L234V, L235A, G236Del, S267E, H268F, S324T, L328F, N297A).

G1044 (SEQ ID NO: 84) is a stradomer on the GL-2045 background comprising 5 point mutations (P238D, D265C, S267E, H268F, S324T).

G1045 (SEQ ID NO: 85) is a stradomer on the GL-2045 background comprising 5 point mutations (P238D, D265P, S267E, H268F, S324T).

G1048 (SEQ ID NO: 86) is a stradomer on the G019 background comprising 5 point mutations (G236R, L328F, S267E, H268F, S324T).

G1047 (SEQ ID NO: 87) is a stradomer on the GL-2045 background comprising 5 point mutations (P238D, L328F, S267E, H268F, S324T).

TABLE 11

Stradomers with Decreased C1q and Canonical FcγR Binding

| Stradomer | SEQ ID NO | Mutated Amino Acids |
|---|---|---|
| G1001 | 78 | S267E, H268F, S324T, N297A |
| G999 | 79 | G236R, S267E, H268F, S324T |
| G1024 | 80 | P238D, S267E, H268F, S324T |
| G1030 | 81 | E233P, L234V, L235A, G236Del, N297A, S267E, H268F, S324T |
| G1031 | 82 | E233P, G236R, S267E, H268F, S324T, N297A |
| G1040 | 83 | E233P, L234V, L235A, G236Del, S267E, H268F, S324T, L328F, N297A |
| G1044 | 84 | P238D, D265C, S267E, H268F, S324T |
| G1045 | 85 | P238D, D265P, S267E, H268F, S324T |
| G1048 | 86 | G236R, L328F, S267E, H268F, S324T |
| G1047 | 87 | P238D, L328F, S267E, H268F, S324T |

Surprisingly, despite comprising the S267E/H268F/S324T triple mutation, the stradomers listed in Table 11 did not bind C1q and did not inhibit CDC, thus further highlighting the unpredictability of a given set of point mutations in the context of a multimerizing stradomer. The results of experiment determining binding to FcγRs and FcRn, binding to C1q, and inhibition of CDC are summarized in Table 12.

TABLE 12

Activity summary of stradomers with Decreased C1q and Canonical FcγR Binding

| | FcγRI Binding | FcγRIIa Binding | FcγRIIb Binding | FcγRIIIa Binding | FcRn Binding (pH 7.4) | C1q* Binding | CDC inhibition |
|---|---|---|---|---|---|---|---|
| G1001 | *** | ** | — | — | *** | ND | (*) |
| G999 | *** | — | ** | — | *** | ND | — |
| G1024 | *** | *** | *** | — | *** | — | — |
| G1030 | — | — | — | — | *** | — | — |
| G1031 | — | — | — | — | ** | — | — |
| G1040 | *** | *** | *** | — | *** | ND | — |
| G1044 | *** | (*) | — | — | *** | ND | — |
| G1045 | *** | — | — | — | *** | — | — |
| G1048 | *** | *** | *** | *** | *** | ND | — |
| G1047 | *** | *** | *** | * | *** | ND | — |

ND = No Data

Example 14

Complement Preferential Stradomer Treatment for Sickle Cell Disease

Complement preferential stradomers G994, G998, G1033, G1022, G1032, G1023, G1006, G1027, and G996 are assessed in a mouse model of Sickle Cell Disease, described in detail in Turhan et all (2004) Blood 103:2397 and Chang et al (2008) Blood 111:915. Briefly, 12-16 week old male SCD mice (Townes SS mice, homozygous Hbatm1 (HBA)Tow and homozygous Hbbtm2(HBG1,HBB*)Tow (M21 genotype) are randomly assigned to groups and either dosed (intravenously) with saline, IVIG (400 mg/kg), hIgG1 (400 mg/kg), albumin (400 mg/kg), or stradomer (G045c, G994, G998 G1003, and G1033, 60 mg/kg) 20 minutes before surgical preparation. Neutrophil adhesion, rolling, and platelet neutrophil aggregates will be analyzed in cremasteric venules. Plasma is collected after terminal blood draw to analyze markers including sE-selectein, sP-selecting, sVCAM-1, and sICAM-1.

The results of the study will show that G994, G998, G1033, G1022, G1032, G1023, G1006, G1027, and G996 significantly decrease SSRBC-WBC interactions/WBC/minute, significantly increase rolling flux by WBC/min or by fraction percent, and significantly improve cumulative survival for the treated group compared with control. Thus, the complement preferential stradomers effectively treat sickle cell disease.

The invention claimed is:

1. A peptide homodimer comprising from amino to carboxy terminus:
   (a) at least one IgG1 Fc domain comprising the amino acid sequence of SEQ ID NO: 2 or SEQ ID NO: 3 with point mutations consisting of S267E, H268F, N297A, and S324T based on the EU index of the IgG1 Fc domain; and
   (b) at least one multimerization domain;
wherein the peptide homodimer retains binding to C1q.

2. The peptide homodimer of claim 1, wherein the multimerization domain is selected from the group consisting of an IgG2 hinge, an isoleucine zipper, and a GPP domain, and is capable of multimerizing said peptide homodimers.

3. The peptide homodimer of claim 1, wherein the multimerization domain creates multimers of said peptide homodimers.

4. The peptide homodimer of claim 3, wherein the multimers of said peptide homodimers are high order multimers.

5. The peptide homodimer of claim 1, wherein the peptide homodimer exhibits preferential binding to complement relative to FcγRI, FcγRIIa, FcγRIIb and/or FcγRIII.

6. The peptide homodimer of claim 1, wherein the peptide homodimer exhibits reduced binding to FcγRI, FcγRII, and/or FcγRIII relative to a peptide homodimer of the same structure that does not comprise point mutations at positions S267, H268, N297, and S324.

7. A compound comprising two or more of the peptide homodimers of claim 1.

8. The peptide homodimer of claim 1, wherein the peptide homodimer binds C1q and inhibits CDC.

9. The peptide homodimer of claim 1, wherein the homodimer comprises, from amino to carboxy terminus, a leader sequence; an IgG1 Fc domain comprising an IgG1 hinge, IgG1CH2, and IgG1 CH3; and an IgG2 hinge.

10. The peptide homodimer of claim 9, wherein the homodimer comprises an amino acid sequence of SEQ ID NO: 14 or SEQ ID NO: 15.

\* \* \* \* \*

SEQUENCE LISTING

```
<160> NUMBER OF SEQ ID NOS: 87

<210> SEQ ID NO 1
<211> LENGTH: 20
<212> TYPE: PRT
<213> ORGANISM: Artificial Sequence
<220> FEATURE:
<223> OTHER INFORMATION: Leader Sequence

<400> SEQUENCE: 1

Met Glu Thr Asp Thr Leu Leu Leu Trp Val Leu Leu Leu Trp Val Pro
1               5                   10                  15

Gly Ser Thr Gly
            20

<210> SEQ ID NO 2
<211> LENGTH: 232
<212> TYPE: PRT
<213> ORGANISM: Homo sapiens

<400> SEQUENCE: 2

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205
```

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 3
<211> LENGTH: 232
<212> TYPE: PRT
<213> ORGANISM: Homo sapiens

<400> SEQUENCE: 3

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 4
<211> LENGTH: 12
<212> TYPE: PRT
<213> ORGANISM: Homo sapiens

<400> SEQUENCE: 4

Glu Arg Lys Cys Cys Val Glu Cys Pro Pro Cys Pro
1               5                   10

<210> SEQ ID NO 5
<211> LENGTH: 41
<212> TYPE: PRT
<213> ORGANISM: Homo sapiens

<400> SEQUENCE: 5

```
Gly Gly Gly Ser Ile Lys Gln Ile Glu Asp Lys Ile Glu Glu Ile Leu
1               5                   10                  15

Ser Lys Ile Tyr His Ile Glu Asn Glu Ile Ala Arg Ile Lys Lys Leu
            20                  25                  30

Ile Gly Glu Arg Gly His Gly Gly Gly
        35                  40
```

<210> SEQ ID NO 6
<211> LENGTH: 16
<212> TYPE: PRT
<213> ORGANISM: Artificial Sequence
<220> FEATURE:
<223> OTHER INFORMATION: GPP multimerization domain

<400> SEQUENCE: 6

```
Gly Pro Pro Gly Pro Pro Gly Pro Pro Gly Pro Pro Gly Pro Pro Gly
1               5                   10                  15
```

<210> SEQ ID NO 7
<211> LENGTH: 264
<212> TYPE: PRT
<213> ORGANISM: Homo sapiens

<400> SEQUENCE: 7

```
Met Glu Thr Asp Thr Leu Leu Leu Trp Val Leu Leu Leu Trp Val Pro
1               5                   10                  15

Gly Ser Thr Gly Glu Pro Lys Ser Cys Asp Lys Thr His Thr Cys Pro
            20                  25                  30

Pro Cys Pro Ala Pro Glu Leu Leu Gly Gly Pro Ser Val Phe Leu Phe
        35                  40                  45

Pro Pro Lys Pro Lys Asp Thr Leu Met Ile Ser Arg Thr Pro Glu Val
50                  55                  60

Thr Cys Val Val Val Asp Val Ser His Glu Asp Pro Glu Val Lys Phe
65                  70                  75                  80

Asn Trp Tyr Val Asp Gly Val Glu Val His Asn Ala Lys Thr Lys Pro
                85                  90                  95

Arg Glu Glu Gln Tyr Asn Ser Thr Tyr Arg Val Val Ser Val Leu Thr
            100                 105                 110

Val Leu His Gln Asp Trp Leu Asn Gly Lys Glu Tyr Lys Cys Lys Val
        115                 120                 125

Ser Asn Lys Ala Leu Pro Ala Pro Ile Glu Lys Thr Ile Ser Lys Ala
130                 135                 140

Lys Gly Gln Pro Arg Glu Pro Gln Val Tyr Thr Leu Pro Pro Ser Arg
145                 150                 155                 160

Glu Glu Met Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser
        195                 200                 205

Phe Phe Leu Tyr Ser Lys Leu Thr Val Asp Lys Ser Arg Trp Gln Gln
210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys Glu Arg Lys Cys
                245                 250                 255

Cys Val Glu Cys Pro Pro Cys Pro
```

260

<210> SEQ ID NO 8
<211> LENGTH: 264
<212> TYPE: PRT
<213> ORGANISM: Homo sapiens

<400> SEQUENCE: 8

Met Glu Thr Asp Thr Leu Leu Leu Trp Val Leu Leu Trp Val Pro
1               5                   10                  15

Gly Ser Thr Gly Glu Pro Lys Ser Cys Asp Lys Thr His Thr Cys Pro
            20                  25                  30

Pro Cys Pro Ala Pro Glu Leu Leu Gly Gly Pro Ser Val Phe Leu Phe
        35                  40                  45

Pro Pro Lys Pro Lys Asp Thr Leu Met Ile Ser Arg Thr Pro Glu Val
    50                  55                  60

Thr Cys Val Val Val Asp Val Ser His Glu Asp Pro Glu Val Lys Phe
65                  70                  75                  80

Asn Trp Tyr Val Asp Gly Val Glu Val His Asn Ala Lys Thr Lys Pro
                85                  90                  95

Arg Glu Glu Gln Tyr Asn Ser Thr Tyr Arg Val Val Ser Val Leu Thr
            100                 105                 110

Val Leu His Gln Asp Trp Leu Asn Gly Lys Glu Tyr Lys Cys Lys Val
        115                 120                 125

Ser Asn Lys Ala Leu Pro Ala Pro Ile Glu Lys Thr Ile Ser Lys Ala
    130                 135                 140

Lys Gly Gln Pro Arg Glu Pro Gln Val Tyr Thr Leu Pro Pro Ser Arg
145                 150                 155                 160

Asp Glu Leu Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser
        195                 200                 205

Phe Phe Leu Tyr Ser Lys Leu Thr Val Asp Lys Ser Arg Trp Gln Gln
    210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys Glu Arg Lys Cys
                245                 250                 255

Cys Val Glu Cys Pro Pro Cys Pro
            260

<210> SEQ ID NO 9
<211> LENGTH: 263
<212> TYPE: PRT
<213> ORGANISM: Homo sapiens

<400> SEQUENCE: 9

Met Glu Thr Asp Thr Leu Leu Leu Trp Val Leu Leu Leu Val Pro Gly
1               5                   10                  15

Ser Thr Gly Glu Arg Lys Cys Cys Val Glu Cys Pro Pro Cys Pro Glu
            20                  25                  30

Pro Lys Ser Cys Asp Lys Thr His Thr Cys Pro Pro Cys Pro Ala Pro
        35                  40                  45

Glu Leu Leu Gly Gly Pro Ser Val Phe Leu Phe Pro Pro Lys Pro Lys

```
                50                  55                  60
Asp Thr Leu Met Ile Ser Arg Thr Pro Glu Val Thr Cys Val Val Val
 65                  70                  75                  80

Asp Val Ser His Glu Asp Pro Glu Val Lys Phe Asn Trp Tyr Val Asp
                 85                  90                  95

Gly Val Glu Val His Asn Ala Lys Thr Lys Pro Arg Glu Glu Gln Tyr
            100                 105                 110

Asn Ser Thr Tyr Arg Val Val Ser Val Leu Thr Val Leu His Gln Asp
        115                 120                 125

Trp Leu Asn Gly Lys Glu Tyr Lys Cys Lys Val Ser Asn Lys Ala Leu
130                 135                 140

Pro Ala Pro Ile Glu Lys Thr Ile Ser Lys Ala Lys Gly Gln Pro Arg
145                 150                 155                 160

Glu Pro Gln Val Tyr Thr Leu Pro Pro Ser Arg Glu Glu Met Thr Lys
                165                 170                 175

Asn Gln Val Ser Leu Thr Cys Leu Val Lys Gly Phe Tyr Pro Ser Asp
            180                 185                 190

Ile Ala Val Glu Trp Glu Ser Asn Gly Gln Pro Glu Asn Asn Tyr Lys
        195                 200                 205

Thr Thr Pro Pro Val Leu Asp Ser Asp Gly Ser Phe Phe Leu Tyr Ser
210                 215                 220

Lys Leu Thr Val Asp Lys Ser Arg Trp Gln Gln Gly Asn Val Phe Ser
225                 230                 235                 240

Cys Ser Val Met His Glu Ala Leu His Asn His Tyr Thr Gln Lys Ser
                245                 250                 255

Leu Ser Leu Ser Pro Gly Lys
            260

<210> SEQ ID NO 10
<211> LENGTH: 264
<212> TYPE: PRT
<213> ORGANISM: Homo sapiens

<400> SEQUENCE: 10

Met Glu Thr Asp Thr Leu Leu Leu Trp Val Leu Leu Leu Trp Val Pro
 1               5                  10                  15

Gly Ser Thr Gly Glu Pro Lys Ser Cys Asp Lys Thr His Thr Cys Pro
                20                  25                  30

Pro Cys Pro Ala Pro Pro Leu Leu Arg Gly Pro Ser Val Phe Leu Phe
            35                  40                  45

Pro Pro Lys Pro Lys Asp Thr Leu Met Ile Ser Arg Thr Pro Glu Val
        50                  55                  60

Thr Cys Val Val Val Asp Val Glu Phe Glu Asp Pro Glu Val Lys Phe
 65                  70                  75                  80

Asn Trp Tyr Val Asp Gly Val Glu Val His Asn Ala Lys Thr Lys Pro
                85                  90                  95

Arg Glu Glu Gln Tyr Asn Ser Thr Tyr Arg Val Val Ser Val Leu Thr
            100                 105                 110

Val Leu His Gln Asp Trp Leu Asn Gly Lys Glu Tyr Lys Cys Lys Val
        115                 120                 125

Thr Asn Lys Ala Leu Pro Ala Pro Ile Glu Lys Thr Ile Ser Lys Ala
130                 135                 140

Lys Gly Gln Pro Arg Glu Pro Gln Val Tyr Thr Leu Pro Pro Ser Arg
145                 150                 155                 160
```

```
Asp Glu Leu Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser
        195                 200                 205

Phe Phe Leu Tyr Ser Lys Leu Thr Val Asp Lys Ser Arg Trp Gln Gln
    210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys Glu Arg Lys Cys
                245                 250                 255

Cys Val Glu Cys Pro Pro Cys Pro
            260

<210> SEQ ID NO 11
<211> LENGTH: 264
<212> TYPE: PRT
<213> ORGANISM: Homo sapiens

<400> SEQUENCE: 11

Met Glu Thr Asp Thr Leu Leu Leu Trp Val Leu Leu Leu Trp Val Pro
1               5                   10                  15

Gly Ser Thr Gly Glu Pro Lys Ser Cys Asp Lys Thr His Thr Cys Pro
            20                  25                  30

Pro Cys Pro Ala Pro Pro Leu Leu Arg Gly Pro Ser Val Phe Leu Phe
        35                  40                  45

Pro Pro Lys Pro Lys Asp Thr Leu Met Ile Ser Arg Thr Pro Glu Val
    50                  55                  60

Thr Cys Val Val Val Asp Val Glu Phe Glu Asp Pro Glu Val Lys Phe
65                  70                  75                  80

Asn Trp Tyr Val Asp Gly Val Glu Val His Asn Ala Lys Thr Lys Pro
                85                  90                  95

Arg Glu Glu Gln Tyr Asn Ser Thr Tyr Arg Val Val Ser Val Leu Thr
            100                 105                 110

Val Leu His Gln Asp Trp Leu Asn Gly Lys Glu Tyr Lys Cys Lys Val
        115                 120                 125

Thr Asn Lys Ala Leu Pro Ala Pro Ile Glu Lys Thr Ile Ser Lys Ala
    130                 135                 140

Lys Gly Gln Pro Arg Glu Pro Gln Val Tyr Thr Leu Pro Pro Ser Arg
145                 150                 155                 160

Glu Glu Met Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser
        195                 200                 205

Phe Phe Leu Tyr Ser Lys Leu Thr Val Asp Lys Ser Arg Trp Gln Gln
    210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys Glu Arg Lys Cys
                245                 250                 255

Cys Val Glu Cys Pro Pro Cys Pro
            260
```

<210> SEQ ID NO 12
<211> LENGTH: 264
<212> TYPE: PRT
<213> ORGANISM: Homo sapiens

<400> SEQUENCE: 12

Met Glu Thr Asp Thr Leu Leu Leu Trp Val Leu Leu Leu Trp Val Pro
1               5                   10                  15

Gly Ser Thr Gly Glu Pro Lys Ser Cys Asp Lys Thr His Thr Cys Pro
            20                  25                  30

Pro Cys Pro Ala Pro Glu Leu Leu Arg Gly Pro Ser Val Phe Leu Phe
        35                  40                  45

Pro Pro Lys Pro Lys Asp Thr Leu Met Ile Ser Arg Thr Pro Glu Val
    50                  55                  60

Thr Cys Val Val Val Asp Val Glu Phe Glu Asp Pro Glu Val Lys Phe
65                  70                  75                  80

Asn Trp Tyr Val Asp Gly Val Glu Val His Asn Ala Lys Thr Lys Pro
                85                  90                  95

Arg Glu Glu Gln Tyr Asn Ser Thr Tyr Arg Val Val Ser Val Leu Thr
            100                 105                 110

Val Leu His Gln Asp Trp Leu Asn Gly Lys Glu Tyr Lys Cys Lys Val
        115                 120                 125

Thr Asn Lys Ala Leu Pro Ala Pro Ile Glu Lys Thr Ile Ser Lys Ala
    130                 135                 140

Lys Gly Gln Pro Arg Glu Pro Gln Val Tyr Thr Leu Pro Pro Ser Arg
145                 150                 155                 160

Asp Glu Leu Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser
        195                 200                 205

Phe Phe Leu Tyr Ser Lys Leu Thr Val Asp Lys Ser Arg Trp Gln Gln
    210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys Glu Arg Lys Cys
                245                 250                 255

Cys Val Glu Cys Pro Pro Cys Pro
            260

<210> SEQ ID NO 13
<211> LENGTH: 264
<212> TYPE: PRT
<213> ORGANISM: Homo sapiens

<400> SEQUENCE: 13

Met Glu Thr Asp Thr Leu Leu Leu Trp Val Leu Leu Leu Trp Val Pro
1               5                   10                  15

Gly Ser Thr Gly Glu Pro Lys Ser Cys Asp Lys Thr His Thr Cys Pro
            20                  25                  30

Pro Cys Pro Ala Pro Glu Leu Leu Gly Gly Pro Ser Val Phe Leu Phe
        35                  40                  45

Pro Pro Lys Pro Lys Asp Thr Leu Met Ile Ser Arg Thr Pro Glu Val
    50                  55                  60

```
Thr Cys Val Val Val Asp Val Glu Phe Glu Asp Pro Glu Val Lys Phe
 65                  70                  75                  80

Asn Trp Tyr Val Asp Gly Val Glu Val His Asn Ala Lys Thr Lys Pro
                 85                  90                  95

Arg Glu Glu Gln Tyr Asn Ser Thr Tyr Arg Val Val Ser Val Leu Thr
            100                 105                 110

Val Leu His Gln Asp Trp Leu Asn Gly Lys Glu Tyr Lys Cys Lys Val
        115                 120                 125

Thr Asn Lys Ala Leu Pro Ala Pro Ile Glu Lys Thr Ile Ser Lys Ala
    130                 135                 140

Lys Gly Gln Pro Arg Glu Pro Gln Val Tyr Thr Leu Pro Pro Ser Arg
145                 150                 155                 160

Asp Glu Leu Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser
        195                 200                 205

Phe Phe Leu Tyr Ser Lys Leu Thr Val Asp Lys Ser Arg Trp Gln Gln
    210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys Glu Arg Lys Cys
                245                 250                 255

Cys Val Glu Cys Pro Pro Cys Pro
            260

<210> SEQ ID NO 14
<211> LENGTH: 264
<212> TYPE: PRT
<213> ORGANISM: Homo sapiens

<400> SEQUENCE: 14

Met Glu Thr Asp Thr Leu Leu Leu Trp Val Leu Leu Leu Trp Val Pro
  1               5                  10                  15

Gly Ser Thr Gly Glu Pro Lys Ser Cys Asp Lys Thr His Thr Cys Pro
                 20                  25                  30

Pro Cys Pro Ala Pro Glu Leu Leu Gly Gly Pro Ser Val Phe Leu Phe
             35                  40                  45

Pro Pro Lys Pro Lys Asp Thr Leu Met Ile Ser Arg Thr Pro Glu Val
     50                  55                  60

Thr Cys Val Val Val Asp Val Glu Phe Glu Asp Pro Glu Val Lys Phe
 65                  70                  75                  80

Asn Trp Tyr Val Asp Gly Val Glu Val His Asn Ala Lys Thr Lys Pro
                 85                  90                  95

Arg Glu Glu Gln Tyr Ala Ser Thr Tyr Arg Val Val Ser Val Leu Thr
            100                 105                 110

Val Leu His Gln Asp Trp Leu Asn Gly Lys Glu Tyr Lys Cys Lys Val
        115                 120                 125

Thr Asn Lys Ala Leu Pro Ala Pro Ile Glu Lys Thr Ile Ser Lys Ala
    130                 135                 140

Lys Gly Gln Pro Arg Glu Pro Gln Val Tyr Thr Leu Pro Pro Ser Arg
145                 150                 155                 160

Asp Glu Leu Thr Lys Asn Gln Val Ser Leu Thr Cys Leu Val Lys Gly
```

```
                165                 170                 175
Phe Tyr Pro Ser Asp Ile Ala Val Glu Trp Glu Ser Asn Gly Gln Pro
            180                 185                 190
Glu Asn Asn Tyr Lys Thr Thr Pro Pro Val Leu Asp Ser Asp Gly Ser
        195                 200                 205
Phe Phe Leu Tyr Ser Lys Leu Thr Val Asp Lys Ser Arg Trp Gln Gln
    210                 215                 220
Gly Asn Val Phe Ser Cys Ser Val Met His Glu Ala Leu His Asn His
225                 230                 235                 240
Tyr Thr Gln Lys Ser Leu Ser Leu Ser Pro Gly Lys Glu Arg Lys Cys
                245                 250                 255
Cys Val Glu Cys Pro Pro Cys Pro
            260

<210> SEQ ID NO 15
<211> LENGTH: 264
<212> TYPE: PRT
<213> ORGANISM: Homo sapiens

<400> SEQUENCE: 15

Met Glu Thr Asp Thr Leu Leu Leu Trp Val Leu Leu Leu Trp Val Pro
1               5                  10                  15
Gly Ser Thr Gly Glu Pro Lys Ser Cys Asp Lys Thr His Thr Cys Pro
            20                  25                  30
Pro Cys Pro Ala Pro Glu Leu Leu Gly Gly Pro Ser Val Phe Leu Phe
        35                  40                  45
Pro Pro Lys Pro Lys Asp Thr Leu Met Ile Ser Arg Thr Pro Glu Val
    50                  55                  60
Thr Cys Val Val Val Asp Val Glu Phe Glu Asp Pro Glu Val Lys Phe
65                  70                  75                  80
Asn Trp Tyr Val Asp Gly Val Glu Val His Asn Ala Lys Thr Lys Pro
                85                  90                  95
Arg Glu Glu Gln Tyr Ala Ser Thr Tyr Arg Val Val Ser Val Leu Thr
            100                 105                 110
Val Leu His Gln Asp Trp Leu Asn Gly Lys Glu Tyr Lys Cys Lys Val
        115                 120                 125
Thr Asn Lys Ala Leu Pro Ala Pro Ile Glu Lys Thr Ile Ser Lys Ala
    130                 135                 140
Lys Gly Gln Pro Arg Glu Pro Gln Val Tyr Thr Leu Pro Pro Ser Arg
145                 150                 155                 160
Glu Glu Met Thr Lys Asn Gln Val Ser Leu Thr Cys Leu Val Lys Gly
                165                 170                 175
Phe Tyr Pro Ser Asp Ile Ala Val Glu Trp Glu Ser Asn Gly Gln Pro
            180                 185                 190
Glu Asn Asn Tyr Lys Thr Thr Pro Pro Val Leu Asp Ser Asp Gly Ser
        195                 200                 205
Phe Phe Leu Tyr Ser Lys Leu Thr Val Asp Lys Ser Arg Trp Gln Gln
    210                 215                 220
Gly Asn Val Phe Ser Cys Ser Val Met His Glu Ala Leu His Asn His
225                 230                 235                 240
Tyr Thr Gln Lys Ser Leu Ser Leu Ser Pro Gly Lys Glu Arg Lys Cys
                245                 250                 255
Cys Val Glu Cys Pro Pro Cys Pro
            260
```

<210> SEQ ID NO 16
<211> LENGTH: 264
<212> TYPE: PRT
<213> ORGANISM: Homo sapiens

<400> SEQUENCE: 16

```
Met Glu Thr Asp Thr Leu Leu Leu Trp Val Leu Leu Leu Trp Val Pro
1               5                   10                  15

Gly Ser Thr Gly Glu Pro Lys Ser Cys Asp Lys Thr His Thr Cys Pro
            20                  25                  30

Pro Cys Pro Ala Pro Pro Leu Leu Arg Gly Pro Ser Val Phe Leu Phe
        35                  40                  45

Pro Pro Lys Pro Lys Asp Thr Leu Met Ile Ser Arg Thr Pro Glu Val
50                  55                  60

Thr Cys Val Val Val Asp Val Ser His Glu Asp Pro Glu Val Lys Phe
65                  70                  75                  80

Asn Trp Tyr Val Asp Gly Val Glu Val His Asn Ala Lys Thr Lys Pro
                85                  90                  95

Arg Glu Glu Gln Tyr Asn Ser Thr Tyr Arg Val Val Ser Val Leu Thr
            100                 105                 110

Val Leu His Gln Asp Trp Leu Asn Gly Lys Glu Tyr Lys Cys Lys Val
        115                 120                 125

Ser Asn Lys Ala Leu Pro Ala Pro Ile Glu Lys Thr Ile Ser Lys Ala
    130                 135                 140

Lys Gly Gln Pro Arg Glu Pro Gln Val Tyr Thr Leu Pro Pro Ser Arg
145                 150                 155                 160

Asp Glu Leu Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser
        195                 200                 205

Phe Phe Leu Tyr Ser Lys Leu Thr Val Asp Lys Ser Arg Trp Gln Gln
    210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys Glu Arg Lys Cys
                245                 250                 255

Cys Val Glu Cys Pro Pro Cys Pro
            260
```

<210> SEQ ID NO 17
<211> LENGTH: 264
<212> TYPE: PRT
<213> ORGANISM: Homo sapiens

<400> SEQUENCE: 17

```
Met Glu Thr Asp Thr Leu Leu Leu Trp Val Leu Leu Leu Trp Val Pro
1               5                   10                  15

Gly Ser Thr Gly Glu Arg Lys Cys Cys Val Glu Cys Pro Pro Cys Pro
            20                  25                  30

Glu Pro Lys Ser Cys Asp Lys Thr His Thr Cys Pro Pro Cys Pro Ala
        35                  40                  45

Pro Glu Leu Leu Gly Gly Pro Ser Val Phe Leu Phe Pro Pro Lys Pro
50                  55                  60
```

```
Lys Asp Thr Leu Met Ile Ser Arg Thr Pro Glu Val Thr Cys Val Val
 65                  70                  75                  80

Val Asp Val Glu Phe Glu Asp Pro Glu Val Lys Phe Asn Trp Tyr Val
                 85                  90                  95

Asp Gly Val Glu Val His Asn Ala Lys Thr Lys Pro Arg Glu Glu Gln
            100                 105                 110

Tyr Asn Ser Thr Tyr Arg Val Val Ser Val Leu Thr Val Leu His Gln
        115                 120                 125

Asp Trp Leu Asn Gly Lys Glu Tyr Lys Cys Lys Val Thr Asn Lys Ala
    130                 135                 140

Leu Pro Ala Pro Ile Glu Lys Thr Ile Ser Lys Ala Lys Gly Gln Pro
145                 150                 155                 160

Arg Glu Pro Gln Val Tyr Thr Leu Pro Pro Ser Arg Glu Glu Met Thr
                165                 170                 175

Lys Asn Gln Val Ser Leu Thr Cys Leu Val Lys Gly Phe Tyr Pro Ser
            180                 185                 190

Asp Ile Ala Val Glu Trp Glu Ser Asn Gly Gln Pro Glu Asn Asn Tyr
        195                 200                 205

Lys Thr Thr Pro Pro Val Leu Asp Ser Asp Gly Ser Phe Phe Leu Tyr
    210                 215                 220

Ser Lys Leu Thr Val Asp Lys Ser Arg Trp Gln Gln Gly Asn Val Phe
225                 230                 235                 240

Ser Cys Ser Val Met His Glu Ala Leu His Asn His Tyr Thr Gln Lys
                245                 250                 255

Ser Leu Ser Leu Ser Pro Gly Lys
            260

<210> SEQ ID NO 18
<211> LENGTH: 264
<212> TYPE: PRT
<213> ORGANISM: Homo sapiens

<400> SEQUENCE: 18

Met Glu Thr Asp Thr Leu Leu Leu Trp Val Leu Leu Leu Trp Val Pro
1               5                   10                  15

Gly Ser Thr Gly Glu Pro Lys Ser Cys Asp Lys Thr His Thr Cys Pro
                20                  25                  30

Pro Cys Pro Ala Pro Glu Leu Leu Gly Gly Pro Ser Val Phe Leu Phe
            35                  40                  45

Pro Pro Lys Pro Lys Asp Thr Leu Met Ile Ser Arg Thr Pro Glu Val
        50                  55                  60

Thr Cys Val Val Val Asp Val Glu Phe Glu Asp Pro Glu Val Lys Phe
 65                  70                  75                  80

Asn Trp Tyr Val Asp Gly Val Glu Val His Asn Ala Lys Thr Lys Pro
                 85                  90                  95

Arg Glu Glu Gln Tyr Asn Ser Thr Tyr Arg Val Val Ser Val Leu Thr
            100                 105                 110

Val Leu His Gln Asp Trp Leu Asn Gly Lys Glu Tyr Lys Cys Lys Val
        115                 120                 125

Thr Asn Lys Ala Leu Pro Ala Pro Ile Glu Lys Thr Ile Ser Lys Ala
    130                 135                 140

Lys Gly Gln Pro Arg Glu Pro Gln Val Tyr Thr Leu Pro Pro Ser Arg
145                 150                 155                 160

Asp Glu Leu Thr Lys Asn Gln Val Ser Leu Thr Cys Leu Val Lys Gly
                165                 170                 175
```

Phe Tyr Pro Ser Asp Ile Ala Val Glu Trp Glu Ser Asn Gly Gln Pro
            180                 185                 190

Glu Asn Asn Tyr Lys Thr Thr Pro Val Leu Asp Ser Asp Gly Ser
            195                 200                 205

Phe Phe Leu Tyr Ser Lys Leu Thr Val Asp Lys Ser Arg Trp Gln Gln
            210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys Glu Arg Lys Cys
                245                 250                 255

Cys Val Glu Cys Pro Pro Cys Pro
            260

<210> SEQ ID NO 19
<211> LENGTH: 264
<212> TYPE: PRT
<213> ORGANISM: Homo sapiens

<400> SEQUENCE: 19

Met Glu Thr Asp Thr Leu Leu Leu Trp Val Leu Leu Leu Trp Val Pro
1               5                   10                  15

Gly Ser Thr Gly Glu Pro Lys Ser Cys Asp Lys Thr His Thr Cys Pro
            20                  25                  30

Pro Cys Pro Ala Pro Pro Val Ala Gly Gly Pro Ser Val Phe Leu Phe
            35                  40                  45

Pro Pro Lys Pro Lys Asp Thr Leu Met Ile Ser Arg Thr Pro Glu Val
50                  55                  60

Thr Cys Val Val Val Asp Val Glu Phe Glu Asp Pro Glu Val Lys Phe
65                  70                  75                  80

Asn Trp Tyr Val Asp Gly Val Glu Val His Asn Ala Lys Thr Lys Pro
                85                  90                  95

Arg Glu Glu Gln Tyr Ala Ser Thr Tyr Arg Val Val Ser Val Leu Thr
            100                 105                 110

Val Leu His Gln Asp Trp Leu Asn Gly Lys Glu Tyr Lys Cys Lys Val
            115                 120                 125

Thr Asn Lys Ala Leu Pro Ala Pro Ile Glu Lys Thr Ile Ser Lys Ala
130                 135                 140

Lys Gly Gln Pro Arg Glu Pro Gln Val Tyr Thr Leu Pro Pro Ser Arg
145                 150                 155                 160

Asp Glu Leu Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190

Glu Asn Asn Tyr Lys Thr Thr Pro Val Leu Asp Ser Asp Gly Ser
            195                 200                 205

Phe Phe Leu Tyr Ser Lys Leu Thr Val Asp Lys Ser Arg Trp Gln Gln
            210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys Glu Arg Lys Cys
                245                 250                 255

Cys Val Glu Cys Pro Pro Cys Pro
            260

<210> SEQ ID NO 20
<211> LENGTH: 264
<212> TYPE: PRT
<213> ORGANISM: Homo sapiens

<400> SEQUENCE: 20

Met Glu Thr Asp Thr Leu Leu Leu Trp Val Leu Leu Leu Trp Val Pro
1               5                   10                  15

Gly Ser Thr Gly Glu Pro Lys Ser Cys Asp Lys Thr His Thr Cys Pro
            20                  25                  30

Pro Cys Pro Ala Pro Glu Leu Leu Gly Gly Asp Ser Val Phe Leu Phe
        35                  40                  45

Pro Pro Lys Pro Lys Asp Thr Leu Met Ile Ser Arg Thr Pro Glu Val
    50                  55                  60

Thr Cys Val Val Val Asp Val Glu Phe Glu Asp Pro Glu Val Lys Phe
65                  70                  75                  80

Asn Trp Tyr Val Asp Gly Val Glu Val His Asn Ala Lys Thr Lys Pro
                85                  90                  95

Arg Glu Glu Gln Tyr Ala Ser Thr Tyr Arg Val Val Ser Val Leu Thr
            100                 105                 110

Val Leu His Gln Asp Trp Leu Asn Gly Lys Glu Tyr Lys Cys Lys Val
        115                 120                 125

Thr Asn Lys Ala Leu Pro Ala Pro Ile Glu Lys Thr Ile Ser Lys Ala
    130                 135                 140

Lys Gly Gln Pro Arg Glu Pro Gln Val Tyr Thr Leu Pro Pro Ser Arg
145                 150                 155                 160

Asp Glu Leu Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser
        195                 200                 205

Phe Phe Leu Tyr Ser Lys Leu Thr Val Asp Lys Ser Arg Trp Gln Gln
    210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys Glu Arg Lys Cys
                245                 250                 255

Cys Val Glu Cys Pro Pro Cys Pro
            260

<210> SEQ ID NO 21
<211> LENGTH: 264
<212> TYPE: PRT
<213> ORGANISM: Homo sapiens

<400> SEQUENCE: 21

Met Glu Thr Asp Thr Leu Leu Leu Trp Val Leu Leu Leu Trp Val Pro
1               5                   10                  15

Gly Ser Thr Gly Glu Pro Lys Ser Cys Asp Lys Thr His Thr Cys Pro
            20                  25                  30

Pro Cys Pro Ala Pro Glu Ala Ala Gly Gly Pro Ser Val Phe Leu Phe
        35                  40                  45

Pro Pro Lys Pro Lys Asp Thr Leu Met Ile Ser Arg Thr Pro Glu Val
    50                  55                  60

Thr Cys Val Val Val Asp Val Glu Phe Glu Asp Pro Glu Val Lys Phe

```
                65                  70                  75                  80
Asn Trp Tyr Val Asp Gly Val Glu Val His Asn Ala Lys Thr Lys Pro
                    85                  90                  95
Arg Glu Glu Gln Tyr Ala Ser Thr Tyr Arg Val Val Ser Val Leu Thr
                    100                 105                 110
Val Leu His Gln Asp Trp Leu Asn Gly Lys Glu Tyr Lys Cys Lys Val
                    115                 120                 125
Thr Asn Lys Ala Leu Pro Ala Pro Ile Glu Lys Thr Ile Ser Lys Ala
            130                 135                 140
Lys Gly Gln Pro Arg Glu Pro Gln Val Tyr Thr Leu Pro Pro Ser Arg
145                 150                 155                 160
Asp Glu Leu Thr Lys Asn Gln Val Ser Leu Thr Cys Leu Val Lys Gly
                    165                 170                 175
Phe Tyr Pro Ser Asp Ile Ala Val Glu Trp Glu Ser Asn Gly Gln Pro
                    180                 185                 190
Glu Asn Asn Tyr Lys Thr Thr Pro Pro Val Leu Asp Ser Asp Gly Ser
                    195                 200                 205
Phe Phe Leu Tyr Ser Lys Leu Thr Val Asp Lys Ser Arg Trp Gln Gln
            210                 215                 220
Gly Asn Val Phe Ser Cys Ser Val Met His Glu Ala Leu His Asn His
225                 230                 235                 240
Tyr Thr Gln Lys Ser Leu Ser Leu Ser Pro Gly Lys Glu Arg Lys Cys
                    245                 250                 255
Cys Val Glu Cys Pro Pro Cys Pro
                    260

<210> SEQ ID NO 22
<211> LENGTH: 264
<212> TYPE: PRT
<213> ORGANISM: Homo sapiens

<400> SEQUENCE: 22

Met Glu Thr Asp Thr Leu Leu Leu Trp Val Leu Leu Leu Trp Val Pro
1               5                   10                  15
Gly Ser Thr Gly Glu Pro Lys Ser Cys Asp Lys Thr His Thr Cys Pro
                    20                  25                  30
Pro Cys Pro Ala Pro Glu Ala Ala Gly Gly Pro Ser Val Phe Leu Phe
                    35                  40                  45
Pro Pro Lys Pro Lys Asp Thr Leu Met Ile Ser Arg Thr Pro Glu Val
            50                  55                  60
Thr Cys Val Val Val Asp Val Glu Phe Glu Asp Pro Glu Val Lys Phe
65                  70                  75                  80
Asn Trp Tyr Val Asp Gly Val Glu Val His Asn Ala Lys Thr Lys Pro
                    85                  90                  95
Arg Glu Glu Gln Tyr Ala Ser Thr Tyr Arg Val Val Ser Val Leu Thr
                    100                 105                 110
Val Leu His Gln Asp Trp Leu Asn Gly Lys Glu Tyr Lys Cys Lys Val
                    115                 120                 125
Thr Asn Lys Ala Leu Pro Ala Pro Ile Glu Lys Thr Ile Ser Lys Ala
            130                 135                 140
Lys Gly Gln Pro Arg Glu Pro Gln Val Tyr Thr Leu Pro Pro Ser Arg
145                 150                 155                 160
Glu Glu Met Thr Lys Asn Gln Val Ser Leu Thr Cys Leu Val Lys Gly
                    165                 170                 175
```

```
Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser
        195                 200                 205

Phe Phe Leu Tyr Ser Lys Leu Thr Val Asp Lys Ser Arg Trp Gln Gln
    210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys Glu Arg Lys Cys
                245                 250                 255

Cys Val Glu Cys Pro Pro Cys Pro
            260

<210> SEQ ID NO 23
<211> LENGTH: 264
<212> TYPE: PRT
<213> ORGANISM: Homo sapiens

<400> SEQUENCE: 23

Met Glu Thr Asp Thr Leu Leu Leu Trp Val Leu Leu Leu Trp Val Pro
1               5                   10                  15

Gly Ser Thr Gly Glu Pro Lys Ser Cys Asp Lys Thr His Thr Cys Pro
            20                  25                  30

Pro Cys Pro Ala Pro Pro Leu Leu Arg Gly Pro Ser Val Phe Leu Phe
        35                  40                  45

Pro Pro Lys Pro Lys Asp Thr Leu Met Ile Ser Arg Thr Pro Glu Val
    50                  55                  60

Thr Cys Val Val Val Asp Val Glu Phe Glu Asp Pro Glu Val Lys Phe
65                  70                  75                  80

Asn Trp Tyr Val Asp Gly Val Glu Val His Asn Ala Lys Thr Lys Pro
                85                  90                  95

Arg Glu Glu Gln Tyr Asn Ser Thr Tyr Arg Val Val Ser Val Leu Thr
            100                 105                 110

Val Leu His Gln Asp Trp Leu Asn Gly Lys Glu Tyr Lys Cys Lys Val
        115                 120                 125

Thr Asn Lys Ala Phe Pro Ala Pro Ile Glu Lys Thr Ile Ser Lys Ala
    130                 135                 140

Lys Gly Gln Pro Arg Glu Pro Gln Val Tyr Thr Leu Pro Pro Ser Arg
145                 150                 155                 160

Asp Glu Leu Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser
        195                 200                 205

Phe Phe Leu Tyr Ser Lys Leu Thr Val Asp Lys Ser Arg Trp Gln Gln
    210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys Glu Arg Lys Cys
                245                 250                 255

Cys Val Glu Cys Pro Pro Cys Pro
            260

<210> SEQ ID NO 24
```

```
<211> LENGTH: 264
<212> TYPE: PRT
<213> ORGANISM: Homo sapiens

<400> SEQUENCE: 24

Met Glu Thr Asp Thr Leu Leu Leu Trp Val Leu Leu Leu Trp Val Pro
1               5                   10                  15

Gly Ser Thr Gly Glu Pro Lys Ser Cys Asp Lys Thr His Thr Cys Pro
            20                  25                  30

Pro Cys Pro Ala Pro Glu Leu Leu Gly Gly Asp Ser Val Phe Leu Phe
        35                  40                  45

Pro Pro Lys Pro Lys Asp Thr Leu Met Ile Ser Arg Thr Pro Glu Val
    50                  55                  60

Thr Cys Val Val Val Gly Val Glu Phe Glu Asp Pro Glu Val Lys Phe
65                  70                  75                  80

Asn Trp Tyr Val Asp Gly Val Glu Val His Asn Ala Lys Thr Lys Pro
                85                  90                  95

Arg Glu Glu Gln Tyr Asn Ser Thr Tyr Arg Val Val Ser Val Leu Thr
            100                 105                 110

Val Leu His Gln Asp Trp Leu Asn Gly Lys Glu Tyr Lys Cys Lys Val
        115                 120                 125

Thr Asn Lys Ala Leu Pro Ala Pro Ile Glu Lys Thr Ile Ser Lys Ala
    130                 135                 140

Lys Gly Gln Pro Arg Glu Pro Gln Val Tyr Thr Leu Pro Pro Ser Arg
145                 150                 155                 160

Glu Glu Met Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser
        195                 200                 205

Phe Phe Leu Tyr Ser Lys Leu Thr Val Asp Lys Ser Arg Trp Gln Gln
    210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys Glu Arg Lys Cys
                245                 250                 255

Cys Val Glu Cys Pro Pro Cys Pro
            260

<210> SEQ ID NO 25
<211> LENGTH: 264
<212> TYPE: PRT
<213> ORGANISM: Homo sapiens

<400> SEQUENCE: 25

Met Glu Thr Asp Thr Leu Leu Leu Trp Val Leu Leu Leu Trp Val Pro
1               5                   10                  15

Gly Ser Thr Gly Glu Pro Lys Ser Cys Asp Lys Thr His Thr Cys Pro
            20                  25                  30

Pro Cys Pro Ala Pro Glu Leu Leu Gly Gly Asp Ser Val Phe Leu Phe
        35                  40                  45

Pro Pro Lys Pro Lys Asp Thr Leu Met Ile Ser Arg Thr Pro Glu Val
    50                  55                  60

Thr Cys Val Val Val Trp Val Glu Phe Glu Asp Pro Glu Val Lys Phe
65                  70                  75                  80
```

```
Asn Trp Tyr Val Asp Gly Val Glu Val His Asn Ala Lys Thr Lys Pro
                85                  90                  95
Arg Glu Glu Gln Tyr Asn Ser Thr Tyr Arg Val Val Ser Val Leu Thr
            100                 105                 110
Val Leu His Gln Asp Trp Leu Asn Gly Lys Glu Tyr Lys Cys Lys Val
        115                 120                 125
Thr Asn Lys Ala Leu Pro Ala Pro Ile Glu Lys Thr Ile Ser Lys Ala
    130                 135                 140
Lys Gly Gln Pro Arg Glu Pro Gln Val Tyr Thr Leu Pro Pro Ser Arg
145                 150                 155                 160
Glu Glu Met Thr Lys Asn Gln Val Ser Leu Thr Cys Leu Val Lys Gly
                165                 170                 175
Phe Tyr Pro Ser Asp Ile Ala Val Glu Trp Glu Ser Asn Gly Gln Pro
            180                 185                 190
Glu Asn Asn Tyr Lys Thr Thr Pro Pro Val Leu Asp Ser Asp Gly Ser
        195                 200                 205
Phe Phe Leu Tyr Ser Lys Leu Thr Val Asp Lys Ser Arg Trp Gln Gln
    210                 215                 220
Gly Asn Val Phe Ser Cys Ser Val Met His Glu Ala Leu His Asn His
225                 230                 235                 240
Tyr Thr Gln Lys Ser Leu Ser Leu Ser Pro Gly Lys Glu Arg Lys Cys
                245                 250                 255
Cys Val Glu Cys Pro Pro Cys Pro
                260

<210> SEQ ID NO 26
<211> LENGTH: 263
<212> TYPE: PRT
<213> ORGANISM: Homo sapiens

<400> SEQUENCE: 26

Met Glu Thr Asp Thr Leu Leu Leu Trp Val Leu Leu Leu Trp Val Pro
1               5                   10                  15
Gly Ser Thr Gly Glu Pro Lys Ser Cys Asp Lys Thr His Thr Cys Pro
            20                  25                  30
Pro Cys Pro Ala Pro Pro Val Ala Gly Pro Ser Val Phe Leu Phe Pro
        35                  40                  45
Pro Lys Pro Lys Asp Thr Leu Met Ile Ser Arg Thr Pro Glu Val Thr
    50                  55                  60
Cys Val Val Val Asp Val Glu Phe Glu Asp Pro Glu Val Lys Phe Asn
65                  70                  75                  80
Trp Tyr Val Asp Gly Val Glu Val His Asn Ala Lys Thr Lys Pro Arg
                85                  90                  95
Glu Glu Gln Tyr Ala Ser Thr Tyr Arg Val Val Ser Val Leu Thr Val
            100                 105                 110
Leu His Gln Asp Trp Leu Asn Gly Lys Glu Tyr Lys Cys Lys Val Thr
        115                 120                 125
Asn Lys Ala Phe Pro Ala Pro Ile Glu Lys Thr Ile Ser Lys Ala Lys
    130                 135                 140
Gly Gln Pro Arg Glu Pro Gln Val Tyr Thr Leu Pro Pro Ser Arg Asp
145                 150                 155                 160
Glu Leu Thr Lys Asn Gln Val Ser Leu Thr Cys Leu Val Lys Gly Phe
                165                 170                 175
Tyr Pro Ser Asp Ile Ala Val Glu Trp Glu Ser Asn Gly Gln Pro Glu
```

```
                      180                 185                 190
Asn Asn Tyr Lys Thr Thr Pro Pro Val Leu Asp Ser Asp Gly Ser Phe
            195                 200                 205

Phe Leu Tyr Ser Lys Leu Thr Val Asp Lys Ser Arg Trp Gln Gln Gly
            210                 215                 220

Asn Val Phe Ser Cys Ser Val Met His Glu Ala Leu His Asn His Tyr
225                 230                 235                 240

Thr Gln Lys Ser Leu Ser Leu Ser Pro Gly Lys Glu Arg Lys Cys Cys
            245                 250                 255

Val Glu Cys Pro Pro Cys Pro
            260

<210> SEQ ID NO 27
<211> LENGTH: 264
<212> TYPE: PRT
<213> ORGANISM: Homo sapiens

<400> SEQUENCE: 27

Met Glu Thr Asp Thr Leu Leu Leu Trp Val Leu Leu Leu Trp Val Pro
1               5                   10                  15

Gly Ser Thr Gly Glu Pro Lys Ser Cys Asp Lys Thr His Thr Cys Pro
            20                  25                  30

Pro Cys Pro Ala Pro Glu Leu Leu Gly Gly Asp Ser Val Phe Leu Phe
            35                  40                  45

Pro Pro Lys Pro Lys Asp Thr Leu Met Ile Ser Arg Thr Pro Glu Val
50                  55                  60

Thr Cys Val Val Val Asp Val Glu Phe Glu Asp Pro Glu Val Lys Phe
65                  70                  75                  80

Asn Trp Tyr Val Asp Gly Val Glu Val His Asn Ala Lys Thr Lys Pro
            85                  90                  95

Arg Glu Glu Gln Tyr Asn Ser Thr Tyr Arg Val Val Ser Val Leu Thr
            100                 105                 110

Val Leu His Gln Asp Trp Leu Asn Gly Lys Glu Tyr Lys Cys Lys Val
            115                 120                 125

Thr Asn Lys Ala Leu Pro Ala Pro Ile Glu Lys Thr Ile Ser Lys Ala
            130                 135                 140

Lys Gly Gln Pro Arg Glu Pro Gln Val Tyr Thr Leu Pro Pro Ser Arg
145                 150                 155                 160

Asp Glu Leu Thr Lys Asn Gln Val Ser Leu Thr Cys Leu Val Lys Gly
            165                 170                 175

Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser
            195                 200                 205

Phe Phe Leu Tyr Ser Lys Leu Thr Val Asp Lys Ser Arg Trp Gln Gln
            210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys Glu Arg Lys Cys
            245                 250                 255

Cys Val Glu Cys Pro Pro Cys Pro
            260

<210> SEQ ID NO 28
<211> LENGTH: 264
```

```
<212> TYPE: PRT
<213> ORGANISM: Homo sapiens

<400> SEQUENCE: 28

Met Glu Thr Asp Thr Leu Leu Leu Trp Val Leu Leu Leu Trp Val Pro
1               5                   10                  15

Gly Ser Thr Gly Glu Pro Lys Ser Cys Asp Lys Thr His Thr Cys Pro
            20                  25                  30

Pro Cys Pro Ala Pro Pro Leu Leu Gln Gly Pro Ser Val Phe Leu Phe
            35                  40                  45

Pro Pro Lys Pro Lys Asp Thr Leu Met Ile Ser Arg Thr Pro Glu Val
        50                  55                  60

Thr Cys Val Val Val Asp Val Ser Phe Glu Asp Pro Glu Val Lys Phe
65                  70                  75                  80

Asn Trp Tyr Val Asp Gly Val Glu Val His Asn Ala Lys Thr Lys Pro
                85                  90                  95

Arg Glu Glu Gln Tyr Asn Ser Thr Tyr Arg Val Val Ser Val Leu Thr
            100                 105                 110

Val Leu His Gln Asp Trp Leu Asn Gly Lys Glu Tyr Lys Cys Lys Val
        115                 120                 125

Thr Asn Lys Ala Leu Pro Ala Pro Ile Glu Lys Thr Ile Ser Lys Ala
130                 135                 140

Lys Gly Gln Pro Arg Glu Pro Gln Val Tyr Thr Leu Pro Pro Ser Arg
145                 150                 155                 160

Asp Glu Leu Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser
        195                 200                 205

Phe Phe Leu Tyr Ser Lys Leu Thr Val Asp Lys Ser Arg Trp Gln Gln
210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys Glu Arg Lys Cys
                245                 250                 255

Cys Val Glu Cys Pro Pro Cys Pro
            260

<210> SEQ ID NO 29
<211> LENGTH: 264
<212> TYPE: PRT
<213> ORGANISM: Homo sapiens

<400> SEQUENCE: 29

Met Glu Thr Asp Thr Leu Leu Leu Trp Val Leu Leu Leu Trp Val Pro
1               5                   10                  15

Gly Ser Thr Gly Glu Pro Lys Ser Cys Asp Lys Thr His Thr Cys Pro
            20                  25                  30

Pro Cys Pro Ala Pro Pro Leu Leu Arg Gly Pro Ser Val Phe Leu Phe
            35                  40                  45

Pro Pro Lys Pro Lys Asp Thr Leu Met Ile Ser Arg Thr Pro Glu Val
        50                  55                  60

Thr Cys Val Val Val Asp Val Ser Phe Glu Asp Pro Glu Val Lys Phe
65                  70                  75                  80
```

```
Asn Trp Tyr Val Asp Gly Val Glu Val His Asn Ala Lys Thr Lys Pro
                85                  90                  95

Arg Glu Glu Gln Tyr Asn Ser Thr Tyr Arg Val Val Ser Val Leu Thr
            100                 105                 110

Val Leu His Gln Asp Trp Leu Asn Gly Lys Glu Tyr Lys Cys Lys Val
        115                 120                 125

Thr Asn Lys Ala Leu Pro Ala Pro Ile Glu Lys Thr Ile Ser Lys Ala
    130                 135                 140

Lys Gly Gln Pro Arg Glu Pro Gln Val Tyr Thr Leu Pro Pro Ser Arg
145                 150                 155                 160

Asp Glu Leu Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser
        195                 200                 205

Phe Phe Leu Tyr Ser Lys Leu Thr Val Asp Lys Ser Arg Trp Gln Gln
    210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys Glu Arg Lys Cys
                245                 250                 255

Cys Val Glu Cys Pro Pro Cys Pro
            260

<210> SEQ ID NO 30
<211> LENGTH: 264
<212> TYPE: PRT
<213> ORGANISM: Homo sapiens

<400> SEQUENCE: 30

Met Glu Thr Asp Thr Leu Leu Leu Trp Val Leu Leu Leu Trp Val Pro
1               5                   10                  15

Gly Ser Thr Gly Glu Pro Lys Ser Cys Asp Lys Thr His Thr Cys Pro
            20                  25                  30

Pro Cys Pro Ala Pro Pro Leu Leu His Gly Pro Ser Val Phe Leu Phe
        35                  40                  45

Pro Pro Lys Pro Lys Asp Thr Leu Met Ile Ser Arg Thr Pro Glu Val
    50                  55                  60

Thr Cys Val Val Val Asp Val Ser Phe Glu Asp Pro Glu Val Lys Phe
65                  70                  75                  80

Asn Trp Tyr Val Asp Gly Val Glu Val His Asn Ala Lys Thr Lys Pro
                85                  90                  95

Arg Glu Glu Gln Tyr Asn Ser Thr Tyr Arg Val Val Ser Val Leu Thr
            100                 105                 110

Val Leu His Gln Asp Trp Leu Asn Gly Lys Glu Tyr Lys Cys Lys Val
        115                 120                 125

Thr Asn Lys Ala Leu Pro Ala Pro Ile Glu Lys Thr Ile Ser Lys Ala
    130                 135                 140

Lys Gly Gln Pro Arg Glu Pro Gln Val Tyr Thr Leu Pro Pro Ser Arg
145                 150                 155                 160

Asp Glu Leu Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190
```

```
Glu Asn Asn Tyr Lys Thr Thr Pro Pro Val Leu Asp Ser Asp Gly Ser
            195                 200                 205

Phe Phe Leu Tyr Ser Lys Leu Thr Val Asp Lys Ser Arg Trp Gln Gln
    210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys Glu Arg Lys Cys
            245                 250                 255

Cys Val Glu Cys Pro Pro Cys Pro
            260

<210> SEQ ID NO 31
<211> LENGTH: 264
<212> TYPE: PRT
<213> ORGANISM: Homo sapiens

<400> SEQUENCE: 31

Met Glu Thr Asp Thr Leu Leu Leu Trp Val Leu Leu Leu Trp Val Pro
1               5                   10                  15

Gly Ser Thr Gly Glu Pro Lys Ser Cys Asp Lys Thr His Thr Cys Pro
            20                  25                  30

Pro Cys Pro Ala Pro Pro Leu Leu Asn Gly Pro Ser Val Phe Leu Phe
        35                  40                  45

Pro Pro Lys Pro Lys Asp Thr Leu Met Ile Ser Arg Thr Pro Glu Val
    50                  55                  60

Thr Cys Val Val Val Asp Val Ser Phe Glu Asp Pro Glu Val Lys Phe
65                  70                  75                  80

Asn Trp Tyr Val Asp Gly Val Glu Val His Asn Ala Lys Thr Lys Pro
                85                  90                  95

Arg Glu Glu Gln Tyr Asn Ser Thr Tyr Arg Val Val Ser Val Leu Thr
            100                 105                 110

Val Leu His Gln Asp Trp Leu Asn Gly Lys Glu Tyr Lys Cys Lys Val
        115                 120                 125

Thr Asn Lys Ala Leu Pro Ala Pro Ile Glu Lys Thr Ile Ser Lys Ala
    130                 135                 140

Lys Gly Gln Pro Arg Glu Pro Gln Val Tyr Thr Leu Pro Pro Ser Arg
145                 150                 155                 160

Asp Glu Leu Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser
        195                 200                 205

Phe Phe Leu Tyr Ser Lys Leu Thr Val Asp Lys Ser Arg Trp Gln Gln
    210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys Glu Arg Lys Cys
                245                 250                 255

Cys Val Glu Cys Pro Pro Cys Pro
            260

<210> SEQ ID NO 32
<211> LENGTH: 264
<212> TYPE: PRT
```

<213> ORGANISM: Homo sapiens

<400> SEQUENCE: 32

```
Met Glu Thr Asp Thr Leu Leu Leu Trp Val Leu Leu Leu Trp Val Pro
1               5                   10                  15

Gly Ser Thr Gly Glu Pro Lys Ser Cys Asp Lys Thr His Thr Cys Pro
            20                  25                  30

Pro Cys Pro Ala Pro Pro Leu Leu Lys Gly Pro Ser Val Phe Leu Phe
        35                  40                  45

Pro Pro Lys Pro Lys Asp Thr Leu Met Ile Ser Arg Thr Pro Glu Val
    50                  55                  60

Thr Cys Val Val Val Asp Val Ser Phe Glu Asp Pro Glu Val Lys Phe
65                  70                  75                  80

Asn Trp Tyr Val Asp Gly Val Glu Val His Asn Ala Lys Thr Lys Pro
                85                  90                  95

Arg Glu Glu Gln Tyr Asn Ser Thr Tyr Arg Val Val Ser Val Leu Thr
            100                 105                 110

Val Leu His Gln Asp Trp Leu Asn Gly Lys Glu Tyr Lys Cys Lys Val
        115                 120                 125

Thr Asn Lys Ala Leu Pro Ala Pro Ile Glu Lys Thr Ile Ser Lys Ala
    130                 135                 140

Lys Gly Gln Pro Arg Glu Pro Gln Val Tyr Thr Leu Pro Pro Ser Arg
145                 150                 155                 160

Asp Glu Leu Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser
        195                 200                 205

Phe Phe Leu Tyr Ser Lys Leu Thr Val Asp Lys Ser Arg Trp Gln Gln
    210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys Gly Arg Lys Cys
                245                 250                 255

Cys Val Glu Cys Pro Pro Cys Pro
            260
```

<210> SEQ ID NO 33
<211> LENGTH: 264
<212> TYPE: PRT
<213> ORGANISM: Homo sapiens

<400> SEQUENCE: 33

```
Met Glu Thr Asp Thr Leu Leu Leu Trp Val Leu Leu Leu Trp Val Pro
1               5                   10                  15

Gly Ser Thr Gly Glu Pro Lys Ser Cys Asp Lys Thr His Thr Cys Pro
            20                  25                  30

Pro Cys Pro Ala Pro Pro Leu Leu Gly Gly Pro Ser Val Phe Leu Phe
        35                  40                  45

Pro Pro Lys Pro Lys Asp Thr Leu Met Ile Ser Arg Thr Pro Glu Val
    50                  55                  60

Thr Cys Val Val Val Asp Val Arg Phe Glu Asp Pro Glu Val Lys Phe
65                  70                  75                  80

Asn Trp Tyr Val Asp Gly Val Glu Val His Asn Ala Lys Thr Lys Pro
```

```
            85                  90                  95
Arg Glu Glu Gln Tyr Asn Ser Thr Tyr Arg Val Val Ser Val Leu Thr
            100                 105                 110

Val Leu His Gln Asp Trp Leu Asn Gly Lys Glu Tyr Lys Cys Lys Val
            115                 120                 125

Thr Asn Lys Ala Leu Pro Ala Pro Ile Glu Lys Thr Ile Ser Lys Ala
            130                 135                 140

Lys Gly Gln Pro Arg Glu Pro Gln Val Tyr Thr Leu Pro Pro Ser Arg
145                 150                 155                 160

Asp Glu Leu Thr Lys Asn Gln Val Ser Leu Thr Cys Leu Val Lys Gly
            165                 170                 175

Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser
            195                 200                 205

Phe Phe Leu Tyr Ser Lys Leu Thr Val Asp Lys Ser Arg Trp Gln Gln
            210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys Glu Arg Lys Cys
            245                 250                 255

Cys Val Glu Cys Pro Pro Cys Pro
            260

<210> SEQ ID NO 34
<211> LENGTH: 264
<212> TYPE: PRT
<213> ORGANISM: Homo sapiens

<400> SEQUENCE: 34

Met Glu Thr Asp Thr Leu Leu Leu Trp Val Leu Leu Leu Trp Val Pro
1               5                   10                  15

Gly Ser Thr Gly Glu Pro Lys Ser Cys Asp Lys Thr His Thr Cys Pro
            20                  25                  30

Pro Cys Pro Ala Pro Pro Leu Leu Gly Gly Pro Ser Val Phe Leu Phe
            35                  40                  45

Pro Pro Lys Pro Lys Asp Thr Leu Met Ile Ser Arg Thr Pro Glu Val
            50                  55                  60

Thr Cys Val Val Val Asp Val Asn Phe Glu Asp Pro Glu Val Lys Phe
65                  70                  75                  80

Asn Trp Tyr Val Asp Gly Val Glu Val His Asn Ala Lys Thr Lys Pro
            85                  90                  95

Arg Glu Glu Gln Tyr Asn Ser Thr Tyr Arg Val Val Ser Val Leu Thr
            100                 105                 110

Val Leu His Gln Asp Trp Leu Asn Gly Lys Glu Tyr Lys Cys Lys Val
            115                 120                 125

Thr Asn Lys Ala Leu Pro Ala Pro Ile Glu Lys Thr Ile Ser Lys Ala
            130                 135                 140

Lys Gly Gln Pro Arg Glu Pro Gln Val Tyr Thr Leu Pro Pro Ser Arg
145                 150                 155                 160

Asp Glu Leu Thr Lys Asn Gln Val Ser Leu Thr Cys Leu Val Lys Gly
            165                 170                 175

Phe Tyr Pro Ser Asp Ile Ala Val Glu Trp Glu Ser Asn Gly Gln Pro
            180                 185                 190
```

```
Glu Asn Asn Tyr Lys Thr Thr Pro Pro Val Leu Asp Ser Asp Gly Ser
            195                 200                 205

Phe Phe Leu Tyr Ser Lys Leu Thr Val Asp Lys Ser Arg Trp Gln Gln
    210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys Glu Arg Lys Cys
            245                 250                 255

Cys Val Glu Cys Pro Pro Cys Pro
            260
```

<210> SEQ ID NO 35
<211> LENGTH: 264
<212> TYPE: PRT
<213> ORGANISM: Homo sapiens

<400> SEQUENCE: 35

```
Met Glu Thr Asp Thr Leu Leu Leu Trp Val Leu Leu Leu Trp Val Pro
1               5                   10                  15

Gly Ser Thr Gly Glu Pro Lys Ser Cys Asp Lys Thr His Thr Cys Pro
            20                  25                  30

Pro Cys Pro Ala Pro Pro Leu Leu Gly Gly Pro Ser Val Phe Leu Phe
        35                  40                  45

Pro Pro Lys Pro Lys Asp Thr Leu Met Ile Ser Arg Thr Pro Glu Val
    50                  55                  60

Thr Cys Val Val Val Asp Val Lys Phe Glu Asp Pro Glu Val Lys Phe
65                  70                  75                  80

Asn Trp Tyr Val Asp Gly Val Glu Val His Asn Ala Lys Thr Lys Pro
                85                  90                  95

Arg Glu Glu Gln Tyr Asn Ser Thr Tyr Arg Val Val Ser Val Leu Thr
            100                 105                 110

Val Leu His Gln Asp Trp Leu Asn Gly Lys Glu Tyr Lys Cys Lys Val
        115                 120                 125

Thr Asn Lys Ala Leu Pro Ala Pro Ile Glu Lys Thr Ile Ser Lys Ala
130                 135                 140

Lys Gly Gln Pro Arg Glu Pro Gln Val Tyr Thr Leu Pro Pro Ser Arg
145                 150                 155                 160

Asp Glu Leu Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser
        195                 200                 205

Phe Phe Leu Tyr Ser Lys Leu Thr Val Asp Lys Ser Arg Trp Gln Gln
    210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys Glu Arg Lys Cys
                245                 250                 255

Cys Val Glu Cys Pro Pro Cys Pro
            260
```

<210> SEQ ID NO 36
<211> LENGTH: 264
<212> TYPE: PRT
<213> ORGANISM: Homo sapiens

<400> SEQUENCE: 36

Met Glu Thr Asp Thr Leu Leu Leu Trp Val Leu Leu Leu Trp Val Pro
1               5                   10                  15

Gly Ser Thr Gly Glu Pro Lys Ser Cys Asp Lys Thr His Thr Cys Pro
            20                  25                  30

Pro Cys Pro Ala Pro Pro Leu Leu Asp Gly Pro Ser Val Phe Leu Phe
        35                  40                  45

Pro Pro Lys Pro Lys Asp Thr Leu Met Ile Ser Arg Thr Pro Glu Val
    50                  55                  60

Thr Cys Val Val Val Asp Val Arg Phe Glu Asp Pro Glu Val Lys Phe
65                  70                  75                  80

Asn Trp Tyr Val Asp Gly Val Glu Val His Asn Ala Lys Thr Lys Pro
                85                  90                  95

Arg Glu Glu Gln Tyr Asn Ser Thr Tyr Arg Val Val Ser Val Leu Thr
            100                 105                 110

Val Leu His Gln Asp Trp Leu Asn Gly Lys Glu Tyr Lys Cys Lys Val
        115                 120                 125

Thr Asn Lys Ala Leu Pro Ala Pro Ile Glu Lys Thr Ile Ser Lys Ala
    130                 135                 140

Lys Gly Gln Pro Arg Glu Pro Gln Val Tyr Thr Leu Pro Pro Ser Arg
145                 150                 155                 160

Asp Glu Leu Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser
        195                 200                 205

Phe Phe Leu Tyr Ser Lys Leu Thr Val Asp Lys Ser Arg Trp Gln Gln
    210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys Glu Arg Lys Cys
                245                 250                 255

Cys Val Glu Cys Pro Pro Cys Pro
            260

<210> SEQ ID NO 37
<211> LENGTH: 264
<212> TYPE: PRT
<213> ORGANISM: Homo sapiens

<400> SEQUENCE: 37

Met Glu Thr Asp Thr Leu Leu Leu Trp Val Leu Leu Leu Trp Val Pro
1               5                   10                  15

Gly Ser Thr Gly Glu Pro Lys Ser Cys Asp Lys Thr His Thr Cys Pro
            20                  25                  30

Pro Cys Pro Ala Pro Pro Leu Leu Arg Gly Pro Ser Val Phe Leu Phe
        35                  40                  45

Pro Pro Lys Pro Lys Asp Thr Leu Met Ile Ser Arg Thr Pro Glu Val
    50                  55                  60

Thr Cys Val Val Val Asp Val Arg Phe Glu Asp Pro Glu Val Lys Phe
65                  70                  75                  80

Asn Trp Tyr Val Asp Gly Val Glu Val His Asn Ala Lys Thr Lys Pro
                85                  90                  95

-continued

Arg Glu Glu Gln Tyr Asn Ser Thr Tyr Arg Val Val Ser Val Leu Thr
                100                 105                 110

Val Leu His Gln Asp Trp Leu Asn Gly Lys Glu Tyr Lys Cys Lys Val
            115                 120                 125

Thr Asn Lys Ala Leu Pro Ala Pro Ile Glu Lys Thr Ile Ser Lys Ala
        130                 135                 140

Lys Gly Gln Pro Arg Glu Pro Gln Val Tyr Thr Leu Pro Pro Ser Arg
145                 150                 155                 160

Asp Glu Leu Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser
        195                 200                 205

Phe Phe Leu Tyr Ser Lys Leu Thr Val Asp Lys Ser Arg Trp Gln Gln
    210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys Glu Arg Lys Cys
                245                 250                 255

Cys Val Glu Cys Pro Pro Cys Pro
            260

<210> SEQ ID NO 38
<211> LENGTH: 264
<212> TYPE: PRT
<213> ORGANISM: Homo sapiens

<400> SEQUENCE: 38

Met Glu Thr Asp Thr Leu Leu Leu Trp Val Leu Leu Leu Trp Val Pro
1               5                   10                  15

Gly Ser Thr Gly Glu Pro Lys Ser Cys Asp Lys Thr His Thr Cys Pro
            20                  25                  30

Pro Cys Pro Ala Pro Pro Leu Leu Arg Gly Pro Ser Val Phe Leu Phe
        35                  40                  45

Pro Pro Lys Pro Lys Asp Thr Leu Met Ile Ser Arg Thr Pro Glu Val
50                  55                  60

Thr Cys Val Val Val Asp Val Asp Phe Glu Asp Pro Glu Val Lys Phe
65                  70                  75                  80

Asn Trp Tyr Val Asp Gly Val Glu Val His Asn Ala Lys Thr Lys Pro
                85                  90                  95

Arg Glu Glu Gln Tyr Asn Ser Thr Tyr Arg Val Val Ser Val Leu Thr
                100                 105                 110

Val Leu His Gln Asp Trp Leu Asn Gly Lys Glu Tyr Lys Cys Lys Val
            115                 120                 125

Thr Asn Lys Ala Leu Pro Ala Pro Ile Glu Lys Thr Ile Ser Lys Ala
        130                 135                 140

Lys Gly Gln Pro Arg Glu Pro Gln Val Tyr Thr Leu Pro Pro Ser Arg
145                 150                 155                 160

Asp Glu Leu Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser

-continued

```
                195                 200                 205

Phe Phe Leu Tyr Ser Lys Leu Thr Val Asp Lys Ser Arg Trp Gln Gln
    210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys Glu Arg Lys Cys
                245                 250                 255

Cys Val Glu Cys Pro Pro Cys Pro
                260

<210> SEQ ID NO 39
<211> LENGTH: 264
<212> TYPE: PRT
<213> ORGANISM: Homo sapiens

<400> SEQUENCE: 39

Met Glu Thr Asp Thr Leu Leu Leu Trp Val Leu Leu Leu Trp Val Pro
1               5                   10                  15

Gly Ser Thr Gly Glu Pro Lys Ser Cys Asp Lys Thr His Thr Cys Pro
                20                  25                  30

Pro Cys Pro Ala Pro Pro Leu Leu Glu Gly Pro Ser Val Phe Leu Phe
            35                  40                  45

Pro Pro Lys Pro Lys Asp Thr Leu Met Ile Ser Arg Thr Pro Glu Val
50                  55                  60

Thr Cys Val Val Val Asp Val Arg Phe Glu Asp Pro Glu Val Lys Phe
65                  70                  75                  80

Asn Trp Tyr Val Asp Gly Val Glu Val His Asn Ala Lys Thr Lys Pro
                85                  90                  95

Arg Glu Glu Gln Tyr Asn Ser Thr Tyr Arg Val Val Ser Val Leu Thr
            100                 105                 110

Val Leu His Gln Asp Trp Leu Asn Gly Lys Glu Tyr Lys Cys Lys Val
        115                 120                 125

Thr Asn Lys Ala Leu Pro Ala Pro Ile Glu Lys Thr Ile Ser Lys Ala
130                 135                 140

Lys Gly Gln Pro Arg Glu Pro Gln Val Tyr Thr Leu Pro Pro Ser Arg
145                 150                 155                 160

Asp Glu Leu Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser
        195                 200                 205

Phe Phe Leu Tyr Ser Lys Leu Thr Val Asp Lys Ser Arg Trp Gln Gln
    210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys Glu Arg Lys Cys
                245                 250                 255

Cys Val Glu Cys Pro Pro Cys Pro
                260

<210> SEQ ID NO 40
<211> LENGTH: 264
<212> TYPE: PRT
<213> ORGANISM: Homo sapiens
```

```
<400> SEQUENCE: 40

Met Glu Thr Asp Thr Leu Leu Leu Trp Val Leu Leu Leu Trp Val Pro
1               5                   10                  15

Gly Ser Thr Gly Glu Pro Lys Ser Cys Asp Lys Thr His Thr Cys Pro
            20                  25                  30

Pro Cys Pro Ala Pro Pro Leu Leu His Gly Pro Ser Val Phe Leu Phe
        35                  40                  45

Pro Pro Lys Pro Lys Asp Thr Leu Met Ile Ser Arg Thr Pro Glu Val
    50                  55                  60

Thr Cys Val Val Val Asp Val Lys Phe Glu Asp Pro Glu Val Lys Phe
65                  70                  75                  80

Asn Trp Tyr Val Asp Gly Val Glu Val His Asn Ala Lys Thr Lys Pro
                85                  90                  95

Arg Glu Glu Gln Tyr Asn Ser Thr Tyr Arg Val Val Ser Val Leu Thr
            100                 105                 110

Val Leu His Gln Asp Trp Leu Asn Gly Lys Glu Tyr Lys Cys Lys Val
        115                 120                 125

Thr Asn Lys Ala Leu Pro Ala Pro Ile Glu Lys Thr Ile Ser Lys Ala
    130                 135                 140

Lys Gly Gln Pro Arg Glu Pro Gln Val Tyr Thr Leu Pro Pro Ser Arg
145                 150                 155                 160

Asp Glu Leu Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser
        195                 200                 205

Phe Phe Leu Tyr Ser Lys Leu Thr Val Asp Lys Ser Arg Trp Gln Gln
    210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys Glu Arg Lys Cys
                245                 250                 255

Cys Val Glu Cys Pro Pro Cys Pro
            260

<210> SEQ ID NO 41
<211> LENGTH: 264
<212> TYPE: PRT
<213> ORGANISM: Homo sapiens

<400> SEQUENCE: 41

Met Glu Thr Asp Thr Leu Leu Leu Trp Val Leu Leu Leu Trp Val Pro
1               5                   10                  15

Gly Ser Thr Gly Glu Pro Lys Ser Cys Asp Lys Thr His Thr Cys Pro
            20                  25                  30

Pro Cys Pro Ala Pro Pro Leu Leu Gln Gly Pro Ser Val Phe Leu Phe
        35                  40                  45

Pro Pro Lys Pro Lys Asp Thr Leu Met Ile Ser Arg Thr Pro Glu Val
    50                  55                  60

Thr Cys Val Val Val Asp Val Gln Phe Glu Asp Pro Glu Val Lys Phe
65                  70                  75                  80

Asn Trp Tyr Val Asp Gly Val Glu Val His Asn Ala Lys Thr Lys Pro
                85                  90                  95
```

```
Arg Glu Glu Gln Tyr Asn Ser Thr Tyr Arg Val Val Ser Val Leu Thr
                100                 105                 110

Val Leu His Gln Asp Trp Leu Asn Gly Lys Glu Tyr Lys Cys Lys Val
            115                 120                 125

Thr Asn Lys Ala Leu Pro Ala Pro Ile Glu Lys Thr Ile Ser Lys Ala
        130                 135                 140

Lys Gly Gln Pro Arg Glu Pro Gln Val Tyr Thr Leu Pro Pro Ser Arg
145                 150                 155                 160

Asp Glu Leu Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser
        195                 200                 205

Phe Phe Leu Tyr Ser Lys Leu Thr Val Asp Lys Ser Arg Trp Gln Gln
210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys Glu Arg Lys Cys
                245                 250                 255

Cys Val Glu Cys Pro Pro Cys Pro
                260

<210> SEQ ID NO 42
<211> LENGTH: 264
<212> TYPE: PRT
<213> ORGANISM: Homo sapiens

<400> SEQUENCE: 42

Met Glu Thr Asp Thr Leu Leu Leu Trp Val Leu Leu Leu Trp Val Pro
1               5                   10                  15

Gly Ser Thr Gly Glu Pro Lys Ser Cys Asp Lys Thr His Thr Cys Pro
            20                  25                  30

Pro Cys Pro Ala Pro Pro Leu Leu Arg Gly Pro Ser Val Phe Leu Phe
        35                  40                  45

Pro Pro Lys Pro Lys Asp Thr Leu Met Ile Ser Arg Thr Pro Glu Val
50                  55                  60

Thr Cys Val Val Val Asp Val Lys Phe Glu Asp Pro Glu Val Lys Phe
65                  70                  75                  80

Asn Trp Tyr Val Asp Gly Val Glu Val His Asn Ala Lys Thr Lys Pro
                85                  90                  95

Arg Glu Glu Gln Tyr Asn Ser Thr Tyr Arg Val Val Ser Val Leu Thr
                100                 105                 110

Val Leu His Gln Asp Trp Leu Asn Gly Lys Glu Tyr Lys Cys Lys Val
            115                 120                 125

Thr Asn Lys Ala Leu Pro Ala Pro Ile Glu Lys Thr Ile Ser Lys Ala
        130                 135                 140

Lys Gly Gln Pro Arg Glu Pro Gln Val Tyr Thr Leu Pro Pro Ser Arg
145                 150                 155                 160

Asp Glu Leu Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser
        195                 200                 205
```

```
Phe Phe Leu Tyr Ser Lys Leu Thr Val Asp Lys Ser Arg Trp Gln Gln
    210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys Glu Arg Lys Cys
                245                 250                 255

Cys Val Glu Cys Pro Pro Cys Pro
            260

<210> SEQ ID NO 43
<211> LENGTH: 264
<212> TYPE: PRT
<213> ORGANISM: Homo sapiens

<400> SEQUENCE: 43

Met Glu Thr Asp Thr Leu Leu Leu Trp Val Leu Leu Leu Trp Val Pro
1               5                   10                  15

Gly Ser Thr Gly Glu Pro Lys Ser Cys Asp Lys Thr His Thr Cys Pro
                20                  25                  30

Pro Cys Pro Ala Pro Pro Leu Leu Arg Gly Pro Ser Val Phe Leu Phe
            35                  40                  45

Pro Pro Lys Pro Lys Asp Thr Leu Met Ile Ser Arg Thr Pro Glu Val
50                  55                  60

Thr Cys Val Val Val Asp Val Gln Phe Glu Asp Pro Glu Val Lys Phe
65                  70                  75                  80

Asn Trp Tyr Val Asp Gly Val Glu Val His Asn Ala Lys Thr Lys Pro
                85                  90                  95

Arg Glu Glu Gln Tyr Asn Ser Thr Tyr Arg Val Val Ser Val Leu Thr
            100                 105                 110

Val Leu His Gln Asp Trp Leu Asn Gly Lys Glu Tyr Lys Cys Lys Val
        115                 120                 125

Thr Asn Lys Ala Leu Pro Ala Pro Ile Glu Lys Thr Ile Ser Lys Ala
    130                 135                 140

Lys Gly Gln Pro Arg Glu Pro Gln Val Tyr Thr Leu Pro Pro Ser Arg
145                 150                 155                 160

Asp Glu Leu Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser
        195                 200                 205

Phe Phe Leu Tyr Ser Lys Leu Thr Val Asp Lys Ser Arg Trp Gln Gln
    210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys Glu Arg Lys Cys
                245                 250                 255

Cys Val Glu Cys Pro Pro Cys Pro
            260

<210> SEQ ID NO 44
<211> LENGTH: 264
<212> TYPE: PRT
<213> ORGANISM: Homo sapiens

<400> SEQUENCE: 44
```

```
Met Glu Thr Asp Thr Leu Leu Leu Trp Val Leu Leu Leu Trp Val Pro
1               5                   10                  15

Gly Ser Thr Gly Glu Pro Lys Ser Cys Asp Lys Thr His Thr Cys Pro
            20                  25                  30

Pro Cys Pro Ala Pro Pro Leu Leu Asp Gly Pro Ser Val Phe Leu Phe
            35                  40                  45

Pro Pro Lys Pro Lys Asp Thr Leu Met Ile Ser Arg Thr Pro Glu Val
        50                  55                  60

Thr Cys Val Val Val Asp Val Lys Phe Glu Asp Pro Glu Val Lys Phe
65                  70                  75                  80

Asn Trp Tyr Val Asp Gly Val Glu Val His Asn Ala Lys Thr Lys Pro
                85                  90                  95

Arg Glu Glu Gln Tyr Asn Ser Thr Tyr Arg Val Val Ser Val Leu Thr
                100                 105                 110

Val Leu His Gln Asp Trp Leu Asn Gly Lys Glu Tyr Lys Cys Lys Val
            115                 120                 125

Thr Asn Lys Ala Leu Pro Ala Pro Ile Glu Lys Thr Ile Ser Lys Ala
130                 135                 140

Lys Gly Gln Pro Arg Glu Pro Gln Val Tyr Thr Leu Pro Pro Ser Arg
145                 150                 155                 160

Asp Glu Leu Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser
            195                 200                 205

Phe Phe Leu Tyr Ser Lys Leu Thr Val Asp Lys Ser Arg Trp Gln Gln
210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys Glu Arg Lys Cys
                245                 250                 255

Cys Val Glu Cys Pro Pro Cys Pro
            260

<210> SEQ ID NO 45
<211> LENGTH: 264
<212> TYPE: PRT
<213> ORGANISM: Homo sapiens

<400> SEQUENCE: 45

Met Glu Thr Asp Thr Leu Leu Leu Trp Val Leu Leu Leu Trp Val Pro
1               5                   10                  15

Gly Ser Thr Gly Glu Pro Lys Ser Cys Asp Lys Thr His Thr Cys Pro
            20                  25                  30

Pro Cys Pro Ala Pro Pro Leu Leu His Gly Pro Ser Val Phe Leu Phe
            35                  40                  45

Pro Pro Lys Pro Lys Asp Thr Leu Met Ile Ser Arg Thr Pro Glu Val
        50                  55                  60

Thr Cys Val Val Val Asp Val Gln Phe Glu Asp Pro Glu Val Lys Phe
65                  70                  75                  80

Asn Trp Tyr Val Asp Gly Val Glu Val His Asn Ala Lys Thr Lys Pro
                85                  90                  95

Arg Glu Glu Gln Tyr Asn Ser Thr Tyr Arg Val Val Ser Val Leu Thr
```

```
            100                 105                 110
Val Leu His Gln Asp Trp Leu Asn Gly Lys Glu Tyr Lys Cys Lys Val
        115                 120                 125

Thr Asn Lys Ala Leu Pro Ala Pro Ile Glu Lys Thr Ile Ser Lys Ala
    130                 135                 140

Lys Gly Gln Pro Arg Glu Pro Gln Val Tyr Thr Leu Pro Pro Ser Arg
145                 150                 155                 160

Asp Glu Leu Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser
        195                 200                 205

Phe Phe Leu Tyr Ser Lys Leu Thr Val Asp Lys Ser Arg Trp Gln Gln
    210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys Glu Arg Lys Cys
                245                 250                 255

Cys Val Glu Cys Pro Pro Cys Pro
            260

<210> SEQ ID NO 46
<211> LENGTH: 264
<212> TYPE: PRT
<213> ORGANISM: Homo sapiens

<400> SEQUENCE: 46

Met Glu Thr Asp Thr Leu Leu Leu Trp Val Leu Leu Leu Trp Val Pro
1               5                   10                  15

Gly Ser Thr Gly Glu Pro Lys Ser Cys Asp Lys Thr His Thr Cys Pro
            20                  25                  30

Pro Cys Pro Ala Pro Pro Leu Leu Gln Gly Pro Ser Val Phe Leu Phe
        35                  40                  45

Pro Pro Lys Pro Lys Asp Thr Leu Met Ile Ser Arg Thr Pro Glu Val
    50                  55                  60

Thr Cys Val Val Val Asp Val Arg Phe Glu Asp Pro Glu Val Lys Phe
65                  70                  75                  80

Asn Trp Tyr Val Asp Gly Val Glu Val His Asn Ala Lys Thr Lys Pro
                85                  90                  95

Arg Glu Glu Gln Tyr Asn Ser Thr Tyr Arg Val Val Ser Val Leu Thr
            100                 105                 110

Val Leu His Gln Asp Trp Leu Asn Gly Lys Glu Tyr Lys Cys Lys Val
        115                 120                 125

Thr Asn Lys Ala Leu Pro Ala Pro Ile Glu Lys Thr Ile Ser Lys Ala
    130                 135                 140

Lys Gly Gln Pro Arg Glu Pro Gln Val Tyr Thr Leu Pro Pro Ser Arg
145                 150                 155                 160

Asp Glu Leu Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser
        195                 200                 205
```

```
Phe Phe Leu Tyr Ser Lys Leu Thr Val Asp Lys Ser Arg Trp Gln Gln
        210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys Glu Arg Lys Cys
                245                 250                 255

Cys Val Glu Cys Pro Pro Cys Pro
            260

<210> SEQ ID NO 47
<211> LENGTH: 264
<212> TYPE: PRT
<213> ORGANISM: Homo sapiens

<400> SEQUENCE: 47

Met Glu Thr Asp Thr Leu Leu Leu Trp Val Leu Leu Leu Trp Val Pro
1               5                   10                  15

Gly Ser Thr Gly Glu Pro Lys Ser Cys Asp Lys Thr His Thr Cys Pro
            20                  25                  30

Pro Cys Pro Ala Pro Pro Leu Leu Lys Gly Pro Ser Val Phe Leu Phe
        35                  40                  45

Pro Pro Lys Pro Lys Asp Thr Leu Met Ile Ser Arg Thr Pro Glu Val
50                  55                  60

Thr Cys Val Val Val Asp Val Lys Phe Glu Asp Pro Glu Val Lys Phe
65                  70                  75                  80

Asn Trp Tyr Val Asp Gly Val Glu Val His Asn Ala Lys Thr Lys Pro
                85                  90                  95

Arg Glu Glu Gln Tyr Asn Ser Thr Tyr Arg Val Val Ser Val Leu Thr
            100                 105                 110

Val Leu His Gln Asp Trp Leu Asn Gly Lys Glu Tyr Lys Cys Lys Val
        115                 120                 125

Thr Asn Lys Ala Leu Pro Ala Pro Ile Glu Lys Thr Ile Ser Lys Ala
    130                 135                 140

Lys Gly Gln Pro Arg Glu Pro Gln Val Tyr Thr Leu Pro Pro Ser Arg
145                 150                 155                 160

Asp Glu Leu Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser
        195                 200                 205

Phe Phe Leu Tyr Ser Lys Leu Thr Val Asp Lys Ser Arg Trp Gln Gln
    210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys Glu Arg Lys Cys
                245                 250                 255

Cys Val Glu Cys Pro Pro Cys Pro
            260

<210> SEQ ID NO 48
<211> LENGTH: 264
<212> TYPE: PRT
<213> ORGANISM: Homo sapiens

<400> SEQUENCE: 48
```

Met Glu Thr Asp Thr Leu Leu Leu Trp Val Leu Leu Leu Trp Val Pro
1               5                   10                  15

Gly Ser Thr Gly Glu Pro Lys Ser Cys Asp Lys Thr His Thr Cys Pro
            20                  25                  30

Pro Cys Pro Ala Pro Pro Leu Leu Lys Gly Pro Ser Val Phe Leu Phe
            35                  40                  45

Pro Pro Lys Pro Lys Asp Thr Leu Met Ile Ser Arg Thr Pro Glu Val
        50                  55                  60

Thr Cys Val Val Val Asp Val Asn Phe Glu Asp Pro Glu Val Lys Phe
65                  70                  75                  80

Asn Trp Tyr Val Asp Gly Val Glu Val His Asn Ala Lys Thr Lys Pro
                85                  90                  95

Arg Glu Glu Gln Tyr Asn Ser Thr Tyr Arg Val Val Ser Val Leu Thr
            100                 105                 110

Val Leu His Gln Asp Trp Leu Asn Gly Lys Glu Tyr Lys Cys Lys Val
            115                 120                 125

Thr Asn Lys Ala Leu Pro Ala Pro Ile Glu Lys Thr Ile Ser Lys Ala
        130                 135                 140

Lys Gly Gln Pro Arg Glu Pro Gln Val Tyr Thr Leu Pro Pro Ser Arg
145                 150                 155                 160

Asp Glu Leu Thr Lys Asn Gln Val Ser Leu Thr Cys Leu Val Lys Gly
            165                 170                 175

Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser
        195                 200                 205

Phe Phe Leu Tyr Ser Lys Leu Thr Val Asp Lys Ser Arg Trp Gln Gln
210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys Glu Arg Lys Cys
            245                 250                 255

Cys Val Glu Cys Pro Pro Cys Pro
            260

<210> SEQ ID NO 49
<211> LENGTH: 264
<212> TYPE: PRT
<213> ORGANISM: Homo sapiens

<400> SEQUENCE: 49

Met Glu Thr Asp Thr Leu Leu Leu Trp Val Leu Leu Leu Trp Val Pro
1               5                   10                  15

Gly Ser Thr Gly Glu Pro Lys Ser Cys Asp Lys Thr His Thr Cys Pro
            20                  25                  30

Pro Cys Pro Ala Pro Pro Leu Leu Asn Gly Pro Ser Val Phe Leu Phe
            35                  40                  45

Pro Pro Lys Pro Lys Asp Thr Leu Met Ile Ser Arg Thr Pro Glu Val
        50                  55                  60

Thr Cys Val Val Val Asp Val Glu Phe Glu Asp Pro Glu Val Lys Phe
65                  70                  75                  80

Asn Trp Tyr Val Asp Gly Val Glu Val His Asn Ala Lys Thr Lys Pro
                85                  90                  95

Arg Glu Glu Gln Tyr Asn Ser Thr Tyr Arg Val Val Ser Val Leu Thr
            100                 105                 110

```
Val Leu His Gln Asp Trp Leu Asn Gly Lys Glu Tyr Lys Cys Lys Val
        115                 120                 125

Thr Asn Lys Ala Leu Pro Ala Pro Ile Glu Lys Thr Ile Ser Lys Ala
    130                 135                 140

Lys Gly Gln Pro Arg Glu Pro Gln Val Tyr Thr Leu Pro Pro Ser Arg
145                 150                 155                 160

Asp Glu Leu Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser
        195                 200                 205

Phe Phe Leu Tyr Ser Lys Leu Thr Val Asp Lys Ser Arg Trp Gln Gln
    210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys Glu Arg Lys Cys
                245                 250                 255

Cys Val Glu Cys Pro Pro Cys Pro
                260

<210> SEQ ID NO 50
<211> LENGTH: 264
<212> TYPE: PRT
<213> ORGANISM: Homo sapiens

<400> SEQUENCE: 50

Met Glu Thr Asp Thr Leu Leu Leu Trp Val Leu Leu Leu Trp Val Pro
1               5                   10                  15

Gly Ser Thr Gly Glu Pro Lys Ser Cys Asp Lys Thr His Thr Cys Pro
            20                  25                  30

Pro Cys Pro Ala Pro Pro Leu Leu Asn Gly Pro Ser Val Phe Leu Phe
        35                  40                  45

Pro Pro Lys Pro Lys Asp Thr Leu Met Ile Ser Arg Thr Pro Glu Val
50                  55                  60

Thr Cys Val Val Val Asp Val Lys Phe Glu Asp Pro Glu Val Lys Phe
65                  70                  75                  80

Asn Trp Tyr Val Asp Gly Val Glu Val His Asn Ala Lys Thr Lys Pro
                85                  90                  95

Arg Glu Glu Gln Tyr Asn Ser Thr Tyr Arg Val Val Ser Val Leu Thr
            100                 105                 110

Val Leu His Gln Asp Trp Leu Asn Gly Lys Glu Tyr Lys Cys Lys Val
        115                 120                 125

Thr Asn Lys Ala Leu Pro Ala Pro Ile Glu Lys Thr Ile Ser Lys Ala
    130                 135                 140

Lys Gly Gln Pro Arg Glu Pro Gln Val Tyr Thr Leu Pro Pro Ser Arg
145                 150                 155                 160

Asp Glu Leu Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser
        195                 200                 205

Phe Phe Leu Tyr Ser Lys Leu Thr Val Asp Lys Ser Arg Trp Gln Gln
```

```
            210                 215                 220
Gly Asn Val Phe Ser Cys Ser Val Met His Glu Ala Leu His Asn His
225                 230                 235                 240

Tyr Thr Gln Lys Ser Leu Ser Leu Ser Pro Gly Lys Glu Arg Lys Cys
                245                 250                 255

Cys Val Glu Cys Pro Pro Cys Pro
                260

<210> SEQ ID NO 51
<211> LENGTH: 264
<212> TYPE: PRT
<213> ORGANISM: Homo sapiens

<400> SEQUENCE: 51

Met Glu Thr Asp Thr Leu Leu Leu Trp Val Leu Leu Leu Trp Val Pro
1               5                   10                  15

Gly Ser Thr Gly Glu Pro Lys Ser Cys Asp Lys Thr His Thr Cys Pro
                20                  25                  30

Pro Cys Pro Ala Pro Pro Leu Leu Arg Gly Pro Ser Val Phe Leu Phe
            35                  40                  45

Pro Pro Lys Pro Lys Asp Thr Leu Met Ile Ser Arg Thr Pro Glu Val
50                  55                  60

Thr Cys Val Val Val Asp Val Asn Phe Glu Asp Pro Glu Val Lys Phe
65                  70                  75                  80

Asn Trp Tyr Val Asp Gly Val Glu Val His Asn Ala Lys Thr Lys Pro
                85                  90                  95

Arg Glu Glu Gln Tyr Asn Ser Thr Tyr Arg Val Val Ser Val Leu Thr
            100                 105                 110

Val Leu His Gln Asp Trp Leu Asn Gly Lys Glu Tyr Lys Cys Lys Val
        115                 120                 125

Thr Asn Lys Ala Leu Pro Ala Pro Ile Glu Lys Thr Ile Ser Lys Ala
130                 135                 140

Lys Gly Gln Pro Arg Glu Pro Gln Val Tyr Thr Leu Pro Pro Ser Arg
145                 150                 155                 160

Asp Glu Leu Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser
        195                 200                 205

Phe Phe Leu Tyr Ser Lys Leu Thr Val Asp Lys Ser Arg Trp Gln Gln
210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys Glu Arg Lys Cys
                245                 250                 255

Cys Val Glu Cys Pro Pro Cys Pro
                260

<210> SEQ ID NO 52
<211> LENGTH: 264
<212> TYPE: PRT
<213> ORGANISM: Homo sapiens

<400> SEQUENCE: 52

Met Glu Thr Asp Thr Leu Leu Leu Trp Val Leu Leu Leu Trp Val Pro
```

```
1               5                   10                  15
Gly Ser Thr Gly Glu Pro Lys Ser Cys Asp Lys Thr His Thr Cys Pro
            20                  25                  30

Pro Cys Pro Ala Pro Glu Leu Leu Gly Gly Pro Ser Val Phe Leu Phe
            35                  40                  45

Pro Pro Lys Pro Lys Asp Thr Leu Met Ile Ser Arg Thr Pro Glu Val
50                  55                  60

Thr Cys Val Val Val Asp Val Ser Phe Glu Asp Pro Glu Val Lys Phe
65                  70                  75                  80

Asn Trp Tyr Val Asp Gly Val Glu Val His Asn Ala Lys Thr Lys Pro
                85                  90                  95

Arg Glu Glu Gln Tyr Asn Ser Ala Tyr Arg Val Val Ser Val Leu Thr
                100                 105                 110

Val Leu His Gln Asp Trp Leu Asn Gly Lys Glu Tyr Lys Cys Lys Val
            115                 120                 125

Thr Asn Lys Ala Leu Pro Ala Pro Ile Glu Lys Thr Ile Ser Lys Ala
130                 135                 140

Lys Gly Gln Pro Arg Glu Pro Gln Val Tyr Thr Leu Pro Pro Ser Arg
145                 150                 155                 160

Asp Glu Leu Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser
            195                 200                 205

Phe Phe Leu Tyr Ser Lys Leu Thr Val Asp Lys Ser Arg Trp Gln Gln
210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys Glu Arg Lys Cys
                245                 250                 255

Cys Val Glu Cys Pro Pro Cys Pro
            260

<210> SEQ ID NO 53
<211> LENGTH: 264
<212> TYPE: PRT
<213> ORGANISM: Homo sapiens

<400> SEQUENCE: 53

Met Glu Thr Asp Thr Leu Leu Leu Trp Val Leu Leu Leu Trp Val Pro
1               5                   10                  15

Gly Ser Thr Gly Glu Pro Lys Ser Cys Asp Lys Thr His Thr Cys Pro
            20                  25                  30

Pro Cys Pro Ala Pro Glu Leu Leu Gly Gly Pro Ser Val Phe Leu Phe
            35                  40                  45

Pro Pro Lys Pro Lys Asp Thr Leu Met Ile Ser Arg Thr Pro Glu Val
50                  55                  60

Thr Cys Val Val Val Asp Val Arg Phe Glu Asp Pro Glu Val Lys Phe
65                  70                  75                  80

Asn Trp Tyr Val Asp Gly Val Glu Val His Asn Ala Lys Thr Lys Pro
                85                  90                  95

Arg Glu Glu Gln Tyr Asn Ser Ala Tyr Arg Val Val Ser Val Leu Thr
                100                 105                 110
```

```
Val Leu His Gln Asp Trp Leu Asn Gly Lys Glu Tyr Lys Cys Lys Val
            115                 120                 125

Thr Asn Lys Ala Leu Pro Ala Pro Ile Glu Lys Thr Ile Ser Lys Ala
        130                 135                 140

Lys Gly Gln Pro Arg Glu Pro Gln Val Tyr Thr Leu Pro Pro Ser Arg
145                 150                 155                 160

Asp Glu Leu Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser
        195                 200                 205

Phe Phe Leu Tyr Ser Lys Leu Thr Val Asp Lys Ser Arg Trp Gln Gln
210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys Glu Arg Lys Cys
                245                 250                 255

Cys Val Glu Cys Pro Pro Cys Pro
            260
```

<210> SEQ ID NO 54
<211> LENGTH: 264
<212> TYPE: PRT
<213> ORGANISM: Homo sapiens

<400> SEQUENCE: 54

```
Met Glu Thr Asp Thr Leu Leu Leu Trp Val Leu Leu Leu Trp Val Pro
1               5                   10                  15

Gly Ser Thr Gly Glu Pro Lys Ser Cys Asp Lys Thr His Thr Cys Pro
            20                  25                  30

Pro Cys Pro Ala Pro Glu Leu Leu Gly Gly Pro Ser Val Phe Leu Phe
        35                  40                  45

Pro Pro Lys Pro Lys Asp Thr Leu Met Ile Ser Arg Thr Pro Glu Val
50                  55                  60

Thr Cys Val Val Val Asp Val Lys Phe Glu Asp Pro Glu Val Lys Phe
65                  70                  75                  80

Asn Trp Tyr Val Asp Gly Val Glu Val His Asn Ala Lys Thr Lys Pro
                85                  90                  95

Arg Glu Glu Gln Tyr Asn Ser Ala Tyr Arg Val Val Ser Val Leu Thr
            100                 105                 110

Val Leu His Gln Asp Trp Leu Asn Gly Lys Glu Tyr Lys Cys Lys Val
        115                 120                 125

Thr Asn Lys Ala Leu Pro Ala Pro Ile Glu Lys Thr Ile Ser Lys Ala
    130                 135                 140

Lys Gly Gln Pro Arg Glu Pro Gln Val Tyr Thr Leu Pro Pro Ser Arg
145                 150                 155                 160

Asp Glu Leu Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser
        195                 200                 205

Phe Phe Leu Tyr Ser Lys Leu Thr Val Asp Lys Ser Arg Trp Gln Gln
210                 215                 220
```

Gly Asn Val Phe Ser Cys Ser Val Met His Glu Ala Leu His Asn His
225                 230                 235                 240

Tyr Thr Gln Lys Ser Leu Ser Leu Ser Pro Gly Lys Glu Arg Lys Cys
                245                 250                 255

Cys Val Glu Cys Pro Pro Cys Pro
            260

<210> SEQ ID NO 55
<211> LENGTH: 264
<212> TYPE: PRT
<213> ORGANISM: Homo sapiens

<400> SEQUENCE: 55

Met Glu Thr Asp Thr Leu Leu Leu Trp Val Leu Leu Leu Trp Val Pro
1               5                   10                  15

Gly Ser Thr Gly Glu Pro Lys Ser Cys Asp Lys Thr His Thr Cys Pro
                20                  25                  30

Pro Cys Pro Ala Pro Glu Leu Leu Gly Gly Pro Ser Val Phe Leu Phe
            35                  40                  45

Pro Pro Lys Pro Lys Asp Thr Leu Met Ile Ser Arg Thr Pro Glu Val
        50                  55                  60

Thr Cys Val Val Val Asp Val Asn Phe Glu Asp Pro Glu Val Lys Phe
65                  70                  75                  80

Asn Trp Tyr Val Asp Gly Val Glu Val His Asn Ala Lys Thr Lys Pro
                85                  90                  95

Arg Glu Glu Gln Tyr Asn Ser Ala Tyr Arg Val Val Ser Val Leu Thr
            100                 105                 110

Val Leu His Gln Asp Trp Leu Asn Gly Lys Glu Tyr Lys Cys Lys Val
        115                 120                 125

Thr Asn Lys Ala Leu Pro Ala Pro Ile Glu Lys Thr Ile Ser Lys Ala
130                 135                 140

Lys Gly Gln Pro Arg Glu Pro Gln Val Tyr Thr Leu Pro Pro Ser Arg
145                 150                 155                 160

Asp Glu Leu Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser
        195                 200                 205

Phe Phe Leu Tyr Ser Lys Leu Thr Val Asp Lys Ser Arg Trp Gln Gln
210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys Glu Arg Lys Cys
                245                 250                 255

Cys Val Glu Cys Pro Pro Cys Pro
            260

<210> SEQ ID NO 56
<211> LENGTH: 264
<212> TYPE: PRT
<213> ORGANISM: Homo sapiens

<400> SEQUENCE: 56

Met Glu Thr Asp Thr Leu Leu Leu Trp Val Leu Leu Leu Trp Val Pro
1               5                   10                  15

Gly Ser Thr Gly Glu Pro Lys Ser Cys Asp Lys Thr His Thr Cys Pro
            20                  25                  30

Pro Cys Pro Ala Pro Glu Leu Leu Gly Gly Pro Ser Val Phe Leu Phe
            35                  40                  45

Pro Pro Lys Pro Lys Asp Thr Leu Met Ile Ser Arg Thr Pro Glu Val
    50                  55                  60

Thr Cys Val Val Val Asp Val Ser Phe Glu Asp Pro Glu Val Lys Phe
65                  70                  75                  80

Asn Trp Tyr Val Asp Gly Val Glu Val His Asn Ala Lys Thr Lys Pro
                85                  90                  95

Arg Glu Glu Gln Tyr Ala Ser Thr Tyr Arg Val Val Ser Val Leu Thr
            100                 105                 110

Val Leu His Gln Asp Trp Leu Asn Gly Lys Glu Tyr Lys Cys Lys Val
        115                 120                 125

Thr Asn Lys Ala Leu Pro Ala Pro Ile Glu Lys Thr Ile Ser Lys Ala
    130                 135                 140

Lys Gly Gln Pro Arg Glu Pro Gln Val Tyr Thr Leu Pro Pro Ser Arg
145                 150                 155                 160

Asp Glu Leu Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser
        195                 200                 205

Phe Phe Leu Tyr Ser Lys Leu Thr Val Asp Lys Ser Arg Trp Gln Gln
    210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys Glu Arg Lys Cys
                245                 250                 255

Cys Val Glu Cys Pro Pro Cys Pro
            260

<210> SEQ ID NO 57
<211> LENGTH: 264
<212> TYPE: PRT
<213> ORGANISM: Homo sapiens

<400> SEQUENCE: 57

Met Glu Thr Asp Thr Leu Leu Leu Trp Val Leu Leu Leu Trp Val Pro
1               5                   10                  15

Gly Ser Thr Gly Glu Pro Lys Ser Cys Asp Lys Thr His Thr Cys Pro
            20                  25                  30

Pro Cys Pro Ala Pro Glu Leu Leu Gly Gly Pro Ser Val Phe Leu Phe
            35                  40                  45

Pro Pro Lys Pro Lys Asp Thr Leu Met Ile Ser Arg Thr Pro Glu Val
    50                  55                  60

Thr Cys Val Val Val Asp Val Lys Phe Glu Asp Pro Glu Val Lys Phe
65                  70                  75                  80

Asn Trp Tyr Val Asp Gly Val Glu Val His Asn Ala Lys Thr Lys Pro
                85                  90                  95

Arg Glu Glu Gln Tyr Ala Ser Thr Tyr Arg Val Val Ser Val Leu Thr
            100                 105                 110

Val Leu His Gln Asp Trp Leu Asn Gly Lys Glu Tyr Lys Cys Lys Val

```
              115                 120                 125
Thr Asn Lys Ala Leu Pro Ala Pro Ile Glu Lys Thr Ile Ser Lys Ala
    130                 135                 140
Lys Gly Gln Pro Arg Glu Pro Gln Val Tyr Thr Leu Pro Pro Ser Arg
145                 150                 155                 160
Asp Glu Leu Thr Lys Asn Gln Val Ser Leu Thr Cys Leu Val Lys Gly
                165                 170                 175
Phe Tyr Pro Ser Asp Ile Ala Val Glu Trp Glu Ser Asn Gly Gln Pro
            180                 185                 190
Glu Asn Asn Tyr Lys Thr Thr Pro Pro Val Leu Asp Ser Asp Gly Ser
                195                 200                 205
Phe Phe Leu Tyr Ser Lys Leu Thr Val Asp Lys Ser Arg Trp Gln Gln
            210                 215                 220
Gly Asn Val Phe Ser Cys Ser Val Met His Glu Ala Leu His Asn His
225                 230                 235                 240
Tyr Thr Gln Lys Ser Leu Ser Leu Ser Pro Gly Lys Glu Arg Lys Cys
                245                 250                 255
Cys Val Glu Cys Pro Pro Cys Pro
            260
```

<210> SEQ ID NO 58
<211> LENGTH: 264
<212> TYPE: PRT
<213> ORGANISM: Homo sapiens

<400> SEQUENCE: 58

```
Met Glu Thr Asp Thr Leu Leu Leu Trp Val Leu Leu Leu Trp Val Pro
1               5                  10                  15
Gly Ser Thr Gly Glu Pro Lys Ser Cys Asp Lys Thr His Thr Cys Pro
                20                  25                  30
Pro Cys Pro Ala Pro Glu Leu Leu Gly Gly Pro Ser Val Phe Leu Phe
            35                  40                  45
Pro Pro Lys Pro Lys Asp Thr Leu Met Ile Ser Arg Thr Pro Glu Val
    50                  55                  60
Thr Cys Val Val Val Asp Val Arg Phe Glu Asp Pro Glu Val Lys Phe
65                  70                  75                  80
Asn Trp Tyr Val Asp Gly Val Glu Val His Asn Ala Lys Thr Lys Pro
                85                  90                  95
Arg Glu Glu Gln Tyr Ala Ser Thr Tyr Arg Val Val Ser Val Leu Thr
            100                 105                 110
Val Leu His Gln Asp Trp Leu Asn Gly Lys Glu Tyr Lys Cys Lys Val
        115                 120                 125
Thr Asn Lys Ala Leu Pro Ala Pro Ile Glu Lys Thr Ile Ser Lys Ala
    130                 135                 140
Lys Gly Gln Pro Arg Glu Pro Gln Val Tyr Thr Leu Pro Pro Ser Arg
145                 150                 155                 160
Asp Glu Leu Thr Lys Asn Gln Val Ser Leu Thr Cys Leu Val Lys Gly
                165                 170                 175
Phe Tyr Pro Ser Asp Ile Ala Val Glu Trp Glu Ser Asn Gly Gln Pro
            180                 185                 190
Glu Asn Asn Tyr Lys Thr Thr Pro Pro Val Leu Asp Ser Asp Gly Ser
                195                 200                 205
Phe Phe Leu Tyr Ser Lys Leu Thr Val Asp Lys Ser Arg Trp Gln Gln
            210                 215                 220
```

```
Gly Asn Val Phe Ser Cys Ser Val Met His Glu Ala Leu His Asn His
225                 230                 235                 240

Tyr Thr Gln Lys Ser Leu Ser Leu Ser Pro Gly Lys Glu Arg Lys Cys
                245                 250                 255

Cys Val Glu Cys Pro Pro Cys Pro
            260

<210> SEQ ID NO 59
<211> LENGTH: 264
<212> TYPE: PRT
<213> ORGANISM: Homo sapiens

<400> SEQUENCE: 59

Met Glu Thr Asp Thr Leu Leu Leu Trp Val Leu Leu Leu Trp Val Pro
1               5                   10                  15

Gly Ser Thr Gly Glu Pro Lys Ser Cys Asp Lys Thr His Thr Cys Pro
            20                  25                  30

Pro Cys Pro Ala Pro Glu Leu Leu Gly Gly Pro Ser Val Phe Leu Phe
        35                  40                  45

Pro Pro Lys Pro Lys Asp Thr Leu Met Ile Ser Arg Thr Pro Glu Val
50                  55                  60

Thr Cys Val Val Val Asp Val Asp Phe Glu Asp Pro Glu Val Lys Phe
65                  70                  75                  80

Asn Trp Tyr Val Asp Gly Val Glu Val His Asn Ala Lys Thr Lys Pro
                85                  90                  95

Arg Glu Glu Gln Tyr Ala Ser Thr Tyr Arg Val Val Ser Val Leu Thr
            100                 105                 110

Val Leu His Gln Asp Trp Leu Asn Gly Lys Glu Tyr Lys Cys Lys Val
        115                 120                 125

Thr Asn Lys Ala Leu Pro Ala Pro Ile Glu Lys Thr Ile Ser Lys Ala
130                 135                 140

Lys Gly Gln Pro Arg Glu Pro Gln Val Tyr Thr Leu Pro Pro Ser Arg
145                 150                 155                 160

Asp Glu Leu Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser
        195                 200                 205

Phe Phe Leu Tyr Ser Lys Leu Thr Val Asp Lys Ser Arg Trp Gln Gln
210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys Glu Arg Lys Cys
                245                 250                 255

Cys Val Glu Cys Pro Pro Cys Pro
            260

<210> SEQ ID NO 60
<211> LENGTH: 264
<212> TYPE: PRT
<213> ORGANISM: Homo sapiens

<400> SEQUENCE: 60

Met Glu Thr Asp Thr Leu Leu Leu Trp Val Leu Leu Leu Trp Val Pro
1               5                   10                  15
```

```
Gly Ser Thr Gly Glu Pro Lys Ser Cys Asp Lys Thr His Thr Cys Pro
            20                  25                  30

Pro Cys Pro Ala Pro Glu Leu Leu Gly Gly Pro Ser Val Phe Leu Phe
        35                  40                  45

Pro Pro Lys Pro Lys Asp Thr Leu Met Ile Ser Arg Thr Pro Glu Val
    50                  55                  60

Thr Cys Val Val Val Asp Val Gln Phe Glu Asp Pro Glu Val Lys Phe
65                  70                  75                  80

Asn Trp Tyr Val Asp Gly Val Glu Val His Asn Ala Lys Thr Lys Pro
                85                  90                  95

Arg Glu Glu Gln Tyr Ala Ser Thr Tyr Arg Val Val Ser Val Leu Thr
            100                 105                 110

Val Leu His Gln Asp Trp Leu Asn Gly Lys Glu Tyr Lys Cys Lys Val
        115                 120                 125

Thr Asn Lys Ala Leu Pro Ala Pro Ile Glu Lys Thr Ile Ser Lys Ala
    130                 135                 140

Lys Gly Gln Pro Arg Glu Pro Gln Val Tyr Thr Leu Pro Pro Ser Arg
145                 150                 155                 160

Asp Glu Leu Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser
        195                 200                 205

Phe Phe Leu Tyr Ser Lys Leu Thr Val Asp Lys Ser Arg Trp Gln Gln
    210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys Glu Arg Lys Cys
                245                 250                 255

Cys Val Glu Cys Pro Pro Cys Pro
            260

<210> SEQ ID NO 61
<211> LENGTH: 264
<212> TYPE: PRT
<213> ORGANISM: Homo sapiens

<400> SEQUENCE: 61

Met Glu Thr Asp Thr Leu Leu Leu Trp Val Leu Leu Leu Trp Val Pro
1               5                   10                  15

Gly Ser Thr Gly Glu Pro Lys Ser Cys Asp Lys Thr His Thr Cys Pro
            20                  25                  30

Pro Cys Pro Ala Pro Glu Leu Leu Arg Gly Pro Ser Val Phe Leu Phe
        35                  40                  45

Pro Pro Lys Pro Lys Asp Thr Leu Met Ile Ser Arg Thr Pro Glu Val
    50                  55                  60

Thr Cys Val Val Val Asp Val Ser His Glu Asp Pro Glu Val Lys Phe
65                  70                  75                  80

Asn Trp Tyr Val Asp Gly Val Glu Val His Asn Ala Lys Thr Lys Pro
                85                  90                  95

Arg Glu Glu Gln Tyr Asn Ser Thr Tyr Arg Val Val Ser Val Leu Thr
            100                 105                 110

Val Leu His Gln Asp Trp Leu Asn Gly Lys Glu Tyr Lys Cys Lys Val
        115                 120                 125
```

-continued

```
Ser Asn Lys Ala Leu Pro Ala Pro Ile Glu Lys Thr Ile Ser Lys Ala
            130                 135                 140

Lys Gly Gln Pro Arg Glu Pro Gln Val Tyr Thr Leu Pro Pro Ser Arg
145                 150                 155                 160

Asp Glu Leu Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser
                195                 200                 205

Phe Phe Leu Tyr Ser Lys Leu Thr Val Asp Lys Ser Arg Trp Gln Gln
            210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys Glu Arg Lys Cys
                245                 250                 255

Cys Val Glu Cys Pro Pro Cys Pro
            260

<210> SEQ ID NO 62
<211> LENGTH: 264
<212> TYPE: PRT
<213> ORGANISM: Homo sapiens

<400> SEQUENCE: 62

Met Glu Thr Asp Thr Leu Leu Leu Trp Val Leu Leu Leu Trp Val Pro
1               5                   10                  15

Gly Ser Thr Gly Glu Pro Lys Ser Cys Asp Lys Thr His Thr Cys Pro
            20                  25                  30

Pro Cys Pro Ala Pro Pro Val Ala Gly Gly Pro Ser Val Phe Leu Phe
        35                  40                  45

Pro Pro Lys Pro Lys Asp Thr Leu Met Ile Ser Arg Thr Pro Glu Val
    50                  55                  60

Thr Cys Val Val Val Asp Val Glu Phe Glu Asp Pro Glu Val Lys Phe
65                  70                  75                  80

Asn Trp Tyr Val Asp Gly Val Glu Val His Asn Ala Lys Thr Lys Pro
                85                  90                  95

Arg Glu Glu Gln Tyr Asn Ser Thr Tyr Arg Val Val Ser Val Leu Thr
            100                 105                 110

Val Leu His Gln Asp Trp Leu Asn Gly Lys Glu Tyr Lys Cys Lys Val
        115                 120                 125

Thr Asn Lys Ala Leu Pro Ala Pro Ile Glu Lys Thr Ile Ser Lys Ala
            130                 135                 140

Lys Gly Gln Pro Arg Glu Pro Gln Val Tyr Thr Leu Pro Pro Ser Arg
145                 150                 155                 160

Asp Glu Leu Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser
                195                 200                 205

Phe Phe Leu Tyr Ser Lys Leu Thr Val Asp Lys Ser Arg Trp Gln Gln
            210                 215                 220

Gly Asn Val Phe Ser Cys Ser Val Met His Glu Ala Leu His Asn His
```

```
                225                 230                 235                 240
Tyr Thr Gln Lys Ser Leu Ser Leu Ser Pro Gly Lys Glu Arg Lys Cys
                245                 250                 255

Cys Val Glu Cys Pro Pro Cys Pro
            260

<210> SEQ ID NO 63
<211> LENGTH: 264
<212> TYPE: PRT
<213> ORGANISM: Homo sapiens

<400> SEQUENCE: 63

Met Glu Thr Asp Thr Leu Leu Leu Trp Val Leu Leu Leu Trp Val Pro
1               5                   10                  15

Gly Ser Thr Gly Glu Pro Lys Ser Cys Asp Lys Thr His Thr Cys Pro
            20                  25                  30

Pro Cys Pro Ala Pro Glu Ala Ala Gly Gly Pro Ser Val Phe Leu Phe
        35                  40                  45

Pro Pro Lys Pro Lys Asp Thr Leu Met Ile Ser Arg Thr Pro Glu Val
    50                  55                  60

Thr Cys Val Val Val Asp Val Glu Phe Glu Asp Pro Glu Val Lys Phe
65                  70                  75                  80

Asn Trp Tyr Val Asp Gly Val Glu Val His Asn Ala Lys Thr Lys Pro
                85                  90                  95

Arg Glu Glu Gln Tyr Asn Ser Thr Tyr Arg Val Val Ser Val Leu Thr
            100                 105                 110

Val Leu His Gln Asp Trp Leu Asn Gly Lys Glu Tyr Lys Cys Lys Val
        115                 120                 125

Thr Asn Lys Ala Leu Pro Ala Pro Ile Glu Lys Thr Ile Ser Lys Ala
    130                 135                 140

Lys Gly Gln Pro Arg Glu Pro Gln Val Tyr Thr Leu Pro Pro Ser Arg
145                 150                 155                 160

Asp Glu Leu Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser
        195                 200                 205

Phe Phe Leu Tyr Ser Lys Leu Thr Val Asp Lys Ser Arg Trp Gln Gln
    210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys Glu Arg Lys Cys
                245                 250                 255

Cys Val Glu Cys Pro Pro Cys Pro
            260

<210> SEQ ID NO 64
<211> LENGTH: 264
<212> TYPE: PRT
<213> ORGANISM: Homo sapiens

<400> SEQUENCE: 64

Met Glu Thr Asp Thr Leu Leu Leu Trp Val Leu Leu Leu Trp Val Pro
1               5                   10                  15

Gly Ser Thr Gly Glu Arg Lys Cys Cys Val Glu Cys Pro Pro Cys Pro
```

```
                20                  25                  30
Glu Pro Lys Ser Cys Asp Lys Thr His Thr Cys Pro Pro Cys Pro Ala
            35                  40                  45
Pro Glu Leu Leu Gly Gly Pro Ser Val Phe Leu Phe Pro Pro Lys Pro
        50                  55                  60
Lys Asp Thr Leu Met Ile Ser Arg Thr Pro Glu Val Thr Cys Val Val
65                  70                  75                  80
Val Asp Val Glu Phe Glu Asp Pro Glu Val Lys Phe Asn Trp Tyr Val
                85                  90                  95
Asp Gly Val Glu Val His Asn Ala Lys Thr Lys Pro Arg Glu Glu Gln
            100                 105                 110
Tyr Asn Ser Thr Tyr Arg Val Val Ser Val Leu Thr Val Leu His Gln
        115                 120                 125
Asp Trp Leu Asn Gly Lys Glu Tyr Lys Cys Lys Val Thr Asn Lys Ala
            130                 135                 140
Phe Pro Ala Pro Ile Glu Lys Thr Ile Ser Lys Ala Lys Gly Gln Pro
145                 150                 155                 160
Arg Glu Pro Gln Val Tyr Thr Leu Pro Pro Ser Arg Asp Glu Leu Thr
                165                 170                 175
Lys Asn Gln Val Ser Leu Thr Cys Leu Val Lys Gly Phe Tyr Pro Ser
            180                 185                 190
Asp Ile Ala Val Glu Trp Glu Ser Asn Gly Gln Pro Glu Asn Asn Tyr
        195                 200                 205
Lys Thr Thr Pro Pro Val Leu Asp Ser Asp Gly Ser Phe Phe Leu Tyr
    210                 215                 220
Ser Lys Leu Thr Val Asp Lys Ser Arg Trp Gln Gln Gly Asn Val Phe
225                 230                 235                 240
Ser Cys Ser Val Met His Glu Ala Leu His Asn His Tyr Thr Gln Lys
                245                 250                 255
Ser Leu Ser Leu Ser Pro Gly Lys
            260

<210> SEQ ID NO 65
<211> LENGTH: 264
<212> TYPE: PRT
<213> ORGANISM: Homo sapiens

<400> SEQUENCE: 65

Met Glu Thr Asp Thr Leu Leu Leu Trp Val Leu Leu Leu Trp Val Pro
1               5                   10                  15
Gly Ser Thr Gly Glu Pro Lys Ser Cys Asp Lys Thr His Thr Cys Pro
            20                  25                  30
Pro Cys Pro Ala Pro Pro Leu Leu Glu Gly Pro Ser Val Phe Leu Phe
        35                  40                  45
Pro Pro Lys Pro Lys Asp Thr Leu Met Ile Ser Arg Thr Pro Glu Val
    50                  55                  60
Thr Cys Val Val Val Asp Val Ser Phe Glu Asp Pro Glu Val Lys Phe
65                  70                  75                  80
Asn Trp Tyr Val Asp Gly Val Glu Val His Asn Ala Lys Thr Lys Pro
                85                  90                  95
Arg Glu Glu Gln Tyr Asn Ser Thr Tyr Arg Val Val Ser Val Leu Thr
            100                 105                 110
Val Leu His Gln Asp Trp Leu Asn Gly Lys Glu Tyr Lys Cys Lys Val
        115                 120                 125
```

```
Thr Asn Lys Ala Leu Pro Ala Pro Ile Glu Lys Thr Ile Ser Lys Ala
            130                 135                 140

Lys Gly Gln Pro Arg Glu Pro Gln Val Tyr Thr Leu Pro Pro Ser Arg
145                 150                 155                 160

Asp Glu Leu Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser
        195                 200                 205

Phe Phe Leu Tyr Ser Lys Leu Thr Val Asp Lys Ser Arg Trp Gln Gln
    210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys Glu Arg Lys Cys
                245                 250                 255

Cys Val Glu Cys Pro Pro Cys Pro
            260

<210> SEQ ID NO 66
<211> LENGTH: 264
<212> TYPE: PRT
<213> ORGANISM: Homo sapiens

<400> SEQUENCE: 66

Met Glu Thr Asp Thr Leu Leu Leu Trp Val Leu Leu Leu Trp Val Pro
1               5                   10                  15

Gly Ser Thr Gly Glu Pro Lys Ser Cys Asp Lys Thr His Thr Cys Pro
            20                  25                  30

Pro Cys Pro Ala Pro Pro Leu Leu Asp Gly Pro Ser Val Phe Leu Phe
        35                  40                  45

Pro Pro Lys Pro Lys Asp Thr Leu Met Ile Ser Arg Thr Pro Glu Val
    50                  55                  60

Thr Cys Val Val Val Asp Val Ser Phe Glu Asp Pro Glu Val Lys Phe
65                  70                  75                  80

Asn Trp Tyr Val Asp Gly Val Glu Val His Asn Ala Lys Thr Lys Pro
                85                  90                  95

Arg Glu Glu Gln Tyr Asn Ser Thr Tyr Arg Val Val Ser Val Leu Thr
            100                 105                 110

Val Leu His Gln Asp Trp Leu Asn Gly Lys Glu Tyr Lys Cys Lys Val
        115                 120                 125

Thr Asn Lys Ala Leu Pro Ala Pro Ile Glu Lys Thr Ile Ser Lys Ala
    130                 135                 140

Lys Gly Gln Pro Arg Glu Pro Gln Val Tyr Thr Leu Pro Pro Ser Arg
145                 150                 155                 160

Asp Glu Leu Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser
        195                 200                 205

Phe Phe Leu Tyr Ser Lys Leu Thr Val Asp Lys Ser Arg Trp Gln Gln
    210                 215                 220

Gly Asn Val Phe Ser Cys Ser Val Met His Glu Ala Leu His Asn His
225                 230                 235                 240
```

Tyr Thr Gln Lys Ser Leu Ser Leu Ser Pro Gly Lys Glu Arg Lys Cys
                    245                 250                 255

Cys Val Glu Cys Pro Pro Cys Pro
            260

<210> SEQ ID NO 67
<211> LENGTH: 264
<212> TYPE: PRT
<213> ORGANISM: Homo sapiens

<400> SEQUENCE: 67

Met Glu Thr Asp Thr Leu Leu Leu Trp Val Leu Leu Leu Trp Val Pro
1               5                   10                  15

Gly Ser Thr Gly Glu Pro Lys Ser Cys Asp Lys Thr His Thr Cys Pro
            20                  25                  30

Pro Cys Pro Ala Pro Pro Leu Leu Gly Gly Pro Ser Val Phe Leu Phe
        35                  40                  45

Pro Pro Lys Pro Lys Asp Thr Leu Met Ile Ser Arg Thr Pro Glu Val
    50                  55                  60

Thr Cys Val Val Val Asp Val Gln Phe Glu Asp Pro Glu Val Lys Phe
65                  70                  75                  80

Asn Trp Tyr Val Asp Gly Val Glu Val His Asn Ala Lys Thr Lys Pro
                85                  90                  95

Arg Glu Glu Gln Tyr Asn Ser Thr Tyr Arg Val Val Ser Val Leu Thr
            100                 105                 110

Val Leu His Gln Asp Trp Leu Asn Gly Lys Glu Tyr Lys Cys Lys Val
        115                 120                 125

Thr Asn Lys Ala Leu Pro Ala Pro Ile Glu Lys Thr Ile Ser Lys Ala
    130                 135                 140

Lys Gly Gln Pro Arg Glu Pro Gln Val Tyr Thr Leu Pro Pro Ser Arg
145                 150                 155                 160

Asp Glu Leu Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser
        195                 200                 205

Phe Phe Leu Tyr Ser Lys Leu Thr Val Asp Lys Ser Arg Trp Gln Gln
    210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys Glu Arg Lys Cys
                245                 250                 255

Cys Val Glu Cys Pro Pro Cys Pro
            260

<210> SEQ ID NO 68
<211> LENGTH: 264
<212> TYPE: PRT
<213> ORGANISM: Homo sapiens

<400> SEQUENCE: 68

Met Glu Thr Asp Thr Leu Leu Leu Trp Val Leu Leu Leu Trp Val Pro
1               5                   10                  15

Gly Ser Thr Gly Glu Pro Lys Ser Cys Asp Lys Thr His Thr Cys Pro
            20                  25                  30

Pro Cys Pro Ala Pro Leu Leu Gly Gly Pro Ser Val Phe Leu Phe
         35                  40                  45

Pro Pro Lys Pro Lys Asp Thr Leu Met Ile Ser Arg Thr Pro Glu Val
50                  55                  60

Thr Cys Val Val Val Asp Val Asp Phe Glu Asp Pro Glu Val Lys Phe
65                  70                  75                  80

Asn Trp Tyr Val Asp Gly Val Glu Val His Asn Ala Lys Thr Lys Pro
                85                  90                  95

Arg Glu Glu Gln Tyr Asn Ser Thr Tyr Arg Val Val Ser Val Leu Thr
            100                 105                 110

Val Leu His Gln Asp Trp Leu Asn Gly Lys Glu Tyr Lys Cys Lys Val
        115                 120                 125

Thr Asn Lys Ala Leu Pro Ala Pro Ile Glu Lys Thr Ile Ser Lys Ala
    130                 135                 140

Lys Gly Gln Pro Arg Glu Pro Gln Val Tyr Thr Leu Pro Pro Ser Arg
145                 150                 155                 160

Asp Glu Leu Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser
        195                 200                 205

Phe Phe Leu Tyr Ser Lys Leu Thr Val Asp Lys Ser Arg Trp Gln Gln
    210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys Glu Arg Lys Cys
                245                 250                 255

Cys Val Glu Cys Pro Pro Cys Pro
            260

<210> SEQ ID NO 69
<211> LENGTH: 264
<212> TYPE: PRT
<213> ORGANISM: Homo sapiens

<400> SEQUENCE: 69

Met Glu Thr Asp Thr Leu Leu Leu Trp Val Leu Leu Leu Trp Val Pro
1               5                   10                  15

Gly Ser Thr Gly Glu Pro Lys Ser Cys Asp Lys Thr His Thr Cys Pro
            20                  25                  30

Pro Cys Pro Ala Pro Leu Leu Gly Gly Pro Ser Val Phe Leu Phe
         35                  40                  45

Pro Pro Lys Pro Lys Asp Thr Leu Met Ile Ser Arg Thr Pro Glu Val
50                  55                  60

Thr Cys Val Val Val Asp Val His Phe Glu Asp Pro Glu Val Lys Phe
65                  70                  75                  80

Asn Trp Tyr Val Asp Gly Val Glu Val His Asn Ala Lys Thr Lys Pro
                85                  90                  95

Arg Glu Glu Gln Tyr Asn Ser Thr Tyr Arg Val Val Ser Val Leu Thr
            100                 105                 110

Val Leu His Gln Asp Trp Leu Asn Gly Lys Glu Tyr Lys Cys Lys Val
        115                 120                 125

Thr Asn Lys Ala Leu Pro Ala Pro Ile Glu Lys Thr Ile Ser Lys Ala

```
            130                 135                 140
Lys Gly Gln Pro Arg Glu Pro Gln Val Tyr Thr Leu Pro Pro Ser Arg
145                 150                 155                 160

Asp Glu Leu Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser
                195                 200                 205

Phe Phe Leu Tyr Ser Lys Leu Thr Val Asp Lys Ser Arg Trp Gln Gln
            210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys Glu Arg Lys Cys
                245                 250                 255

Cys Val Glu Cys Pro Pro Cys Pro
            260

<210> SEQ ID NO 70
<211> LENGTH: 264
<212> TYPE: PRT
<213> ORGANISM: Homo sapiens

<400> SEQUENCE: 70

Met Glu Thr Asp Thr Leu Leu Leu Trp Val Leu Leu Leu Trp Val Pro
1               5                   10                  15

Gly Ser Thr Gly Glu Pro Lys Ser Cys Asp Lys Thr His Thr Cys Pro
                20                  25                  30

Pro Cys Pro Ala Pro Pro Leu Leu Gly Gly Pro Ser Val Phe Leu Phe
            35                  40                  45

Pro Pro Lys Pro Lys Asp Thr Leu Met Ile Ser Arg Thr Pro Glu Val
50                  55                  60

Thr Cys Val Val Val Asp Val Glu Phe Glu Asp Pro Glu Val Lys Phe
65                  70                  75                  80

Asn Trp Tyr Val Asp Gly Val Glu Val His Asn Ala Lys Thr Lys Pro
                85                  90                  95

Arg Glu Glu Gln Tyr Asn Ser Thr Tyr Arg Val Val Ser Val Leu Thr
            100                 105                 110

Val Leu His Gln Asp Trp Leu Asn Gly Lys Glu Tyr Lys Cys Lys Val
        115                 120                 125

Thr Asn Lys Ala Leu Pro Ala Pro Ile Glu Lys Thr Ile Ser Lys Ala
130                 135                 140

Lys Gly Gln Pro Arg Glu Pro Gln Val Tyr Thr Leu Pro Pro Ser Arg
145                 150                 155                 160

Asp Glu Leu Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser
                195                 200                 205

Phe Phe Leu Tyr Ser Lys Leu Thr Val Asp Lys Ser Arg Trp Gln Gln
            210                 215                 220

Gly Asn Val Phe Ser Cys Ser Val Met His Glu Ala Leu His Asn His
225                 230                 235                 240
```

Tyr Thr Gln Lys Ser Leu Ser Leu Ser Pro Gly Lys Glu Arg Lys Cys
                245                 250                 255

Cys Val Glu Cys Pro Pro Cys Pro
            260

<210> SEQ ID NO 71
<211> LENGTH: 264
<212> TYPE: PRT
<213> ORGANISM: Homo sapiens

<400> SEQUENCE: 71

Met Glu Thr Asp Thr Leu Leu Leu Trp Val Leu Leu Leu Trp Val Pro
1               5                   10                  15

Gly Ser Thr Gly Glu Pro Lys Ser Cys Asp Lys Thr His Thr Cys Pro
            20                  25                  30

Pro Cys Pro Ala Pro Pro Leu Leu Asp Gly Pro Ser Val Phe Leu Phe
        35                  40                  45

Pro Pro Lys Pro Lys Asp Thr Leu Met Ile Ser Arg Thr Pro Glu Val
    50                  55                  60

Thr Cys Val Val Val Asp Val Gln Phe Glu Asp Pro Glu Val Lys Phe
65                  70                  75                  80

Asn Trp Tyr Val Asp Gly Val Glu Val His Asn Ala Lys Thr Lys Pro
                85                  90                  95

Arg Glu Glu Gln Tyr Asn Ser Thr Tyr Arg Val Val Ser Val Leu Thr
            100                 105                 110

Val Leu His Gln Asp Trp Leu Asn Gly Lys Glu Tyr Lys Cys Lys Val
        115                 120                 125

Thr Asn Lys Ala Leu Pro Ala Pro Ile Glu Lys Thr Ile Ser Lys Ala
    130                 135                 140

Lys Gly Gln Pro Arg Glu Pro Gln Val Tyr Thr Leu Pro Pro Ser Arg
145                 150                 155                 160

Asp Glu Leu Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser
        195                 200                 205

Phe Phe Leu Tyr Ser Lys Leu Thr Val Asp Lys Ser Arg Trp Gln Gln
    210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys Glu Arg Lys Cys
                245                 250                 255

Cys Val Glu Cys Pro Pro Cys Pro
            260

<210> SEQ ID NO 72
<211> LENGTH: 264
<212> TYPE: PRT
<213> ORGANISM: Homo sapiens

<400> SEQUENCE: 72

Met Glu Thr Asp Thr Leu Leu Leu Trp Val Leu Leu Leu Trp Val Pro
1               5                   10                  15

Gly Ser Thr Gly Glu Pro Lys Ser Cys Asp Lys Thr His Thr Cys Pro
            20                  25                  30

```
Pro Cys Pro Ala Pro Pro Leu Leu Gln Gly Pro Ser Val Phe Leu Phe
        35                  40                  45

Pro Pro Lys Pro Lys Asp Thr Leu Met Ile Ser Arg Thr Pro Glu Val
 50                  55                  60

Thr Cys Val Val Val Asp Val Asp Phe Glu Asp Pro Glu Val Lys Phe
 65                  70                  75                  80

Asn Trp Tyr Val Asp Gly Val Glu Val His Asn Ala Lys Thr Lys Pro
                 85                  90                  95

Arg Glu Glu Gln Tyr Asn Ser Thr Tyr Arg Val Val Ser Val Leu Thr
                100                 105                 110

Val Leu His Gln Asp Trp Leu Asn Gly Lys Glu Tyr Lys Cys Lys Val
            115                 120                 125

Thr Asn Lys Ala Leu Pro Ala Pro Ile Glu Lys Thr Ile Ser Lys Ala
130                 135                 140

Lys Gly Gln Pro Arg Glu Pro Gln Val Tyr Thr Leu Pro Pro Ser Arg
145                 150                 155                 160

Asp Glu Leu Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser
        195                 200                 205

Phe Phe Leu Tyr Ser Lys Leu Thr Val Asp Lys Ser Arg Trp Gln Gln
210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys Glu Arg Lys Cys
                245                 250                 255

Cys Val Glu Cys Pro Pro Cys Pro
                260

<210> SEQ ID NO 73
<211> LENGTH: 264
<212> TYPE: PRT
<213> ORGANISM: Homo sapiens

<400> SEQUENCE: 73

Met Glu Thr Asp Thr Leu Leu Leu Trp Val Leu Leu Leu Trp Val Pro
 1               5                  10                  15

Gly Ser Thr Gly Glu Pro Lys Ser Cys Asp Lys Thr His Thr Cys Pro
                20                  25                  30

Pro Cys Pro Ala Pro Pro Leu Leu Asp Gly Pro Ser Val Phe Leu Phe
            35                  40                  45

Pro Pro Lys Pro Lys Asp Thr Leu Met Ile Ser Arg Thr Pro Glu Val
 50                  55                  60

Thr Cys Val Val Val Asp Val Asp Phe Glu Asp Pro Glu Val Lys Phe
 65                  70                  75                  80

Asn Trp Tyr Val Asp Gly Val Glu Val His Asn Ala Lys Thr Lys Pro
                 85                  90                  95

Arg Glu Glu Gln Tyr Asn Ser Thr Tyr Arg Val Val Ser Val Leu Thr
                100                 105                 110

Val Leu His Gln Asp Trp Leu Asn Gly Lys Glu Tyr Lys Cys Lys Val
            115                 120                 125

Thr Asn Lys Ala Leu Pro Ala Pro Ile Glu Lys Thr Ile Ser Lys Ala
130                 135                 140
```

```
Lys Gly Gln Pro Arg Glu Pro Gln Val Tyr Thr Leu Pro Pro Ser Arg
145                 150                 155                 160

Asp Glu Leu Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser
            195                 200                 205

Phe Phe Leu Tyr Ser Lys Leu Thr Val Asp Lys Ser Arg Trp Gln Gln
210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys Glu Arg Lys Cys
            245                 250                 255

Cys Val Glu Cys Pro Pro Cys Pro
            260

<210> SEQ ID NO 74
<211> LENGTH: 264
<212> TYPE: PRT
<213> ORGANISM: Homo sapiens

<400> SEQUENCE: 74

Met Glu Thr Asp Thr Leu Leu Leu Trp Val Leu Leu Leu Trp Val Pro
1               5                   10                  15

Gly Ser Thr Gly Glu Pro Lys Ser Cys Asp Lys Thr His Thr Cys Pro
            20                  25                  30

Pro Cys Pro Ala Pro Glu Leu Leu Gly Gly Pro Ser Val Phe Leu Phe
            35                  40                  45

Pro Pro Lys Pro Lys Asp Thr Leu Met Ile Ser Arg Thr Pro Glu Val
50                  55                  60

Thr Cys Val Val Val Asp Val Glu Phe Glu Asp Pro Glu Val Lys Phe
65                  70                  75                  80

Asn Trp Tyr Val Asp Gly Val Glu Val His Asn Ala Lys Thr Lys Pro
            85                  90                  95

Arg Glu Glu Gln Tyr Asn Ser Ala Tyr Arg Val Val Ser Val Leu Thr
            100                 105                 110

Val Leu His Gln Asp Trp Leu Asn Gly Lys Glu Tyr Lys Cys Lys Val
        115                 120                 125

Thr Asn Lys Ala Leu Pro Ala Pro Ile Glu Lys Thr Ile Ser Lys Ala
    130                 135                 140

Lys Gly Gln Pro Arg Glu Pro Gln Val Tyr Thr Leu Pro Pro Ser Arg
145                 150                 155                 160

Asp Glu Leu Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser
            195                 200                 205

Phe Phe Leu Tyr Ser Lys Leu Thr Val Asp Lys Ser Arg Trp Gln Gln
210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys Glu Arg Lys Cys
```

```
                        245                 250                 255
Cys Val Glu Cys Pro Pro Cys Pro
            260
```

<210> SEQ ID NO 75
<211> LENGTH: 264
<212> TYPE: PRT
<213> ORGANISM: Homo sapiens

<400> SEQUENCE: 75

```
Met Glu Thr Asp Thr Leu Leu Leu Trp Val Leu Leu Trp Val Pro
  1               5                  10                  15

Gly Ser Thr Gly Glu Pro Lys Ser Cys Asp Lys Thr His Thr Cys Pro
             20                  25                  30

Pro Cys Pro Ala Pro Glu Leu Leu Gly Gly Pro Ser Val Phe Leu Phe
         35                  40                  45

Pro Pro Lys Pro Lys Asp Thr Leu Met Ile Ser Arg Thr Pro Glu Val
 50                  55                  60

Thr Cys Val Val Val Asp Val Gln Phe Glu Asp Pro Glu Val Lys Phe
 65                  70                  75                  80

Asn Trp Tyr Val Asp Gly Val Glu Val His Asn Ala Lys Thr Lys Pro
                 85                  90                  95

Arg Glu Glu Gln Tyr Asn Ser Ala Tyr Arg Val Val Ser Val Leu Thr
            100                 105                 110

Val Leu His Gln Asp Trp Leu Asn Gly Lys Glu Tyr Lys Cys Lys Val
        115                 120                 125

Thr Asn Lys Ala Leu Pro Ala Pro Ile Glu Lys Thr Ile Ser Lys Ala
130                 135                 140

Lys Gly Gln Pro Arg Glu Pro Gln Val Tyr Thr Leu Pro Pro Ser Arg
145                 150                 155                 160

Asp Glu Leu Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser
        195                 200                 205

Phe Phe Leu Tyr Ser Lys Leu Thr Val Asp Lys Ser Arg Trp Gln Gln
210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys Glu Arg Lys Cys
                245                 250                 255

Cys Val Glu Cys Pro Pro Cys Pro
            260
```

<210> SEQ ID NO 76
<211> LENGTH: 264
<212> TYPE: PRT
<213> ORGANISM: Homo sapiens

<400> SEQUENCE: 76

```
Met Glu Thr Asp Thr Leu Leu Leu Trp Val Leu Leu Trp Val Pro
  1               5                  10                  15

Gly Ser Thr Gly Glu Pro Lys Ser Cys Asp Lys Thr His Thr Cys Pro
             20                  25                  30

Pro Cys Pro Ala Pro Glu Leu Leu Gly Gly Pro Ser Val Phe Leu Phe
```

```
                35                  40                  45
Pro Pro Lys Pro Lys Asp Thr Leu Met Ile Ser Arg Thr Pro Glu Val
    50                  55                  60

Thr Cys Val Val Val Asp Val Asp Phe Glu Asp Pro Glu Val Lys Phe
65                  70                  75                  80

Asn Trp Tyr Val Asp Gly Val Glu Val His Asn Ala Lys Thr Lys Pro
                85                  90                  95

Arg Glu Glu Gln Tyr Asn Ser Ala Tyr Arg Val Val Ser Val Leu Thr
            100                 105                 110

Val Leu His Gln Asp Trp Leu Asn Gly Lys Glu Tyr Lys Cys Lys Val
        115                 120                 125

Thr Asn Lys Ala Leu Pro Ala Pro Ile Glu Lys Thr Ile Ser Lys Ala
    130                 135                 140

Lys Gly Gln Pro Arg Glu Pro Gln Val Tyr Thr Leu Pro Pro Ser Arg
145                 150                 155                 160

Asp Glu Leu Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser
        195                 200                 205

Phe Phe Leu Tyr Ser Lys Leu Thr Val Asp Lys Ser Arg Trp Gln Gln
    210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys Glu Arg Lys Cys
                245                 250                 255

Cys Val Glu Cys Pro Pro Cys Pro
            260

<210> SEQ ID NO 77
<211> LENGTH: 264
<212> TYPE: PRT
<213> ORGANISM: Homo sapiens

<400> SEQUENCE: 77

Met Glu Thr Asp Thr Leu Leu Leu Trp Val Leu Leu Leu Trp Val Pro
1               5                   10                  15

Gly Ser Thr Gly Glu Pro Lys Ser Cys Asp Lys Thr His Thr Cys Pro
            20                  25                  30

Pro Cys Pro Ala Pro Glu Leu Leu Gly Gly Pro Ser Val Phe Leu Phe
        35                  40                  45

Pro Pro Lys Pro Lys Asp Thr Leu Met Ile Ser Arg Thr Pro Glu Val
    50                  55                  60

Thr Cys Val Val Val Asp Val His Phe Glu Asp Pro Glu Val Lys Phe
65                  70                  75                  80

Asn Trp Tyr Val Asp Gly Val Glu Val His Asn Ala Lys Thr Lys Pro
                85                  90                  95

Arg Glu Glu Gln Tyr Asn Ser Ala Tyr Arg Val Val Ser Val Leu Thr
            100                 105                 110

Val Leu His Gln Asp Trp Leu Asn Gly Lys Glu Tyr Lys Cys Lys Val
        115                 120                 125

Thr Asn Lys Ala Leu Pro Ala Pro Ile Glu Lys Thr Ile Ser Lys Ala
    130                 135                 140
```

```
Lys Gly Gln Pro Arg Glu Pro Gln Val Tyr Thr Leu Pro Pro Ser Arg
145                 150                 155                 160

Asp Glu Leu Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser
        195                 200                 205

Phe Phe Leu Tyr Ser Lys Leu Thr Val Asp Lys Ser Arg Trp Gln Gln
    210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys Glu Arg Lys Cys
                245                 250                 255

Cys Val Glu Cys Pro Pro Cys Pro
            260
```

```
<210> SEQ ID NO 78
<211> LENGTH: 264
<212> TYPE: PRT
<213> ORGANISM: Homo sapiens

<400> SEQUENCE: 78

Met Glu Thr Asp Thr Leu Leu Leu Trp Val Leu Leu Leu Trp Val Pro
1               5                   10                  15

Gly Ser Thr Gly Glu Arg Lys Cys Cys Val Glu Cys Pro Pro Cys Pro
                20                  25                  30

Glu Pro Lys Ser Cys Asp Lys Thr His Thr Cys Pro Pro Cys Pro Ala
            35                  40                  45

Pro Glu Leu Leu Gly Gly Pro Ser Val Phe Leu Phe Pro Pro Lys Pro
        50                  55                  60

Lys Asp Thr Leu Met Ile Ser Arg Thr Pro Glu Val Thr Cys Val Val
65                  70                  75                  80

Val Asp Val Glu Phe Glu Asp Pro Glu Val Lys Phe Asn Trp Tyr Val
                85                  90                  95

Asp Gly Val Glu Val His Asn Ala Lys Thr Lys Pro Arg Glu Glu Gln
            100                 105                 110

Tyr Ala Ser Thr Tyr Arg Val Val Ser Val Leu Thr Val Leu His Gln
        115                 120                 125

Asp Trp Leu Asn Gly Lys Glu Tyr Lys Cys Lys Val Thr Asn Lys Ala
    130                 135                 140

Leu Pro Ala Pro Ile Glu Lys Thr Ile Ser Lys Ala Lys Gly Gln Pro
145                 150                 155                 160

Arg Glu Pro Gln Val Tyr Thr Leu Pro Pro Ser Arg Glu Glu Met Thr
                165                 170                 175

Lys Asn Gln Val Ser Leu Thr Cys Leu Val Lys Gly Phe Tyr Pro Ser
            180                 185                 190

Asp Ile Ala Val Glu Trp Glu Ser Asn Gly Gln Pro Glu Asn Asn Tyr
        195                 200                 205

Lys Thr Thr Pro Pro Val Leu Asp Ser Asp Gly Ser Phe Phe Leu Tyr
    210                 215                 220

Ser Lys Leu Thr Val Asp Lys Ser Arg Trp Gln Gln Gly Asn Val Phe
225                 230                 235                 240

Ser Cys Ser Val Met His Glu Ala Leu His Asn His Tyr Thr Gln Lys
                245                 250                 255
```

Ser Leu Ser Leu Ser Pro Gly Lys
            260

<210> SEQ ID NO 79
<211> LENGTH: 264
<212> TYPE: PRT
<213> ORGANISM: Homo sapiens

<400> SEQUENCE: 79

Met Glu Thr Asp Thr Leu Leu Leu Trp Val Leu Leu Leu Trp Val Pro
1               5                   10                  15

Gly Ser Thr Gly Glu Arg Lys Cys Cys Val Glu Cys Pro Pro Cys Pro
            20                  25                  30

Glu Pro Lys Ser Cys Asp Lys Thr His Thr Cys Pro Pro Cys Pro Ala
        35                  40                  45

Pro Glu Leu Leu Arg Gly Pro Ser Val Phe Leu Phe Pro Pro Lys Pro
    50                  55                  60

Lys Asp Thr Leu Met Ile Ser Arg Thr Pro Glu Val Thr Cys Val Val
65                  70                  75                  80

Val Asp Val Glu Phe Glu Asp Pro Glu Val Lys Phe Asn Trp Tyr Val
                85                  90                  95

Asp Gly Val Glu Val His Asn Ala Lys Thr Lys Pro Arg Glu Glu Gln
            100                 105                 110

Tyr Asn Ser Thr Tyr Arg Val Val Ser Val Leu Thr Val Leu His Gln
        115                 120                 125

Asp Trp Leu Asn Gly Lys Glu Tyr Lys Cys Lys Val Thr Asn Lys Ala
    130                 135                 140

Leu Pro Ala Pro Ile Glu Lys Thr Ile Ser Lys Ala Lys Gly Gln Pro
145                 150                 155                 160

Arg Glu Pro Gln Val Tyr Thr Leu Pro Pro Ser Arg Asp Glu Leu Thr
                165                 170                 175

Lys Asn Gln Val Ser Leu Thr Cys Leu Val Lys Gly Phe Tyr Pro Ser
            180                 185                 190

Asp Ile Ala Val Glu Trp Glu Ser Asn Gly Gln Pro Glu Asn Asn Tyr
        195                 200                 205

Lys Thr Thr Pro Pro Val Leu Asp Ser Asp Gly Ser Phe Phe Leu Tyr
    210                 215                 220

Ser Lys Leu Thr Val Asp Lys Ser Arg Trp Gln Gln Gly Asn Val Phe
225                 230                 235                 240

Ser Cys Ser Val Met His Glu Ala Leu His Asn His Tyr Thr Gln Lys
                245                 250                 255

Ser Leu Ser Leu Ser Pro Gly Lys
            260

<210> SEQ ID NO 80
<211> LENGTH: 263
<212> TYPE: PRT
<213> ORGANISM: Homo sapiens

<400> SEQUENCE: 80

Met Glu Thr Asp Thr Leu Leu Leu Trp Val Leu Leu Val Pro Gly
1               5                   10                  15

Ser Thr Gly Glu Arg Lys Cys Cys Val Glu Cys Pro Pro Cys Pro Glu
            20                  25                  30

Pro Lys Ser Cys Asp Lys Thr His Thr Cys Pro Pro Cys Pro Ala Pro
        35                  40                  45

```
Glu Leu Leu Gly Gly Asp Ser Val Phe Leu Phe Pro Pro Lys Pro Lys
            50                  55                  60
Asp Thr Leu Met Ile Ser Arg Thr Pro Glu Val Thr Cys Val Val Val
 65                  70                  75                  80
Asp Val Glu Phe Glu Asp Pro Glu Val Lys Phe Asn Trp Tyr Val Asp
                85                  90                  95
Gly Val Glu Val His Asn Ala Lys Thr Lys Pro Arg Glu Glu Gln Tyr
            100                 105                 110
Asn Ser Thr Tyr Arg Val Val Ser Val Leu Thr Val Leu His Gln Asp
            115                 120                 125
Trp Leu Asn Gly Lys Glu Tyr Lys Cys Lys Val Thr Asn Lys Ala Leu
130                 135                 140
Pro Ala Pro Ile Glu Lys Thr Ile Ser Lys Ala Lys Gly Gln Pro Arg
145                 150                 155                 160
Glu Pro Gln Val Tyr Thr Leu Pro Pro Ser Arg Glu Glu Met Thr Lys
                165                 170                 175
Asn Gln Val Ser Leu Thr Cys Leu Val Lys Gly Phe Tyr Pro Ser Asp
            180                 185                 190
Ile Ala Val Glu Trp Glu Ser Asn Gly Gln Pro Glu Asn Asn Tyr Lys
            195                 200                 205
Thr Thr Pro Pro Val Leu Asp Ser Asp Gly Ser Phe Phe Leu Tyr Ser
210                 215                 220
Lys Leu Thr Val Asp Lys Ser Arg Trp Gln Gln Gly Asn Val Phe Ser
225                 230                 235                 240
Cys Ser Val Met His Glu Ala Leu His Asn His Tyr Thr Gln Lys Ser
                245                 250                 255
Leu Ser Leu Ser Pro Gly Lys
            260

<210> SEQ ID NO 81
<211> LENGTH: 264
<212> TYPE: PRT
<213> ORGANISM: Homo sapiens

<400> SEQUENCE: 81

Met Glu Thr Asp Thr Leu Leu Leu Trp Val Leu Leu Leu Trp Val Pro
 1               5                  10                  15
Gly Ser Thr Gly Glu Pro Lys Ser Cys Asp Lys Thr His Thr Cys Pro
             20                  25                  30
Pro Cys Pro Ala Pro Pro Val Ala Gly Gly Pro Ser Val Phe Leu Phe
         35                  40                  45
Pro Pro Lys Pro Lys Asp Thr Leu Met Ile Ser Arg Thr Pro Glu Val
 50                  55                  60
Thr Cys Val Val Val Asp Val Glu Phe Glu Asp Pro Glu Val Lys Phe
 65                  70                  75                  80
Asn Trp Tyr Val Asp Gly Val Glu Val His Asn Ala Lys Thr Lys Pro
                 85                  90                  95
Arg Glu Glu Gln Tyr Ala Ser Thr Tyr Arg Val Val Ser Val Leu Thr
            100                 105                 110
Val Leu His Gln Asp Trp Leu Asn Gly Lys Glu Tyr Lys Cys Lys Val
            115                 120                 125
Thr Asn Lys Ala Leu Pro Ala Pro Ile Glu Lys Thr Ile Ser Lys Ala
130                 135                 140
Lys Gly Gln Pro Arg Glu Pro Gln Val Tyr Thr Leu Pro Pro Ser Arg
```

```
        145                 150                 155                 160
Asp Glu Leu Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
                180                 185                 190

Glu Asn Asn Tyr Lys Thr Thr Pro Val Leu Asp Ser Asp Gly Ser
                195                 200                 205

Phe Phe Leu Tyr Ser Lys Leu Thr Val Asp Lys Ser Arg Trp Gln Gln
        210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys Glu Arg Lys Cys
                245                 250                 255

Cys Val Glu Cys Pro Pro Cys Pro
                260

<210> SEQ ID NO 82
<211> LENGTH: 264
<212> TYPE: PRT
<213> ORGANISM: Homo sapiens

<400> SEQUENCE: 82

Met Glu Thr Asp Thr Leu Leu Leu Trp Val Leu Leu Leu Trp Val Pro
1               5                   10                  15

Gly Ser Thr Gly Glu Pro Lys Ser Cys Asp Lys Thr His Thr Cys Pro
                20                  25                  30

Pro Cys Pro Ala Pro Pro Leu Leu Arg Gly Pro Ser Val Phe Leu Phe
            35                  40                  45

Pro Pro Lys Pro Lys Asp Thr Leu Met Ile Ser Arg Thr Pro Glu Val
        50                  55                  60

Thr Cys Val Val Val Ala Val Glu Phe Glu Asp Pro Glu Val Lys Phe
65                  70                  75                  80

Asn Trp Tyr Val Asp Gly Val Glu Val His Asn Ala Lys Thr Lys Pro
                85                  90                  95

Arg Glu Glu Gln Tyr Ala Ser Thr Tyr Arg Val Val Ser Val Leu Thr
                100                 105                 110

Val Leu His Gln Asp Trp Leu Asn Gly Lys Glu Tyr Lys Cys Lys Val
            115                 120                 125

Thr Asn Lys Ala Leu Pro Ala Pro Ile Glu Lys Thr Ile Ser Lys Ala
        130                 135                 140

Lys Gly Gln Pro Arg Glu Pro Gln Val Tyr Thr Leu Pro Pro Ser Arg
145                 150                 155                 160

Asp Glu Leu Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
                180                 185                 190

Glu Asn Asn Tyr Lys Thr Thr Pro Pro Val Leu Asp Ser Asp Gly Ser
                195                 200                 205

Phe Phe Leu Tyr Ser Lys Leu Thr Val Asp Lys Ser Arg Trp Gln Gln
        210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys Glu Arg Lys Cys
                245                 250                 255
```

Cys Val Glu Cys Pro Pro Cys Pro
            260

<210> SEQ ID NO 83
<211> LENGTH: 264
<212> TYPE: PRT
<213> ORGANISM: Homo sapiens

<400> SEQUENCE: 83

Met Glu Thr Asp Thr Leu Leu Leu Trp Val Leu Leu Leu Trp Val Pro
1               5                   10                  15

Gly Ser Thr Gly Glu Pro Lys Ser Cys Asp Lys Thr His Thr Cys Pro
            20                  25                  30

Pro Cys Pro Ala Pro Pro Val Ala Gly Gly Pro Ser Val Phe Leu Phe
        35                  40                  45

Pro Pro Lys Pro Lys Asp Thr Leu Met Ile Ser Arg Thr Pro Glu Val
50                  55                  60

Thr Cys Val Val Val Asp Val Glu Phe Glu Asp Pro Glu Val Lys Phe
65                  70                  75                  80

Asn Trp Tyr Val Asp Gly Val Glu Val His Asn Ala Lys Thr Lys Pro
                85                  90                  95

Arg Glu Glu Gln Tyr Ala Ser Thr Tyr Arg Val Val Ser Val Leu Thr
            100                 105                 110

Val Leu His Gln Asp Trp Leu Asn Gly Lys Glu Tyr Lys Cys Lys Val
        115                 120                 125

Thr Asn Lys Ala Phe Pro Ala Pro Ile Glu Lys Thr Ile Ser Lys Ala
130                 135                 140

Lys Gly Gln Pro Arg Glu Pro Gln Val Tyr Thr Leu Pro Pro Ser Arg
145                 150                 155                 160

Asp Glu Leu Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser
        195                 200                 205

Phe Phe Leu Tyr Ser Lys Leu Thr Val Asp Lys Ser Arg Trp Gln Gln
210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys Glu Arg Lys Cys
                245                 250                 255

Cys Val Glu Cys Pro Pro Cys Pro
            260

<210> SEQ ID NO 84
<211> LENGTH: 264
<212> TYPE: PRT
<213> ORGANISM: Homo sapiens

<400> SEQUENCE: 84

Met Glu Thr Asp Thr Leu Leu Leu Trp Val Leu Leu Leu Trp Val Pro
1               5                   10                  15

Gly Ser Thr Gly Glu Pro Lys Ser Cys Asp Lys Thr His Thr Cys Pro
            20                  25                  30

Pro Cys Pro Ala Pro Glu Leu Leu Gly Gly Asp Ser Val Phe Leu Phe
        35                  40                  45

```
Pro Pro Lys Pro Lys Asp Thr Leu Met Ile Ser Arg Thr Pro Glu Val
    50                  55                  60

Thr Cys Val Val Cys Val Glu Phe Glu Asp Pro Glu Val Lys Phe
 65              70                  75                  80

Asn Trp Tyr Val Asp Gly Val Glu Val His Asn Ala Lys Thr Lys Pro
                 85                  90                  95

Arg Glu Glu Gln Tyr Asn Ser Thr Tyr Arg Val Val Ser Val Leu Thr
                100                 105                 110

Val Leu His Gln Asp Trp Leu Asn Gly Lys Glu Tyr Lys Cys Lys Val
            115                 120                 125

Thr Asn Lys Ala Leu Pro Ala Pro Ile Glu Lys Thr Ile Ser Lys Ala
            130                 135                 140

Lys Gly Gln Pro Arg Glu Pro Gln Val Tyr Thr Leu Pro Pro Ser Arg
145                 150                 155                 160

Asp Glu Leu Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
                180                 185                 190

Glu Asn Asn Tyr Lys Thr Thr Pro Pro Val Leu Asp Ser Asp Gly Ser
            195                 200                 205

Phe Phe Leu Tyr Ser Lys Leu Thr Val Asp Lys Ser Arg Trp Gln Gln
            210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys Glu Arg Lys Cys
                245                 250                 255

Cys Val Glu Cys Pro Pro Cys Pro
                260

<210> SEQ ID NO 85
<211> LENGTH: 264
<212> TYPE: PRT
<213> ORGANISM: Homo sapiens

<400> SEQUENCE: 85

Met Glu Thr Asp Thr Leu Leu Leu Trp Val Leu Leu Leu Trp Val Pro
 1               5                  10                  15

Gly Ser Thr Gly Glu Pro Lys Ser Cys Asp Lys Thr His Thr Cys Pro
                 20                  25                  30

Pro Cys Pro Ala Pro Glu Leu Leu Gly Gly Asp Ser Val Phe Leu Phe
             35                  40                  45

Pro Pro Lys Pro Lys Asp Thr Leu Met Ile Ser Arg Thr Pro Glu Val
    50                  55                  60

Thr Cys Val Val Val Pro Val Glu Phe Glu Asp Pro Glu Val Lys Phe
 65              70                  75                  80

Asn Trp Tyr Val Asp Gly Val Glu Val His Asn Ala Lys Thr Lys Pro
                 85                  90                  95

Arg Glu Glu Gln Tyr Asn Ser Thr Tyr Arg Val Val Ser Val Leu Thr
                100                 105                 110

Val Leu His Gln Asp Trp Leu Asn Gly Lys Glu Tyr Lys Cys Lys Val
            115                 120                 125

Thr Asn Lys Ala Leu Pro Ala Pro Ile Glu Lys Thr Ile Ser Lys Ala
            130                 135                 140

Lys Gly Gln Pro Arg Glu Pro Gln Val Tyr Thr Leu Pro Pro Ser Arg
145                 150                 155                 160
```

```
Asp Glu Leu Thr Lys Asn Gln Val Ser Leu Thr Cys Leu Val Lys Gly
                165                 170                 175
Phe Tyr Pro Ser Asp Ile Ala Val Glu Trp Glu Ser Asn Gly Gln Pro
            180                 185                 190
Glu Asn Asn Tyr Lys Thr Thr Pro Pro Val Leu Asp Ser Asp Gly Ser
        195                 200                 205
Phe Phe Leu Tyr Ser Lys Leu Thr Val Asp Lys Ser Arg Trp Gln Gln
210                 215                 220
Gly Asn Val Phe Ser Cys Ser Val Met His Glu Ala Leu His Asn His
225                 230                 235                 240
Tyr Thr Gln Lys Ser Leu Ser Leu Ser Pro Gly Lys Glu Arg Lys Cys
                245                 250                 255
Cys Val Glu Cys Pro Pro Cys Pro
            260

<210> SEQ ID NO 86
<211> LENGTH: 263
<212> TYPE: PRT
<213> ORGANISM: Homo sapiens

<400> SEQUENCE: 86

Met Glu Thr Asp Thr Leu Leu Leu Trp Val Leu Leu Leu Val Pro Gly
1               5                   10                  15
Ser Thr Gly Glu Arg Lys Cys Cys Val Glu Cys Pro Pro Cys Pro Glu
                20                  25                  30
Pro Lys Ser Cys Asp Lys Thr His Thr Cys Pro Pro Cys Pro Ala Pro
            35                  40                  45
Glu Leu Leu Arg Gly Pro Ser Val Phe Leu Phe Pro Pro Lys Pro Lys
        50                  55                  60
Asp Thr Leu Met Ile Ser Arg Thr Pro Glu Val Thr Cys Val Val Val
65                  70                  75                  80
Asp Val Glu Phe Glu Asp Pro Glu Val Lys Phe Asn Trp Tyr Val Asp
                85                  90                  95
Gly Val Glu Val His Asn Ala Lys Thr Lys Pro Arg Glu Glu Gln Tyr
                100                 105                 110
Asn Ser Thr Tyr Arg Val Val Ser Val Leu Thr Val Leu His Gln Asp
            115                 120                 125
Trp Leu Asn Gly Lys Glu Tyr Lys Cys Lys Val Thr Asn Lys Ala Phe
130                 135                 140
Pro Ala Pro Ile Glu Lys Thr Ile Ser Lys Ala Lys Gly Gln Pro Arg
145                 150                 155                 160
Glu Pro Gln Val Tyr Thr Leu Pro Pro Ser Arg Glu Glu Met Thr Lys
                165                 170                 175
Asn Gln Val Ser Leu Thr Cys Leu Val Lys Gly Phe Tyr Pro Ser Asp
            180                 185                 190
Ile Ala Val Glu Trp Glu Ser Asn Gly Gln Pro Glu Asn Asn Tyr Lys
        195                 200                 205
Thr Thr Pro Pro Val Leu Asp Ser Asp Gly Ser Phe Phe Leu Tyr Ser
210                 215                 220
Lys Leu Thr Val Asp Lys Ser Arg Trp Gln Gln Gly Asn Val Phe Ser
225                 230                 235                 240
Cys Ser Val Met His Glu Ala Leu His Asn His Tyr Thr Gln Lys Ser
                245                 250                 255
Leu Ser Leu Ser Pro Gly Lys
```

```
<210> SEQ ID NO 87
<211> LENGTH: 264
<212> TYPE: PRT
<213> ORGANISM: Homo sapiens

<400> SEQUENCE: 87

Met Glu Thr Asp Thr Leu Leu Leu Trp Val Leu Leu Leu Trp Val Pro
1               5                   10                  15

Gly Ser Thr Gly Glu Pro Lys Ser Cys Asp Lys Thr His Thr Cys Pro
            20                  25                  30

Pro Cys Pro Ala Pro Glu Leu Leu Gly Gly Asp Ser Val Phe Leu Phe
        35                  40                  45

Pro Pro Lys Pro Lys Asp Thr Leu Met Ile Ser Arg Thr Pro Glu Val
    50                  55                  60

Thr Cys Val Val Val Asp Val Glu Phe Glu Asp Pro Glu Val Lys Phe
65                  70                  75                  80

Asn Trp Tyr Val Asp Gly Val Glu Val His Asn Ala Lys Thr Lys Pro
                85                  90                  95

Arg Glu Glu Gln Tyr Asn Ser Thr Tyr Arg Val Val Ser Val Leu Thr
            100                 105                 110

Val Leu His Gln Asp Trp Leu Asn Gly Lys Glu Tyr Lys Cys Lys Val
        115                 120                 125

Thr Asn Lys Ala Phe Pro Ala Pro Ile Glu Lys Thr Ile Ser Lys Ala
    130                 135                 140

Lys Gly Gln Pro Arg Glu Pro Gln Val Tyr Thr Leu Pro Pro Ser Arg
145                 150                 155                 160

Asp Glu Leu Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser
        195                 200                 205

Phe Phe Leu Tyr Ser Lys Leu Thr Val Asp Lys Ser Arg Trp Gln Gln
    210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys Glu Arg Lys Cys
                245                 250                 255

Cys Val Glu Cys Pro Pro Cys Pro
            260
```